US 10,519,224 B2

(12) United States Patent
Bigal et al.

(10) Patent No.: US 10,519,224 B2
(45) Date of Patent: *Dec. 31, 2019

(54) TREATING HEADACHE COMPRISING ADMINISTERING AN ANTIBODY TO CALCITONIN GENE-RELATED PEPTIDE

(71) Applicant: Teva Pharmaceuticals International GmbH, Jona (CH)

(72) Inventors: Marcelo Bigal, Doylestown, PA (US); Sarah Walter, Redwood City, CA (US); Henry Stern, Woodside, CA (US); Michael Chang, Portola Valley, CA (US)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,900

(22) Filed: Jan. 25, 2018

(65) Prior Publication Data

US 2019/0031745 A1  Jan. 31, 2019

Related U.S. Application Data

(63) Continuation of application No. 14/664,715, filed on Mar. 20, 2015, now Pat. No. 9,896,502.

(60) Provisional application No. 62/119,778, filed on Feb. 23, 2015, provisional application No. 62/083,809, filed on Nov. 24, 2014, provisional application No. 61/968,897, filed on Mar. 21, 2014.

(51) Int. Cl.
*C07K 16/18* (2006.01)
*A61K 39/00* (2006.01)
*A61P 5/22* (2006.01)

(52) U.S. Cl.
CPC ........ *C07K 16/18* (2013.01); *A61K 2039/505* (2013.01); *A61K 2039/545* (2013.01); *C07K 2317/24* (2013.01); *C07K 2317/34* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 5,116,964 A | 5/1992 | Capon et al. | |
| 5,500,362 A | 3/1996 | Robinson et al. | |
| 5,545,806 A | 8/1996 | Longberg et al. | |
| 5,545,807 A | 8/1996 | Surani et al. | |
| 5,569,825 A | 10/1996 | Longberg et al. | |
| 5,625,126 A | 4/1997 | Longberg et al. | |
| 5,633,425 A | 5/1997 | Longberg et al. | |
| 5,661,016 A | 8/1997 | Longberg et al. | |
| 5,750,373 A | 5/1998 | Garrard et al. | |
| 5,821,337 A | 10/1998 | Carter et al. | |
| 5,851,556 A | 12/1998 | Breton et al. | |
| 5,932,215 A | 8/1999 | De Lacharriere et al. | |
| 5,935,586 A | 8/1999 | De Lacharriere et al. | |
| 5,938,586 A | 8/1999 | De Lacharriere et al. | |
| 6,168,809 B1 | 1/2001 | De Lacharriere et al. | |
| 6,313,097 B1 | 11/2001 | Eberlein et al. | |
| 6,344,438 B1 | 2/2002 | De Lacharriere et al. | |
| 6,344,449 B1 | 2/2002 | Rudolf et al. | |
| 6,509,014 B1 | 1/2003 | De Lacharriere et al. | |
| 6,521,609 B1 | 2/2003 | Doods et al. | |
| 6,552,043 B1 | 4/2003 | Patchett et al. | |
| 6,586,458 B1 | 7/2003 | Plachetka | |
| 6,737,056 B1 | 5/2004 | Presta | |
| 6,767,056 B2 | 5/2004 | Presta | |
| 7,109,214 B2 | 9/2006 | Zimmer et al. | |
| 7,384,930 B2 | 6/2008 | Chaturvedula et al. | |
| 7,479,488 B2 | 1/2009 | Mueller et al. | |
| 7,772,224 B2 | 8/2010 | Paone et al. | |
| 8,007,794 B2 | 8/2011 | Zeller et al. | |
| 8,168,592 B2 | 5/2012 | Gegg, Jr. et al. | |
| 8,293,239 B2 | 10/2012 | Poulsen et al. | |
| 8,298,536 B2 | 10/2012 | Poulsen et al. | |
| 8,586,045 B2 | 11/2013 | Zeller et al. | |
| 8,597,649 B2 | 12/2013 | Zeller et al. | |
| 8,623,366 B2 | 1/2014 | Pios et al. | |
| 8,669,368 B2 | 3/2014 | Leahy et al. | |
| 8,734,802 B1 | 5/2014 | Zeller et al. | |

(Continued)

FOREIGN PATENT DOCUMENTS

| | | |
|---|---|---|
| CA | 2563687 | 11/2005 |
| CL | 2013003336 | 6/2014 |

(Continued)

OTHER PUBLICATIONS

Wong et al., Cephalalgia, 2013; vol. 33, No. 11 pp. 964, Abstract # LBP12 presented at the 2013 International Headache Congress, Boston MA (Year: 2013).*
U.S. Appl. No. 13/621,981, filed Sep. 18, 2012, Poulsen et al.
U.S. Appl. No. 14/612,117, filed Feb. 2, 2015, Zeller et al.
U.S. Appl. No. 60/753,044, filed Dec. 22, 2005, Benschop et al.
U.S. Appl. No. 13/623,206, filed Sep. 20, 2012, Poulsen et al.
U.S. Appl. No. 13/835,394, filed Mar. 25, 2013, Zeller et al.
U.S. Appl. No. 14/855,959, filed Sep. 16, 2015, Pios et al.
U.S. Appl. No. 15/879,900, filed Jan. 25, 2008, Bigal et al.
"A study of LY2951742 in Participants with Episodic Cluster Headache," Clinical Trials.gov, last verified Mar. 2016, 6 pages.

(Continued)

*Primary Examiner* — Christina M Borgeest
(74) *Attorney, Agent, or Firm* — Fish & Richardson P.C.

(57) ABSTRACT

The invention features methods for preventing or treating CGRP associated disorders such as vasomotor symptoms and/or headaches (e.g., migraine, cluster headache, and tension headache) by administering an anti-CGRP antagonist antibody. Compositions for use in the disclosed methods are also provided. Antagonist antibody G1 and antibodies derived from G1 directed to CGRP are also described.

23 Claims, 23 Drawing Sheets

Specification includes a Sequence Listing.

(56) References Cited

U.S. PATENT DOCUMENTS

| | | |
|---|---|---|
| 9,115,194 B2 | 8/2015 | Zeller et al. |
| 9,266,951 B2 | 2/2016 | Zeller et al. |
| 9,328,167 B2 | 5/2016 | Poulsen et al. |
| 9,328,168 B2 | 5/2016 | Zeller et al. |
| 9,340,614 B2 | 5/2016 | Zeller et al. |
| 9,346,881 B2 | 5/2016 | Zeller et al. |
| 9,365,648 B1 | 6/2016 | Zeller et al. |
| 9,505,838 B2 | 11/2016 | Allan et al. |
| 9,884,907 B2 | 2/2018 | Zeller et al. |
| 9,884,908 B2 | 2/2018 | Zeller et al. |
| 9,890,210 B2 | 2/2018 | Zeller et al. |
| 9,890,211 B2 | 2/2018 | Zeller et al. |
| 2002/0162125 A1 | 10/2002 | Salmon et al. |
| 2002/0164707 A1 | 11/2002 | Adamou et al. |
| 2003/0069231 A1 | 4/2003 | Rudolf et al. |
| 2003/0194404 A1 | 10/2003 | Greenfeder et al. |
| 2005/0234054 A1 | 10/2005 | Mueller et al. |
| 2006/0183700 A1 | 8/2006 | Vater et al. |
| 2009/0220489 A1 | 9/2009 | Zeller et al. |
| 2010/0172895 A1 | 7/2010 | Boone et al. |
| 2011/0054150 A1* | 3/2011 | Poulsen ............... C07K 16/18 530/389.1 |
| 2011/0257371 A1* | 10/2011 | Poulsen ............... C07K 16/18 530/387.3 |
| 2011/0305711 A1 | 10/2011 | Poulsen et al. |
| 2012/0009192 A1* | 1/2012 | Zeller ................... C07K 16/26 424/135.1 |
| 2012/0225075 A1* | 9/2012 | Pios ...................... C07K 16/26 424/139.1 |
| 2012/0294797 A1 | 11/2012 | Kovacevich et al. |
| 2012/0294802 A1 | 11/2012 | Russo et al. |
| 2012/0294822 A1 | 11/2012 | Russo et al. |
| 2013/0216535 A1 | 8/2013 | Zeller et al. |
| 2013/0295087 A1 | 11/2013 | Poulsen et al. |
| 2013/0295088 A1 | 11/2013 | Poulsen et al. |
| 2014/0147438 A1 | 5/2014 | Zeller et al. |
| 2014/0308290 A1 | 10/2014 | Pios et al. |
| 2014/0314767 A1 | 10/2014 | Pios et al. |
| 2015/0050267 A1 | 2/2015 | Zeller et al. |
| 2015/0216535 A1 | 8/2015 | Herbowy et al. |
| 2015/0259415 A1 | 9/2015 | Allan et al. |
| 2015/0266948 A1 | 9/2015 | Bigal et al. |
| 2015/0291690 A1 | 10/2015 | Zeller et al. |
| 2015/0302690 A1 | 10/2015 | Poulsen et al. |
| 2015/0307607 A1 | 11/2015 | Bigal et al. |
| 2015/0322142 A1 | 12/2015 | Zeller et al. |
| 2015/0361171 A1 | 12/2015 | Zeller et al. |
| 2015/0361172 A1 | 12/2015 | Zeller et al. |
| 2015/0361173 A1 | 12/2015 | Zeller et al. |
| 2015/0376286 A1 | 12/2015 | Boone et al. |
| 2016/0168244 A1 | 2/2016 | Zeller et al. |
| 2017/0073403 A1 | 3/2017 | Allan et al. |
| 2017/0073412 A1 | 3/2017 | Pios et al. |

FOREIGN PATENT DOCUMENTS

| | | | |
|---|---|---|---|
| CL | 2017002686 | 10/2017 | |
| CL | 2017001379 | 12/2017 | |
| CN | 1308676 | 5/2001 | |
| CN | 1671711 | 9/2005 | |
| CN | 101309704 | 11/2008 | |
| CN | 103421114 | 12/2013 | |
| EP | 0212432 | 3/1987 | |
| EP | 1031350 | 8/2000 | |
| EP | 1556020 | 7/2005 | |
| EP | 1770091 | 4/2007 | |
| EP | 2380592 | 10/2011 | |
| EP | 2579894 A1 | 4/2013 | |
| EP | 2709662 A1 | 3/2014 | |
| EP | 2709663 A2 | 3/2014 | |
| EP | 2710039 A2 | 3/2014 | |
| JP | H07196700 A | 8/1995 | |
| JP | H08268874 A | 10/1996 | |
| JP | 2007523870 | 8/2007 | |
| JP | 2009515942 | 4/2009 | |
| RU | 2329062 | 7/2008 | |
| WO | WO 1991/000737 | 1/1991 | |
| WO | WO 1994/021665 A1 | 9/1994 | |
| WO | WO 1995/05468 A1 | 2/1995 | |
| WO | WO 1996/004928 A1 | 2/1996 | |
| WO | WO 1996/33735 A1 | 10/1996 | |
| WO | WO 1997/009046 A1 | 3/1997 | |
| WO | WO 1997/041223 A1 | 11/1997 | |
| WO | WO 1998/003534 A1 | 1/1998 | |
| WO | WO 1998/009630 A1 | 3/1998 | |
| WO | WO 1998/011128 A1 | 3/1998 | |
| WO | WO 1998/056779 A1 | 12/1998 | |
| WO | WO 1999/058572 A1 | 11/1999 | |
| WO | WO 2000/018764 A1 | 4/2000 | |
| WO | WO 2001/027160 | 4/2001 | |
| WO | WO 2003/027252 | 4/2003 | |
| WO | WO 2003/093472 A2 | 11/2003 | |
| WO | WO 2003/104236 A1 | 12/2003 | |
| WO | WO 2004/003019 A2 | 1/2004 | |
| WO | WO 2004/014351 A2 | 2/2004 | |
| WO | WO 2004/050683 A2 | 6/2004 | |
| WO | WO 2004/082602 A2 | 9/2004 | |
| WO | WO 2004/082605 A2 | 9/2004 | |
| WO | WO 2004/082678 A1 | 9/2004 | |
| WO | WO 2004/083187 A1 | 9/2004 | |
| WO | WO 2004/087649 A2 | 10/2004 | |
| WO | WO 2004/091514 A2 | 10/2004 | |
| WO | WO 2004/092166 A2 | 10/2004 | |
| WO | WO 2004/092168 A1 | 10/2004 | |
| WO | WO 2004/097421 | 11/2004 | |
| WO | WO 2005/009962 A1 | 2/2005 | |
| WO | WO 2005/041757 | 5/2005 | |
| WO | WO 2005/100360 A1 | 10/2005 | |
| WO | WO 2006/077212 A1 | 7/2006 | |
| WO | WO 2007/025212 A2 | 3/2007 | |
| WO | WO 2007/025286 A2 | 3/2007 | |
| WO | WO 2007/035906 A2 | 3/2007 | |
| WO | WO 2007/048026 A2 | 4/2007 | |
| WO | WO 2007/061676 A2 | 5/2007 | |
| WO | WO2007054809 * | 5/2007 | ............ C07K 16/00 |
| WO | WO 2007/076336 A1 | 7/2007 | |
| WO | WO 2008/011190 A1 | 1/2008 | |
| WO | WO 2008/097824 | 8/2008 | |
| WO | WO 2009/055350 | 4/2009 | |
| WO | WO2009/109908 * | 9/2009 | ............ A61K 39/395 |
| WO | WO2009/109911 * | 9/2009 | ............ A61K 39/395 |
| WO | WO 2010/006168 A2 | 1/2010 | |
| WO | WO 2010/075238 A1 | 7/2010 | |
| WO | WO 2011/024113 A1 | 3/2011 | |
| WO | WO2011156324 * | 12/2011 | ............ A61K 39/395 |
| WO | WO 2012/162243 A2 | 11/2012 | |
| WO | WO 2012/162253 A2 | 11/2012 | |
| WO | WO 2012/162257 A2 | 11/2012 | |
| WO | WO 2013/028635 A1 | 2/2013 | |
| WO | WO 2014/145650 A1 | 9/2014 | |
| WO | WO 2014/146074 A2 | 9/2014 | |
| WO | WO 2015/003122 A2 | 1/2015 | |
| WO | WO 2016/044224 A1 | 3/2016 | |
| WO | WO 2016/171742 | 10/2016 | |
| WO | WO 2016/205037 | 12/2016 | |

OTHER PUBLICATIONS

"Declaration of Marcelo Bigal, M.D., Ph.D.," European Patent No. EP1957106 B1, EP Application No. 06809207, dated Feb. 3, 2015, 41 pages.

AAN (American Academy of Neurology), "New Drugs Offer Hope for Migraine Prevention," AAN 66th Annual Meeting Abstract, Apr. 22, 2014, 1 pages.

Abstracts of the XII Congress of the International Headache Society, IHC 2005, Oct. 9-12, 2005, Cephalalgia 25:923, Oct. 9-12, 2005, 3 pages.

Adam et al., "Severity of mucosal inflammation as a predictor for alterations of visceral sensory function in a rat model," Pain 123(1-2):179-86, Jul. 2006, 8 pages.

Adwanikar et al., "Spinal CGRP1 receptors contribute to supraspinally organized pain behavior and pain-related sensitization of amygdala neurons," Pain 132(1-2):53-66, Nov. 2007, 14 pages.

(56) References Cited

OTHER PUBLICATIONS

Aiyar et al., "Pharmacology of SB-273779, a nonpeptide calcitonin gene-related peptide 1 receptor antagonist," J Pharmacolog Exp Therap 296(3):768-775, 2001, 8 pages.
Al-Lazikani et al., "Standard conformations for the canonical structures of immunoglobulins," J Mol Biol 273(4):927-948, Nov. 7, 1997, 22 pages.
Almagro and Strohl, "Antibody engineering: humanization, affinity maturation, and selection technique," Therapeutic Monoclonal Antibodies Chapter 13, pp. 311-334, 2009, 24 pages.
Amara et al., "Expression in brain of a messenger RNA encoding a novel neuropeptide homologous to calcitonin gene-related peptide," Science 229(4718):1094-1097, Sep. 13, 1985, 4 pages.
Ambalavanar et al., "Deep tissue inflammation upregulates neuropeptides and evokes nociceptive behaviors which are modulated by a neuropeptide antagonist," Pain 120(1-2):53-68, Jan. 2006, 16 pages.
American Headache Society, "Initial Results for LY2951742, A New Investigational Medicine for Migraine Prevention," 2014. Available at URL: <http://www.americanheadachesociety.org/initial_results_for_ly2951742_a_new_investigational_medicine_for_migraine_prevention>. Accessed May 15, 2014, 2 pages.
An, "Therapeutic Monoclonal Antibodies From Bench to Clinic," Wiley Chapter 31, pp. 711-762, 2009, 55 pages.
Andrew et al., "Monoclonal antibodies distinguishing alpha and beta forms of calcitonin gene-related peptide," J Immunol Methods 134(1):87-94, Nov. 6, 1990, 8 pages.
Armour et al., "Recombinant human IgG molecules lacking Fcγ receptor I binding and monocyte triggering activities," Eur J Immunol 29(8):2613-2624, Aug. 1999, 12 pages.
Arulmani et al., "Calcitonin gene-related peptide and its role in migraine pathophysiology," Eur J Pharmacol 500(1-3):315-330, Oct. 1, 2004, 16 pages.
Arulmozhi et al., "Migraine: current concepts and emerging therapies," Vascul Pharmacol 43(3):176-187, Sep. 2005, 12 pages.
Asahina et al., "Specific induction of cAMP in Langerhans cells by calcitonin gene-related peptide: Relevance to functional effects," Proceed Nat Acad Sci USA 92(18):8323-8327, Aug. 1995, 5 pages.
Ashina et al., "Calcitonin gene-related peptide levels during nitric oxide-induced headache in patients with chronic tension-type headache," Eur J Neurol 8(2):173-178, Mar. 2001, 6 pages.
Ashina et al., "Evidence for increased plasma levels of calcitonin gene-related peptide in migraine outside of attacks," Pain 86(1-2):133-138, May 2000, 6 pages.
Ashina et al., "Plasma levels of calcitonin gene-related peptide in chronic tension-type headache," Neurology 55(9):1335-1340, Nov. 2000, 6 pages.
ATCC website search for PTA-6866 deposit, Oct. 22, 2010, 1 page.
ATCC website search for PTA-6867 deposit, Oct. 22, 2010, 1 pages.
Aziz, "Visceral hypersensitivity: fact or fiction," Gastroenterology 131(2):661-664, Aug. 2006, 4 pages.
Balint and Larrick, "Antibody engineering by parsimonious mutagenesis," Gene 137(1):109-118, Dec. 1993, 10 pages.
Bard et al., "Peripherally administered antibodies against amyloid beta-peptide enter the central nervous system and reduce pathology in a mouse model of Alzheimer disease," Nat Med 6(8):916-919, Aug. 2000, 4 pages.
Bell, "Calcitonin Gene-Related Peptide Receptor Antagonists: New Therapeutic Agents for Migraine," J Med Chem 57(19):7838-7858, Jun. 24, 2014, 21 pages.
Bennett et al., "Alleviation of mechanical and thermal allodynia by CGRP(8-37) in a rodent model of chronic central pain," Pain 86(1-2):163-175, May 2000, 13 pages.
Benschop et al., "Development of a novel antibody to calcitonin gene-related peptide for the treatment of osteoarthritis-related pain," Osteoarthritis Cartilage 22(4):578-585, Apr. 2014, 8 pages.
Bigal et al., "Calcitonin gene-related peptide (CGRP) and migraine current understanding and state of development", Headache: The Journal of Head and Face Pain 53(8):1230-4244, Sep. 2013, 15 pages.

Bigal et al., "Cardiovascular and hemodynamic parameters in women following prolonged CGRP inhibition using LBR-101, a monoclonal antibody against CGRP," Cephalalgia 34(12):968-976, Oct. 2014, 9 pages.
Bigal et al., "Emerging drugs for lnigraine prophylaxis and treatment," MedGenMed 8(2): 31, May 4, 2006, 12 pages.
Bigal et al., "Migraine in the Triptan Era: Lessons From Epidemiology, Pathophysiology, and Clinical Science", Headache 49:S21-S33, Feb. 2009, 13 pages.
Bigal et al., "Migraine in the Triptan Era: Progresses achieved, lessons learned and future developments," Arquivos de Neuro-Psiquiatria 67(2-B):559-569, Jun. 2009, 11 pages.
Bigal et al., "Monoclonal Antibodies for Migraine: Preventing Calcitonin Gene-Related Peptide Activity ," CNS Drugs, 28(5): 389-399, Mar. 2014, 11 pages.
Bigal et al., "New Migraine preventive options: an update with pathophysiological considerations," Rev Hosp Clin Fae Med Sao Paulo 57(6):293-298, Nov.-Dec. 2002, 6 pages.
Bigal et al., "Safety and tolerability of LBR-101, a humanized monoclonal antibody that blocks the binding of CGRP to its receptor: Results of the Phase 1 program," Cephalalgia 34(7):483-492, Dec. 23, 2013, 10 pages.
Bigal et al., "TEV-48125 for the preventive treatment of chronic migraine," Neurology 87(1):41-48, Jul. 5, 2016, 8 pages.
Bigal, "Experimental Agent Boosts Hope for Monoclonal Antibody Treatment of Migraine," Neurology Reviews 22(5):5, May 6, 2014, 3 pages.
Bird et al., "Single-chain antigen-binding proteins," Science 242(4877):423-426, Oct. 21, 1988, 5 pages.
Boerner et al., "Production of antigen-specific human monoclonal antibodies from in vitro-primed human splenocytes," J Immunol 147(1):86-95, Jul. 1, 1991, 10 pages.
Botox Package Insert, "BLA STN 103000/5215—FDA Approved Labeling Text," Oct. 2010, 25 pages.
Bowen et al., "Tumor necrosis factor-alpha stimulation of calcitonin gene-related peptide expression and secretion from rat trigeminal ganglion neurons," J Neurochem 96(1):65-77, Jan. 2006, 13 pages.
Brain and Edvinsson, "Chapter 16: Calcitonin Gene-Related Peptide and Other Peptides," The Headaches, Third Edition, pp. 159-164, 2006, 8 pages.
Brain and Grant, "Vascular actions of calcitonin gene-related peptide and adrenomedullin," Physiol Rev 84(3):903-934, Jul. 2004, 32 pages.
Brain, "Calcitonin gene-related peptide (CGRP) antagonists: blockers of neuronal transmission in migraine," Brit J Pharmacol 142(7):1053-1054, Aug. 2004, 2 pages.
Brandes et al., "Topiramate for Migraine Prevention," J Am Med Assoc 291(8):965-973, Feb. 25, 2004, 9 pages.
Brody et al., "Aptamers as therapeutic and diagnostic agents," Reviews in Molecular Biotechnology 74(1):5-13, Mar. 2000, 9 pages.
Brorson et al., "Mutational analysis of avidity and fine specificity of anti-levan antibodies," J Immunol 163(12):6694-6701, Dec. 15, 1999, 9 pages.
Brummell et al., "Probing the combining site of an anti-carbohydrate antibody by saturation-mutagenesis: role of the heavy-chain CDR3 residues," Biochemistry, 32(4):1180-1187, Feb. 2, 1993, 2 pages.
Buckley et al., "The partial inhibition of inflammatory responses induced by capsaicin using the Fab fragment of a selective calcitonin gene-related peptide antiserum in rabbit skin," Neuroscience 48(4):963-968, Jun. 1992, 6 pages.
Burks et al., "In vitro scanning saturation mutagenesis of an antibody binding pocket," Proc Natl Acad Sci USA 94(2):412-417, Jan. 21, 1997, 6 pages.
Burstein and Jakubowski, "Analgesic Triptan Action in an Animal Model of Intracranial Pain: A Race against the Development of Central Sensitization," Ann Neurol 55(1):27-36, Jan. 2004, 8 pages.
Burstein et al., "Defeating Migraine Paine with Triptans: A Race against the Development of Cutaneous Allodynia," Ann Neurol 55(1):19-26, Jan. 2004, 8 pages.
Buse et al., "Psychiatric comorbidities of episodic and chronic migraine," J Neurl 260:1960-1969, Nov. 2013, 11 pages.

(56) References Cited

OTHER PUBLICATIONS

Capel et al., "Heterogeneity of human IgG Fc receptors," Immunomethods 4(1):25-34, Feb. 1994, 10 pages.
Caraceni et al., "Pain measurement tools and methods in clinical research in palliative care: recommendations of an Expert Working Group of the European Association of Palliative Care," J Pain Symptom Manage 23(3):239-255, Mar. 2002, 17 pages.
Carter, "Potent antibody therapeutics by design," Nature Reviews Immunology 6(5):343-57, May 2006, 20 pages.
Casset et al., "A peptide mimetic of an anti-CD4 monoclonal antibody by rational design," Biochem Biophys Res Commun 307(1):198-205, Jul. 18, 2003, 8 pages.
Chen et al., "Generation and analysis of random point mutations in an antibody CDR2 sequence: many mutated antibodies lose their ability to bind antigen," J Exp Med 176(3):855-866, Sep. 1992, 12 pages.
Chen et al., "Selection and analysis of an optimized anti-VEGF antibody: crystal structure of an affinity-matured Fab in complex with antigen," J Mol Biol 293(4):865-881, Nov. 5, 1999, 17 pages.
Chothia et al., "Conformations of immunoglobulin hypervariable regions," Nature 342(6252):877-883, Dec. 21-28, 1989, 7 pages.
Clynes et al., "Fc receptors are required in passive and active immunity to melanoma," Proc Natl Acad Sci USA 95(2):652-656, Jan. 20, 1998, 5 pages.
Cole et al., "The EBV-hybridoma technique and its application to human lung cancer," Monoclonal Antibodies and Cancer Therapy 27:77-96, 1985, 20 pages.
Colman, "Effects of amino acid sequence changes on antibody-antigen interactions," Res Immunol 145(1):33-36, Jan. 1994, 4 pages.
Conner et al., "Interaction of calcitonin-gene-related peptide with its receptors," Biochem Soc Trans 30(4):451-455, Aug. 2002, 5 pages.
Correia, "Stability of IgG isotypes in serum," mAbs 2(3):221-232, May/Jun. 2010, 12 pages.
Covell et al., "Pharmacokinetics of monoclonal immunoglobulin G1, F(ab')2, and Fab' in mice," Cancer Res 46(8):3969-3978, Aug. 1986, 10 pages.
Davies and Riechmann, "Affinity improvement of single antibody VH domains: residues in all three hypervariable regions affect antigen binding," Immunotechnology 2(3):169-179, Sep. 1996, 11 pages.
Davletov et al., "Beyond BOTOX: advantages and lilnitations of individual botulinum neurotoxins," Trends Neurosci 28(8):446-452, Aug. 2005, 7 pages.
De Felice et al., "Opiate-induced persistent pronociceptive trigeminal neural adaptations: potential relevance to opiate-induced medication overuse headache," Cephalalgia 29(12):1277-1284, May 2009, 9 pages.
De Haas et al., "Fc gamma receptors of phagocytes," J Lab Clin Med 126(4):330-341, Oct. 1995, 12 pages.
De Pascalis et al., "Grafting of "abbreviated" complementarity-determining regions containing specificity-determining residues essential for ligand contact to engineer a less immunogenic humanized monoclonal antibody," J Immunol 169(6):3076-3084, Sep. 15, 2002, 9 pages.
Declaration Dr. Jes Olesen No. 2, dated Feb. 7, 2016, 15 pages.
Declaration Dr. Marcelo Bigal and Dr. Bigal's Cirruculum Vitae, dated Mar. 2, 2015, 41 pages.
Declaration of Dr. Jes Olesen regarding EP1957106, dated Jul. 11, 2014, 58 pages.
Declaration of Dr. Leonard Presta regarding EP1957106, dated Jul. 11, 2014, 53 pages.
Declaration of Dr. Robert Benschop regarding EP1957106, dated Jul. 16, 2014, 13 pages.
Delafoy et al., "Interactive involvement of brain derived neurotrophic factor, nerve growth factor, and calcitonin gene related peptide in colonic hypersensitivity in the rat," Gut 55(7):940-945, Jul. 2006, 6 pages.
Deleu, "Guidelines for the prevention of migraine," Saudi Med J 20(7):495-500, Jul. 1999.
Denekas et al., "Inhibition of stimulated meningeal blood flow by a calcitonin gene-related peptide binding mirror-image RNA oligonucleotide," Brit J Pharmacol 148(4):536-543, Jun. 2006, 8 pages.
Dockray et al., "Immunoneutralization studies with calcitonin gene-related peptide," Ann N Y Acad Sci 657:258-267, Jun. 30, 1992, 10 pages.
Dodick et al., "OnabotulinumtoxinA for Treatment of Chronic Migraine: Pooled Results From the Double-Blind, Randomized, Placebo-Controlled Phases of the PREEMPT Clinical Program," Headache 50(6):921-936, Jun. 2010, 16 pages.
Dodick et al., "Safety and efficacy of ALD403, an antibody to calcitonin gene-related peptide, for the prevention of frequent episodic migraine: a randomised, double-blind, placebo-controlled, exploratory phase 2 trial," Lancet Neurol 13(11):1100-1107, Nov. 2014, 8 pages.
Dodick et al., "Safety and efficacy of LY2951742, a monoclonal antibody to calcitonin gene-related peptide, for the prevention of migraine: a phase 2, randomised, double-blind, placebo-controlled study," Lancet Neurol 13(9):885-892, Sep. 2014, 8 pages.
Dodick et al., Authors' reply re Site of effect of LY2951742 for migraine prophylaxis. Www.thelancet.com/neueology. vol. 14, 32-33, Jan. 2015, 3 pages.
Dolgin, "Antibody drugs set to revive flagging migraine target," Nat Rev Drug Discov 12(4):249-250, Apr. 2013, 2 pages.
Doods et al., "Pharmacological profile of BIBN4096BS, the first selective small molecule CGRP antagonist," Brit J Pharmacol 129(3):420-423, Feb. 2000, 4 pages.
Dressler et al., "Botulinum toxin: mechanisms of action," Eur Neurol 53(1):3-9, 2005, 6 pages.
Dufner et al., "Harnessing phage and ribosome display for antibody optimisation," Trends Biotechnol 24(11):523-529, Nov. 2006, 7 pages.
Durham and Vause, "Calcitonin gene-related peptide (CGRP) receptor antagonists in the treatment of migraine", CNS Drugs 24(7):539-548, Jul. 2010, 12 pages.
Durham et al., "CGRP-receptor antagonists—a fresh approach to migraine therapy?" N Eng J Med 350(11):1073-1075, Mar. 11, 2004, 3 pages.
Edvinsson and Hargreaves, "Chapter 31: CGRP Involvement in Migraines," in The Headaches, Third Edition, pp. 289-299, 2006, 13 pages.
Edvinsson and Tfelt-Hansen, "The blood-brain barrier in migraine treatment," Cephalalgia 28(12):1245-1258, Dec. 2008, 14 pages.
Edvinsson and Uddman, "Neurobiology in primary headaches," Brain Res Rev 48(3):438-456, Jun. 2005, 19 pages.
Edvinsson et al., "Effect of the CGRP receptor antagonist BIBN4096BS in human cerebral., coronary and omental arteries and in SK-N-MC cells," Eur J Pharmacol 434(1-2):49-53, Jan. 2, 2002, 5 pages.
Edvinsson et al., "Inhibitory effect of BIBN4096BS, CGRP8-37, a CGRPantibody and an RNA-Spiegelmer on CGRP induced vasodilatation in the perfused and non-perfused rat middle cerebral artery," Brit J Pharmacol 150(5):633-640, Mar. 2007, 8 pages.
Edvinsson, "Blockade of CGRP receptors in the intracranial vasculature: a new target in the treatment of headache," Cephalalgia 24:611-622, 2004, 12 pages.
Edvinsson, "CGRP blockers in migraine therapy: where do they act?" Brit J Pharmacol 155(7):967-969, Dec. 2008, 3 pages.
Edvinsson, "Clinical Data on the CGRP Antagonist BIBN4096BS for Treatment of Migraine Attacks," CNS Drug Reviews 11(1):69-76, Mar. 2005, 8 pages.
Eftekhari et al., "Localization of CGRP, CGRP receptor, PACAP and glutamate in trigeminal ganglion. Relation to the blood-brain barrier", Brain Research 1600:93-109, Mar. 2015, 5 pages.
El Vidge, "Anti-CGRP antibodies for migraine tum industry heads," Nat Biotechnol 32(8):707, Aug. 2014, 1 page.
Elshourbagy et al., "Molecular cloning and characterization of the porcine calcitonin gene-related peptide receptor," Endocrinology 139(4):1678-1683, Apr. 1998, 6 pages.
Escott and Brain, "Effect of a calcitonin gene-related peptide antagonist ($CGRP_{8-37}$) on skin vasodilatation and oedema induced by stimulation of the rat saphenous nerve," Brit J Pharmacol 110(2):772-776, Oct. 1993, 5 pages.

(56) References Cited

OTHER PUBLICATIONS

Escott et al., "Trigeminal ganglion stimulation increases facial skin blood flow in the rat: a major role for calcitonin gene-related peptide," Brain Res 669(1):93-99, Jan. 9, 1995, 7 pages.
European Notice of Opposition in European Patent No. 1957106, dated Jul. 11, 2014, 56 pages.
European Notice of Opposition in European Patent No. 1957106, dated Jul. 16, 2014, 51 pages.
European Office Action in Application No. 10754584, dated Dec. 16, 2013, 6 pages.
European Search Report in Application No. 11166787.9, dated May 8, 2012, 7 pages.
Evidence of Publication Date of Edvinsson, CNS Drug Reviews 11(1):69-76, 2005, 1 page.
Extended European Search Report in Application No. 15765287.6, dated Aug. 8, 2017, 8 pages.
Extended European Search Report in Application No. 16154411.9, dated Jul. 18, 2016, 8 pages.
Extended European Search Report in Application No. 17152503.3, dated May 3, 2017, 13 pages.
Fanciullacci et al., "Increase in plasma calcitonin gene-related peptide from the extracerebral circulation during nitroglycerin-induced cluster headache attack," Pain 60(2):119-123, Feb. 1995, 5 pages.
Felson et al., "The American College of Rheumatology preliminary core set of disease activity measures for rheumatoid arthritis clinical trials. The Committee on Outcome Measures in Rheumatoid Arthritis Clinical Trials," Arthritis Rheum 36(6):729-740, Jun. 1993, 12 pages.
Fischer et al., "The Nonpeptide Calcitonin Gene-Related Peptide Receptor Antagonist BIBN4096BS Lowers the Activity of Neurons with Meningeal Input in the Rat Spinal Trigeminal Nucleus," J Neurosci 25(25):5877-5883, Jun. 22, 2005, 7 pages.
Forster and Dockray, "The role of calcitonin gene-related peptide in gastric mucosal protection in the rat," Exp Physiol 76(4):623-626, Jul. 1991, 4 pages.
Francis et al., "The irritable bowel severity scoring system: a simple method of monitoring irritable bowel syndrome and its progress," Aliment Pharmacol Ther 11(2):395-402, Apr. 1997, 8 pages.
Fries et al., "The dimensions of health outcomes: the health assessment questionnaire, disability and pain scales," J Rheumatol 9(5):789-793, Sep.-Oct. 1982, 6 pages.
Frobert et al. "A sensitive sandwich enzyme immunoassay for calcitonin gene-related peptide (CGRP): characterization and application," Peptides 20(2):275-284, Feb. 1999, 10 pages.
Gallai et al., "Vasoactive peptide levels in the plasma of young migraine patients with and without aura assessed both interictally and ictally," Cephalalgia 15(5):384-390, Oct. 15, 1995, 7 pages.
Gay et al., "Interleukin-6 genetic ablation protects from trinitrobenzene sulfonic acid-induced colitis in mice," NeuroImmunoModulation 13(2):114-121, 2006, 8 pages.
Geppetti et al., "CGRP and migraine: neurogenic inflammation revisited," J Headache Pain 6(2):61-70, Apr. 2005, 10 pages.
Giamberadino and Marrtelletti, "Emerging drugs for migraine treatment," Expert Opininon 20(1):137-147, 2015, 11 pages.
Giffin et al., "Effect of the adenosine A 1 receptor agonist GR79236 on trigeminal nociception with blink reflex recordings in healthy human subjects," Cephalalgia 23(4):287-292, May 2003, 6 pages.
Goadsby and Hargreaves, "Refractory Migraine and Chronic Migraine: Pathophysiological Mechanisms", Headache 48:799-804, 2008, 8 pages.
Goadsby et al., "Migraine—Current Understanding and Treatment," N Eng J Med 346(4):257-270, Jan. 24, 2002, 14 pages.
Goadsby et al., "Vasoactive peptide release in the extracerebral circulation of humans during migraine headache," Ann Neurol 28(2):183-187, Aug. 1990, 5 pages.
Goadsby, "Calcitonin Gene-Related Peptide Antagonists as Treatments of Migraine and Other Primary Headaches," Drugs 65(18):2557-2567, Dec. 2005, 11 pages.
Goadsby, "Can we Develop Neurally Acting Drugs for the Treatment of Migraine?" Nat Rev Drug Discov 4:741-750, Sep. 2005, 10 pages.
Goadsby, "New targets in the acute treatment of headache," Curr Opin Neurol 18(3):283-288, Jun. 2005, 6 pages.
Goadsby, "Pathophysiology of cluster headache: a trigeminal autonomic cephalgia," Lancet Neurology 1:251-257, 2002, 7 pages.
Goadsby, "Pathophysiology of Migraine", Neurol Clin 27:335-360, May 2009, 6 pages.
Grennan and Jayson, "Rheumatoid arthritis," Textbook of Pain pp. 397-407, 1994, 15 pages.
Gupta et al., "Improvement of the closed cranial window model in rats by intracarotid infusion of signalling molecules implicated in migraine," Cephalalgia 30(1):27-36, Apr. 28, 2009, 10 pages.
Guyer et al., "Immunoglobulin binding by mouse intestinal epithelial cell receptors," J Immunol 117(2):587-593, Aug. 1976, 8 pages.
Hakala et al., "Modelling constrained calcitonin gene-related peptide analogues," Protein Eng 9(2):143-148, Feb. 1996, 6 pages.
Hay et al., "A comparison of the actions of BIBN4096BS and $CGRP_{8-37}$ on CGRP and adrenomedullin receptors expressed on SK-N-MC, L6, col. 29 and Rat 2 cells," Brit J Pharmacol 137(1):80-86, Sep. 2002, 7 pages.
Hay et al., "Determinants of 1-Piperidinecarboxamide, N-[2-[[5-Amino-1[[4-(4-pyridinyl)-1-piperazinyl]carbonyl]pentyl]amino]-1-[(3,5-dibromo-4-hydroxyphenyl)methyl]-2-oxoethyl]-4-(1,4-dihydro-2-oxo-3(2H)-quinazolinyl) (BIBN4096BS) Affinity for Calcitonin Gene-Related Peptide and Amylin Receptors—The Role of Receptor Activity Modifying Protein 1," Mol Pharmacol 70(6):1984-1991, Dec. 2006, 8 pages.
Hay et al., "Pharmacological Discrimination of Calcitonin Receptor: Receptor Activity-Modifying Protein Complexes," Mol Pharmacol 67(5):1655-1665, May 2005, 11 pages.
Hershey et al., "Investigation of the species selectivity of a nonpeptide CGRP receptor antagonist using a novel pharmacodynamic assay," Regulatory Peptides 127(1):71-77, Apr. 2005, 7 pages.
Ho et al., "CGRP and its receptors provide new insights into migraine pathophysiology," Nat Rev Neurol 6:573-582, Oct. 2010, 10 pages.
Hogue et al., "Pathophysiology and first-line treatment of osteoarthritis," Ann Pharmacother 36(4):679-686, Apr. 2002, 8 pages.
Holm et al., "Functional mapping and single chain construction of the anti-cytokeratin 8 monoclonal antibody TS1," Mol Immunol 44(6):1075-1084, Feb. 2007, 10 pages.
Holman et al., "Human alpha- and beta-CGRP and rat alpha-CGRP are coronary vasodilators in the rat," Peptides 7(2):231-235, Mar.-Apr. 1986, 5 pages.
Holt et al., "Domain antibodies: proteins for therapy," Trends Biotechnol 21(11):484-490, Nov. 2003, 7 pages.
Hong et al., "Pharmacological coupling and functional role for CGRP receptors in the vasodilation of rat pial arterioles," Am J Phsyiol 270(1):H317-H323, Jan. 1, 1996, 6 pages.
Hong et al., "Pharmacological evidence that calcitonin gene-related peptide is implicated in cerebral autoregulation," Am J Physiology—Heart Circ Physiol 266(1):H11-H16, 1994, 6 pages.
Honore et al., "Murine models of inflammatory, neuropathic and cancer pain each generates a unique set of neurochemical changes in the spinal cord and sensory neurons," Neuroscience 98(3):585-598, 2000, 14 pages.
Hoogenboom and Winter, "By-passing immunisation. Human antibodies from synthetic repertoires of germline VH gene segments rearranged in vitro," J Mol Biol 227(2):381-388, Sep. 20, 1992, 8 pages.
Hostetler et al., "In Vivo Quantification of Calcitonin Gene-Related Peptide Receptor Occupancy by Telcagepant in Rhesus Monkey and Human Brain Using the Positron Emission Tomography Tracer [11C]MK-4232," J Pharmacol Experim Therapeut 347(2):478-486, Nov. 1, 2013, 9 pages.
Hruby, "Designing Peptide Receptor Agonists and Antagonists," Nat Rev Drug Discov 1:835-858, Nov. 2002, 14 pages.
Hurley, "CGRP Drug Improves Wellness on Headache-Free Days, Study Finds," Neurology Today, p. 31, Jul. 7, 2016, 1 page.
Huston et al., "Protein engineering of antibody binding sites: recovery of specific activity in an anti-digoxin single-chain Fv

(56) References Cited

OTHER PUBLICATIONS analogue produced in *Escherichia coli*," Proc Natl Acad Sci USA 85(16):5879-5883, Aug. 1988, 5 pages.
Hutchings, "Theraputic antibodies directed at G protein-coupled receptors," mAbs 2(6):594-606, Nov./Dec. 2010, 14 pages.
Image of the CGRP signaling pathway, cited by Examiner Christina M. Borgeest in U.S. Appl. No. 14/711,705, filed Apr. 8, 2016, 2 pages, from physrev.physiology.org/content/physrev/94/4/1099/F2.large.jpg.
International Preliminary Report on Patentability in Application No. PCT/IB2006/003181, dated May 14, 2008, 9 pages.
International Search Report and Written Opinion in Application No. PCT/IB2006/003181, dated May 9, 2007, 14 pages.
International Search Report and Written Opinion in Application No. PCT/IB2009/050849, dated Jul. 31, 2009, 6 pages.
International Search Report and Written Opinion in Application No. PCT/IB2009/050852, dated Jul. 29, 2009, 12 pages.
International Search Report and Written Opinion in Application No. PCT/IB2010/053787, dated Nov. 11, 2010, 12 pages.
International Search Report and Written Opinion in Application No. PCT/US2015/021887, dated Jul. 8, 2015, 12 pages.
Janeway and Travers, Immunobiology: The Immune System in Health and Disease, Garland Publishing. p. G-2, 1994, 3 pages.
Jang et al., "The structural basis for DNA binding by an anti-DNA autoantibody," Mol Immunol 35(18):1207-1217, Dec. 1998, 11 pages.
Jansen-Olesen, "Animal Migraine Models for Drug Development: Status and Future Perspectives," CNS Drugs 27(12):1049-1068, Dec. 2013, 20 pages.
Jefferis, "Glycosylation of recombinant antibody therapeutics," Biotechnology Progress, American Institute of Chemical Engineers 21(1):11-16, Jan. 1, 2005, 6 pages.
Juhasz et al., "NO-induced migraine attack: strong increase in plasma calcitonin gene-related peptide (CGRP) concentration and negative correlation with platelet serotonin release," Pain 106(3):461-470, Dec. 2003, 10 pages.
Juhl et al., "Effect of two novel CGRP-binding compounds in a closed cranial window rat model," Europ J Pharmacol 657(1-2):117-124, Jul. 12, 2007, 8 pages.
Kar et al., "Increased calcitonin gene-related peptide (CGRP), substance P, and EYKephalin immunoreactivities in dorsal spinal cord and loss of CGRP-immunoreactive motoneurons in arthritic rats depend on intact peripheral nerve supply," J Mol Neurosci 3(1):7-18, 1991, 12 pages.
Katz et al., "Measurement of pain," Surg Clin North Am 79(2):231-252, Apr. 1999, 12 pages.
Kawamura et al., "Antinociceptive effect of intrathecally administered antiserum against calcitonin gene-related peptide on thermal and mechanical noxious stimuli in experimental hyperalgesic rats," Brain Res 497(1):199-203, Sep. 11, 1989, 5 pages.
Kipriyanov, "Generation of antibody molecules through antibody engineering," Methods Mol Biol 207:3-25, 2003, 23 pages.
Kobayashi et al., "Tryptophan H33 plays an important role in pyrimidine (6-4) pyrimidone photoproduct binding by a high-affinity antibody," Protein Eng 12(10):879-884, Oct. 1999, 6 pages.
Kohler and Milstein, "Continuous cultures of fused cells secreting antibody of predefined specificity," Nature 256(5517):495-497, Aug. 7, 1975, 3 pages.
Kraljevic et al., "Accelerating drug discovery," European Molecular Biology Organization (EMBO) reports, 5(9): 837-842, Sep. 2004, 6 pages.
Kruuse et al., "Plasma levels of cAMP, cGMP and CGRP in sildenafil-induced headache," Cephalalgia 24(7):547-553, Jul. 2004, 7 pages.
Kumar et al., "Molecular cloning and expression of the Fabs of human autoantibodies in *Escherichia coli*. Determination of the heavy or light chain contribution to the anti-DNA/-cardiolipin activity of the Fab," J Biol Chem 275(45):35129-35139, Nov. 10, 2000, 8 pages.

Kuraishi et al., "Antinociception induced in rats by intrathecal administration of antiserum against calcitonin gene-related peptide," Neurosci Lett 92(3):325-329, Oct. 17, 1988, 5 pages.
Lassen et al., "CGRP may play a causative role in migraine," Cephalalgia 22(1):54-61, Feb. 2002, 8 pages.
Lassen et al., "Comorbidity," Poster Presentations, Cephalagia 23:581-762, 2003, 1 page.
Lassen et al., "Involvement of calcitonin gene-related peptide in migraine: regional cerebral blood flow and blood flow velocity in migraine patients," J Headache Pain 9(3):151-157, Jun. 2008, 7 pages.
Letter from Patentee's representative dated Feb. 12, 2013, 4 pages.
Levy et al., "Calcitonin Gene-Related Peptide Does Not Excite or Sensitize Meningeal Nociceptors: Implications for the Pathophysiology of Migraine," Annal Neurol 58(5):698-705, Nov. 2005, 8 pages.
Levy et al., "Disruption of communication between peripheral and central trigeminovascular neurons mediates the antimigraine action of 5HT1B/1D receptor agonists," PNAS 101(12):4274-4279, Mar. 23, 2004, 6 pages.
Li et al., "Calcitonin gene-related peptide stimulation of nitric oxide synthesis and release from trigeminal ganglion glial cells," Brain Res 1196:22-32, Feb. 27, 2008.
Little et al., "Of mice and men: hybridoma and recombinant antibodies," Immunol Today 21(8):364-370, Aug. 2000, 7 pages.
Longstreth et al., "Functional bowel disorders," Gastroenterology 130(5):1480-1491, Apr. 2006, 15 pages.
Louis et al., "Antibodies to calcitonin-gene related peptide reduce inflammation induced by topical mustard oil but not that due to carrageenin in the rat," Neurosci Lett 102(2-3):257-260, Jul. 31, 1989, 4 pages.
Louis et al., "The role of substance P and calcitonin gene-related peptide in neurogenic plasma extravasation and vasodilatation in the rat," Neuroscience 32(3):581-586, 1989, 6 pages.
MacCallum et al., "Antibody-antigen interactions: contact analysis and binding site topography," J Mol Biol 262(5):732-745, Oct. 11, 1996, 14 pages.
Mallee et al., "Receptor activity-modifying protein 1 determines the species selectivity of non-peptide CGRP receptor antagonists," J Biol Chem 277(16):14294-14298, Apr. 19, 2002, 8 pages.
Marks et al., "By-passing immunization. Human antibodies from V-gene libraries displayed on phage," J Mol Biol 222(3):581-597, Dec. 5, 1991, 17 pages.
Marquez de Prado and Russo, "CGRP receptor antagonists: A new frontier of anti-migraine medications," Drug Discov Today Ther Strateg 3(4):593-597, 2006, 8 pages.
Marshall et al., "Human and rat alpha-CGRP but not calcitonin cause mesenteric vasodilatation in rats," Eur J Pharmacol 123(2):217-222, Apr. 16, 1986, 6 pages.
Mason et al., "Induction of Migraine-Like Photophobic Behaviour in Mice by Both Peripheral and Central CGRP Mechanisms", The Journal of Neuroscience 37(1):204-216, Jan. 4, 2017, 13 pages.
May, "Cluster headache: pathogenesis, diagnosis, and management," Lancet 366:843-855, 2005, 13 pages.
McCafferty et al., "Phage antibodies: filamentous phage displaying antibody variable domains," Nature 348(6301):552-554, Dec. 6, 1990, 3 pages.
McLatchie et al., "RAMPs regulate the transport and ligand specificity of the calcitoninreceptor-like receptor," Nature 393(6683):333-339, May 28, 1998, 7 pages.
Medhurst et al., "A rat model of bone cancer pain," Pain 96(1-2):129-140, Mar. 2002, 12 pages.
Meenan et al., "The arthritis impact measurement scales. Further investigations of a health status measure," Arthritis Rheum 25(9):1048-1053, Sep. 1982, 6 pages.
Mense, "Pathophysiology of low back pain and the transition to the chronic state—experimental data and new concepts," Schmerz 15(6):413-417, Dec. 2001, Article in German, 5 pages.
Merck manual., Pain, 17th Ed. p. 1367, #167. (in Japanese with Engish translation), 1999, 5 pages.
Merskey et al., "Classification of Chronic Pain, Descriptions of Chronic Pain Syndromes and Definitions of Pain Terms," IASP Task Force on Taxonomy 1994. 2nd Edition. 238 pages.

(56) References Cited

OTHER PUBLICATIONS

Moore and Salvatore, "Targeting a family B GPCR/RAMP receptor complex: CGRP receptor antagonists and migraine," Brit J Pharmacol 166(1):66-78, Apr. 10, 2012, 13 pages.
Morell et al., "Metabolic properties of IgG subclasses in man," J Clin Invest 49(4):673-680, Apr. 1970, 8 pages.
Mulderry et al., "Differential expression of alpha-CGRP and beta-CGRP by primary sensory neurons and enteric autonomic neurons of the rat," Neuroscience 25(1):195-205, Apr. 1988, 11 pages.
Mullins et al., "Characterization of a calcitonin gene-related peptide (CGRP) receptor on mouse bone marrow cells," Regul Pept 49(1):65-72, Nov. 19, 1993 (Abstract only), 1 page.
Nakamura-Craig and Gill, "Effect of neurokinin A, substance P and calcitonin gene related peptide in peripheral hyperalgesia in the rat paw," Neurosci Lett 124(1):49-51, Mar. 11, 1991, 3 pages.
Notice from the European Patent Office dated Oct. 2, 2015, concerning the staying of proceedings due to referral G 1/15, 2 pages.
Olesen and Ashina, "Emerging migraine treatments and drug targets," Trends Pharmacol Sci 32(6):352-359, Jun. 2011, 8 pages.
Olesen and Hargreaves, "CGRP Involvement in Migraines," The Headaches, Lippincott Williams & Wilkins, Chapter 31, pp. 289-299, Oct. 1, 2005, 13 pages.
Olesen et al., "Calcitonin gene-related peptide receptor antagonist BIBN 4096 BS for the acute treatment of migraine," N Eng J Med 350(11):1104-1110, Mar. 11, 2004, 7 pages.
Olesen et al., "Origin of pain in migraine: evidence for peripheral sensitisation," Lancet Neruol 8(7):679-690, Jul. 2009, 12 pages.
Olesen, "The treatment of acute migraine," Rev Neurol (Paris) 161(6-7):679-680, Jul. 2005, 2 pages.
Oshinsky et al., "Episodic dural stimulation in awake rats: a model for recurrent headache," Headache 47(7):1026-1036, Jul.-Aug. 2007, 17 pages.
Pacharinsak et al., "Animal models of cancer pain," Comp Med 58(3):220-233, Jun. 2008, 14 pages.
Papadopoulous et al., "Binding and neutralization of vascular endothelial growth factor (VEGF) and related ligands by VEGF Trap, ranibizumab and bevacizumab," Angiogenesis 15(2):171-185, Jun. 2015, 15 pages.
Park et al., "Alteration of cancer pain-related signals by radiation: proteomic analysis in an animal model with cancer bone invasion," Int J Radiation Oncol Biol Phys 61(5):1523-1534, Apr. 2005, 12 pages.
Paulus et al., "Analysis of improvement in individual rheumatoid arthritis patients treated with disease-modifying antirheumatic drugs, based on the findings in patients treated with placebo. The Cooperative Systematic Studies of Rheumatic Diseases Group," Arthritis Rheum 33(4):477-484, Apr. 1990, 8 pages.
Peroutka, "Neurogenic Inflammation and Migraine: Implications for Therapeutics," Mol Interv 5(5):304-311, Oct. 2005, 8 pages.
Peskar et al., "A monoclonal antibody to calcitonin gene-related peptide abolishes capsaicin-induced gastroprotection," Eur J Pharmacol 250(1):201-203, Nov. 30, 1993, 3 pages.
Petersen et al., "BIBN4096BS Antagonizes Human α-calcitonin Gene Related Peptide-induced Headache and Extracerebral Artery Dilatation," Clin Pharmacol Ther 77(3):202-213, Mar. 7, 2005, 12 pages.
Petersen et al., "Effect of hypotension and carbon dioxide changes in an improved genuine closed cranial window rat model," Cephalalgia 25(1):23-29, Jan. 2005, 7 pages.
Petersen et al., "Inhibitory effect of BIBN4096BS on cephalic vasodilatation induced by CGRP or transcranial electrical stimulation in the rat," Brit J Pharmacol 143(6):697-704, Nov. 2004, 8 pages.
Petersen et al., "Presence and function of the calcitonin gene-related peptide receptor on rat pial arteries investigated in vitro and in vivo," Cephalalgia 25(6):424-432, Jun. 2005, 9 pages.
Petersen et al., "The CGRP-antagonist, BIBN4096BS does not affect cerebral or systemic haemodynamics in healthy volunteers," Cephalalgia 25(2):139-147, Feb. 2005, 9 pages.
Petersen et al., "The effect of the nonpeptide CGRP-antagonist, BIBN4096BS on human-alpha CGRP induced headache and hemodynamics in healthy volunteers," Cephalagia 23:725, 2003, 1 page.
Plessas et al., "Migraine-like episodic pain behavior in a dog: can dogs suffer from migraines?" J Vet Intern Med 27(5):1034-1040, Sep.-Oct. 2013, 7 pages.
Plourde et al., "Calcitonin gene-related peptide in viscerosensitive response to colorectal distension in rats," Am J Physiol 273(1 Pt 1):G191-G196, Jul. 1997, 7 pages.
Poyner et al., "Structural determinants for binding to CGRP receptors expressed by human SK-N-MC and Col 29 cells: studies with chimeric and other peptides," Brit J Pharmacol 124(8):1659-1666, Aug. 1998, 8 pages.
Prewett et al., "The biologic effects of C225, a chimeric monoclonal antibody to the EGFR, on human prostate carcinoma," J Immunother Emphasis Tumor Immunol 19(6):419-427, Nov. 1996, 9 pages.
Pringsheim, "Canadian Headache Society guideline for migraine prophylaxis," Canadian J Neruol Sci 36:S1-S2, Mar. 2012, 2 pages.
Ravetch et al., "Fc receptors," Annu Rev Immunol 9:457-492, 1991, 36 pages.
Reichert et al., "Monoclonal Antibody Successes in the Clinic," Nature Biotechnology 23(9): 1073-1078, Sep. 2005, 6 pages.
Reinshagen et al., "Calcitonin gene-related peptide mediates the protective effect of sensory nerves in a model of colonic injury," J Pharmacol Exp Ther 286(2):657-661, Aug. 1998, 5 pages.
Reuter et al., "Experimental models of migraine," Funct Neurol 15(S3):9-18, 2000, 10 pages.
Roon et al., "No Acute Antimigraine Efficacy of CP-122,288, a Highly Potent Inhibitor of Neurogenic Inflammation: Results of Two Randomized, Double-Blind, Placebo-Controlled Clinical Trials," Ann Neurol 47(2):238-241, Feb. 2000, 4 pages.
Rovero et al., "CGRP Antagonist Activity of Short C-Terminal Fragments of Human aCGRP, CGRP(23-37) and CGRP(19-37)," Peptides 13(5):1025-1027, Sep.-Oct. 1992, 3 pages.
Rozen, "Cluster headache: diagnosis and treatment," Curr Pain Headache Rep 9:135-140, 2005, 6 pages.
Rudikoff et al., "Single amino acid substitution altering antigen-binding specificity," Proc Natl Acad Sci USA 79(6):1979-1983, Mar. 1982, 5 pages.
Russo, "Calcitonin gene-related peptide (CGRP): a new target for migraine," Annu Rev Pharmacol Toxicol 55:533-552, 2015, 23 pages.
Saleh et al., "Phase I trial of the chimeric anti-GD2 monoclonal antibody ch14.18 in patients with malignant melanoma," Hum Antibodies Hybridomas 3(1):19-24, Jan. 1992, 6 pages.
Schaible et al., "Mechanisms of pain in arthritis," Ann N Y Acad Sci 966:343-354, Jun. 2002, 16 pages.
Seong et al., "Radiation-induced alteration of pain-related signals in an animal model with bone invasion from cancer," Ann N Y Acad Sci 1030:179-186, Dec. 2004, 8 pages.
Shaw et al., "The effect of monoclonal antibodies to calcitonin gene-related peptide (CGRP) on CGRP-induced vasodilatation in pig coronary artery rings," Brit J Pharmacol 106:196-198, 1992, 3 pages.
Sheets et al., "Efficient construction of a large nonimmune phage antibody library: the production of high-affinity human single-chain antibodies to protein antigens," Proc Natl Acad Sci USA 95(11):6157-6162, May 26, 1998, 7 pages.
Silberstein et al., "Efficacy and Safety of Topiramate for the Treatment of Chronic Migraine: A Randomized, Double-Blind, Placebo-Controlled Trial," Headache 170-180, Feb. 2007, 11 pages.
Silberstein et al., "Evidence-based guideline update: Pharmacologic treatment for episodic migraine prevention in adults," Am Acad Neurol 78:1337-1345, Apr. 24, 2012, 12 pages.
Silberstein, "Emerging target-based paradigms to prevent and treat migraine," Clin Pharmacol Ther 93(1):78-85, Jan. 2013, 8 pages.
Smith et al., "Reversal of advanced digoxin intoxication with Fab fragments of digoxin-specific antibodies," N Eng J Med 294(15):797-800, Apr. 8, 1976, 4 pages.
Smith-Gill et al., "Contributions of immunoglobulin heavy and light chains to antibody specificity for lysozyme and two haptens," J Immunol 139(12):4135-4144, Dec. 15, 1987, 10 pages.

(56) References Cited

OTHER PUBLICATIONS

Song et al., "Light chain of natural antibody plays a dominant role in protein antigen binding," Biochem Biophys Res Commun 268(2):390-394, Feb. 16, 2000, 5 pages.
Sprenger and Goadsby, "Migraine pathogenesis and state of pharmacological treatment options," BMC Med 7(71), 5 pages, Nov. 16, 2009, 5 pages.
Stjernsward et al., "The World Health Organization Cancer Pain and Palliative Care Program. Past, present, and future," J Pain Symptom Manage 12(2):65-72, Aug. 1996, 8 pages.
Storer et al., "Calcitonin gene-related peptide (CGRP) modulates nociceptive trigeminovascular transmission in the cat," Brit J Pharmacol 142(7):1171-1181, Aug. 2004, 11 pages.
Szabat et al., "Production and characterization of monoclonal antibody against human calcitonin gene-related peptide (CGRP) and its immunohistochemical application to salivary glands," Histochemical Journal 26:317-326, 1994, 10 pages.
Takhshid et al., "Characterization and effects on cAMP accumulation of adrenomedullin and calcitonin gene-related peptide (CGRP) receptors in dissociated rat spinal cord cell culture," Brit J Pharmacol 148(4):459-468, Jun. 2006, 10 pages.
Tamura et al., "Structural correlates of an anti carcinoma antibody: identification of specificity-determining residues (SDRs) and development of a minimally immunogenic antibody variant by retention of SDRs only," J Immunol 164(3):1432-1441, Feb. 1, 2000, 11 pages.
Tan et al., "Calcitonin gene-related peptide as an endogenous vasodilator: immunoblockade studies in vivo with an anti-calcitonin gene-related peptide monoclonal antibody and it's Fab' fragment," Clinical Science 89(6):565-573, Dec. 1, 1995, 9 pages.
Tan et al., "Demonstration of the neurotransmitter role of calcitonin gene-related peptides (CGRP) by immunoblockade with anti-CGRP monoclonal antibodies," Brit J Pharmacol 111(3):703-710, Mar. 1994, 8 pages.
Tepper et al., "Botulinum neurotoxin type A in the preventive treatment of refractory headache: a review of 100 consecutive cases," Headache 44(8):794-800, Sep. 2004, 8 pages.
Teva Press Release, "Teva to Aquire Labrys Biologies, Inc.: Novel Migraine Prophylaxis Treatment Adds Significant New Dimension to Teva's growing Pain Care Franchise," RSS Content, 2014, 4 pages.
Textbook of Pain Levine et al., Textbook of Pain pp. 45-56, 1994, 17 pages.
Textbook of Pain McCarthy et al., Textbook of Pain pp. 387-395, 1994, 15 pages.
Tfelt-Hansen and Olesen, "Possible site of action of CGRP antagonists in migraine," Cephalalgia 31(6):748-750, Apr. 2011, 3 pages.
Tfelt-Hansen, "Site of effect of LY2951742 for migraine prophylaxis," Lancet Neurol 14(1):31-32, Jan. 2015, 2 pages.
Troltzsch et al., "The calcitonin gene-related peptide (CGRP) receptor antagonist BIBN4096BS reduces neurogenic increases in dural blood flow," European Journal of Pharmacology 562:103-110, 2007, 8 pages.
Tvedskov et al., "CGRP receptor antagonist olcegepant (BIBN4096BS) does not prevent glyceryl trinitrate-induced migraine," Cephalalgia 30(11):1346-1353, Nov. 2010, 8 pages.
Tvedskov et al., "No Increase of Calcitonin Gene-Related Peptide in Jugular Blood during Migraine", Annals of Neurobilogy, vol. 58, No. 4, Oct. 2005, 8 pages.
Tvedskov et al., "The prophylactic effect of valproate on glyceryltrinitrate induced migraine," Cephalalgia 24(7):576-585, Jul. 2004, 10 pages.
Tzabazis et al., "Antihyperalgesic effect of a recombinant herpes virus encoding antisense for calcitonin gene-related peptide," Anesthesiology 106(6):1196-1203, Jun. 2007, 8 pages.
Van Wijngaarden et al, "Inhibitors of Ocular Neovascularization: Promises and Potential Problems," JAMA, American Medical Association 293(12):1509-1513, Mar. 2005, 5 pages.
Vater and Klussmann, "Toward third-generation aptamers: Spieglemers and their therapeutic prospects," Curr Opin Drug Discov & Devel 6(2):253-261, Mar. 2003, 9 pages.

Vater et al., "Short bioactive Spiegelmers to migraine-associated calcitonin gene-related peptide rapidly identified by a novel approach: tailored-SELEX," Nucleic Acids Res 31(21):e130, Nov. 1, 2003, 7 pages.
Vaughan et al., "Human antibodies with sub-nanomolar affinities isolated from a large non-immunized phage display library," Nat Biotechnol 14(3):309-314, Mar. 1996, 6 pages.
Vecsei et al., "CGRP antagonists and antibodies for the treatment of migraine," Expert opinion on investigational drugs 24(1):31-41, Jan. 2, 2015, 12 pages.
Verkman, "Drug discovery in academia," Am J Physiol Cell Physiol 286:C465-C47, Mar. 2004, 10 pages.
Vermeersch et al., "Translational Pharmacodynamics of Calcitonin Gene-Related Peptide Monoclonal Antibody LY2951742 in a Capsaicin-Induced Dermal Blood Flow Model", J Pharmacol Exp Ther 354:350-357, Sep. 2015, 8 pages.
Vincent et al., "Molecular targets for autoimmune and genetic disorders of neuromuscular transmission," Eur J Biochem 267(23):6717-6728, Dec. 2000, 12 pages.
Vollbracht et al., "The pipeline in headache therapy," CNS Drugs 27(9):717-729, Sep. 2013, 13 pages.
Vugmeyster et al., "Pharmacokinetics and toxicology of therapeutic proteins: Advances and challenges", World J Biolog Chem 3(4):73-92, Apr. 26, 2012, 20 pages.
Wacnik et al., "Tumor-induced mechanical hyperalgesia involves CGRP receptors and altered innervation and vascularization of DsRed2 fluorescent hindpaw tumors," Pain 115(1-2):95-106, May 2005, 6 pages.
Waeber et al., "Migraine as an inflammatory disorder", Neurology 64(10 Suppl 2):S9-15, May 2005, 7 pages.
Walker and Hay, "CGRP in the trigeminovascular system: a role for CGRP, adrenomedullin and amylin receptors?" British Journal of Pharmacology 170(7):1293-1307, Dec. 2013, 15 pages.
Walter and Bigal, "TEV-48125: a Review of a Monoclonal CGRP antibody in Development for the Preventative Treatment of Migraine," Curr Pain Headache Rep 19:6, Mar. 2015, 6 pages.
Walter et al., "Evaluation of cardiovascular parameters in cynomolgus monkeys following IV administration of LBR-101, a monoclonal antibody against calcitonin gene-related peptide," MAbs 6(4):871-878, Jul.-Aug. 2014, 9 pages.
Ward et al., "Binding activities of a repertoire of single immunoglobulin variable domains secreted from *Escherichia coli*," Nature 341(6242):544-546, Oct. 12, 1989, 3 pages.
Wick et al., "Transient receptor potential vanilloid 1, calcitonin gene-related peptide, and substance P mediate nociception in acute pancreatitis," Am J Physiol Gastrointest Liver Physiol 290(5):G959-G969, May 2006, 11 pages.
Williamson et al., "Sumatriptan inhibits neurogenic vasodilation of dural blood vessels in the anaesthetized rat—intravital microscope studies," Cephalalgia 17(4):525-531, Jun. 1997, 12 pages.
Winkler et al., "Changing the antigen binding specificity by single point mutations of an anti-p24 (HIV-1) antibody," J Immunol 165(8):4505-4514, Oct. 15, 2000, 11 pages.
Witte, "The madness of migraine," Scientific American Mind 39-43, Dec. 2006-Jan. 2007, 6 pages.
Wong et al., "Monoclonal antibody to rat alpha-CGRP: production, characterization, and in vivo immunoneutralization activity," Hybridoma 12(1):93-106, Feb. 1993, 14 pages.
Wong et al., "Preparation of a monoclonal antibody to rat alpha-CGRP for in vivo immunoneutralization of peptides," Ann N Y Acad Sci 657:525-527, Jun. 30, 1992, 3 pages.
Wu et al., "Development and potential of non-peptide antagonists for calcitonin-gene-related peptide (CGRP) receptors: evidence for CGRP receptor heterogeneity," Biochem Soc Trans 30(4):468-473, Aug. 2002, 6 pages.
Wu et al., "Humanization of a murine monoclonal antibody by simultaneous optimization of framework and CDR residues," J Mol Biol 294(1):151-162, Nov. 19, 1999, 12 pages.
Xu, "Study on the Mechanism of SP and CGRP in the Chronic Pain and Knee Joint," Master Thesis. Guangxi Medical University. May 2005. (In Chinese with Engish abstract), 57 pages.

(56) References Cited

OTHER PUBLICATIONS

Zeller et al., "CGRP function-blocking antibodies inhibit neurogenic vasodilatation without affecting heart rate or arterial blood pressure in the rat," Brit J Pharmacol 155(7):1093-1103, Dec. 2008, 11 pages.
Zhang et al., "Rheumatoid factor specificity of a VH3-encoded antibody is dependent on the heavy chain CDR3 region and is independent of protein A binding," J Immunol 161(5):2284-2289, Sep. 1, 1998, 7 pages.
Zhang et al., "Sensitization of calcitonin gene-related peptide receptors by receptor activity-modifying protein-1 in the trigeminal ganglion," J Neurosci 27(10):2693-2703, Mar. 7, 2007, 11 pages.
Zhang, "Therapeutic Protein Protein-Drug Interactions: An FDA Perspective," Office of Clinical Pharmacology Office of Translational Sciences CDER, FDA Jun. 4, 2012.
Zittel et al., "Role of spinal afferents and calcitonin gene-related peptide in the postoperative gastric ileus in anesthetized rats," Ann Surg 219(1):79-87, Jan. 1994, 9 pages.
"Emerging Concepts in GPCR Research and Their Implication for Drug Discovery," Wiley Handbook of Current and Emerging Drug Therapies vol. 1-4: 369-386, 2007, 18 pages.
"Guidance for Industry—Estimating the Maximum Safe Starting Dose in Initial Clinical Trials for Therapeutics in Adult Healthy Volunteers," U.S. Department of Health and Human Services, Food and Drug Administration, Center for Drug Evaluation and Research (CDER), Jul. 2005, 30 pages.
"Physician's Desk Reference," PDR, 58 Edition, 2004, 39 pages.
"Physician's Desk Reference," PDR, 59 Edition, 2005, 28 pages.
Abbott, "Astrocyte-endothelial interactions and blood-brain barrier permeability", Journal of Anatomy 200(6):629-638, Jun. 2002, 10 pages.
Abbott, "Chapter 15: Comparative Physiology of the Blood-Brain Barrier", Physiology and Pharmacology of the Blood-Brain Barrier, pp. 371-396, 1992, 26 pages.
Abbott, "Evidence for bulk flow of brain interstitial fluid: significance for physiology and pathology", Neurochemistry International 45(4):545-552, Sep. 2004, 8 pages.
ACHE' [online], "Migraine Attack: The Four Phases / ACHE," available on or before Aug. 1, 2014, retrieved on Oct. 13, 2015, retrieved from URL <http://www.achenet.org/resources/migraine_attack_the_four_phases>, 4 pages.
Adams et al., "Monoclonal antibody therapy of cancer", Nature Biotechnology 23(9):1147-1157, Sep. 2005, 11 pages.
Adelman et al., "Comparison of rizatriptan and other triptans on stringent measures of efficacy," Neurology vol. 57, 1377-83, Oct. 2001, 8 pages.
Afridi et al., "Glyceryl trinitrate triggers premonitory symptoms in migraineurs", Pain 110:675-680, Aug. 2004, 6 pages.
Afridi et al., "Verapamil and lymphomatoid papulosis in chronic cluster headache", Journal of Neurology 251:473-475, Apr. 2004, 3 pages.
Aggarwal, "Signalling pathways of the TNF superfamily: a double-edged sword," Natural Review of Immunol., vol. 3, 745-756, Sep. 2003, 12 pages.
Ahn and Basbaum, "Where do triptans act in the treatment of migraine?" Pain 115: 1-4, May 2005, 4 pages.
Ahn and Goadsby, "Animal Models of Headache," The Headaches 213-219 2006, 2013, 7 pages.
Aiyar et al., "A cDNA encoding the calcitonin gene-related peptide type 1 receptor," the Journal of Biological Chemisty, vol. 271, No. 19, May 1996, 6 pages.
Akerman and Goadsby, "Topiramate inhibits cortical spreading depression in rat and cat: impact in migraine aura", Neuroreport 16:1383-1387, Aug. 2005, 5 pages.
Akerman et al., "Oxygen inhibits neuronal activation in the trigeminocervical complex after stimulation of trigeminal autonomic reflex but not during direct dural activation of trigeminal afferents," Headache 49; 1131-1143, Sep. 2009, 13 pages.

Akerman et al., "The effect of adrenergic compounds on neurogenic dural vasodilation", European Journal of Pharmacology 424(1):53-58, Aug. 2001, 6 pages.
Akerman et al., "The effect of adrenergic compounds on neurogenic vasodilation of dural meningeal vessels," Cephalalgia 20: 281-283, Jul. 2000, 2 pages.
Akerman et al., "The effect of anti-migraine compounds on nitric oxide induced dilation of dural meningeal vessels", European Journal of Pharmacology 452:223-228, Oct. 2002, 6 pages.
Akerman et al., "Topiramate inhibits trigeminovascular activation: an intravital microscopy study", British Journal of Pharmacology 146:7-14, Sep. 2005, 8 pages.
Alberts et al., "Molecular Biology of the Cell," p. G-34, 4th Edition, Garland Science, Taylor & Francis Group, New York, 2002, 5 pages.
Alexander et al., "Calcitonin, amylin, CGRP and adrenomedullin," British Journal of Pharmacology, 158(Suppl. 1), Nov. 2009, 2 pages.
Allen et al., "Calcitonin Gene-Related Peptide and Reperfusion Injury," Journal of Orthopaedic Research, vol. 15, No. 2, Mar. 1997, 6 pages.
Allt et al., "Is the pial microvessel a good model for blood-brain barrier studies?" Brain Research Reviews, vol. 24:67-76, Jun. 1997, 10 pages.
Andreou et al., "Animal models of headache: from bedside to bench and back to bedside," Expert Reviews Neurother. 10(3) 389-411, Mar. 2010, 23 pages.
Annequin et al., "Last-Minute Poster Presentations", Cephalalgia 25:1189-1205, Dec. 2005, 7 pages.
Antonaci et al., "Recent advances in migraine therapy," Springer Plus 2016, No. 5, 637, May 2016, 14 pages.
Arfors et al., "Microvascular transport of macromolecules in normal and inflammatory conditions", Acta Physiol Scand Suppl., 463:93-103, 1979, 11 pages.
Armour et al., "Pharmacological characterization of receptor-activity-modifying proteins (RAMPs) and the human calcitonin receptor", J Pharmacol Toxicol 42: 217-224, Dec. 1999, 8 pages.
Arndt et al., "CGRP Antagonism—A Valid New Concept for the Treatment of Migraine Pain," Neuropeptides vol. 38, No. 2-3, Apr./Jun. 2004, 6 pages.
Arulmani et al., "Lack of effect of the adenosine A1 receptor agonist, GR79236, on capsaicininduced CGRP release in anaesthetized pigs," Cephalalgia 25(11):1082-1090, Nov. 2005, 9 pages.
Asghar et al., "Dilation by CGRP of middle meningeal artery and reversal by sumatriptan in normal volunteers," Neurology 75(17):1520-1526, Oct. 26, 2010, 7 pages.
Asghar et al., "Effect of CGRP and sumatriptan on the BOLD response in visual cortex," Journal of Headache Pain 13(2):159-166, Mar. 2012, 8 pages.
Ashina, "Calcitonin Gene-Related Peptide in Tention-Type Headache," The Scientific World 2:1527-1531, Jun. 2002, 6 pages.
Ashina, "Vascular changes have a primary role in migraine," Cephalalgia 32(5):428-430, Apr. 2012, 3 pages.
Ashkenazi et al., "Headache management for the pain specialist," Regional Anethesia and Pain Medicine, vol. 29, No. 5, Sep.-Oct. 2004, 14 pages.
Ashkenazi et al., "The evoling management of migraine," Current Opinion in Neurology, Jun. 2003, 5 pages.
Askenazi et al., "Botulinum toxin and other new approached to migraine therapy," Annual Review of Medicine, vol. 55, Feb. 2004, 14 pages.
ATCC website search for PTA-6866 deposit, Jan. 22, 2010, 1 page.
ATCC website search for PTA-6867 deposit, Jan. 22, 2010, 1 page.
Aubrée-Lecat et al., "Influence of Barrier-Crossing Limitations on the Amount of Macromolecular Drug Taken up by its Target", Journal of Pharmacokinetics and Biopharmaceutics 21 1 75-98, Feb. 1993, 24 pages.
Augustin et al., "Differentiation of endothelial cells: Analysis of the constitutive and activated endothelial cell phenotypes," BioEssays vol. 16(12), Dec. 1994, 6 pages.
Avastin (bevacizumab), "Prescribing Information," Feb. 2004, 27 pages.
Avastin® (bevacizumab) EMA, "Scientific Discussion," EMEA 2005, 61 pages.

(56) References Cited

OTHER PUBLICATIONS

Ayata et al., "Suppression of cortical spreading depression in migraine prophylaxis", Annals of Neurology 59(4):652-661, Apr. 2006, 10 pages.
Bahra et al., "Oral zolmitriptan is effective in the acute treatment of cluster headache," presented in part at the annual meeting of the American Academy of Neurology, Apr. 17-24, 1999, Neurology 54:1832-1839, May 2000, 8 pages.
Ballabh et al., "The Blood-brain barrier: an overview—structure regulation and clinical implications," Neurobiology of Disease, vol. 16(1), 1-13, Jun. 2004, 13 pages.
Benemei et al., "CGRP receptors in the control of pain and inflammation," Current Opinion in Pharmacology, 9:9-14, Feb. 2009, 6 pages.
Bergerot et al., "Animal models of migraine: looking at the component parts of a complex disorder", European Journal of Neuroscience 24(6):1517-1534, Sep. 2006, 18 pages.
Bernstein et al., "Sensitization of the Trigeminovascular Pathway: Perspective and Implications to Migraine Pathophysiology," Journal Clinical Neurology, 8:89-99, Jun. 2012, 11 pages.
Bexxar (131 I-tositumomab), "Prescribing Information," Corixa Corporation and GlaxoSmithKline, Jun. 2003, 49 pages.
Bhaskar et al., "Recent progress in migraine pathophysiology: role of cortical spreading depression and magnetic resonance imaging", European Journal of Neuroscience 38(11):3540-3551, Dec. 2013, 12 pages.
Bigal, "Safety, tolerability, and efficacy of TEV-48125 for preventive treaetment of high-frequency episodic migraine: a multicentre, randomised, double-blind, placebo-controlled, phase 2b study," neurology atricles Lancet Neurology, Sep. 30, 2015, 1081-1090, 10 pages.
Bjarnadottir, "Comprehensive repertoire and phylogenetic analysis of the G protein-coupled receptors in human and mouse", Genomics 88(3):263-273, Sep. 2006, 11 pages.
Boel et al., "Functional human monoclonal antibodies of all isotypes constructed from phage display library-derived single-chain Fv antibody fragments," Journal of Immunology Methods, vol. 236(1-2), May 2000, 14 pages.
Bolay et al., "Intrinsic brain activity triggers trigeminal meningeal afferents in a migraine model," Nature medicine 8(2):136, Feb. 2002, 7 pages.
Boross et al., "IgA EGFR antibodies mediate tumor klling in vivo," EMBO Molecular Medicine, vol. 5, Aug. 2013, 14 pages.
Bousser and Welch, "Relation between migraine and stroke," Lancet Neurology, vol. 4, Sep. 2005, 10 pages.
Boyce and Hill, "Substance P ($NK_1$) Receptor Antagonists—Analgesics or Not?" Handbook of Experimental Pharmacology Stress, Immunology and Behaviour, 2004, 23 pages.
Brain et al., "CGRP receptors: a headache to study, but will antagonists prove therapeutic in migraine?", Trends in Pharmaceutical Sciences 23(2): 51-53, Feb. 2002, 3 pages.
Brain et al., "Calcitonin Gene-Related Peptide is a Potent Vasodilator," Nature vol. 313: 54-56, Jan. 1985, 3 pages.
Breeze et al., "Solution structure of human calcitonin gene-related peptide by 1H NMR and distance geometry with retrained molecular dynamics," BioChemistry, vol. 30(2): 575-82, Jan. 1991, 8 pages.
Brekke and Sandlie, "Therapeutic Antibodies for Human Diseases at the Dawn of the Twenty-First Century," Nature Reviews, Drug Discovery, vol. 2, Jan. 2003, 11 pages.
British National Formulary, "British National Formulary, 52nd Edition," pp. 234-239, BMJ Publishing Group with RPS Publishing, Sep. 2006, 8 pages.
Brown and Morice, "Clinical Pharmacology of Vasodilator Peptides", Journal of Cardiovascular Pharmacology 10 Suppl 12:S82-87, Feb. 1987, 6 pages.
Bruera et al., "Cancer pain," JAMA 290(18):2476-2479, Nov. 12, 2003, 4 pages.

Brüggemann et al., "Comparison of the Effector Functions of Human Immunoglobulins Using a Matched Set of Chimeric Antibodies," Journal of Exp. Med. 166: 1351-1361, Nov. 1987, 11 pages.
Buntinx et al., "Development of anti-migraine therapeutics using the capsaicin-induced dermal blood flow model," Brit J Clin Pharmacol 80(5):992-1000, Oct. 6, 2015, 9 pages.
Buzzi and Moskowitz, "The Pathophysiology of Migraine: Year 2005," Journal of Headache Pain, vol. 6, pp. 105-111, Jun. 2005, 7 pages.
Buzzi et al., "The antimigraine drug, sumatriptan (GR43175), selectively blocks neurogenic plasma extravasation from blood vessels in dura mater," British Journal of Pharmacology, 99(1):202-206, Jan. 1990, 5 pages.
Bylund and Toews, "Radioligand Bingind Methods: Practical Guide and Tips," Invited Review, American J. Physiological, 265: L421-L429, Nov. 1993, 9 pages.
Byrne, "Chapter 6: Neuromuscular and Synaptic Transmission," in Essential Medical Physiology, 3rd Edition, Elsevier Academic Press, Amsterdam, 2003, 28 pages.
Cady and Dodick, "Diagnosis and Treatment of Migraine," Mayo Clinical Proceedings, vol. 77, Mar. 2002, 7 pages.
Caekebeke et al., "The antimigraine drug sumatriptan increases blood flow veolocity in large cerebral arteries during migraine attacks," Neurology, vol. 42, 1522-26, Aug. 1992, 6 pages.
Cardarelli et al., "Binding to CD20 by Anti-B1 antibody or F(ab')(2) is Sufficient for Induction of Apoptosis in B-Cell Lines," Cancer Immunol. Immunother. 51: 15-24, Mar. 2002, 10 pages.
Carter et al., "Humanization of an Anti-p185HER2 Antibody for Human Cancer Therapy," Proceedings of the National Academy of Sciences of the United States of America, vol. 89, May 1992, 5 pages.
Carter, "Improving the Efficacy of Antibody-Based Cancer Therapies," Nature Reviews Cancer, vol. 1, Nov. 2001, 12 pages.
Catty, "Antibodies vol. 1: A practical approach," Chapter 1-4, Practical Approach Series, 1988, 90 pages.
Catty, "Antibodies vol. II: A Practical Approach," Chapter 4: ELISA and related enzyme immunoassays, 1989, 60 pages.
Cervero et al., "Visceral pain," Lancet 353(9170):2145-2148, Jun. 19, 1999, 4 pages.
Chan et al., "Glutamate receptor antagonists in the management of migraine," Drugs vol. 72(11): 1165-76, Jul. 2014, 12 pages.
Chan et al., "Therapeutic antibodies for autoimmunity and inflammation," Nature Reviews: Immunology 10(5):301-316, May 2010, 16 pages.
Chapman, "PEGylated antibodies and antibody fragments for improved therapy: a review," Advanced Drug Deliv. Rev., vol. 54(4): 531-545, Jun. 2002, 15 pages.
Chapman, "Therapeutic antibody fragments with prolonged in vivo half-lives," Nature America, Nature BioTechnology, vol. 17, Aug. 1999, 4 pages.
Charles, "Migraine is not primarily a vascular disorder," Cephalalgia 32(5):431-432, Apr. 20, 2012, 2 pages.
Charles, "Vasodilation out of the picture as a cause of migraine headache", Lancet Neurol 12(5):419-420, May 2013, 2 pages.
Chen et al., "Use of Constitutive G Protein-Coupled Receptor Activity for Drug Discovery," Molecular Pharmacology 57(1):125-134, Jan. 2000, 10 pages.
Chester and Hawkins, "Clinical Issues in Antibody Design," Trends Biotechnol. vol. 13: 294-300, Aug. 1995, 7 pages.
Chiba et al., "Calcitonin gene-relatd peptide receptor antagonist human CGRP-(8-37)," American Journal of Physiology: Endocrine and Metabolism, vol. 256:E331-35, Feb. 1989, 7 pages.
Cittadini et al., "Effectiveness of intranasal zolmitriptan in acute cluster headache. A randomized, placebo-controlled, double-blind crossover study", Archives of Neurology 63:1537-1542, Nov. 2006, 6 pages.
Cole et al., "Human IgG2 Variants of Chimeric Anti-CD3 are Nonmitogenic to T cells," J. Immunol. 159: 3613-3621, 1997, 10 pages.
Conner et al., "Characterization of CGRP Receptor Binding", Current Protocols in Pharmacology 24:1-30, Sep. 2004, 11 pages.

(56) References Cited

OTHER PUBLICATIONS

Connor et al., "GR205171 Clinical Study Group: Clinical evaluation of a novel, potent, CNS penetrating NK receptor antagonist in the acute treatment of migraine," Cephalalgia 18, 1998, 1 page.
Connor et al., "Interaction of calcitonin-gene-related peptide with its receptors," Biochemical Scoeity Transactions, vol. 30, Part 4, Aug. 2002, 5 pages.
Cruickshank et al., "β-Adrenoreceptor-Blocking Agents and the Blood-Brain Barrier," Clinical Science, pp. 453s-455s, vol. 59, Dec. 1980, 3 pages.
Cumberbatch et al., "Differential effects of the 5HT 1B/1D receptor agonist naratriptan on trigeminal versus spinal nociceptive responses," Cephalalgia 18:659-663, Dec. 1998, 5 pages.
Cumberbatch et al., "Dural vasodilation causes a sensitization of rat caudal trigeminal neurones in vivo that is blocked by a 5-HT$_{1B/1D}$ agonist," British Journal of Pharmacology 126:1478-1486, 1999, 9 pages.
Cumberbatch et al., "Reversal of behavioral and electrophysiological correlates of experimental peripheral neuropathy by the NK1 receptor antagonist GR205171 in rats," Neuropharmacology 37:1535-1543, Dec. 1998, 9 pages.
Cumberbatch et al., "Rizatriptan has central antinociceptive effects against durally evoked responses", European Journal of Pharmacology 328:37-40, Jun. 1997, 4 pages.
Cumberbatch et al., "The effects of 5-HT1A, 5-HT1B and 5-HT1D receptor agonists on trigeminal nociceptive neurotransmission in anaesthetized rats", European Journal of Pharmacology 362(1):43-46, Nov. 1998, 4 pages.
Cutrer et al., "Priorities for triptan treatment attributes and the implications for seleting an oral triptan for acute migraine: a study of US primary care physicians (the TRIPSTAR Project)", Clinical Therapeutics 26:1533-1545, Sep. 2004, 13 pages.
D.H.E. 45 and Migranal (dihydroergotamine mesylate, USP), "Prescribing Information," Novartis, N5-929 S-032 S-033, Jul. 31, 2002, 37 pages.
D'Amico et al., "When should "chronic migraine" be considered "refractory" to pharmacological prophylaxis?" Neurol Sci Suppl. 1:S55-S58, 2008, 4 pages.
Dahlof et al., "Within-patient consistency of response of rizatriptan for treating migraine," Neurology vol. 55, 1511-1516, Nov. 2000, 7 pages.
D'Amico and Tepper, "Prophylaxis of migraine: general principles and patient acceptance", Neuropsychiatric Disease and Treatment 4(6):1155-1167, Dec. 2008, 14 pages.
Davis et al., "Fundamentals of Neurologic Disease," pp. 204-207, Demos Medical Publishing Inc., 2005, 6 pages.
Davis et al., "The Tortuous Road to an Ideal CGRP function blocker for the treatment of migraine", Current Topics in Medicinal Chemistry 8(16):1468-1479, Nov. 2008, 12 pages.
De Prado et al., "CGRP receptor antagonists: a new frontier of anti-migraine medications," Drug Discovery Today: Therapeutic Strategies, Nervous System Disorders, vol. 3, No. 4, Winter 2006, 5 pages.
De Vries et al., "Genetic biomarkers of migraine," Headache, Jul.-Aug. 2006, 10 pages.
Dechant et al., "Chimeric IgA antibodies against HLA class II effectively trigger lymphoma cell killing," Blood vol. 100, No. 13, Dec. 2002, 7 pages.
Dechant et al., "IgA antibodies for cancer therapy," Critical Review in Oncology/Hematology vol. 39, Jul.-Aug. 2001, 9 pages.
Deckert-Schluter et al., "Crucial role of TNF receptor type-1 (p55), but not of TNF receptor type-2 (p75) in murine toxoplamosis," Journal of Immunology, vol. 160: 3427-3436, Jul. 1990, 11 pages.
Delves et al, "Chapter 3: Antibodies," Roitt's Essential Immunology, Blackwell Publishing, 2006, 24 pages.
Dennis et al., "hCGRP8-37: a calcitonin gene-related peptide antagonist revelead calcitonin gene-related peptide receptor hetrogeneity in brain and periphery," Journal of Pharmacology Exp. Ther. vol. 254(1), Jul. 1990, 6 pages.
Dennis et al., "Strutcture-Activity Profile of Calcitonin Gene-Related Peptide in Peripheral and Brain Tissues. Evidence for Receptor Multiplicity," The Journal of Pharmacology and Experimental Theraperutics 251(2):718-725, 1989, 8 pages.
Di Angelantonio et al., "A Novel Class of Peptides with Facilitating Action on Neuronal Nicotinic Receptors of Rat Chromaffin Cells in Vitro: Functional and Molecular Dynamic Studies," Molecular Pharmacology 61(1):43-54, 2002, 12 pages.
Diener et al., "New therapeutic approaches for the prevention and treatment of migraine", Lancet Neurology, vol. 14:1010-1022, Oct. 2015, 14 pages.
Diener et al., "RPR100893, a Substance-P antagonist, is not effective in the treatment of migraine attacks," Cephalalgia, vol. 23, Apr. 2003, 3 pages.
Djavadi-Ohaniance et al., "Chapter 4: Measuring Antibody Affinity in Solution," in Antibody Engineering: A Practical Approach 77-117, 1st ed. 1996, 42 pages.
Dodick and Silberstein, "Central sensitization theory of migraine: clinical implications," Headache, Nov. 2006, 10 pages.
Dodick et al., "Botulinum neurotoxin for the treatment of migraine and other primary headache disorders," Clinics in Dermatology, Apr. 2004, 6 pages.
Dodick et al., "Cardiovascular tolerability and safety of triptans: a review of clinical data," Headache, May 2004, 11 pages.
Dodick et al., "Cluster Headache," Cephalalgia, Nov. 2000, 17 pages.
Dodick et al., "Consensus Statement: Cardiovascular Safety Profile of Triptans (5-HT1B/1D Agonists) in the Acute Treatment of Migraine," Headache 44(5):414-425, May 2004, 12 pages.
Dodick et al., "Is there a preferred triptan?" Headache, Jan. 2002, 7 pages.
Dodick et al., "Predictors of migraine headache recurrence: a pooled analysis from the eletriptan database," Headache, vol. 48(2), 184-193, Feb. 2008, 10 pages.
Dodick et al., "Prioritizing treatment attributes and their impact on selecting an oral triptan: results from the TRIPSTAR project," Current Pain and Headache Reports 8:435-442, Dec. 2004, 8 pages.
Doenicke et al., "Possible benefit of GR43175, a novel 5-HT1-like receptor agonist, for the acute treatment of severe migraine," Lancet vol. 331 No. 8598, Jun. 11, 1988, 3 pages.
Doods, "Development of CGRP antagonists for the treatment of migraine," Current Opinion in Investigation Drugs, Sep. 2001, 8 pages.
Drossman et al., "Functional Bowel Disorders, A multicenter comparison of health status and development of illness severity index," Digestive Diseases and Sciences 40(5):986-995, May 1995.
Dubel et al., "Chapter 1: Therapeautic Antibodies—from Past to Future," Handbook of Therapeutic Antibodies, Second edition Chapter 1:1-14, 2014, 14 pages.
Durham and Russo, "Regulation of Calcitonin Gene-Related Peptide Secretion by a Serotonergic Antimigraine Drug," Journal of Neuroscience, vol. 19, pp. 3423-3429, May 1, 1999, 7 pages.
Durham, "Calcitonin Gene-Related Peptide (CGRP) and Migraine," Emerging Neural Theories of Migraine Pathogenesis, Headache 46(1): S3-S8, Jun. 2006, 6 pages.
Durham, "CGRP receptor antagonists: A new choice for acutre treatment of migraine?" Current Opinion in Investigational Drugs 5(7):731-735, Jul. 2004, 5 pages.
Durham, "Inihibition of Calcitonin Gene-Related Peptide Function: A Promising Strategy for Treating Migraine," Headache 38(8):1269-1275, Sep. 2008, 7 pages.
Duvernoy and Risold, "The cirumventricular organs: An atlas of comparative anatomy and vascularization," Brain Research Reviews vol. 56(1), Nov. 2007, 29 pages.
Ebersberger et al., "Release of Substance P, Calcitonin Gene-Related Peptide and Prostaglandin E2 from Rat Dura Mater Enchephali Following Electrical and Chemical Stimulation in Vitro," Neuroscience, vol. 89(3):901-907, Mar. 1999, 7 pages.
Edvinsson and Goadsby, "Neuropeptides in migraine and cluster headache," Cephalalgia vol. 14, 1994, 8 pages.

(56) References Cited

OTHER PUBLICATIONS

Edvinsson et al. "Characterisation of the effects of a non-peptide CGRP receptor antagonist in SK-N-MC cells and isolated human cerebral arteries," European Journal of Pharmacology 415:39-44, 2001, 6 pages.
Edvinsson et al., "Amylin localisation effects on cerebral arteries and on local cerebral blood flow in the cat," Scientific World Journal, vol. 1: 168-180, May 2001, 14 pages.
Edvinsson et al., "Calcintonin Gene-Related Peptide (CGRP) in Cerebrovascular Disease," Scientific World Journal, vol. 2, May 30, 2002, 7 pages.
Edvinsson et al., "Innervation of the human middle meningeal artery immunohistochemistry, ultrastructure, and role of endotherlium for vasomotility," Peptides vol. 19(7),1998, 13 pages.
Edvinsson et al., "Measurement of vasoactive neuropeptides in biological materials: Problems and pitfalls from 30 years of experience and novel future approaches," Cephalalgia 30(6):761-766, Jun. 2010, 7 pages.
Edvinsson, "CGRP receptor antagonists and antibodies against CGRP and its receptor in migraine treatment," Brit J Clin Pharmacol 80(2):193-199, Aug. 2015, 7 pages.
Edvinsson, "New therapeutic target in primary headaches—blocking the CGRP receptor," Expert Opinion Ther Targets 7(3):377-338, Jun. 2003, 7 pages.
Edvinsson, "Novel migraine therapy with calcitonin gene-regulated peptide rececptor antagonists", Expert Opinion on Therapeutic Targets 11(9):1179-1188, Sep. 2007, 11 pages.
Edvinsson, "The journey to establish CGRP as a migraine target: a retrospective view," Headache 55(9):1249-1255, Oct. 2015, 7 pages.
Ekbom et al., "Treatment of Acute Cluster Headache with Sumatriptan," New England Journal of Medicine, vol. 325(5), Aug. 1, 1991, 5 pages.
Elgert, "Immunology: Understanding the Immune System," 1st Edition, 58-78, Wiley-Liss Inc, 1996, 24 pages.
Elliott et al., "Nociceptive Neuropeptide Increases and Periorbital Allodynia in a Model of Traumatic Brain Injury," Headache 52(6):96-984, Jun. 2012, 28 pages.
Emilien and Maloteaux, "Current Therapeutic Uses and Potential of β-Adrenoreceptor Agonists and Antagonists," European Journal of Clinical Pharmacology, vol. 53, pp. 389-404, Feb. 1998, 16 pages.
Enger et al., "Dynamics in ionic shifts in cortical spreading depression", Cerebral Cortex 25(11):4469-4476, Nov. 2015, 8 pages.
EP Opposition: Interlocutory Decision in Opposition Proceedings against European Patent No. 1957106, dated Feb. 1, 2017, 63 pages.
European Medicines Agency, "Scientific conclusions and ground for variation of the terms of the marketing authorisations of suspension for the marketing authorisations, as application, taking into considerings the approved inidcated for each product," available on or before Jan. 18, 2012, 7 pages.
Evers et al., "EFNS guideline on the drug treatment of migraine—report of an EFNS task force," European Journal of Neurology 13:560-572, Jun. 2006, 13 pages.
Faraci et al., "Vascular responses of dura mater," American Journal of Physiology, Jul. 1989, 5 pages.
Feniuk et al., "The selective carotid arterial vasoconstrictor action of GR43175 in anaesthetized dogs," British Journal of Pharmacology 96(1):83-90, Jan. 1989, 8 pages.
Ferrara et al., "Discovery and Development of Bevacizumab, an Anti-VEGF Antibody for Treating Cancer," Nature Review Drug Discovery, vol. 3: 391-400, May 2004, 10 pages.
Ferrari et al., "5-HT1 receptors in migraine pathophysiology and treatment," European Journal of Neurology vol. 2(1):5-21, Mar. 1995, 17 pages.
Ferrari et al., "Acute treatment of migraine attacks," Current Opinion in Neurology, 8(3):237-4, Jun. 1995, 6 pages.
Ferrari et al., "Cerebral blood flow during migraine attacks without aura and effect of sumatriptan," Arch Neurol vol. 135-139, Feb. 1995, 5 pages.
Ferrari et al., Clinical and experimental effects of sumatriptan in humans. Trends in Pharmacol Sci 14:129-133, Apr. 1993, 5 pages.
Ferrari et al., "Clinical effects and mechanism of action of sumatriptan in migraine," Clinical Neurology and Neurosurgery, 94(suppl):S73-S77, 1992, 5 pages.
Ferrari et al., "Combinatie van een triptaan met een NSAID bij migraine," Ned Tijdsch Geneeskd, 151, 36, Sep. 2007, 2 pages.
Ferrari et al., "Efficacy of ICS 205-930, a novel 5-Hydroxytryptamine3 (5HT3) receptor antagonist, in the prevention of migraine attacks. A complex answer to a simple question," Pain vol. 45:283-291, Jun. 1991, 9 pages.
Ferrari et al., "From molecules to migraine patient," proceedings of the 2nd International Congress of the European Headache Federation in Liege, Jun. 1994, Cephalalgia Oct. 1995, 43 pages.
Ferrari et al., "Methionine-Enkephalin in migraine and tension headache. Differences between classic migraine, common migraine and tension headache, and changes during attacks," presented in part at the 6th International Migraine Symposium, Oct. 1986, Headache 30:160-164, 1990, 5 pages.
Ferrari et al., "Migraine pathophysiology lessons from mouse models and human genetics," Lancet Neurology, vol. 14, Jan. 2015, 16 pages.
Ferrari et al., "Monoamine oxidase, phenosulphotransferase and serotonin metabolism in common and classic migraine and tension headache," Cephalalgia 7,suppl.6:144-146, 1987, 3 pages.
Ferrari et al., "Neuro-excitatory plasma aminoacids are elevated in migraine," Neurology 40:1582-1586, Oct. 1990, 5 pages.
Ferrari et al., "Oral sumatriptan: effect of a second dose, incidence and treatment of headache recurrences," Cephalalgia 14:330-338, Oct. 1994, 9 pages.
Ferrari et al., "Oral triptans (serotonin 5OHT 1B/1D agonists) in acute migraine treatment: a meta-analysis of 53 trials," The Lancet 358(9294):1668-175, Nov. 2001, 8 pages.
Ferrari et al., "Plasma aminoacids in common and classic migraine and tension headache," Cephalalgia vol. 7, suppl.6:246-247, 1987, 2 pages.
Ferrari et al., "Release of platelet Met-enkephalin, but not serotonin, in migraine. A platelet-response unique to migraine patients?" Journal of the Neurological Sciences, vol. 93:51-60, Oct. 1989, 10 pages.
Ferrari et al., "Sumatriptan in the treatment of migraine," Neurology 1993;43(suppl 3):S43-47, Jun. 1993, 6 pages.
Ferrari et al., "The genetics of migraine: implication for treatment approaches," J Neural Transm Suppl. (63):111-27, 2002, 18 pages.
Ferrari et al., "The use of multiattribute decision models in evaluating triptan treatment options in migraine," J Neurology 252:1026-1032, Sep. 2005, 7 pages.
Ferrari et al., "Triptan medications to treat acute migraine," Lancet vol. 359: 1152-53, Mar. 30, 2002, 1 page.
Ferrari et al., "Triptans (serotonin, 5-HT 1B/1D agonists) in migraine: detailed results and methods of a meta-analysis of 53 trials," Cephalalgia 22(8):633-658, Oct. 2002, 26 pages.
Ferrari, "Should we advise patients to treat migrain attacks early: methodologic issues," European Neurology, vol. 53, suppl 1, May 3, 2005, 5 pages.
Ferrari, "311C90: Increasing the options for therapy with effective acute antimigraine 5HT1B/1D receptor agonists," Neurology, Mar. 1997, 4 pages.
Ferrari, "Current perspectives on effective migraine treatments: are small clinical differences important for patients?" Drugs of Today (Barc) vol. 39 Suppl D:37-41, 2003, 4 pages.
Ferrari, "From genetics to prophylaxis," Cephalalgia 17(suppl 17):2-5, Jun. 1997, 4 pages.
Ferrari, "How to assess and compare drugs in the management of migraine: success rates in terms of response and recurrence," Cephalalgia, 19 Suppl 23:2-8, Mar. 1999, 7 pages.
Ferrari, "Migraine," Lancet, vol. 351, Apr. 4, 1998, 9 pages.
Ferrari, "Rizatriptan: a new milestone in migraine treatment. Introduction," Cephalalgia 20 Suppl 1:1, Nov. 2000, 19 pages.
Ferrari, "Should we advise patients to treat migraine attacks early?" Cephalalgia, Nov. 2004, 3 pages.
Ferrari, "The clinical effectiveness of 311C90 in the acute treatment of migraine," Eur Neurol 36(suppl 2):4-7, 1996, 4 pages.

(56) References Cited

OTHER PUBLICATIONS

Ferrari, "Treatment of migraine attacks with sumatriptan: The Subcutaneous Sumatriptan International Study Group," the New England Journal of Medicine, vol. 325:316-321, Aug. 1, 1991, 6 pages.

Ferro et al., "A comparison of the contractile effects of 5-hydroxytryptamine, sumatriptan and MK-462 on human coronary artery in vitro," British Journal of Pharmacology 40(3):245-251, Sep. 1995, 7 pages.

Fewou et al., "The pre-synaptic motor nerve terminal as a site for antibody-mediated neurotoxicity in autoimmune neuropathies and synaptopathies," Journal of Anatomy 224(1):36-4, Jan. 2014, 9 pages.

Flower, "Modelling G-protein-coupled receptors for drug design," Biochimica et Biophysica Acta 1422: 207-234, Nov. 1999, 28 pages.

Foord and Craig, "Isolation and characterisation of a human calcitonin-gene-related-peptide receptor," European Journal of Biochemistry 170 1-2 373-9, Dec. 1987, 7 pages.

Foord et al., "New methods for researching accessory proteins," Journal of Molecular Neuroscience, vol. 26, Issue 2-3, Jun. 2005, 12 pages.

Foote et al., "Antibody Framework Residues Affecting the Conformation of the Hypervariable Loops," Journal of Molecular Biology, vol. 224, Mar. 1992, 13 pages.

Foulkes et al., "Differential vasodilator profile of calcitonin gene-related peptide in porcine large and small diameter coronary artery rings," European Journal of Pharmacology, 201, 143-149, Aug. 1991, 7 pages.

Friend et al., "Phase I Study of an Engineered Aglycosylated Humanized CD3 Antibody in Renal Transplant Rejection," Transplantation vol. 68, No. 11, Dec. 15, 1999, 6 pages.

Gardiner et al., "Antagonistic effect of Human α-CGRP [8-37] on the in vivo regional haemodynamic actions of human α-CGRP," Biochemical and Biophysical Research Communications 171(3):938-943, Sep. 28, 1990, 6 pages.

Gardiner et al., "Haemodynamic effects of human α-calcitonin gene-related peptide following administration of endothelin-1 or NG-nitro-L-arginine methyl ester in conscious rats," British Journal of Pharmacoloy 103(1):1256-662, May 1991, 7 pages.

Gardiner et al., "Regional haemodynamic effects of calcitonin gene-related peptide," American Journal of Physiology—Regulatory, Integrative and Comparative Physiology 256(2):R332-R338, Feb. 1989, 7 pages.

Gardiner et al., "Regional haemodynamic effects of human α- and β-calcitonin gene-related peptide in conscious Wistar rats," British Journal of Pharmacology 98(4):1225-132, Dec. 1989, 8 pages.

Garg and Balthasar, "Investigation of the Influence of FcRn on the distribution of IgG to the brain," The AAPS Journal, vol. II, No. 3 553-557, Sep. 2009, 5 pages.

Garlick and Renkin, "Transport of large molecules from plasma to intersititial fluid and lymph in dogs," American Journal of Physiology vol. 219, No. 6, Dec. 1970, 11 pages.

Gavilondo and Larrick, "Antibody Engineering at the Millennium," BioTechniques 29: 128-145, Jul. 2000, 15 pages.

GE Healthcare, "Biacore Sensor Surface Handbook," BR-1005-71 Edition AB, 2005, 100 pages.

Geerligs et al., "The influence of different adjuvants on the immune response to a synthetic peptide comprising amino acid resides 9-21 of herpes simplex virus type 1 glycoprotein D.," Journal of Immunological Methods, vol. 124, 95-102, Nov. 1989, 8 pages.

Ghatta et al., "Calcitonin gene related peptide: Understanding its role," Indian Journal of Pharmacology, vol. 36, Issue 5, Oct. 2004, 7 pages.

Gijsman et al., "Dihydoergotamine nasal spray," Neurology 45: 397-98, Feb. 1995, 2 pages.

Gijsman et al., "Double-blind, placebo-controlled, dose-finding study of rizatriptan (MK-462) in the acute treatment of migraine," Cephalalgia 17:647-51, Oct. 1997, 9 pages.

Gijsman et al., "Pharmacokinetic and pharmacodynamic profile of oral and intravenous meta-chlorophenylpiperazine in healthy volunters," J Clin Psychopharmacol 1998;18:289-95, Aug. 1998, 14 pages.

Goadsby and Boes, "Chronic daily headache," J Neurol Neurosurg Psychiatry 72(Suppl II):ii2-ii5, Jun. 2002, 4 pages.

Goadsby and Boes, "New daily persistent headache," Journal of Neurology Neurosurgery Psychiatry 72(Suppl II): ii6-ii9, Jun. 2002, 4 pages.

Goadsby and Edvinsson, "Human in vivo Evidence for Trigeminovascular Activation in Cluster Headache:—Neuropeptide Changes and Effects of Acute Attacks Therapies," Brain vol. 117: 427-434, 1994, 8 pages.

Goadsby and Edvinsson, "The Trigeminovascular System and Migraine: Studies Characterizing Cerebrovascular and Neuropeptide Changes Seen in Humans and Cats," Annals of Neurology, 33(1): 48-56, Jan. 1993, 9 pages.

Goadsby and Kernick, "Chapter 4: The migraine attack," in Headache: A Practical Manual (Oxford Care Manuals) 2009, 18 pages.

Goadsby and Ramadan, "Potential New Drugs for Acute and Prophylactic Treatment of Migraines," The Headaches, 3rd Edition, Chapter 60, 569-576, 2006, 8 pages.

Goadsby et al., "Chapter 6: Treatment of headache and prophylaxis," in The Effective of Management written by Andrew Dowson, Aesculapius Medical Press, 1999, 16 pages.

Goadsby et al., "Chapter 61: Migraine," in Diseases of the Nervous System: Clinical Neumscience and Therapeutic Principles, Third Edition, vol. I, 2002, 9 pages.

Goadsby et al., "Extracranial vasodilatation mediated by vasoactive intestinal polypeptide (VIP)," Brain Research 329(1-2):285-288, Mar. 1985, 4 pages.

Goadsby et al., "Mechanisms and Management of Headache," CME Neurology—I, Journal of Royal College of Physicians of London, vol. 33, No. 3, pp. 228-234, May-Jun. 1999, 7 pages.

Goadsby et al., "Towards a definition of intractable headache for use in clinical practice and trails," Cephalalgia, vol. 26: 1168-1170, Sep. 2006, 3 pages.

Goadsby et al., "Treatment of a Migraine," New England Journal of Medicine, vol. 347, No. 10, Sep. 5, 2002, 3 pages.

Goadsby et al., "TRIPSTAR: Prioritizing triptan treatment attributes in migraine management," Acta Neurologica Scandinavica 110:137-143, Sep. 2004, 7 pages.

Goadsby, "Advances in the understanding of headache," British Medical Bulletin 73-74:83-92, Jan. 2005, 10 pages.

Goadsby, "Chapter 55: Primary neurovascular headache," in Textbook of Pain Wall and Melzack Neurovascular Headache, pp. 851-874, 2006, 24 pages.

Goadsby, "Cortical Spreading Depression—Better Understanding and More Questions," Journal of Neurophysiol, vol. 97, Apr. 4, 2007, 1 page.

Goadsby, "Efficacy and safety of topiramate for the treatment of chronic migraine: a randomized, double-blind placebo-controlled trial", Headache 47(2):170-180, Feb. 2007, 11 pages.

Goadsby, "Eletriptan in acute migraine: a double-blind, placebo-controlled comparison to sumatriptan," Neurology 54:156-163, Jan. 2000, 8 pages.

Goadsby, "Incredible progress for an era of better migraine care," Nat Rev Neurol 11(11):621-622, Nov. 2015, 2 pages.

Goadsby, "Migraine Pathophysiology," Headache vol. 45(Suppl. 1), Apr. 2005, 11 pages.

Goadsby, "Migraine, Aura, and Cortical Spreading Depression: Why are we still talking about it?" Annals of Neurology 49(1):4-6, Jan. 2001, 3 pages.

Goadsby, "Migraine: emerging treatment options for preventive and acute attack therapy," Expert Opinion on emerging drugs 11(3):419-427, Sep. 2006, 9 pages.

Goadsby, "New directions in migraine research," Journal of Clinical Neuroscience 9:116, Jul. 2002, 6 pages.

Goadsby, "Post-triptan Era for the Treatment of Acute Migraine," Current Pain and Headache Reports 8(5):393-398, Oct. 2004, 6 pages.

Goadsby, "Recent advances in the diagnosis and management of migraine," BMJ 332:25-29, Jan. 7, 2006, 5 pages.

(56) References Cited

OTHER PUBLICATIONS

Goadsby, "Recent advances in understanding migraine mechanisms, molecules and therapeutics," Trends in Molecular Medicine 13(1):39-44, Jan. 2007, 6 pages.
Goadsby, "The vascular theory of migraine—a great story wrecked by the facts," Brain: A Journal of Neurology, 132:6-7, Jan. 2009, 2 pages.
Goadsby, "Therapeutic Prospects for Migraine: Can Paradise Be Regained?" Ann Neurol 74:423-434, Sep. 2013, 12 pages.
Goadsby, "Trigeminal autonomic cephalalgias (TACs)", Acta Neurologica Belgica 101:10-19, Mar. 2001, 10 pages.
Goadsby, Silberstein, Dodick, "Chronic Daily Headache for Clinicians," Chapters 1-6, 11, 18, Jul. 2005, 112 pages.
Goldberg and Silberstein, "Targeting CGRP: A New Era for Migraine Treatment," CNS Drugs 29: 443-452, Jun. 2015, 10 pages.
Goldstein et al., "Considerations for animal models of blast-related traumatic brain injury and chronic traumatic encephalopathy," Alzheimer's Res & Ther 6:64, Sep. 5, 2014, 10 pages.
Goldstein et al., "Ineffectiveness of neurokinin-1 antagonist in acute migraine: a crossover study," Cephalagia, Nov. 1997, 11 pages.
Goldstein et al., "Lanepitant, an NK-1 antagonist, in migraine prevention," Cephalalgia vol. 21, Mar. 2001, 5 pages.
Goldstein et al., "Selective seratonin 1F (5-HT1F) receptor agonist LY334370 for acute migraine a randomised controlled trial," Lancet vol. 358, Oct. 13, 2001, 5 pages.
Goldstein et al., "Biological Efficacy of a Chimeric Antibody to the Epidermal Growth Factor Receptor in a Human Tumor Xenograft Model," Clinical Cancer Research, vol. 1: 1311-1318, Nov. 1995, 9 pages.
Goyal and Hirano, "The enteric nervous system," Mechanism of Disease, Review Article, The New England Journal of Medicine 334(17):1106-1115, Apr. 25, 1996, 10 pages.
Graham et al., "Mechanism of migraine headache and action of ergotamine tartrate," Arch NeurPhsych, vol. 39 Issue 4, Apr. 1938, 27 pages.
Green et al., U.S. Appl. No. 60/753,004, filed Dec. 22, 2005, 18 pages.
Gupta et al., "Antibodies against G-protein coupled receptors: novel uses in screening and drug development," Comb Chem High Throughput Screen 11(6): 463-467, Jul. 2008, 9 pages.
Gupta et al., "Intravital microscopy on a closed cranial window in mice: a model to study trigeminovascular mechanisms involved in migraine," Cephalalgia 26:1294-12303, Nov. 2006, 10 pages.
Haan et al., "Lisinopril heeft geen relevant preventief effect bij migraine,"Ned Tijdsch Geneeskd, vol. 15, 755, 2001, 3 pages.
Haar et al., "Crystal Structure of the Ectodomain Complex of the CGRP Receptor, a Class-B GPCR, Reveals the Site of Drug Antagonism," Structure 18: 1083-1093, Sep. 8, 2010, 11 pages.
Hamann and Berger, "Chapter 12: Mylotarg—The First Antibody-Targeted Chemotherapy Agent," in: Pagé M. (eds) Tumor Targeting in Cancer Therapy. Cancer Drug Discovery and Development. Humana Press, Totowa, NJ. 2002, 16 pages.
Hargreaves and Shepheard, "Pathophysiology of Migraine—New Insights," Can. J. Neurol. Sci. 26(3): S12-S19, Nov. 1999, 8 pages.
Hargreaves, "New Migraine and Pain Research," American Headache Society 47(Suppl 1):S26-S43, Apr. 2007, 18 pages.
Harlow, "Using Antibodies: A Laboratory Manual," Chapters 1, 2, 11, Cold Spring Harbor Laboratory Press, 1999, 64 pages.
Hasbak et al., "Investigation of GCRP Receptors and Peptide Pharmacology in Human Coronary Arteries: Characterization with a Nonpeptide Antagonist," the Journal of Pharmacology and Experimental Therapeutics, vol. 34: 326-33, Jan. 2003, 9 pages.
Hay et al., "CGRP modulation for RAMPS," Pharmacology and Therapeutics 109:173-197, 2006, 25 pages.
Hay et al., "International Union of Pharmacology. LXIX. Status of the Calcitonin Gene-Related Peptide Subtype 2 Receptor," Pharmacological Reviews 60(2):143-145, 2008, 3 pages.
Haydon and Carmignoto, "Astrocyte Control of Synaptic Transmission and Neurovascular Coupling," Physiological Reviews 86(3):1009-1031, Jul. 2006, 23 pages.
Haywood et al., "Vasculature of the normal and arthritic synovial joint," Histology and Histopathology, Cellular Molecular Biology, vol. 16: 277-284, Jan. 2001, 8 pages.
Hepp et al., "Systematic Review of Migraine Prophylaxis Adherence and Persistence", Journal of Managed Care Pharmacy 20(1):22-33, Jan. 2004, 12 pages.
Herceptin® (trastuzumab) Prescribing Information, Genentech Inc, Sep. 1998, 2 pages.
Herzenberg et al., "Chapter 12: Antibody-Antigen Binding: Structure-Function Relationships Viewed at Atomic Scale Resolution," in Weir's Handbook of Experimental Immunology—vol. I: Immunochemistry and Molecular Immunology, 2007, 49 pages.
Herzenberg et al., "Weir's Handbook of Experimental Immunology—vol. IV: The Integrated Immune System," 1997, 121 pages.
Hilairet et al., "Protein-protein Interaction and not Glycosylation Determines the Binding Selectivity of Heterodimers between the Calcitonin Receptor-like Receptor and the Receptor Activity-modifying Proteins," Journal of Biological Chemistry, Aug. 2001, 8 pages.
Hill and Oliver, "Neuropeptide and Kinin Antagonists," HEP 177: 181-216, 2006, 36 pages.
Hill, "New Targets for Analgesic Drugs," Chapter 36, proceedings of the 10th World Congress on Pain, Progress in Pain Research and Management 24: 419-436, 2003, 18 pages.
Hill, "$NK_1$ (substance P) receptor antagonists—why are they not analgesic in humans?," TiPS 21:244-246, Jul. 2000, 3 pages.
Hinton et al., "An Engineered human IgG1 Antibody with Longer Serum Half-Life," The Journal of Immunology, Jan. 2006, 11 pages.
Ho et al., "Efficacy and tolerability of MK-0974 (telcagepant), a new oral antagonist of calcitonin gene-related receptor, compared with zolmitriptan for acute migraine: a randomised, placebo-controlled, parallel-treatment trial," Lancet vol. 372: 2115-2123, Dec. 2008, 9 pages.
Hoare, Mechanisms of peptide and nonpeptide ligand binding to Class B G-protein-coupled receptors, Drug Discovery Today 10(6):417-427, Mar. 2005, 11 pages.
Hoelig et al., "A novel CGRP-neutralizing Spiegelmer attenauates neurogenic plasma protein extravasation," British Journal of Pharmacology 172:3086-3098, 2015, 13 pages.
Hoff et al., "A breathtaking headache," Journal of Neurology and Neurosurgery Psychiatry, vol. 75: 506-509, Apr. 2004, 6 pages.
Hollenstein et al., "Insights into the structure of class B GPCRs," Cell Press, Trends in Pharmacological Sciences, vol. 35(1):12-22, Jan. 2014, 11 pages.
Holt et al., "Anti-serum albumin domain antibodies for extending the half-lives of short lived drugs," Protein Engineering, Design and Selection, vol. 21(5): 283-288, May 2008, 6 pages.
Hopkins, "The druggable genome," Nature Reviews: Drug Discovery, Nature Publishing Group, vol. 1, Sep. 2002, 4 pages.
Hu et al., "A new view of Starling's hypothesis at the microstructural level," Microvascular Research Vo. 58:281-304, Nov. 1999, 24 pages.
Hubbard et al., "Identification of the epitopes of calcitonin gene-related peptide (CGRP) for two anti-CGRP monoclonal antibodies by 2D NMR," Protein Science 6: 1945-1952, Sep. 1997, 8 pages.
Huls et al., "Antitumor Immune Effector Mechanisms Recruited by Phage Display-derived Fully Human IgG1 and IgA1 Monoclonal Antibodies," Cancer Research vol. 59, Nov. 15, 1999, 8 pages.
Humphrey et al., "Chapter 32: Consistency of pain relief over multiple migraine attacks following treatment with rizatriptan & Chapter 40: Clinical efficacy and tolerability of the triptans—discussion summary," in The Triptans—Novel Drugs for Migraine, Oxford University Press, 2001, 12 pages.
Humphrey et al., "Preclinical Studies on the Anti-Migraine Drug, Sumatriptan," Eur. Neurol., vol. 31, No. 5, pp. 282-290, 1991, 9 pages.
Humphrey et al., "Serotonin and Migraine," Annals N.Y. Acad. Science, vol. 600, Issue 1, pp. 587-600, Oct. 1990, 14 pages.
Humphrey et al., "GR43175, a selective agonist for the 5-HT1-like receptor in dog isolated saphenous vein," Br. J. Pharmacol. 94, 1123-1132, Aug. 1988, 10 pages.

(56) References Cited

OTHER PUBLICATIONS

Idusogie et al., "Mapping of the C1q binding site on rituxan, a chimeric antibody with a human IgG1 Fc," J Immunol 15;164(8):4178-84, Apr. 15, 2000.
International Classification of Diseases and Related Health Problems: Version for 2005 (ICD), 10 pages.
International Classification of Diseases and Related Health Problems: Version for 2006 (ICD), 10 pages.
International Search Report and Written Opinion in Application No. PCT/IB2017/055777, dated Jan. 11, 2018, 15 pages.
International Search Report and Written Opinion issued in International Application No. PCT/US2018/020536 dated Jun. 18, 2018, 19 pages.
International Search Report and Written Opinion issued in International Application No. PCT/US2018/020537 dated Jun. 7, 2018, 17 pages.
Iovino et al., "Safety, Tolerability and Pharmacokinetics of BIBN 4096 BS, the First Selective Small Molecule Calcitonin Gene-Related Peptide Receptor Antagonist, Following Single Intravenous Administration in Healthy Volunteers," Cephalalgia, 24: 645-656, Aug. 2004, 12 pages.
Irani et al., "Molecular properties of human IgG subclasses and their implications for designing therapeutic monoclonal antibodies against infectious diseases," Molecular Immunology, 67: 171-182, Oct. 2015, 12 pages.
Irie et al., "Phase I pilot clinical trial for human IgM monoclonal antibody to ganglioside GM3 in patients with metastatic melanoma," Cancer Immunol. Immunother vol. 53, Feb. 2004, 8 pages.
Irimia et al., "Refractory migraine in a headache clinic population," BMC Neurol 11:94, 2011, 6 pages.
Janeway and Travers, "Immunobiology: The Immune System in Health and Disease, Second Edition," Chapter 2, 3 and 12, Current Biology Ltd./Garland Publishing Inc., 1996, 134 pages.
Janeway et al., "Immunobiology, 5th Edition: The Immune Systems in Health and Disease," pp. 123-154, Garland Publishing, Taylor and Francis Group, 2001, 35 pages.
Janeway et al., "Immunobiology, 5th Edition: The Immune Systems in Health and Disease," pp. 341-380, Garland Publishing, Taylor and Francis Group, 2001, 44 pages.
Janeway et al., "Immunobiology, 5th Edition: The Immune Systems in Health and Disease," pp. 626-627, Garland Publishing, Taylor and Francis Group, 2001, 5 pages.
Janeway et al., "Immunobiology, 5th Edition: The Immune Systems in Health and Disease," pp. 93-122 Garland Publishing, Taylor and Francis Group, 2001, 34 pages.
Jefferis, "Antibody terapeutics: isotype and glycoform selection," Expert Opinion Biol Ther, vol. 7, No. 9, 1401-1413, Sep. 2007, 13 pages.
Jefferis, "The antibody paradigm: present and future development as a scaffold for biopharmaceutical drugs", Biotechnology and Genetic Engineering Reviews 26:1-42, Jul. 2009, 43 pages.
Jhee, "Pharmacokinetics and pharmacodynamics of the triptan antimigraine agents: a comparative review," Drug Disposition, Pharmacokinet, vol. 40, Issue 3, Feb. 2001, 17 pages.
Johnstone et al., "The Effect of Temperature on the Binding Kinetics and Equilibrium Constants of Monoclonal Antibodies to Cell Surface Antigens," Molecular Immunology, vol. 27, No. 4, Apr. 1990, 7 pages.
Jones et al., "Replacing the Complementarity-Determining Regions in a Human Antibody with Those from a Mouse," Nature vol. 321, May 29, 1986, 4 pages.
Kajekar et al., "Effect of a 5-HT1 receptor agonist, CP-122,288, on oedema formation induced by stimulation of the rat saphenous nerve," British Journal of Pharmacology 115(1):1-2, May 1995, 2 pages.
Kane et al., "A mouse model of human repetitive mild traumatic brain injury," J Neurosci Meth 203(1):41-49, Jan. 15, 2012, 24 pages.

Kaube et al., "Inhibition by sumatriptan of central trigeminal neurons only after blood-brain barrier disruption," British Journal of Pharmacology 109 788-792, Jul. 1993, 5 pages.
Keller et al., "Lack of Efficacy of the Substance P (Neurokinin1 Receptor) Antagonist Aprepitant in the Treatment of Major Depressive Disorder," Biological Psychiatry 59(3):216-223, Feb. 2005, 8 pages.
Kelley, "Thermodynamics of Protein-Protein Interaction Studied by Using BIAcore and Single-Site Mutagenesis," Methods: A companion to methods in Enzymology, vol. 6, Issue 2, 111-120, Jun. 1994, 10 pages.
Kenakin and Onaran, "The ligand paradox between affinity and efficacy: can you be there and not make a difference?" TRENDS in Pharmaceutical Sciences 23(6): 275-280, Jun. 2002, 6 pages.
Kenakin, "Drug Efficacy at G Protein-Coupled Receptors," Annu Rev Pharmacol Toxicol 42: 349-379, 2002, 33 pages.
Kenakin, "Efficacy of G-protein-coupled receptors," Nature Reviews, Drug Discovery, vol. 1, Macmillan Magazines, Feb. 2002, 8 pages.
Kenakin, "G-Protein Coupled Receptors as Allosteric Machines," Receptors and Channels 10: 51-60, 2004, 10 pages.
Kenakin, "New concepts in pharmacological efficacy of 7TM receptors: IUPHAR review 2," British Journal of Pharmacology, vol. 168(3), Feb. 2013, 22 pages.
Kenakin, "Principles: Receptor Theory in Pharmacology," TRENDS in Pharmacological Sciences 25(4) 186-224, Apr. 2004, 7 pages.
Kenney et al., "Influence of adjuvants on the quantity, affinity, isotype and epitope specificity of murine antibodies," Journal of Immunological Methods, 121, 157-166, Jul. 1989, 10 pages.
Kernick et al., "Cluster headache in primary care: unmissable, underdiagnosed and undertreated," British Journal of General Practice, 56(528):486-487, Jul. 2006, 2 pages.
Kettleborough et al., "Humanization of a Mouse Monoclonal Antibody by CDR-Grafting: The Importance of Framework Residues on Loop Conformation," Protein Engineering, vol. 4, No. 7, Oct. 1991, 11 pages.
Khazaeli et al., "Human Immune Response to Monoclonal Antibodies," Journal of Immunotherapy, 15:42-52, Jan. 1994, 11 pages.
Kim et al., "Antibody Engineering for the Development of Therapeutic Antibodies," Molecules and Cells, vol. 20, No. 1, Aug. 2005, 13 pages.
Kipriyanov and Le Gall, "Generation and Production of Engineered Antibodies," Molecular Biotechnology, vol. 26, Jan. 2004, 22 pages.
Knauf et al., "Relationship of effective molecular size to systemic clearence in rats of recombinant interleukin-2 chemical modified with water-soluble polymers," The Journal of Biological Chemistry, vol. 263, No. 29, Issue of Oct. 15, 1988, 7 pages.
Knight et al., "4991W93 inhibits release of calcitonin gene-related peptide in the cat but only at doses with 5HT1B/1D receptor agonist activity," Neuropharmacology 40:520-525, Mar. 2001, 6 pages.
Knight et al., "Pharmacodynamic Enhancement of the Anti-Platelet Antibody Fab Abciximab by Site-Specific Pegylation," Platelets 15(7), Nov. 2004, 11 pages.
Knudsen et al., "Chapter 5: Morphology, Physiology and Pathophysiology of the brain barrier," in Basic Mechanisms of Migraine, 1988.
Kobeissy, "Chapter 13: Characterization and Management of Headache after Mild Traumatic Brain Injury," Brain Neurotrauma: Molecular, Neuropsychological, and Rehabilitaion Aspects. Boca Raton (FL):CRC Press/Taylor & Francis, 2015, 13 pages.
Krogsgaard-Larsen et al., "Textbook of Drug Design and Discovery," p. 7-8, Taylor and Francis, 2002, 4 pages.
Kruit et al., "Brain stem and cerebellar hyperintense lesions in migraine," Stroke 37:1109-1112, Feb. 2006, 4 pages.
Kruit et al., "Iron accumulation in deep brain nuclei in migraine: a population-based magnetic resonance imaging study," Cephalalgia 29:351-359, Mar. 2009, 14 pages.
Kruit et al., "Migraine as a Risk Factor for Subclinical Brain Lesions," JAMA vol. 291: 427-434, Jan. 28, 2004, 8 pages.
Kruit et al., "Migraine as a risk factor for white matter lesions, silent infarctions, and ischemic stroke: the evidence for a link," Headache Currents, vol. 2, No. 3;62-71, Jun. 2005, 9 pages.
Kruit et al., "MRI findings in migraine," Revue Neurologique 161,6/7:661-666, 2005, 5 pages.

(56) References Cited

OTHER PUBLICATIONS

Kurosawa et al., "Increase of meningeal blood flow after electrical stimulation of rat dura mater encephali: mediation by calcitonin gene-related peptide," British Journal of Pharmacology 114:1397-1402, Apr. 1995, 6 pages.
Kurth et al., "Migraine and Rish of Cardiovascular Disease in Women," JAMA vol. 296(3), Jul. 19, 2006, 10 pages.
Lassen et al., "Nitric oxide synthase inhibition in migraine," Lancet, vol. 349, Feb. 1997, 2 pages.
Laukkanen et al., "Hevein-specific recombinant IgE from human single-chain antibody phage display libraries," Journal of Immunological Methods, vol. 278:271-281, Jul. 2003, 11 pages.
Launer et al., "The prevalence and characteristics of migraine in a population-based cohort, the GEM study," Neurology vol. 53: 537-542, Aug. 1999, 17 pages.
Lauritzen, "Pathophysiology of the migraine aura: The spreading depression theory," Oxford University Press, Feb. 1994, 12 pages.
Leavy, "Therapeutic antibodies: past, present and future," Nature Reviews: Immunology 10(5):297, May 2010, 1 pages.
Léger et al., "Humanization of a Mouse Antibody against Human Alpha-4 Integrin: A Potential Therapeutic for the Treatment of Multiple Sclerosis," Human Antibodies vol. 8: 3-16, Mar. 1, 1997, 14 pages.
Lenzer et al., "FDA advisers warn: COX2 inhibitors increase risk of heart attack and stroke," BMJ, vol. 330, Feb. 26, 2005, 1 page.
Levine and Taiwo, "Inflammatory pain," Textbook of Pain, pp. 45-56, 1994, 17 pages.
Levy et al., "Octreotide is not effective in the acute treatment of migraine," Cephalalgia 25:48-55, Jan. 2005, 8 pages.
Li and Schwartz, "The TNFa transgenic mouse model of inflammatory arthritis," Springer Seminars in Immunopathology, Aug. 2003, 15 pages.
Lin et al., "Preclinical pharmacokinetics, interspecies scaling and tissue distribution of a humanized monoclonal antibody against vascular endothelial growth factor," Journal of Pharmacology and Experimental Therapeutics, 288:371-378, Jan. 1999, 8 pages.
Lipinski et al., "Experimental and computational approaches to estimate solubility and permeability in drug discovery and development settings," Advanced Drug Delivery Reviews, vol. 23: 3-25, Jan. 1997, 24 pages.
Lipton and Stewart, "Acute migraine therapy: do doctors understand what patients with migraine want from therapy," Headache vol. 39, Suppl. 2: S20-S26, Aug. 1999, 7 pages.
Lipton et al., "Classification of primary headaches," Journal of Neurology, vol. 63, Views and Reviews, Aug. 2004, 9 pages.
Lipton et al., "Double-blind clinical trials of oral triptans versus other classes of acute migraine medication," Cephalalgia 24:321-332, May 2004, 12 pages.
Lipton et al., "Eager for better migraine therapies", Neurology 83:954-955, Sep. 9, 2014, 3 pages.
Lipton et al., "How treatment priorities influence triptan preferences in clinical practice: perspectives of migraine sufferers, neurologists, and primary care physicians," Current Medical Research and Opinion 21:413-424, Mar. 2005, 12 pages.
Lipton et al., "Migraine practice patterns among neurologists," Neurology, Jun. 2004, 7 pages.
Lipton et al., "Migraine prevalence, disease burden, and the need for preventive therapy", Neurology. 68(5):343-9, Jan. 30, 2007, 8 pages.
Lipton et al., "Migraine,.Identifying and removing barriers to care," Neurology vol. 44, Suppl. 4, S63-S68, Jun. 1994, 6 pages.
Lipton et al., "Moving Forward—Essential Questions for the Next 10 Years," Headache 49:S43-S46, Feb. 2009, 4 pages.
Lipton et al., "The role of headache-related disability in migraine management," Neurology 56(Supp 1):S35-S42, 2001, 8 pages.
Lipton et al., "Treatment preferences and the selection of acute migraine medications: results from a populatin-based survey," Journal of Headache Pain, vol. 5, Issue 2, Aug. 2004, 8 pages.
Lipton et al., "Why headache treatment fails?" Neurology 60:1064-1070, Apr. 2003, 7 pages.
Lipton, "CGRP antagonists in the acute treatment of migraine", The Lancet Neurology 3:332, Jun. 2004, 1 page.
Lodish et al., "Molecular Cell Biology," 5th Edition, W.H. Freeman and Company, pp. 537-539, 2004, 4 pages.
Longmore et al., "5-HT1D receptor agonsits and human coronary artery reactivity in vitro crossover comparisons of 5-HT and sumatriptan with rizatriptan and L-741,519," Br J Clin Pharmacol 42:431-441, 1996, 11 pages.
Longmore et al., "Comparison of the vasoconstrictor effects of the selective 5-HT1D-receptor agonist L-775,606 with the mixed 5-HT1B/1D-receptor agonist sumatriptan and 5-HT in human isolatd coronary artery," J Clin Pharmacol 49:126-131, 2000, 6 pages.
Longmore et al., "Effects of two truncated forms of human calcitonin-gene related peptide: implications for receptor classification," European Journal of Pharmacology 265:53-59, Nov. 1994, 7 pages.
Lucas, "Posttraumatic Headache: Clinical Characterization and Management," Curr Pain Headache Rep 19:48, Aug. 18, 2015, 9 pages.
Luykx et al., "Are mirgraineurs at increased risk of adverse drug responses?: A meta-analytic comparison of topiramate-related adverse drug reactions in epilepsy and migraine," Clinical Pharmacology & Therapeutics, vol. 85, No. 3, Mar. 2009, 6 pages.
Ma et al., "Colocalization of CGRP with 5-HT 1B/1D receptors and substance P in trigeminal ganglion neurons in rats," European Journal of Neuroscience 13:2099-2104, Jun. 2001, 6 pages.
MaassenVanDenBrink et al., "5-HT1B-receptor polymorphism and clinical response to sumatriptan," Headache, vol. 38:288-91, Apr. 1998, 4 pages.
MaassenVanDenBrink et al., "Augmented contraction of the human isolated coronary artery by sumatriptan: a possile role for endogenous thromboxane," British Journal of Pharmacology, vol. 119:855-62, Nov. 1996, 8 pages.
MabCampath® (alemtuzumab), "Scientific Discussion," EMEA 2005, 22 pages.
MacEwan, "TNF receptor subtype signaling differences and cellular consequences," Cell Signal vol. 14, 477-492, Jun. 2002, 16 pages.
MacGregor et al., "Guidelines for All Healthcare Professionals in the Diagnosis and Management of Migraine," British Association for the Study of Headaches (BASH), Sep. 2010, 53 pages.
Macolino et al., "Mechanical alloydnia induced by traumatic brain injury is inependent of restraint stress," J Neurosci Meth 226:139-146, Apr. 15, 2014, 8 pages.
Maini and Feldmann, "How Does Infliximab Work in Rheumatoid Arthritis?" Arthritis Research, vol. 4, Suppl. 2, Mar. 27, 2002, 7 pages.
Malik et al., "Research Submission—Acute migraine treatment: patterns of use and satisfaction in clinical population," Headache, May 2006, 8 pages.
Manack et al., "The Evolution of Chronic Migraine: Classification and Nomenclature", Headache 49:1206-1213, Sep. 2009, 8 pages.
Manack et al., "Chronic Migraine: Epidemiology and Disease Burden," Curr Pain Headache Rep 15:70-78, Feb. 2011, 9 pages.
Mankarious et al., "The half-lives of IgG subclasses and specific antibodies in patients with primary immunodeficiency who are receiving intravenously administered immunoglobulin," J Lab of Clinical Medicine, vol. 112, No. 5, Nov. 1998, 7 pages.
Marks et al., "By-passing immunization: building high affinity human antibodies by chain shuffling," Biotechnol 10(7):779-783, Jul. 1992, 17 pages.
Martinelletti et al., "The Global Campaign (GC) to reduce the burden of headache worldwide: The international team for specialist education (ITSE)," Journal of Headache Pain, vol. 6(4), Jul. 20, 2005, 3 pages.
Mason et al., "Release of the Predicted Calcitonin Gene-Related Peptide from Cultured Rat Trigeminal Ganglion Cells," Nature vol. 308: 653-655, Apr. 1984, 3 pages.
Matharu and Goadsby, "Trigeminal autonomic cephalalgias," J Neurol Neurosurf Psychiatry 72)Suppl II);ii19-ii26, 2002, 8 pages.
Matharu et al., "Verapamil-induced gingival enlargement in cluster headache," Journal of Neurology, Neruosurgery, and Psychiatry 76:124-127, Jan. 2005, 4 pages.

(56) References Cited

OTHER PUBLICATIONS

May et al., "EFNS guidelines on the treatment of cluster headache and other trigeminalautonomic cephalalgias," European Journal of Neurology 13:1066-1077, Oct. 2006, 12 pages.
May et al., "PET and MRA findings in cluster headache and MRA in experimental pain," Neurology 55:1328-1335, Nov. 2000, 8 pages.
Maynard and Georgiou, "Antibody Engineering," Annu. Rev. Biomed. Eng. 2: 339-376, 2000, 38 pages.
McCarthy et al., "Osteoarthritis," Textbook of Pain, pp. 387-395, 1994, 15 pages.
McCulloch et al., "Calcitonin gene-related peptide: Functional role in cerebrovascular regulation," Proc Natl Acad Sci USA 83:5731-5735, Aug. 1986, 5 pages.
Messlinger et al., "Abstracts of the XII Congress of the International Headache Society/ IHC 2005," Cephalalgia, Believe in Headache Relief, IHC 2005 Kyoto, Oct. 2005, 193 pages.
Messlinger et al., "Inhibition of neurogenic blood flow increases in the rat cranial dura mater by a CGRP-binding Spiegelmer," Cephalalgia 25;923, Oct. 2005, 3 pages.
Messlinger et al., "Poster-Inhibition of neurogenic blood flow increases in the rat cranial dua mater by a CGRP-binding Spiegelmer," Cephalalgia 25:923, Oct. 2005, 1 page.
Michelson et al., "Lack of efficacy of L-759274, a novel neurokinin 1 (subtance P) receptor antagonist, for the treatment of generalized anxiety disorder," International Journal of Neuropsychopharmacology 16(1):1-11, Feb. 2013, 11 pages.
Mitsikostas et al., "New players in the preventive treatment of migraine," BMC Medicine, vol. 13, No. 1, Nov. 10, 2015, 7 pages.
Morara et al., "Calcitonin Gene-Related Peptide Receptor Exprssion in the Neurons and Glia of Developing Rat Cerebellum: An Autoradiographic and Immunohistochemical Analysis," Neuroscience 100(2):381-391, 2000, 11 pages.
Moreno et al., "Efficacy of the non-peptide antagonist BIBN4096BS in blocking CGRP-induced dilations in human and bovine cerebral arteries," Neuropharmacology 42(4):568-576, Mar. 2002, 9 pages.
Morrison et al., "Chimeric human antibody molecules: Mouse antigen-binding domains with human constant region domains," Proceedings of the National Academy of Science, USA, vol. 81(21), Nov. 1984, 5 pages.
Moskowitz, "Interpreting vessel diameter changes in vascular headaches," Cephalalgia, Feb. 1992, 3 pages.
Moskowitz, "Neurogenic versus vascular mechanisms of sumatriptan and ergot alkaloids in migraine", Trends in Pharmacological Sciences 13(8):307-311, Aug. 1992, 5 pages.
Nestorov, "Clinical pharmacokinetics of tumor necrosis factor antagonists," The Journal of Rheumatology 74:13-18, Mar. 2005, 7 pages.
Nilsson et al., "Placebo response rates in cluster headache trials, a review," Cephalalgia 23:504-510, Sep. 2003, 7 pages.
Norman et al., "A placebo-controlled, in-clinic study to explore the preliminary safety and efficacy of intravenous L-758,298 (a prodrug of the NK1 receptor antagonist L-754,030) in the acute treatment of migraine," Cephalalgia 18, Poster Presentations, 1998, 1 page.
Notice of Opposition to European Patent No. EP3045182 B1, European Application No, 16154418.4 dated Dec. 7, 2018, 43 pages.
Nyholt et al., "A high-density association screen of 155 ion transport genes for involvement with common migraine," Human Molecular Genetics, 17: 3318-3331, Nov. 2008, 14 pages.
O'Connell et al., "On the role of the C-terminus of α-calcitonin-gene-related-peptide (αCGRP) The Structure of des-phenylalaninamide[37] -αCGRP and it's interatction with the CGRP receptor," Biochem J 291:205-210, 1993, 6 pages.
Odink et al., "F229: Plasma aminoacids in common and classic migraine and tension headache," Neurochemistry Int., 13,suppl. 1:155-56, 1988, 1 pages.
Olesen (and the First Headache Classification Subcommittee Members), "The International Classification of Headache Disorders: 2rd Edition," Blackwell Publishing, 2004, 150 pages.
Olesen and Goadsby, "The Headaches: Third Edition," Chapters 2, 9, 10, 16, 22, 28, 30, 31, 33, 47, 48, 49, 50-60, 2005, 259 pages.
Olesen et al., "Brief Report—New appendix criteria open for a broader concept of chronic migraine," Cephalalgia 26: 742-746, Jun. 2006, 5 pages.
Olesen et al., "The international Classiication of Headache Disorders, 3rd edition (beta version)," Headache Classification Committee of the International Headache Society, Cephalalgia, Jul. 2013, 180 pages.
Olesen et al., "Timing and Topography of Cerebral Blood Flow, Aura, and the Headache during Migraine Attacks," Ann Neurol. vol. 28, No. 6, Dec. 1990, 8 pages.
Olesen et al., "S26 CGRP Antagonism as a New Therapeutic Principle in Acute Migraine," Neuropeptides 38: 110-131, No. 2-3, Apr./Jun. 2004, 6 pages.
Olesen, "Chapter 11: Chronic Migraine," in Classification and Diagnosis of Headache Disorders, Oxford University Press 2005, 8 pages.
Olesen, "In-depth characterization of CGRP receptors in human intracranial arteries," European Journal of Pharmacology, vol. 481, Nov. 2003, 10 pages.
Oliver et al., "Immunohistochemical Localization of Calcitonin Receptor-Like Receptor and Receptor Activity-Modifying Proteins in the Human Cerebral Vasculature," Journal of Cerebral Blood Flow & Metabolism 22: 620-629, May 2002, 10 pages.
Oliver et al., "Distribution of novel CGRP1 receptor and adrenomedullin receptor mRNAs in the rat central nervous system," Molecular Brain Research 57: 149-154, Jun. 1998, 6 pages.
Oliver et al., "Regional and cellular localization of calcitonin gene-related peptide-receptor component protin mRNA in the guinea-pig central nervous system," Molecular Brain Research 66:201-210, Mar. 1999, 6 pages.
Ophoff et al., "P/Q-type Ca2+ channel defects in migraine, ataxia and epilepsy," Trends in Pharmacological Sciences vol. 19:121-127, Apr. 1998, 7 pages.
Ophoff et al., "The impact of pharmacogenetics for migraine," European Journal of Pharmacology, vol. 413:1-10, Feb. 2001, 10 pages.
Opposition dated Dec. 4, 2018 in European Patent No. EP3045182 B1, Eurpean Application No. 16154418.4 dated Dec. 4, 2018, 19 pages.
Overington et al., "How many drug targets are there?" Nature Reviews: Drug Discovery 5(12):993-996, Dec. 2006, 4 pages.
Overy and Tansey, "Migraine: Diagnosis, Treatment and Understanding c. 1960-2010," vol. 49, Queen Mary University of London, 2013, 149 pages.
Parameswaran et al., "Activation of multiple mitogen-activation protein kinases by recombinant calcitonin gene-related peptide receptor," European Journal of Pharmacology, vol. 389(2-3): 125-30, Feb. 2000, 6 pages.
Pardridge, "CNS Drug Design Based on Principles of Blood-Brain Barrier Transport," Journal of Neurochemistry, vol. 70 No. 5, 1781-1792, May 1998, 12 pages.
Pardridge, "The Blood-Brain Barrier: Bottleneck in Brain Drug Development," NeuroRx: The Journal of American Society for Experimental NeuroTherapeutics, vol. 2, 3-14, Jan. 2005, 12 pages.
Parsons et al., "Tonabersat (SB-220453) a novel benzopyran with anticonvulsant properties attenuates trigeminal nerve-induced neurovascular reflexes," British Journal of Pharmacology 132:1549-1557, Apr. 2001, 9 pages.
Paus and Winter, "Mapping epitopes and antigenicity by site-directed masking", PNAS 103(24):9172-9177, Jun. 13, 2006, 6 pages.
Pietrobon et al., "Pathophysiology of migraine," Annual Review of Physiology 75:365-391, 2013, 30 pages.
Pietrobon, "Migraine: New Molecular Mechanisms," The Neuroscientist 11(4):373-386, Aug. 2005, 14 pages.
Pilgrim, "Methodology of Clinical Trials of Sumatriptan in Migraine and Cluster Headache," European Neurology 31(5):295-299, 1991, 5 pages.
Poduslo et al., "Macromolecular permeability across the blood-nerve and blood-brain barriers," PNAS, vol. 91:5705-5709, Jun. 1994, 5 pages.

(56) References Cited

OTHER PUBLICATIONS

Pollack, "F.D.A. Approves a Multiple Sclerosis Drug," New York Times, Nov. 24, 2004, 4 pages.
Poyner et al., "CGRP receptors: beyond the CGRP(1)-CGRP(2) subdivision," Trends in Pharmacological Sciences, vol. 22, No. 5, May 2001, 1 page.
Poyner et al., "International Union of Pharmacology. XXXII. The Mammalian Calcitonin Gene-Related Peptides, Adrenomedullin, Amylin, and Calcitonin Receptors," Pharmacological Reviews 54(2)233-246, Jun. 2002, 14 pages.
Poyner et al., "The CGRP Family: Calcitonin Gene-Related Peptide (CGRP), Amylin and Andrenomedullin," Molecular Biology Intelligence Unit 10, Chapters 1-7, and 15-16, 2000, 88 pages.
Poyner, "Calcitonin Gene-Related Peptide: Multiple actions, multiple receptors," Pharmacology & Therapeutics 56(1):23-51, Feb. 1992, 29 pages.
Presta, "Selection, Design, and Engineering of Therapeutic Antibodies," Journal of Allergy and Clinical Immunology, vol. 116, Issue 4, 731-736, Oct. 2005, 6 pages.
Projan et al., "Small Molecules for Small Minds? The Case for Biologic Pharmaceuticals," Expert Opinion Biol. Ther. 4:1345-1350, Aug. 2004, 7 pages.
Purves et al., "Neuroscience: Third Edition," pp. 763-773, Sinauer Associates, Inc., 2004, 14 pages.
Qiao and Grider, "Up-regulation of calcitonin gene-related peptide and receptor tyroside kinase TrkB in rat bladder afferent neurons following TNBS," Experimental Neurology, vol. 204, Apr. 2004, 13 pages.
Queen et al., "A Humanized Antibody that Binds to the Interleukin 2 Receptor," Proceedings of the National Academy of Sciences of the United States of America, vol. 86: 10029-10033, Dec. 1989, 5 pages.
Raddant et al., "Calcitonin gene-related peptide in migraine: intersection of peripheral inflammation and central modulation", Expert Reviews in Molecular Medicine 13, Nov. 2011, 22 pages.
Rader et al., "Chemically Programmed Monoclonal Antibodies for Cancer Therapy: Adaptor Immunotherapy Based on a Covalent Antibody Catalyst," Proc. Natl. Acad. Science. USA, vol. 100, No. 9, pp. 5396-5400, Apr. 29, 2003, 5 pages.
Ramadan and Buchanan, "New and future migraine therapy," Pharmacology and Therapeutics, 112(1):199-212, Oct. 2006, 14 pages.
Rang, "Pharmacology: 5th Edition," Chapters 2, 3, 9 ,13, 31, Elsevier Science Limited, 2003, 76 pages.
Rapp et al., "Botulinum Toxin Type A Inhibits Cacitonin Gene-Related Peptide Release from Isolated Rat Bladder," Journal of Urology, American Urological Association, vol. 175, No. 1138-1142, Mar. 2006, 5 pages.
Ray and Wolff, "Experimental Studies of Headache," Archives of Surgery, vol. 41, No. 4, Oct. 1940, 44 pages.
Recober and Goadsby, "Calcitonin gene-related peptide (CGRP): a molecular link between obesity and migraine?", Drug News Perspect 23(2),112-117, Mar. 2010, 9 pages.
Reff et al., "Depletion of B Cells in vivo by a Chimeric Mouse Human Monoclonal Antibody to CD20," Blood vol. 83, No. 2, 435-445, Jan. 15, 1994, 12 pages.
Remicade (infliximab), "Prescribing Information," 5007 & 5090 Combined (clean copy): FDA Revisions on Dec. 13, 2004, 32 pages.
Reuter, "Anti-CGRP antibodies: a new approach to migraine prevention," The Lancet 13(9):857-859, Sep. 2014, 3 pages.
Riechers II et al., "Post-traumatic headaches," Handbook of Clinical Neurology 128:567-578, Dec. 2014, 12 pages.
Rist et al., "CGRP 27-37 analogues with high affinity to the CGRP1 receptor show antagonistic properties in a rat blood flow assay," Regul. Pept. vol. 79: 153-58, Feb. 1999, 8 pages.
Rist et al., "From Micromolar to Nanomolar Affinity: A Systematic Approach to Identify the Binding Site of CGRP at the Human Calcitonin Gene-Related Peptide 1 Receptor," J. Med. Chem. 41: 117-123, Jan. 1998, 7 pages.

Ritter et al., "A Textbook of Clinical Pharmacology: 4th Edition," Chapters 16, 22, 24, Oxford Univeristy Press, 1999, 25 pages.
RituxanTM (rituximab) Prescribing Information, Nov. 1997, 2 pages.
Rizzoli, "Synaptic Vesicle Pools," Nature Reviews: Neuroscience, vol. 6, Jan. 2005, 13 pages.
Roon et al., "Bovine isolated middle cerebral artery contrations to antimigraine drugs," Naunyn-Schmiedeberg's Arch Pharmacol vol. 360:591-596, Nov. 1999, 6 pages.
Roon et al., "Pharmacokinetic profile of alniditan nasal spray during and outside migraine attacks," Br J Clin Pharmacol vol. 47:285-290, Mar. 1999, 6 pages.
Russell et al., "Calcitonin Gene-related paptide: physiology and pathophysiology," Physiolog Rev 94(4):1099-1142, Oct. 1, 2014, 44 pages.
Salman et al., "An Improved Protocol for Coupling Synthetic Peptides to Carrier Proteins for Antibody Production Using DMF to Solubilize Peptides," Journal of Biomolecular Techniques 18:173-176, Jul. 2007, 4 pages.
Sanchez del Rio et al., "How to pick optimal acute treatment for migraine headache," Current Pain and Headache Reports, vol. 5, Apr. 2001, 9 pages.
Sandborn and Yednock, "Novel Approaches to Treating Inflammatory Bowel Disease: Targeting Alpha-4 Integrin," The American Journal of Gastroenterology, vol. 98, No. 11, Nov. 2003, 11 pages.
Sandor, "Nervous control of the cerebrovascular system: doubt and facts," Neurochemistry International 35:237-259, 1999, 23 pages.
Santora et al., "Characterization of Noncovalent Complexes of Recombinant Human Monoclonal Antibody and Antigen Using Cation Exchange, Size Exclusion Chromatography, and BIAcore," Analytical Biochemistry, 229: 119-129, Dec. 2001, 11 pages.
Saper et al., "DHE in the Pharmacotheraphy of Migraine Potential for a Larger Role," Headache vol. 46(Suppl. 4), Nov. 2006, 9 pages.
Saxena et al., "5HT1-like receptor agonists and the pathophysiology of migraine," Trends Pharmacol Sci vol. 10,5:200-204, May 1989, 5 pages.
Saxena et al., "Effects of tertatolol, a β-adrenoceptor antagonist with agonist affinity at 5-HT1A receptors, in an animal model of migraine: comparison with propanolol and pindolol," European Journal of Pharmacology, 220, Sep. 1992, 8 pages.
Scher et al., "Cardiovascular risk factors and migraine. The GEM population-based study," Neurlogy 64:614-620, Feb. (2 of 2) 2005, 7 pages.
Schmitz et al., "Frontal lobe structure and executive function in migraine patients," Neuroscience Letters, 1:440(2):92-6, Aug. 2008, 5 pages.
Schoenen et al., "Neurophysical features of the migrainous brain," Features of the Migrainous Brain, Neurol Sci, vol. 27, S77-S81, May 2006, 5 pages.
Schoenen et al., "No effect of eletriptan administration during the aura phase of migraine," European Journal of Neurology, vol. 11, 671-677, Oct. 2004, 7 pages.
Schoenen et al., "When should triptans be taken during a migraine attack?" Leading Article, CNS Drugs, vol. 15(8), Aug. 2001, 5 pages.
Schoonman et al., "Chapter 1: The prevalence of premonitory symptoms in migraine: a questionnaire study in 461 patients," Cephalalgia 26;1209-1213, 2006, 8 pages.
Schoonman et al., "Chapter 3: Normobaric hypoxia and nitroglycerin as trigger factors for migraine," Cephalalgia, vol. 26(7):816-9, Jul. 2006, 8 pages.
Schoonman et al., "Gabapentin in Migraine Prophylaxis: Is it Effective and Well Tolerated?" Headache, vol. 42, Issue 3, Mar. 2002, 1 page.
Schoonman et al., "Is stress a trigger factor for migraine?" Psychoneuroendocrinology 32(5):532-538, Jun. 2007, 7 pages.
Schoonman et al., "Magnetic resonance angiography of the human middle meningeal artery: implications for migraine," Journal of Magnetic Resonance Imagining, 24:918-921, Oct. 2006, 4 pages.
Schoonman et al., "Migraine headache is not associated with cerebral or meningeal vasodilatation—a 3T magnetic resonance angiography study," Brain 131:2192-2200, Aug. 2008, 9 pages.

(56) References Cited

OTHER PUBLICATIONS

Schueren et al., "Reproductivity of the capsaicin-induced dermal blood flow response as assessed by laser Doppler perfusion imaging," Br J Clin Pharmacol 64(5):580-590, 2007, 11 pages.

Schulman et al., "Defining Refractory Migraine and Refractory Chronic Migraine: Proposed Criteria From the Refractory Headache Special Interest Section of the American Headache Society", Headache 48:778-782, 2008, 6 pages.

Schytz et al., "PACAP38 induces migraine-like attacks in patients with migraine without aura," Brain, vol. 132 (part 1): 16-25, Jan. 2009, 10 pages.

Scimemi and Beato, "Determining the Neurotransmitter Concentration Profile at Active Synapses", Molecular Neurobiology 40(3): 289-306, Oct. 2009, 18 pages.

Scott et al., "Sumatriptan and cerebral perfusion in healthy volunteers," British Journal of Clinical Pharmacology 33(4):401-404, Apr. 1992, 4 pages.

seekingalpha.com' [online], "Teva Pharmaceutical Industries (TEVA) Q3 2017 Results—Earnings Call Transcript," available on or before Nov. 2, 2017, retrieved on Dec. 11, 2018, retrieved from URL: <https://seekingalpha.com/article/4119613-teva-pharmaceutical-industries-teva-q3-2017-results-earnings-call-transcript#question-answer-session>, 3 pages.

Seifert et al., "Chapter 7: (Patho)physiological and Therapeutic Relevance of Constitutive Activity and Inverse Agonism at G Protein-Coupled Receptors" in G-Protein-Coupled Receptors as Drug Targets: Analysis of Activation and Constitutive Activity, vol. 24, 2006, 11 pages.

Seon et al., "Isolation, Structure, Synthesis, and Activity of a New Member of the Calcitonin Gene-related Peptide Family from Frog Skin and Molecular Cloining of Its Precursor," The Journal of Biological Chemistry 275(8):5934-5940, 2000, 8 pages.

Shapiro and Goadsby, "The long drought the dearth public funding for headache research," Cephalalgia, vol. 27, Sep. 2007, 4 pages.

Shawket et al., "Prolonged effect of CGRP in Raynaud's patients: a double-blind randomised comparison with protacyclin," Br J Clin Pharmac 32:209-213, 1991, 5 pages.

Shawket et al., "Selective Suprasensitivity to Calcitonin-Gene-Related Peptide in the Hands in Raynaud's Phenomenon," The Lancet 1354-1385, Dec. 9, 1989, 4 pages.

Shepheard et al., "Possible antimigraine mechanisms of action of the 5HT1F receptor agonist LY334370," Cephalalgia 19:851-858, Dec. 1999, 8 pages.

Shepherd and Dean, "Monoclonal Antiobodies: A Practical Approach," Chapters 1, 2, 12, 13, 20, 21, Oxford University Press, Jul. 13, 2000, 151 pages.

Shevel, "The Extracranial Vascular Theory of Migraine—A Great Story Confirmed by the Facts," Headache vol. 51, Mar. 2011, 9 pages.

Shields and Goadsby, "Seritonin receptors modulate trigeminovascular responses in ventroposteromedial nucleus of thalamus: a migraine target?" Neurobiology of Disease 23:491-501, Sep. 2006, 11 pages.

Shields et al, "Inhibition of Allergic Reactions with Antibodies to IgE," International Archives for Allergy and Immunology, 107: 308-312, May-Jun. 1995, 5 pages.

Sigma-Aldrich, "Biochemicals & Reagents for Life Science Research" pp. 350-352, 2004, 7 pages.

Silberstein et al., "Advances in the understanding of the pathophysiology headache," Neurology, vol. 42(suppl.2): 6-10, Mar. 1992, 5 pages.

Silberstein et al., "Botulinum toxin type A for the prophylactic treatment of chronic daily headache: a randomized, double-blind, placebo-controlled trial," Mayo Clinic Proceedings, Sep. 2005, 12 pages.

Silberstein et al., "Chapter 5: Pathophysiology of Headache, Chapter 6: Genetics of Headache, Chapter 9: Migraine—Diagnosis and Treatment & Chapter 12: Cluster Headache—Diagnosis, Management and Treatment," in Wolff's Headache and other head pain: Seventh Edition, Oxford Press 2001, 180 pages.

Silberstein et al., "CNS effects of sumatriptan and rizatriptan," Cephalalgia, Jan. 2004, 2 pages.

Silberstein et al., "From migraine mechanisms to innovative therapeutic drugs," Neurology, vol. 64 (Suppl 2), May 2005, 3 pages.

Silberstein et al., "Migraine: preventive treatment," Cephalalgia, vol. 22, Sep. 2002, 22 pages.

Silberstein et al., "Preventive treatment of migraine," Neurology, 60(Suppl 2):S38-S44, 2003, 7 pages.

Silberstein et al., "Removing barriers to appropriate migraine treatment: formulary limitaions and triptan package size," Headache, Oct. 2005, 5 pages.

Silberstein et al., "Section 2: Primary Headache Disorders, Chapter 6: Migraine: diagnosis and treatment," in Headache in Primary Care, Isis Medical Media, 1999, 32 pages.

Silberstein, "Cardiovascular risk factors associated with migraine," Lancet Neurol, Jul. 2005, 2 pages.

Silberstein, "Chronic migraine: diagnosis and management strategy," Reviews in Neuological Diseases, vol. 1, No. 3, Summer 2004, 6 pages.

Silberstein, "Current Preventive Therapy: Preventive treatment mechanism," Headache Currents, vol. 3, No. 5, Sep./Oct. 2006, 8 pages.

Silberstein, "Migraine pathophysiology and its clinical implications," Cephalalgia, 24 Suppl. 2, Feb. 2004, 6 pages.

Silberstein, "Migraine prevention medication reduces resource utilization," Research Submissions: Headache, Mar. 2003, 8 pages.

Silberstein, "Migraine," Lancet, vol. 363, Jan. 2044, 11 pages.

Silberstein, "Migraine: preventive treatment," Current Medical Research and Opinion, vol. 17, Suppl. 1, S87-93, 2001, 7 pages.

Silberstein, "Preventive treatment of headaches," Current Opinion in Neurology, Jun. 2005, 4 pages.

Silberstein, "Preventive treatment of migraine," Review in Neurological Diseases, vol. 2, No. 4, Fall 2005, 9 pages.

Silberstein, "Preventive treatment of migraine," Trends in Pharmacological Sciences, vol. 27, No. 8, Aug. 2006, 6 pages.

Silberstein, "Review of botulinum toxin type A and its clinical applications in migraine headache," Expert Opinion Phermacother, vol. 2 (10), Oct. 2001, 6 pages.

Silberstein, "The International Classification of Headache Disorders, 2nd Edition (ICHD-II)—revision of criteria for 8.2 Medication-overuse headache," Cephalalgia, Jun. 2005, 6 pages.

Silberstein, "Topiramate in migraine prevention," Headache, Apr. 2005, 9 pages.

Silberstein,"A new Frontier for headache," Frontiers in Neurology, vol. 1, Article 135, p. 1, Oct. 2, 2010, 1 pages.

Silberstein, "Migraine," Discovery Medicine, Jul. 12, 2009, pp. 1.

Silberstein, "Preventive Migraine Treatment," Continuum, 21(4);973-989, Aug. 2015, 17 pages.

Simulect® (basiliximab), "Prescribing Information," Novartis Pharmaceuticals Corporation, May 1998, 7 pages.

Sixt et al., "Calcitonin gene-related peptide receptor antagonist olcegepant acts in the spinal trigeminal nucleus," Brain 132:3134-3141, Nov. 2009, 8 pages.

Smith et al., "An immunocytochemical investigation of human trigeminal nucleus caudalis: CGRP, substance P and $5\text{-}HT_{1D}$-receptor immunoreactivities are expressed by trigeminal sensory fibres," Cephalalagia 22:242-432, Jul. 2002, 10 pages.

Sparey, "Embracing partnerships: the Merck philosophy", Biopartnering Magazine, Spring 2006, 3 pages.

Spillner, "Recombinant IgE antibody engineering to target EGFR," Cancer Immunology Immunother. vol. 61(9), Sep. 2012, 9 pages.

Stam, "Migraine: new treatment options from molecular biology," Expert Rev Neurotherapeutrics, 5(5), Sep. 2005, 9 pages.

St-Amour et al., "Brain bioavailability of human intravenous immunoglobulin and its transport through the murine blood-brain barrier," Journal of Cerebral Blood Flow and Metabolism, 33(12):1983-92, Dec. 2013, 10 pages.

Steiner et al., "BASH Guidelines for Diagnosis and Management of Migraine, Tension-Type Headache, Cluster Headache and Medication-Overuse Headache: third edition," 2010, 53 pages.

Steiner et al., "BASH Management Guidelines: Guidelines for all Doctors in the Diagnosis and Management of Migraine and Tension-Type Headache (2nd edition)," BASH Management Guidelines, Mar. 2000, 31 pages.

(56) References Cited

OTHER PUBLICATIONS

Steiner et al., "The prevalence and disability burden of adult migraine in England and their relationships to age, gender and ethnicity," Cephalalgia, vol. 23, Sep. 2003, 9 pages.
Sternini, "Enteric and Visceral Afferent CGRP Neurons, Targets of Innercation and Differential Expression Patterns," Annals New York Academy of Sciences 170-185, 1992, 17 pages.
Strecker et al., "Nitric Oxide Releases Calcitonin-Gene-Related Peptide from Rat Dura mater Encephali Promoting Increases in Meningeal Blood Flow," Journal of Vascular Research 39:489-496, Nov.-Dec. 2002, 8 pages.
Strorer and Goadsby, "Topiramate inhibits trigeminovascular neurons in the cat," Cephalalgia 24:1049-1056, Dec. 2004, 8 pages.
Struthers et al., "Human calcitonin gene related peptide: a potent endogenous vasodilator in man," Clinical Science 70:389-393, 1986, 5 pages.
Subramanian, "Antibodies vol. 2—Novel Technologies and Therapeutic Use," Springer Science+Business Media New York, Jan. 2004, 239 pages.
Supowit et al., "Calcitonin Gene-Related Peptide Protects Against Hypertension-Induced Heart and Kidney Damage," Hypertension, vol. 45:109-14, Jan. 2005, 8 pages.
Swillens, "Interpretation of Binding Curves Obtained with High Receptor Concentrations: Practical Aid for Computer Analysis," Molecular Pharmacology 47:1197-1203, 1995, 7 pages.
Synagis® (palivizumab) EMA Scientific Discussion, 2004, 19 pages.
Tajti et al., "Migraine and neuropeptides," Neuropeptides 52:19-30, Aug. 2015, 12 pages.
Tao and Morrison, "Studies of Aglycosylated Chimeric Mouse-Human Ig:. Role of Carbohydrate in the Structure and Effector Functions Mediated by the Human IgG Constant Region," Journal of Immunology, 143: 2595-2601, No. 8, Oct. 15, 1989, 8 pages.
Tepper et al., "Mechanisms of Action of the 5-HT 1B/1D Receptor Agonists," Neurological Review, Arch. Neurol. vol. 59, pp. 1084-1088, Jul. 2002, 5 pages.
Terwindt et al., "Hemiplegic and basilar-type migraine: current and future treatment," Headache Currents No. 4:97-99, Jul.-Aug. 2006, 4 pages.
Terwindt et al., "Migraine en cardiovasculair risico," Ned Tijdsch Geneeskd 151(37) 2029-2031, 2007, 3 pages.
Terwindt et al., "The impact of migraine on quality of life in the general population. The GEM study," Neurology vol. 55:624-629, Sep. 2000, 6 pages.
Teva Pharmaceutical Industries, "Teva announces U.S. Approval of AJOVY (fremanezumab-vfrm) injection, the first and only anti-CGRP treatment with both quarterly and monthly dosing for the prevention of migraine in Adults," Teva Pharmaceutical Industries Ltd., available on or before Sep. 14, 2018, 8 pages.
Tfelt-Hansen et al., "Calcitonin gene-related peptide in blood is it increased in the external jugular vein during migraine and cluster headace: A review," Journal of Headache Pain, vol. 10, Jun. 2009, 7 pages.
Tfelt-Hansen et al., "Ergotamine in the acute treatment of migraine—a review and European consensus," Brain 123:9-18, Jan. 2000, 10 pages.
Tfelt-Hansen et al., "Guidelines for controlled trials of drugs in migraine: second edition," Cephalalgia vol. 20:765-786, Nov. 2000, 22 pages.
Tfelt-Hansen, "Site of effect of LY2951742 for migraine prophylaxis," The Lancet, 14:31-33, Jan. 2015 (includes Authors' reply), 2 pages.
Tsai et al., "Cerebral arterial innervation by nerve fibers containing CGRP: I. Distribution and Origin of CGRP Perivascular Innervation in the Rat," The Journal of Comparative Neurology, vol. 271: 435-444, May 1988, 10 pages.
Tsurushita et al., "Design of Humanized Antibodies: From anti-Tac to Zenapax," Methods 36: 69-83, May 2005, 15 pages.
Tuma, "Phase I Antibodie Risks: Trial Safety Explained," Journal of Natural Cancer Inst. vol. 98(14): 956-98, Jul. 19, 2006, 3 pages.

Tysabri (natalizumab), "Prescribing Information," Biogen Idec Inc., Nov. 2004, 11 pages.
Tysabri® Letter from the Food and Drug Administration, Nov. 2004, 7 pages.
Uddman et al., "Calcitonin gene-related peptide (CGRP) pervascular distribution and vasodilatory effects," Regulatory Peptides, vol. 15, Aug. 1986, 23 pages.
Uddman et al., "Innverevation of the feline cerebral vasculatur by nerve fibers containing CGRP," Neuroscience Letters, vol. 62, Nov. 1985, 6 pages.
Urban et al., "Functional Selectivity and Classical Concepts of Quantitative pharmacology," The Journal of Pharmacology and Experimental Therapeutics 320(1):1-13, Jan. 2007, 13 pages.
Vajdos et al., "Comprehensive functional maps of the antigen-binding site of an anti-ErbB2 antibody obtained with shotgun scanning mutagenesis," J Mol Biol 320(2):415-428, Jul. 5, 2002, 14 pages.
Van der Kamp et al., "Interictal cortical hyperexcitability in migraine patients demonstrated with transcranial magnetic stimulation," Journal of the Neurological Sciences, vol. 139:106-110, Jul. 1996, 5 pages.
Van der Schueren, "Reproducibility of the capsaicin-induced dermal blood flow response as assessed by laser Doppler perfusion imaging," British Journal of Clinical Pharmacology 64:580-590, Nov. 2007, 11 pages.
Van Dijk et al., "Human antibodies as next generation therapeutics," Current Opinion in Chemical Biology, vol. 5: 368-374, Aug. 2001, 7 pages.
Van Dijk et al., "No confirmation of visual evoked potential diagnostic test for migraine," Lancet vol. 337 i:517-518, Mar. 2, 1991, 2 pages.
Van Dijk et al., "Visual evoked potentials and background EEG activity in migraine," Headache 31:392-395, Jun. 1991, 4 pages.
Van Regenmortal et al., "Improving the Quality of BIACORE-Based Affinity Measurements," Dev. Biol. (Basel), 112: 141-151, 2003, 11 pages.
Van Valen et al., "Calcitonin Gene-Related Peptide (CGRP) Receptors are Linked to Cyclic Adenosine Monophosphate Production in SK-N-MC Human Neuroblastoma Cells," Neuroscience Letters 119: 195-198, Nov. 1990, 4 pages.
Van Vliet et al., "Cardiovascular autonomic function tests in cluster headache," Cephalalgia 26:329-331, Mar. 2006, 3 pages.
Van Vliet et al., "Evaluating the IHS criteria for cluster headache—a comparison between patients meeting all criteria and patients failing one criterion," Cephalalgia 26: 241-245, Mar. 2006, 5 pages.
Van Vliet et al., "Features involved in the diagnostic delay of cluster headache," J Neurol Neurosurg Psychiatry vol. 74(8):1123-1125, Aug. 2003, 3 pages.
Van Vliet et al., "Intranasal sumatriptan in cluster headache," Neurology 60:-633, Feb. (2 of 2) 2003, 5 pages.
Verhoeff et al., "Dopamine D2-receptor imaging with 123I-Iodobenzamide SPECT in migraine patients abusing ergotamine: does ergotamine cross blood brain barrier?" Cephalalgia 13:325-329, Oct. 1993, 5 pages.
Visser et al., "311C90, A new central and peripherally acting 5-HT1D receptor agonist in the acute oral treatment of migraine: a double blind, placebo-controlled, dose-range finding study," presented in part at the 10th Migraine Trust, Sep. 5-8, 1994, Neurology, Feb. 1996, 5 pages.
Visser et al., "Clinical trials and therapeutics, Pharmacokinetic and pharmacodynamic profiles of sumatriptan in migraine patients with headache recurrence or no response," Clinical Pharmacology and Therapeutics, vol. 60, No. 4, Oct. 1996, 9 pages.
Visser et al., "Subcutaneous Sumatriptan International Study Group. Treatment of migraine attacks with migraine attacks with subcutaneous sumatriptan: first placebo-controlled study," Cephalalgia 12:308-314, Oct. 1992, 6 pages.
Visser et al., "Sumatriptan in clinical practice: a 2-year review of 453 migraine patients," Neurology 47:46-51, Jul. 1996, 7 pages.
Visser et al., "Sumatriptan non-responders: a survey in 366 migraine patients," Headache vol. 36:471-475, Sep. 1996, 5 pages.
Wang and Yu, "Postictal headache in epileptic patients," Molecular & Cellular Epilepsy vol. 1, e197, 2014, 5 pages.

(56) References Cited

OTHER PUBLICATIONS

Wang et al., "Monoclonal antibody pharmacokinetics and pharmacodynamics", Clinical Pharmacology and Therapeutics, 84(5), 548-558, Nov. 2008, 11 pages.
Weiner et al., "Monoclonal antibodies: versatile platforms for cancer immunotherapy", Nature Reviews: Immunology 10(5):317-327, May 2010, 11 pages.
Weir et al., "Forming antibody fragments to mediate specific therapeutic functions," Biochemical society transations vol. 30, part 4, Aug. 2002, 5 pages.
Welch, "MRI of the occipital cortex, red nucleus, and substantia nigra during visual aura of migraine," Neuology, vol. 51:1465-1469, Nov. 1998, 5 pages.
Werry and Aman, "Practitioner's Guide to Psychoactive Drugs for Children and Adolescents, 2nd Edition," Plenum Publishing Corporation, pp. 42-50, 1999, 11 pages.
Werther et al., "Humanization of an Anti-lymphocyte Function-Associated Antigen (LFA)-1 Monoclonal Antibody and Reengineering of the Humanized Antibody for Binding to Rhesus LFA-1," J. Immunol. 157: 4986-4995, Dec. 1996, 10 pages.
Wicher et al., "Immunogenicity of Three Recombinant Treponema pallidum Antigens Examined in Guinea Pigs," Int. Arch. Allergy Appl. Immunol. 89 128-135, 1989, 8 pages.
Wiendels and Ferrari, "Treating migraine attacks asap: concept and methodological issues," Progress in Neurotherapeutics and Neuropsychopharmacology, vol. 1 p. 53-61, Jan. 2006, 9 pages.
Wiendels et al., "Chapter 2: Chronic frequent headache in the general population—prevalence and associated factors & Chapter 3: Chronic frequent headaches in the general population—comorbidity and quality of life," Cephalalgia vol. 26:1434-1442, 2006, 161 pages.
Wiig et al., "Interstitial Fluid and Lymph Formation and transport," Physiological Review, vol. 92, Jul. 2012, 56 pages.
Wild et al., "Determination of the Human Cytochrome P450 Isoforms Involved in the Metabolism of Zolmitriptan," Xenobiotica, vol. 29, pp. 847-857, Aug. 1999, 12 pages.
Williamson et al., "Intravital microscope studies on the effects of neurokinin agonists and calcitonin gene-related peptide on dural vessel diameter in the anaesthetized rat," Cephalalgia 17(4):518-524, Jun. 1997, 14 pages.
Williamson et al., "Role of opioid receptors in neurogenic dural vasodilation and sensitization of trigeminal neurons in anaesthetized rats," British Journal of Pharmacology 133 807-814, Jul. 2001, 8 pages.
Williamson et al., "The Novel Anti-Migraine Agent Rizatriptan Inhibits Neurogenic Dural Vasodilation and Extravasation," European Journal of Pharmacology, vol. 328, pp. 61-64, Jun. 1997, 4 pages.
Wimalawansa et al., "Isolation, Purification, and Characterization of Calcitonin Gene-Related Peptide Receptor," Peptides 14:691-699, 1993, 9 pages.
Wimalawansa, "Cacitonin Gene-Related Peptide and Its Receptors: Molecular Genetics, Physiology, Pathophysiology, and Therapeutic Potentials," Endocrine Reviews 17(5):553-585, Oct. 1996, 33 pages.
Wisskrichen et al., "Bioactive β-bend structures for the antagonist hα CGRP $_{8-37}$ at the CGRP$_1$ receptor of the rat pulmonary artery," British Journal of Pharmaology 129:1049-+1055, 2000, 7 pages.
Woods et al., "Bilateral spreading cerebral hypoperfusion during spontaneous migraine and headache," the New England Journal of Medicine, Brief Report, vol. 331, No. 25, Dec. 1994, 4 pages.
World Health Organization (WHO), "General policies for monoclonal antibodies," INN Working Document 09.251 Revised, Dec. 2009, 4 pages.
World Health Organization (WHO), "WHO Drug Information," WHO Drug Information vol. 30, No. 2, 2016, 187 pages.
World Health Organization, "The use of stems in the selection of international nonproprietary names (INN) for pharmaceutical substances," Programme on International Nonproprietary Names (INN), 2006, 170 pages.
Wright and Morrison, "Effect of Glycosylation on Antibody Function: Implications for Genetic Engineering," Trends Biotechnology 15: 26-32, Jan. 1997, 7 pages.
Wu et al., "Stepwise in vitro Affinity Maturation of Vitaxin, an alphavbeta3-Specific Humanized mAb," Proc. Natl. Acad. Sci. USA 95: 6037-42, May 1998, 6 pages.
Wu et al., "Ultra-Potent Antibodies Against Respiratory Syncytial Virus: Effects of Binding Kinetics and Binding Valence on Viral Neutralization," J. Mol. Biol. 350: 126-144, Jul. 2005, 19 pages.
Wyon et al., "Urinary Excretion of Calcitonin Gene-related Peptide in Males with Hot Flushes after Castration for Carcinoma of the Prostate," Scand J Urol Nephrol 35:92-96, May 2001, 5 pages.
Xu et al., "Essential role of the TNF-TNFR2 cognate interation in mouse dendritic cell-natural killer cell crosstalk," Blood, vol. 109, No. 8, Apr. 2007, 10 pages.
Yang et al., "CDR Walking Mutagenesis for the Affinity Maturation of a Potent Human Anti-HIV-1 Antibody into the Picomolar Range," J. Mol. Biol. 254: 392-403, Dec. 1995, 12 pages.
Yeomans et al., U.S. Appl. No. 60/711,950, filed Aug. 26, 2005, 47 pages.
Young et al., "Transcranial Doppler: technique and application to headache," Headache, Mar. 1992, 7 pages.
Zanetti and Capra, "The Antibodies vol. 1," Chapters 2, 3, 4, 5, 6, Harwood Academic Publishers, 1995, 137 pages.
ZevalinTM (ibritumomab tiuxetan) Prescribing Information, Dec. 21, 2001, 38 pages.
Zhang et al. "Activation of meningeal nociceptors by cortical spreading depression: implicaions for migraine with aura." Journal of Neuroscience 30(26):8807-8814, Jun. 2010, 16 pages.
Zhang et al., "Activation of central trigeminovascular neurons by cortical spreading depression", Annals of neurology 69(5):855-865, May 2011, 16 pages.
Zomig (zolmitriptan) tablets and Zomig-ZMT (zolmitriptan) Orally Disintegrating Tablets, "Prescribing Information," AstraZeneca 2000, last revised: Feb. 12, 2001, 28 pages.
Zwetsloot et al., "Blood flow velocities in the vertebrobasilar system during migraine attacks—a transcranial Doppler study," Cephalalgia vol. 12:29-32, Feb. 1992, 4 pages.
Zwetsloot et al., "Blood Flow velocity changes in migraine attacks—a transcranial doppler study," Cephalalgia vol. 11:103-107, May 1991, 5 pages.
Zwetsloot et al., "Lack of asymmetry of middle cerebral artery blood flow velocity in unilateral migraine," Stroke, vol. 24, No. 9, Sep. 1993, 4 pages.
Zwetsloot et al., "Vascular reactivity during migraine attacks: a transcranial Doppler study," Headache, Oct. 1991, 3 pages.
*Eli Lilly and Company v Teva Pharmaceauticals International GMBH*, "Declaration of Dr. Andrew Charles," Case No., IPR2018-01711, U.S. Pat. No. 9,884,907, Oct. 1, 2018, 114 pages.
*Eli Lilly and Company v Teva Pharmaceuticals International GMBH*,"Declaration of Andrew Charles, M.D.," Case No. IPR2018-01422, U.S. Pat. No. 9,340,614, Aug. 7, 2018, 93 pages .
*Eli Lilly and Company v Teva Pharmaceuticals International GMBH*, "Declaration of Andrew Charles, M.D.," Case No. IPR2018-01424, U.S. Pat. No. 9,346,881, Aug. 7, 2018, 99 pages.
*Eli Lilly and Company v Teva Pharmaceuticals International GMBH*, "Declaration of Andrew Charles, M.D.," Case No. IPR2018-01426, U.S. Pat. No. 9,890,211, Aug. 8, 2018, 100 pages.
*Eli Lilly and Company v Teva Pharmaceuticals International GMBH*,"Declaration of Andrew Charles, M.D.," Case No. IPR2018-01427, U.S. Pat. No. 8,597,649, Aug. 8, 2018, 94 pages.
*Eli Lilly and Company v Teva Pharmaceuticals International GMBH*, "Declaration of Andrew Charles, M.D.," IPR2018-01423, U.S. Pat. No. 9,266,951, Aug. 7, 2018, 98 pages.
*Eli Lilly and Company v Teva Pharmaceuticals International GMBH*, "Declaration of Andrew Charles, M.D.," IPR2018-01425, U.S. Pat. No. 9,890,210, Aug. 8, 2018, 93 pages.
*Eli Lilly and Company v Teva Pharmaceuticals International GMBH*, "Declaration of Andrew Charles, M.D.," IPR2018-01710, U.S. Pat. No. 8,586,045 on Sep. 27, 2018, 113 pages.
*Eli Lilly and Company v. Teva Pharmaceuticals International GMBH*, "Declaration of Dr. Andrew Charles," Case No. IPR2018-01712, U.S. Pat. No. 9,884,908, Oct. 1, 2018, 119 pages.

(56) References Cited

OTHER PUBLICATIONS

*Eli Lilly and Company* v *Teva Pharmaceauticals International GMBH*, "Declaration of Dr. Alain P. Vasserot, Ph.D.," Case No. IPR2018-01711, U.S. Pat. No. 9,884,907, Sep. 27, 2018, 78 pages.
*Eli Lilly and Company* v *Teva Pharmaceuticals International GMBD*, "Declaration of Alain P. Vasserot," Case No. IPR2018-01710, U.S. Pat. No. 8,586,045 on Sep. 9, 2019, 86 pages.
*Eli Lilly and Company* v *Teva Pharmaceuticals International GMBH*, "Declaration of Alain P. Vasserot," Case No. IPR2018-01423, U.S. Pat. No. 9,266,951, Aug. 2018, 80 pages.
*Eli Lilly and Company* v *Teva Pharmaceuticals International GMBH*, "Declaration of Alain P. Vasserot," Case No. IPR2018-01424, U.S. Pat. No. 9,346,881, Aug. 2018, 85 pages.
*Eli Lilly and Company* v *Teva Pharmaceuticals International GMBH*, "Declaration of Alain P. Vasserot," Case No. IPR2018-01425, U.S. Pat. No. 9,890,210, Aug. 2018, 75 pages.
*Eli Lilly and Company* v *Teva Pharmaceuticals International GMBH*, "Declaration of Alain P. Vasserot," Case No. IPR2018-01426, U.S. Pat. No. 9,890,211, Aug. 2018, 93 pages.
*Eli Lilly and Company* v *Teva Pharmaceuticals International GMBH*, "Declaration of AlainP. Vasserot," Case No. IPR2018-01427, U.S. Pat. No. 8,597,649, Aug. 2018, 88 pages.
*Eli Lilly and Company* v *Teva Pharmaceuticals International GMBH.*, "Declaration of Alain P. Vasserot," Case No. IPR2018-01422, U.S. Pat. No. 9,340,614, Aug. 2018, 78 pages.
*Eli Lilly and Company* v. *Teva Pharmaceuticals International GMBH*, "Declaration of Dr. Alain P. Vasserot," Case No. IPR2018-01712, U.S. Pat. No. 9,884,908, Sep. 27, 2018, 93 pages.
*Eli Lilly and Company* v *Teva Pharmaceauticals International GMBH*, "Petitioner's Exhibit List as of Oct. 1, 2018," Case No., IPR2018-01711, U.S. Pat. No. 9,884,907, Oct. 1, 2018, 20 pages.
*Eli Lilly and Company* v *Teva Pharmaceuticals International GMBH*, "Petitioner's Exhibit List as of Sep. 28, 2018," Case No. IPR2018-01710, U.S. Pat. No. 8,586,045 on Sep. 28, 2018, 21 pages.
*Eli Lilly and Company* v *Teva Pharmaceuticals International GMBH*, "Petitioner's Exhibit List as of Aug. 8, 2018," Case No. IPR2018-01422, U.S. Pat. No. 9,340,614, dated Aug. 8, 2018, 20 pages.
*Eli Lilly and Company* v *Teva Pharmaceuticals International GMBH*, "Petitioner's Exhibit List as of Aug. 8, 2018," Case No. IPR2018-01423, U.S. Pat. No. 9,266,951, dated Aug. 8, 2018, 18 pages.
*Eli Lilly and Company* v *Teva Pharmaceuticals International GMBH*,"Petitioner's Exhibit List as of Aug. 8, 2018," Case No. IPR2018-01424, U.S. Pat. No. 9,346,881, dated Aug. 8, 2018, 19 pages.
*Eli Lilly and Company* v *Teva Pharmaceuticals International GMBH*, "Petitioner's Exhibit List as of Aug. 8, 2018," Case No. IPR2018-01425, U.S. Pat. No. 9,890,210, dated Aug. 8, 2018, 20 pages.
*Eli Lilly and Company* v *Teva Pharmaceuticals International GMBH*, "Petitioner's Exhibit List as of Aug. 8, 2018," Case No. IPR2018-01426, U.S. Pat. No. 9,890,211, dated Aug. 8, 2018, 21 pages.
*Eli Lilly and Company* v *Teva Pharmaceuticals International GMBH*, "Petitioner's Exhibit List as of Aug. 8, 2018," Case No. IPR2018-01427, U.S. Pat. No. 8,597,649, dated Aug. 8, 2018, 19 pages.
*Eli Lilly and Company* v. *Teva Pharmaceuticals International GMBH*, "Petitioner's Exhibit List of Oct. 1, 2018," Case No., IPR2018-01712, U.S. Pat. No. 9,884,908, Oct. 1, 2018, 21 pages.
*Eli Lilly and Company* v *Teva Pharmaceuticals International GMBH*, "Petition for Inter Parte Review," Case No. IPR2018-01711, U.S. Pat. No. 9,884,907, filed Oct. 1, 2018, 74 pages.
*Eli Lilly and Company* v *Teva Pharmaceuticals International GMBH*, "Petition for Inter Partes Review," Case No. IPR2018-01422, U.S. Pat. No. 9,340,614, dated Aug. 8, 2018, 71 pages.
*Eli Lilly and Company* v *Teva Pharmaceuticals International GMBH*, "Petition for Inter Partes Review," Case No. IPR2018-01423, U.S. Pat. No. 9,266,951, dated Aug. 8, 2018, 76 pages.
*Eli Lilly and Company* v *Teva Pharmaceuticals International GMBH*, "Petition for Inter Partes Review," Case No. IPR2018-01424, U.S. Pat. No. 9,346,881, dated Aug. 8, 2018, 78 pages.
*Eli Lilly and Company* v *Teva Pharmaceuticals International GMBH*, "Petition for Inter Partes Review," Case No. IPR2018-01425, U.S. Pat. No. 9,890,210, dated Aug. 8, 2018, 67 pages.
*Eli Lilly and Company* v *Teva Pharmaceuticals International GMBH*, "Petition for Inter Partes Review," Case No. IPR2018-01426, U.S. Pat. No. 9,890,211, dated Aug. 8, 2018, 77 pages.
*Eli Lilly and Company* v *Teva Pharmaceuticals International GMBH*, "Petition for Inter Partes Review," Case No. IPR2018-01427, U.S. Pat. No. 8,597,649, dated Aug. 8, 2018, 76 pages.
*Eli Lilly and Company* v *Teva Pharmaceuticals International GMBH*, "Petition for Inter Partes Review," Case No. IPR2018-01710, U.S. Pat. No. 8,586,045 on Sep. 28, 2018, 79 pages.
*Eli Lilly and Company* v. *Teva Pharmaceuticals International GMBH*, "Petition for Inter Partes Review," Case No., IPR2018-01712, U.S. Pat. No. 9,884,908, Oct. 1, 2018, 79 pages.

\* cited by examiner

Figure 1

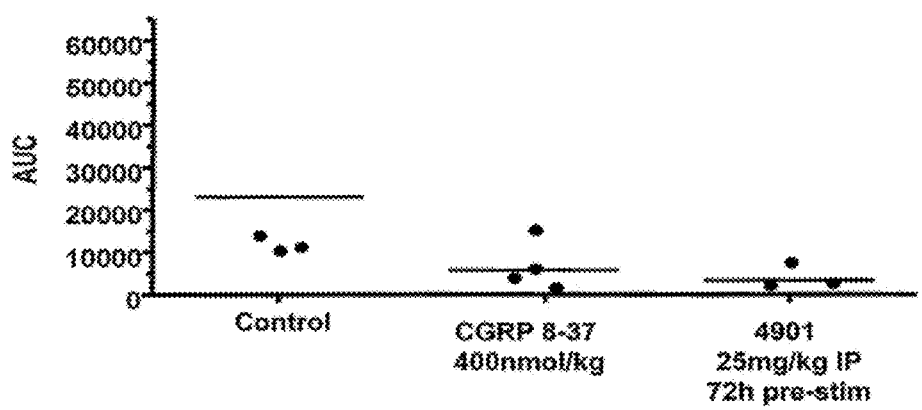

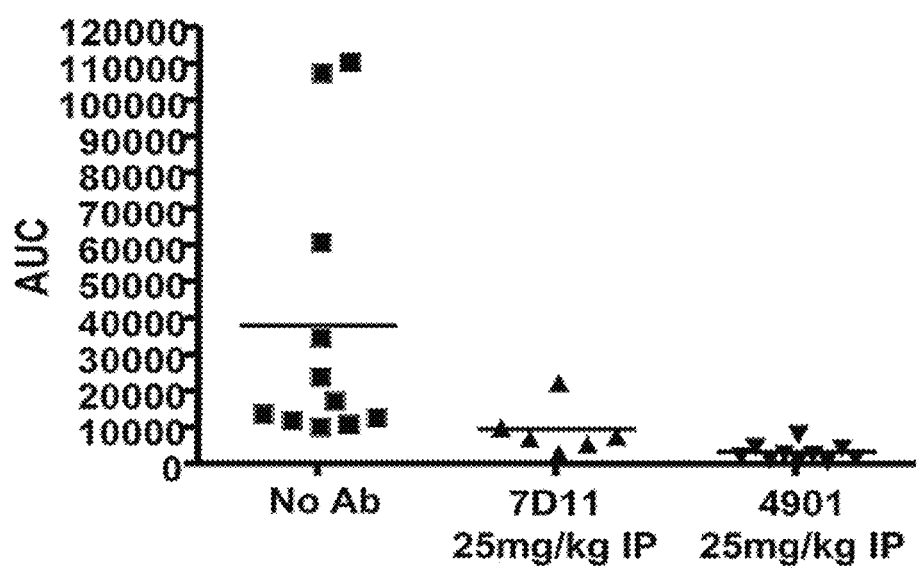

Figure 5

Bold=Kabat CDR
<u>Underline=Chothia CDR</u>

G1 Heavy chain

```
1       5        10        15        20        25    H1  30
E V Q L V E S S G G G L V Q P G G S L R L S C A A S G F T F S 31      35        40        45        50    H2    55        60
N Y W I S W V R Q A P G K G L E W V A R I R S K S D A S A T 61      65        70        75        80        85        90
H Y A E A V K G R F T I S R D N A K N S L Y L Q M N S L R A 91      95       100   H3   105       110       115       120
E D T A V Y Y C L A Y F D Y G L A I Q N Y W G Q G T L V T V 121 122
S S
```

G1 Light chain

```
1       5        10        15        20        25    L1  30
E I V L T Q S P A T L S L S P G E R A T L S C K A S K R V T 31      35        40        45    L2    50        55        60
T Y V S W Y Q Q K P G Q A P R L L I Y G A S N R Y L G I P A 61      65        70        75        80        85        90
R F S G S G S G T D F T L T I S S L E P E D F A V Y Y C S Q

91  L3  95       100       105  107
S Y N Y P Y T F G Q G T K L E I K
```

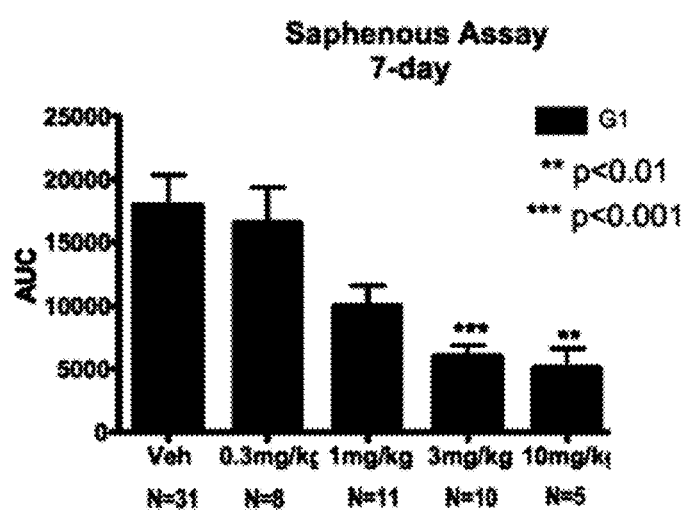

SEQUENCE LISTING

<160> NUMBER OF SEQ ID NOS: 79

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Thr Phe Ser Asn Tyr Trp Ile Ser
1               5                   10

<210> SEQ ID NO 4
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 4

Glu Ile Arg Ser Glu Ser Asp Ala Ser Ala Thr His Tyr Ala Glu Ala
1               5                   10                  15

Val Lys Gly

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Phe Asp Tyr Gly Leu Ala Ile Gln Asn Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Lys Arg Val Thr Thr Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ala Ser Asn Arg Tyr Leu
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gln Ser Tyr Asn Tyr Pro Tyr Thr
1               5

<210> SEQ ID NO 9
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaagttcagc tggttgaatc cggtggtggt ctggttcagc caggtggttc cctgcgtctg      60
```

```
tcctgcgctg cttccggttt caccttctcc aactactgga tctcctgggt tcgtcaggct      120
cctggtaaag gtctggaatg ggttgctgaa atccgttccg aatccgacgc gtccgctacc      180
cattacgctg aagctgttaa aggtcgtttc accatctccc gtgacaacgc taagaactcc      240
ctgtacctgc agatgaactc cctgcgtgct gaagacaccg ctgtttacta ctgcctggct      300
tactttgact acggtctggc tatccagaac tactggggtc agggtaccct ggttaccgtt      360
tcctcc                                                                 366

<210> SEQ ID NO 10
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gaaatcgttc tgacccagtc cccggctacc ctgtccctgt ccccaggtga acgtgctacc       60
ctgtcctgca aagcttccaa acgggttacc acctacgttt cctggtacca gcagaaaccc      120
ggtcaggctc ctcgtctgct gatctacggt gcttccaacc gttacctcgg tatcccagct      180
cgtttctccg gttccggttc cggtaccgac ttcaccctga ccatctcctc cctggaaccc      240
gaagacttcg ctgtttacta ctgcagtcag tcctacaact accctacac cttcggtcag      300 ggtaccaaac tggaaatcaa a                                                321

<210> SEQ ID NO 11
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Phe Arg Val Val
            290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
            35                  40                  45

Tyr Gly Ala Ser Asn Arg Tyr Leu Gly Ile Pro Ala Arg Phe Ser Gly
            50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr

```
            85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210
```

<210> SEQ ID NO 13
<211> LENGTH: 1347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
gaagttcagc tggttgaatc cggtggtggt ctggttcagc caggtggttc cctgcgtctg     60
tcctgcgctg cttccggttt caccttctcc aactactgga tctcctgggt tcgtcaggct    120
cctggtaaag gtctggaatg gttgctgaa atccgttccg aatccgacgc gtccgctacc    180
cattacgctg aagctgttaa aggtcgtttc accatctccc gtgacaacgc taagaactcc    240
ctgtacctgc agatgaactc cctgcgtgct gaagacaccg ctgtttacta ctgcctggct    300
tactttgact acggtctggc tatccagaac tactggggtc agggtaccct ggttaccgtt    360
tcctccgcct ccaccaaggg cccatctgtc ttccccactgg ccccatgctc cgcagcacc     420 tccgagagca cagccgccct gggctgcctg gtcaaggact acttcccaga acctgtgacc    480
gtgtcctgga actctggcgc tctgaccagc ggcgtgcaca ccttcccagc tgtcctgcag    540
tcctcaggtc tctactccct cagcagcgtg gtgaccgtgc catccagcaa cttcggcacc    600
cagacctaca cctgcaacgt agatcacaag ccaagcaaca ccaaggtcga caagaccgtg    660
gagagaaagt gttgtgtgga gtgtccacct tgtccagccc ctccagtggc cggaccatcc    720
gtgttcctgt tccctccaaa gccaaaggac accctgatga tctccagaac cccagaggtg    780
acctgtgtgg tggtggacgt gtcccacgag gacccagagg tgcagttcaa ctggtatgtg    840
gacggagtgg aggtgcacaa cgccaagacc aagccaagag aggagcagtt caactccacc    900
ttcagagtgg tgagcgtgct gaccgtggtg caccaggact ggctgaacgg aaaggagtat    960
aagtgtaagg tgtccaacaa gggactgcca tccagcatcg agaagaccat ctccaagacc   1020
aagggacagc caagagagcc acaggtgtat accctgcccc catccagaga ggagatgacc   1080
aagaaccagg tgtccctgac ctgtctggtg aagggattct atccatccga catcgccgtg   1140
gagtgggagt ccaacggaca gccagagaac aactataaga ccaccctcc aatgctggac   1200 tccgacggat ccttcttcct gtattccaag ctgaccgtgg acaagtccag atggcagcag   1260
```

```
ggaaacgtgt tctcttgttc cgtgatgcac gaggccctgc acaaccacta tacccagaag    1320
agcctgtccc tgtctccagg aaagtaa                                        1347
```

<210> SEQ ID NO 14
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gaaatcgttc tgacccagtc cccggctacc ctgtccctgt ccccaggtga acgtgctacc     60
ctgtcctgca aagcttccaa cgggttacc acctacgttt cctggtacca gcagaaaccc    120
ggtcaggctc ctcgtctgct gatctacggt gcttccaacc gttacctcgg tatcccagct    180
cgtttctccg gttccggttc cggtaccgac ttcaccctga ccatctcctc cctggaaccc    240
gaagacttcg ctgtttacta ctgcagtcag tcctacaact accccctacac cttcggtcag    300 ggtaccaaac tggaaatcaa acgcactgtg gctgcaccat ctgtcttcat cttccctcca    360
tctgatgagc agttgaaatc cggaactgcc tctgttgtgt gcctgctgaa taacttctat    420
ccgcgcgagg ccaaagtaca gtggaaggtg ataacgccc tccaatccgg taactcccag    480
gagagtgtca cagagcagga cagcaaggac agcacctaca gcctcagcag caccctgacc    540
ctgagcaaag cagactacga aaacacaaa gtctacgcct gcgaagtcac ccatcagggc    600
ctgagttctc cagtcacaaa gagcttcaac cgcggtgagt gctaa                    645
```

<210> SEQ ID NO 15
<211> LENGTH: 37
<212> TYPE: PRT
<213> ORGANISM: Homo sapiens
<220> FEATURE:
<223> OTHER INFORMATION: C-term amidated

<400> SEQUENCE: 15

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35
```

<210> SEQ ID NO 16
<211> LENGTH: 30
<212> TYPE: PRT
<213> ORGANISM: Homo sapiens
<220> FEATURE:
<223> OTHER INFORMATION: C-term amidated

<400> SEQUENCE: 16

```
Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30
```

<210> SEQ ID NO 17
<211> LENGTH: 19
<212> TYPE: PRT
<213> ORGANISM: Homo sapiens
<220> FEATURE:
<223> OTHER INFORMATION: C-term amidated

<400> SEQUENCE: 17

Ser Gly Gly Val Val Lys Asn Asn Phe Val Pro Thr Asn Val Gly Ser
1               5                   10                  15

Lys Ala Phe

<210> SEQ ID NO 18
<211> LENGTH: 19
<212> TYPE: PRT
<213> ORGANISM: Homo sapiens
<220> FEATURE:
<223> OTHER INFORMATION: C-term amidated

<400> SEQUENCE: 18

Ser Gly Gly Val Val Lys Asn Asn Phe Val Ala Thr Asn Val Gly Ser
1               5                   10                  15

Lys Ala Phe

<210> SEQ ID NO 19
<211> LENGTH: 19
<212> TYPE: PRT
<213> ORGANISM: Homo sapiens
<220> FEATURE:
<223> OTHER INFORMATION: C-term amidated

<400> SEQUENCE: 19

Ser Gly Gly Val Val Lys Asn Asn Phe Val Pro Thr Asn Val Gly Ser
1               5                   10                  15

Ala Ala Phe

<210> SEQ ID NO 20
<211> LENGTH: 19
<212> TYPE: PRT
<213> ORGANISM: Homo sapiens
<220> FEATURE:
<223> OTHER INFORMATION: C-term amidated

<400> SEQUENCE: 20

Ser Gly Gly Val Val Lys Asn Asn Phe Val Pro Thr Asn Val Gly Ser
1               5                   10                  15

Glu Ala Phe

<210> SEQ ID NO 21
<211> LENGTH: 19
<212> TYPE: PRT
<213> ORGANISM: Homo sapiens
<220> FEATURE:
<223> OTHER INFORMATION: C-term amidated

<400> SEQUENCE: 21

Ser Gly Gly Val Val Lys Asn Asn Phe Val Pro Thr Asn Val Gly Ser
1               5                   10                  15

Met Ala Phe

<210> SEQ ID NO 22
<211> LENGTH: 19
<212> TYPE: PRT
<213> ORGANISM: Homo sapiens
<220> FEATURE:
<223> OTHER INFORMATION: C-term amidated

<400> SEQUENCE: 22

Ser Gly Gly Val Val Lys Asn Asn Phe Val Pro Thr Asn Val Gly Ser

```
1               5                   10                  15

Gln Ala Phe

<210> SEQ ID NO 23
<211> LENGTH: 19
<212> TYPE: PRT
<213> ORGANISM: Homo sapiens
<220> FEATURE:
<223> OTHER INFORMATION: C-term amidated

<400> SEQUENCE: 23

Ser Gly Gly Val Val Lys Asn Asn Phe Val Pro Thr Asn Val Gly Ser
1               5                   10                  15

Lys Ala Ala

<210> SEQ ID NO 24
<211> LENGTH: 14
<212> TYPE: PRT
<213> ORGANISM: Homo sapiens
<220> FEATURE:
<223> OTHER INFORMATION: C-term amidated

<400> SEQUENCE: 24

Asn Asn Phe Val Pro Thr Asn Val Gly Ser Lys Ala Phe Ala
1               5                   10

<210> SEQ ID NO 25
<211> LENGTH: 13
<212> TYPE: PRT
<213> ORGANISM: Homo sapiens
<220> FEATURE:
<223> OTHER INFORMATION: C-term amidated

<400> SEQUENCE: 25

Asn Asn Phe Val Pro Thr Asn Val Gly Ser Lys Ala Phe
1               5                   10

<210> SEQ ID NO 26
<211> LENGTH: 13
<212> TYPE: PRT
<213> ORGANISM: Homo sapiens
<220> FEATURE:
<223> OTHER INFORMATION: C-term amidated

<400> SEQUENCE: 26

Asn Asn Ala Val Pro Thr Asn Val Gly Ser Lys Ala Phe
1               5                   10

<210> SEQ ID NO 27
<211> LENGTH: 13
<212> TYPE: PRT
<213> ORGANISM: Homo sapiens
<220> FEATURE:
<223> OTHER INFORMATION: C-term amidated

<400> SEQUENCE: 27

Asn Asn Phe Ala Pro Thr Asn Val Gly Ser Lys Ala Phe
1               5                   10

<210> SEQ ID NO 28
<211> LENGTH: 13
<212> TYPE: PRT
<213> ORGANISM: Homo sapiens
<220> FEATURE:
<223> OTHER INFORMATION: C-term amidated
```

```
<400> SEQUENCE: 28

Asn Asn Phe Val Ala Thr Asn Val Gly Ser Lys Ala Phe
1               5                   10

<210> SEQ ID NO 29
<211> LENGTH: 13
<212> TYPE: PRT
<213> ORGANISM: Homo sapiens
<220> FEATURE:
<223> OTHER INFORMATION: C-term amidated

<400> SEQUENCE: 29

Asn Asn Phe Val Pro Ala Asn Val Gly Ser Lys Ala Phe
1               5                   10

<210> SEQ ID NO 30
<211> LENGTH: 13
<212> TYPE: PRT
<213> ORGANISM: Homo sapiens
<220> FEATURE:
<223> OTHER INFORMATION: C-term amidated

<400> SEQUENCE: 30

Asn Asn Phe Val Pro Thr Ala Val Gly Ser Lys Ala Phe
1               5                   10

<210> SEQ ID NO 31
<211> LENGTH: 13
<212> TYPE: PRT
<213> ORGANISM: Homo sapiens
<220> FEATURE:
<223> OTHER INFORMATION: C-term amidated

<400> SEQUENCE: 31

Asn Asn Phe Val Pro Thr Asn Ala Gly Ser Lys Ala Phe
1               5                   10

<210> SEQ ID NO 32
<211> LENGTH: 13
<212> TYPE: PRT
<213> ORGANISM: Homo sapiens
<220> FEATURE:
<223> OTHER INFORMATION: C-term amidated

<400> SEQUENCE: 32

Asn Asn Phe Val Pro Thr Asn Val Ala Ser Lys Ala Phe
1               5                   10

<210> SEQ ID NO 33
<211> LENGTH: 13
<212> TYPE: PRT
<213> ORGANISM: Homo sapiens
<220> FEATURE:
<223> OTHER INFORMATION: C-term amidated

<400> SEQUENCE: 33

Asn Asn Phe Val Pro Thr Asn Val Gly Ala Lys Ala Phe
1               5                   10

<210> SEQ ID NO 34
<211> LENGTH: 13
<212> TYPE: PRT
<213> ORGANISM: Homo sapiens
<220> FEATURE:
<223> OTHER INFORMATION: C-term amidated

<400> SEQUENCE: 34
```

```
Asn Asn Phe Val Pro Thr Asn Val Gly Ser Lys Ala Ala
1               5                   10
```

<210> SEQ ID NO 35
<211> LENGTH: 12
<212> TYPE: PRT
<213> ORGANISM: Homo sapiens
<220> FEATURE:
<223> OTHER INFORMATION: C-term amidated

<400> SEQUENCE: 35

```
Asn Phe Val Pro Thr Asn Val Gly Ser Lys Ala Phe
1               5                   10
```

<210> SEQ ID NO 36
<211> LENGTH: 19
<212> TYPE: PRT
<213> ORGANISM: Homo sapiens

<400> SEQUENCE: 36

```
Ser Gly Gly Val Val Lys Asn Asn Phe Val Pro Thr Asn Val Gly Ser
1               5                   10                  15

Lys Ala Phe
```

<210> SEQ ID NO 37
<211> LENGTH: 18
<212> TYPE: PRT
<213> ORGANISM: Homo sapiens

<400> SEQUENCE: 37

```
Ser Gly Gly Val Val Lys Asn Asn Phe Val Pro Thr Asn Val Gly Ser
1               5                   10                  15

Lys Ala
```

<210> SEQ ID NO 38
<211> LENGTH: 36
<212> TYPE: PRT
<213> ORGANISM: Homo sapiens

<400> SEQUENCE: 38

```
Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala
        35
```

<210> SEQ ID NO 39
<211> LENGTH: 19
<212> TYPE: PRT
<213> ORGANISM: Homo sapiens

<400> SEQUENCE: 39

```
Ala Cys Asp Thr Ala Thr Cys Val Thr His Arg Leu Ala Gly Leu Leu
1               5                   10                  15

Ser Arg Ser
```

<210> SEQ ID NO 40
<211> LENGTH: 13
<212> TYPE: PRT
<213> ORGANISM: Homo sapiens

```
<400> SEQUENCE: 40

Ala Cys Asp Thr Ala Thr Cys Val Thr His Arg Leu Ala
1               5                   10

<210> SEQ ID NO 41
<211> LENGTH: 37
<212> TYPE: PRT
<213> ORGANISM: Rattus sp.
<220> FEATURE:
<223> OTHER INFORMATION: C-term amidated

<400> SEQUENCE: 41

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Glu Ala Phe
            35

<210> SEQ ID NO 42
<211> LENGTH: 19
<212> TYPE: PRT
<213> ORGANISM: Rattus sp.
<220> FEATURE:
<223> OTHER INFORMATION: C-term amidated

<400> SEQUENCE: 42

Ser Gly Gly Val Val Lys Asp Asn Phe Val Pro Thr Asn Val Gly Ser
1               5                   10                  15

Glu Ala Phe

<210> SEQ ID NO 43
<211> LENGTH: 37
<212> TYPE: PRT
<213> ORGANISM: Homo sapiens
<220> FEATURE:
<223> OTHER INFORMATION: C-term amidated

<400> SEQUENCE: 43

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
            35

<210> SEQ ID NO 44
<211> LENGTH: 37
<212> TYPE: PRT
<213> ORGANISM: Rattus sp.
<220> FEATURE:
<223> OTHER INFORMATION: C-term amidated

<400> SEQUENCE: 44

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Lys Ala Phe
            35

<210> SEQ ID NO 45
```

```
<211> LENGTH: 32
<212> TYPE: PRT
<213> ORGANISM: Homo sapiens
<220> FEATURE:
<223> OTHER INFORMATION: C-term amidated

<400> SEQUENCE: 45

Cys Gly Asn Leu Ser Thr Cys Met Leu Gly Thr Tyr Thr Gln Asp Phe
 1               5                  10                  15

Asn Lys Phe His Thr Phe Pro Gln Thr Ala Ile Gly Val Gly Ala Pro
             20                  25                  30

<210> SEQ ID NO 46
<211> LENGTH: 37
<212> TYPE: PRT
<213> ORGANISM: Homo sapiens
<220> FEATURE:
<223> OTHER INFORMATION: C-term amidated

<400> SEQUENCE: 46

Lys Cys Asn Thr Ala Thr Cys Ala Thr Gln Arg Leu Ala Asn Phe Leu
 1               5                  10                  15

Val His Ser Ser Asn Asn Phe Gly Ala Ile Leu Ser Ser Thr Asn Val
             20                  25                  30

Gly Ser Asn Thr Tyr
         35

<210> SEQ ID NO 47
<211> LENGTH: 52
<212> TYPE: PRT
<213> ORGANISM: Homo sapiens
<220> FEATURE:
<223> OTHER INFORMATION: C-term amidated

<400> SEQUENCE: 47

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
             20                  25                  30

Phe Thr Asp Lys Asp Lys Asp Asn Val Ala Pro Arg Ser Lys Ile Ser
         35                  40                  45

Pro Gln Gly Tyr
     50

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Leu Leu Gly
 1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49
```

Glu Leu Leu Gly
1

<210> SEQ ID NO 50
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Pro Val Ala
1

<210> SEQ ID NO 51
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Glu Leu Leu
1

<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Phe Leu Gly
1

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Arg, Trp, Gly, Leu or Asn
<220> FEATURE:
<221> NAME/KEY: MOD_RES
<222> LOCATION: (7)..(7)
<223> OTHER INFORMATION: Thr, Ala, Asp, Gly, Arg, Ser, Trp or Val

<400> SEQUENCE: 53

Lys Ala Ser Lys Xaa Val Xaa Thr Tyr Val Ser
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Gly or Ala
<220> FEATURE:
<221> NAME/KEY: MOD_RES
<222> LOCATION: (2)..(2)
<223> OTHER INFORMATION: Ala or His
<220> FEATURE:
<221> NAME/KEY: MOD_RES
<222> LOCATION: (7)..(7)
<223> OTHER INFORMATION: Leu, Thr, Ile or Ser

<400> SEQUENCE: 54

Xaa Xaa Ser Asn Arg Tyr Xaa
1               5

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Glu, Arg, Lys, Gln or Asn
<220> FEATURE:
<221> NAME/KEY: MOD_RES
<222> LOCATION: (8)..(8)
<223> OTHER INFORMATION: Ala, Gly, Asn, Glu, His, Ser, Leu, Arg, Cys,
      Phe, Tyr, Val, Asp or Pro
<220> FEATURE:
<221> NAME/KEY: MOD_RES
<222> LOCATION: (9)..(9)
<223> OTHER INFORMATION: Ser, Gly, Thr, Tyr, Cys, Glu, Leu, Ala, Pro,
      Ile, Asn, Arg, Val, Asp or Met
<220> FEATURE:
<221> NAME/KEY: MOD_RES
<222> LOCATION: (12)..(12)
<223> OTHER INFORMATION: His or Phe
<220> FEATURE:
<221> NAME/KEY: MOD_RES
<222> LOCATION: (15)..(15)
<223> OTHER INFORMATION: Glu or Asp

<400> SEQUENCE: 55

Glu Ile Arg Ser Xaa Ser Asp Xaa Xaa Ala Thr Xaa Tyr Ala Xaa Ala
1               5                   10                  15

Val Lys Gly

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 56

His His His His His His
1               5

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Gly Ser Gly Gly Gly Gly Ser Gly Gly Gly Gly Ser
```

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys
            100                 105
```

<210> SEQ ID NO 59
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Asp Thr Arg Tyr Ile Gln Lys Phe
    50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser
        115
```

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Glu Tyr His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asp Ala Leu Pro Pro
                85                  90                  95

Thr Phe Gly Gln Gly Thr Lys Leu Glu Ile Lys
            100                 105

<210> SEQ ID NO 61
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
50                  55                  60

Ala Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Ser Tyr Trp Gly Gln Gly
            100                 105                 110

Thr Leu Val Thr Val Ser Ser
        115

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Asp Ile Ser Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asp Ala Leu Pro Pro
                 85                  90                  95

Thr Phe Gly Gly Gly Thr Lys Val Glu Ile Lys
            100                 105
```

<210> SEQ ID NO 63
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Gln Val Gln Leu Val Gln Ser Gly Ala Glu Val Lys Lys Pro Gly Ser
 1               5                  10                  15

Ser Val Lys Val Ser Cys Lys Ala Ser Gly Tyr Thr Phe Gly Asn Tyr
             20                  25                  30

Trp Met Gln Trp Val Arg Gln Ala Pro Gly Gln Gly Leu Glu Trp Met
         35                  40                  45

Gly Ala Ile Tyr Glu Gly Thr Gly Lys Thr Val Tyr Ile Gln Lys Phe
     50                  55                  60

Ala Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Asp Tyr Val Ser Gly Phe Gly Tyr Trp Gly Gln Gly
            100                 105                 110

Thr Thr Val Thr Val Ser Ser
        115
```

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Arg Pro Ile Asp Lys Tyr
             20                  25                  30

Leu Asn Trp Tyr Gln Gln Lys Pro Gly Lys Ala Pro Lys Leu Leu Ile
         35                  40                  45

Tyr Tyr Thr Ser Glu Tyr His Ser Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asp Ala Leu Pro Pro
                 85                  90                  95

Thr Phe Gly Gln Gly Thr Lys Leu Glu Ile Lys
            100                 105
```

<210> SEQ ID NO 65

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Leu Val Thr Val Ser Ser
        115

<210> SEQ ID NO 66
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asp Lys Tyr
            20                  25                  30

Leu Asn Trp Tyr Gln Gln Lys Pro Gly Lys Ala Pro Lys Leu Leu Ile
        35                  40                  45

Tyr Tyr Thr Ser Gly Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Ala Leu Pro Pro
                85                  90                  95

Thr Phe Gly Gly Gly Thr Lys Val Glu Ile Lys
            100                 105

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Gln Ser Gly Ala Glu Val Lys Lys Pro Gly Ser
1               5                   10                  15
```

Ser Val Lys Val Ser Cys Lys Ala Ser Gly Tyr Thr Phe Gly Asn Tyr
            20                  25                  30

Trp Met Gln Trp Val Arg Gln Ala Pro Gly Gln Gly Leu Glu Trp Met
        35                  40                  45

Gly Ala Ile Tyr Glu Gly Thr Gly Lys Thr Val Tyr Ile Gln Lys Phe
    50                  55                  60

Ala Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Asp Tyr Val Ser Gly Phe Gly Tyr Trp Gly Gln Gly
            100                 105                 110

Thr Thr Val Thr Val Ser Ser
            115

<210> SEQ ID NO 68
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Thr Lys Val Glu Ile Lys
            100                 105                 110

Arg

<210> SEQ ID NO 69
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu

```
                65                  70                  75                  80
Gln Met Asn Ser Leu Arg Ala Glu Asp Thr Ala Val Tyr Phe Cys Ala
                    85                  90                  95

Arg Gly Asp Ile Trp Gly Gln Gly Thr Leu Val Thr Val Ser Ser
                100                 105                 110

<210> SEQ ID NO 70
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
                20                  25                  30

Tyr Leu Ala Trp Tyr Gln Gln Lys Pro Gly Lys Val Pro Lys Gln Leu
            35                  40                  45

Ile Tyr Ser Thr Ser Thr Leu Ala Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
                100                 105                 110

Arg

<210> SEQ ID NO 71
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
                20                  25                  30

Tyr Met Gln Trp Val Arg Gln Ala Pro Gly Lys Gly Leu Glu Trp Val
            35                  40                  45

Gly Val Ile Gly Ile Asn Asp Asn Thr Tyr Tyr Ala Ser Trp Ala Lys
        50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
                100                 105                 110

<210> SEQ ID NO 72
<211> LENGTH: 113
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 72

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr Asp Asn Asn
            20                  25                  30

Tyr Leu Ala Trp Tyr Gln Gln Lys Pro Gly Lys Val Pro Lys Gln Leu
        35                  40                  45

Ile Tyr Ser Thr Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Ser
                85                  90                  95

Ser Gly Asp Cys Phe Val Phe Gly Gly Gly Thr Lys Val Glu Ile Lys
            100                 105                 110

Arg

<210> SEQ ID NO 73
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Val Ser Gly Leu Asp Leu Ser Ser Tyr
            20                  25                  30

Tyr Met Gln Trp Val Arg Gln Ala Pro Gly Lys Gly Leu Glu Trp Val
        35                  40                  45

Gly Val Ile Gly Ile Asn Asp Asn Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 74
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Leu Thr Gln Thr Pro Ser Val Ser Ala Ala Val Gly Ser
1               5                   10                  15

Thr Val Thr Ile Asn Cys Gln Ala Ser Gln Ser Val Tyr His Asn Thr
            20                  25                  30

Tyr Leu Ala Trp Tyr Gln Gln Lys Pro Gly Gln Pro Pro Lys Gln Leu
```

```
            35                  40                  45

Ile Tyr Asp Ala Ser Thr Leu Ala Ser Gly Val Pro Ser Arg Phe Ser
     50                   55                  60

Gly Ser Gly Ser Gly Thr Gln Phe Thr Leu Thr Ile Ser Gly Val Gln
65                   70                  75                  80

Cys Asn Asp Ala Ala Ala Tyr Tyr Cys Leu Gly Ser Tyr Asp Cys Thr
                 85                  90                  95

Asn Gly Asp Cys Phe Val Phe Gly Gly Gly Thr Glu Val Val Val Lys
            100                 105                 110

Arg

<210> SEQ ID NO 75
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Ser Leu Glu Glu Ser Gly Gly Arg Leu Val Thr Pro Gly Thr Pro
1               5                   10                  15

Leu Thr Leu Thr Cys Ser Val Ser Gly Ile Asp Leu Ser Gly Tyr Tyr
            20                  25                  30

Met Asn Trp Val Arg Gln Ala Pro Gly Lys Gly Leu Glu Trp Ile Gly
        35                  40                  45

Val Ile Gly Ile Asn Gly Ala Thr Tyr Tyr Ala Ser Trp Ala Lys Gly
    50                  55                  60

Arg Phe Thr Ile Ser Lys Thr Ser Ser Thr Val Asp Leu Lys Met
65                  70                  75                  80

Thr Ser Leu Thr Thr Glu Asp Thr Ala Thr Tyr Phe Cys Ala Arg Gly
                85                  90                  95

Asp Ile Trp Gly Pro Gly Thr Leu Val Thr Val Ser Ser
            100                 105

<210> SEQ ID NO 76
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Leu Thr Gln Ser Pro Ser Ser Leu Ser Ala Ser Val Gly Asp
1               5                   10                  15

Arg Val Thr Ile Asn Cys Gln Ala Ser Gln Ser Val Tyr His Asn Thr
            20                  25                  30

Tyr Leu Ala Trp Tyr Gln Gln Lys Pro Gly Lys Val Pro Lys Gln Leu
        35                  40                  45

Ile Tyr Asp Ala Ser Thr Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Val Ala Thr Tyr Tyr Cys Leu Gly Ser Tyr Asp Cys Thr
                85                  90                  95

Asn Gly Asp Cys Phe Val Phe Gly Gly Gly Thr Lys Val Glu Ile Lys
            100                 105                 110
```

Arg

<210> SEQ ID NO 77
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Leu Ser Gly Tyr
            20                  25                  30

Tyr Met Asn Trp Val Arg Gln Ala Pro Gly Lys Gly Leu Glu Trp Val
        35                  40                  45

Gly Val Ile Gly Ile Asn Gly Ala Thr Tyr Tyr Ala Ser Trp Ala Lys
    50                  55                  60

Gly Arg Phe Thr Ile Ser Arg Asp Asn Ser Lys Thr Thr Val Tyr Leu
65                  70                  75                  80

Gln Met Asn Ser Leu Arg Ala Glu Asp Thr Ala Val Tyr Phe Cys Ala
                85                  90                  95

Arg Gly Asp Ile Trp Gly Gln Gly Thr Leu Val Thr Val Ser Ser
            100                 105                 110

<210> SEQ ID NO 78
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Thr Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Ser Ala Val Val Phe Gly Gly Gly Thr Lys Leu Thr Val Leu
            100                 105                 110

<210> SEQ ID NO 79
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Glu Ser Gly Gly Gly Val Val Gln Pro Gly Arg

```
1               5                   10                  15
Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Ser Phe Asp Gly Ser Ile Lys Tyr Ser Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
            85                  90                  95

Ala Arg Asp Arg Leu Asn Tyr Tyr Asp Ser Ser Gly Tyr Tyr His Tyr
            100                 105                 110

Lys Tyr Tyr Gly Met Ala Val Trp Gly Gln Gly Thr Thr Val Thr Val
            115                 120                 125

Ser Ser
    130
```

TREATING HEADACHE COMPRISING ADMINISTERING AN ANTIBODY TO CALCITONIN GENE-RELATED PEPTIDE

CROSS REFERENCE TO RELATED APPLICATIONS

This application is a continuation application of U.S. patent application Ser. No. 14/664,715, filed on Mar. 20, 2015, which claims priority to U.S. Provisional Patent Application No. 61/968,897, filed Mar. 21, 2014, U.S. Provisional Patent Application No. 62/083,809, filed Nov. 24, 2014 and U.S. Provisional Patent Application No. 62/119,778 filed Feb. 23, 2015, which applications are incorporated herein by reference in their entireties for all purposes.

REFERENCE TO SEQUENCE LISTING

The instant application contains a Sequence Listing which has been submitted in ASCII format via EFS-Web and is hereby incorporated by reference in its entirety. The sequence listing contains no new matter. Said ASCII copy, created on Sep. 21, 2018, is named 43612_0006003_Seq_List.txt and is 50 Kilobytes in size.

BACKGROUND

CGRP (calcitonin gene-related peptide) is a 37 amino acid neuropeptide, which belongs to a family of peptides that includes calcitonin, adrenomedullin and amylin. In humans, two forms of CGRP ($\alpha$-CGRP and $\beta$-CGRP) exist and have similar activities. They vary by three amino acids and exhibit differential distribution. At least two CGRP receptor subtypes may also account for differential activities. CGRP is a neurotransmitter in the central nervous system, and has been shown to be a potent vasodilator in the periphery, where CGRP-containing neurons are closely associated with blood vessels. CGRP-mediated vasodilatation is also associated with neurogenic inflammation, as part of a cascade of events that results in extravasation of plasma and vasodilation of the microvasculature and is present in migraine.

CGRP has been noted for its possible connection to vasomotor symptoms (Wyon et al. Scand. J. Urol. Nephrol. 35: 92-96 (2001); Wyon et al. Menopause 7(1):25-30 (2000)). Vasomotor symptoms (VMS), such as hot flushes and night sweats, are the most common symptoms associated with menopause, occurring in 60% to 80% of all women following natural or surgically-induced menopause. Hot flushes are likely to be an adaptive response of the central nervous system (CNS) to declining sex steroids (Freedman Am. J. Human Biol. 13:453-464 (2001)). To date, the most effective therapies for flushes are hormone-based treatments, including estrogens and/or some progestins. Hormonal treatments can be effective for alleviating flushes, but are not appropriate for all women. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., 3.sup.rd Int'l Symposium on Recent Advances in Urological Cancer Diagnosis and Treatment-Proceedings, Paris, France: SCI: 3-7 (1992)).

Men also experience hot flushes following steroid hormone (androgen) withdrawal. This is true in cases of age-associated androgen decline (Katovich, et al., Proceedings of the Society for Experimental Biology & Medicine, 1990, 193(2): 129-35) as well as in extreme cases of hormone deprivation associated with treatments for prostate cancer (Berendsen, et al., European Journal of Pharmacology, 2001, 419(1): 47-54). As many as one-third of these patients will experience persistent and frequent symptoms severe enough to cause significant discomfort and inconvenience.

CGRP is a potent vasodilator that has been implicated in the pathology of other vasomotor symptoms, such as forms of vascular headache, including migraines (with or without aura) and cluster headache. Durham, N. Engl. J. Med. 350:1073-1075, 2004. The serum levels of CGRP in the external jugular vein are elevated in patients during migraine headache. Goadsby et al., Ann. Neurol. 28:183-7, 1990. Intravenous administration of human $\alpha$-CGRP induced headache and migraine in patients suffering from migraine without aura, suggesting that CGRP has a causative role in migraine. Lassen et al., Cephalalgia 22:54-61, 2002.

Possible CGRP involvement in migraine has been the basis for the development and testing of a number of compounds that inhibit release of CGRP (e.g., sumatriptan), antagonize at the CGRP receptor (e.g., dipeptide derivative BIBN4096BS (Boerhringer Ingelheim); CGRP(8-37)), or interact with one or more of receptor-associated proteins, such as, receptor activity membrane protein (RAMP) or receptor component protein (RCP), both of which affect binding of CGRP to its receptors. Brain, S. et al., Trends in Pharmacological Sciences 23:51-53, 2002. Alpha-2 adrenoceptor subtypes and adenosine A1 receptors also control (inhibit) CGRP release and trigeminal activation (Goadsby et al., Brain 125:1392-401, 2002). The adenosine A1 receptor agonist GR79236 (metrafadil), which has been shown to inhibit neurogenic vasodilation and trigeminal nociception in humans, may also have anti-migraine activity (Arulmani et al., Cephalalgia 25:1082-1090, 2005; Giffin et al., Cephalalgia 23:287-292, 2003.)

Confounding this theory is the observation that treatment with compounds that exclusively inhibit neurogenic inflammation (e.g., tachykinin NK1 receptor antagonists) or trigeminal activation (e.g., $5HT_{1D}$ receptor agonists) have been shown to be relatively ineffective as acute treatments for migraine, leading some investigators to question whether inhibiting release of CGRP is the primary mechanism of action of effective anti-migraine treatments. Arulmani et al., Eur. J. Pharmacol. 500:315-330, 2004.

Migraine is a complex, common neurological condition that is characterized by severe, episodic attacks of headache and associated features, which may include nausea, vomiting, sensitivity to light, sound or movement. In some patients, the headache is preceded or accompanied by an aura. The headache pain may be severe and may also be unilateral in certain patients.

Migraine attacks are disruptive to daily life. In US and Western Europe, the overall prevalence of migraine sufferers is 11% of the general population (6% males; 15-18% females). Furthermore, the median frequency of attacks in an individual is 1.5/month. While there are a number of treatments available to alleviate or reduce symptoms, preventive therapy is recommended for those patients having more than 3-4 attacks of migraine per month. Goadsby et al. New Engl. J. Med. 346(4): 257-275, 2002.

The variety of pharmacologic interventions that have been used to treat migraine and the variability in responses among patients are a testament to the diverse nature of this disorder. Thus, such relatively non-selective drugs as ergot alkaloids (e.g., ergotamine, dihydroergotamine, methysergide), which exhibit serotonergic, as well as adrenergic, noradrenergic and dopaminergic activity, have been used for over eighty years to treat migraine. Other treatments include opiates (e.g., oxycodone) and 3-adrenergic antagonists (e.g., propranolol). Some patients, usually those with milder symptoms, are able to control their symptoms with non-prescription remedies such as one or more non-steroidal anti-inflammatory agents (NSAIDs), such as a combination of aspirin, acetaminophen and caffeine (e.g., Excedrin® Migraine).

More recently, some migraine patients have been treated with topiramate, an anticonvulsant that blocks voltage-dependent sodium channels and certain glutamate receptors (AMPA-kainate), potentiates GABA-A receptor activity, and blocks carbonic anhydrase. The relatively recent success of serotonin 5HT-1B/1D and/or 5HT-la receptor agonists, such as sumatriptan, in some patients has led researchers to propose a serotonergic etiology of the disorder. Unfortunately, while some patients respond well to this treatment, others are relatively resistant to its effects.

It has been postulated that a dysfunction of an ion channel in the aminergic brainstem nuclei underlies the disorder, however, the precise pathophysiology of migraine is not yet well understood. One form of migraine, familial hemiplegic migraine, has been shown to be associated with missense mutations in the al subunit of the voltage-gated P/Q-type calcium channel, and it is thought likely that other ion-channel mutations will also be found in other populations of patients. While dilation of blood vessels is associated with and exacerbates the pain symptoms of migraine, such neurovascular events are now thought to be a result of, rather than causative of, the condition. Overall, dysfunction of brainstem pathways modulating sensory input is considered to be a unifying feature of migraine. Goadsby, P. J. et al., New Engl. J. Med. 346(4): 257-275, 2002.

BRIEF SUMMARY

In some aspects, the invention disclosed herein concerns anti-CGRP antagonist antibodies and methods of using anti-CGRP antagonist antibodies for treating or preventing vasomotor symptoms. Examples of vasomotor symptoms are provided herein, such as hot flush. In some cases, anti-CGRP antagonist antibodies are used for treating or preventing a headache, such as migraine with or without aura, hemiplegic migraine, cluster headaches, migrainous neuralgia, chronic headaches, tension headaches, and headaches resulting from other medical conditions (such as infection or increased pressure in the skull due to a tumor).

In one aspect, the present invention provides a method for treating or preventing at least one vasomotor symptom in an individual comprising administering to the individual an effective amount of an anti-CGRP antagonist antibody.

In one aspect, the present invention provides a method for treating or preventing headache (e.g., migraine and cluster headache) in an individual comprising administering to the individual an effective amount of an anti-CGRP antagonist antibody.

In another aspect, the invention provides a method for ameliorating, controlling, reducing incidence of, or delaying the development or progression of headache (e.g., migraine and cluster headache) in an individual comprising administering to the individual an effective amount of an anti-CGRP antagonist antibody.

In one aspect, the invention provides a method of treating or reducing incidence of at least one vasomotor symptom and/or headache in a subject. In one embodiment, the method comprises administering to the subject on a plurality of days an amount of monoclonal antibody (e.g., monoclonal anti-CGRP-antagonist antibody) that modulates the CGRP pathway, wherein the amount administered on each of the plurality of days is less than 1000 mg. In one embodiment, the method comprises administering to the subject on a plurality of days an amount of monoclonal antibody (e.g., monoclonal anti-CGRP-antagonist antibody) that modulates the CGRP pathway, wherein the amount administered on each of the plurality of days is between 100-2000 mg. In some embodiments, the headache is migraine headache (e.g. chronic migraine headache or episodic migraine headache). In some embodiments, two of the plurality of days are more than seven days apart. In some embodiments, the incidence of headache is reduced for at least seven days after a single administration. In some embodiments, the amount of the monoclonal antibody administered on a first day is different than (e.g. more than) the amount of the monoclonal antibody administered on a second day. In some embodiments, the subject is administered less than 3 doses per month. In some embodiments, the administering is subcutaneous administration. In some embodiments, the administering is intravenous administration. In some embodiments, the administering comprises utilizing a pre-filled syringe comprising the amount of the monoclonal antibody. In some embodiments, the monoclonal antibody is formulated at a concentration of 150 mg/mL. In some embodiments, the monoclonal antibody is administered in a volume of less than 2 mL. In some embodiments, the amount of monoclonal antibody is less than 1000 mg. In some embodiments, monthly headache hours experienced by the subject after said administering is reduced by 40 or more hours (e.g. 45, 50, 55, 60, 65, 70, 75, 80, or more) from a pre-administration level in the subject. Monthly headache hours may be reduced by more than 60 hours. In some embodiments, monthly headache hours experienced by the subject after said administering are reduced by 25% or more (e.g. 30%, 35%, 40%, 45%, 50%, or more) relative to a pre-administration level in the subject. Monthly headache hours may be reduced by 40% or more. In some embodiments, monthly headache days experienced by the subject after said administering is reduced by 3 or more days (e.g. 3, 4, 5, 6, 7, 8, 9, 10, 11, 12, 13, 14, 15, 16, 17, 18, 19, 20 or more days) from a pre-administration level in the subject. In some embodiments, the method further comprises administering to the subject a second agent simultaneously or sequentially with the monoclonal antibody. The second agent can be any of 5-HT1 agonists, triptans, ergot alkaloids, and non-steroidal anti-inflammatory drugs. In some embodiments, the second agent is an agent taken by the subject prophylactically. In some embodiments, monthly use of the second agent by the subject is decreased by at least 15% after administering the monoclonal antibody. In some embodiments, the second agent is a triptan. In some embodiments, the subject is a human. In some embodiments, the monoclonal antibody is a human or humanized monoclonal antibody. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a method of decreasing a number of monthly headache hours experienced by a subject. In one embodiment, the method comprises administering to the subject an amount of a monoclonal antibody that modulates the CGRP pathway, wherein the monoclonal antibody is in an amount effective to decrease the number of monthly headache hours by at least 20 (e.g. 25, 30, 35, 40, 45, 50, 55, 60, 65, 70 or more headache hours) after a single dose. In some embodiments, the number of monthly headache hours is reduced by at least about 50 hours. In one embodiment, the method comprises administering to the subject an amount of a monoclonal antibody that modulates the CGRP pathway, wherein the monoclonal antibody is in an amount effective to decrease the number of monthly headache hours by at least 15% (e.g. 20%, 25%, 30%, 35%, 40%, or more) after a single dose. In some embodiments, the number of monthly headache hours is reduced by at least about 30%. In some embodiments, the monoclonal antibody is an anti-CGRP antagonist antibody. In some embodiments, the amount of the monoclonal antibody is less than 1000 mg. In some embodiments, the subject is administered fewer than 3 doses per month. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL. In some embodiments, the subject is human. In some embodiments, the monoclonal antibody is human or humanized. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a method of decreasing a number of monthly headache days experienced by a subject. In one embodiment, the method comprises administering to the subject an amount of a monoclonal antibody that modulates the CGRP pathway, wherein the monoclonal antibody is in an amount effective to decrease the number of monthly headache days by at least 3 (e.g. 3, 4, 5, 6, 7, 8, 9, 10, 11, 12, 13, 14, 15, 16, 17, 18, 19, 20 or more headache days) after a single dose. In some embodiments, the number of monthly headache days is reduced by at least about 6 headache days. In some embodiments, the monoclonal antibody is an anti-CGRP antagonist antibody. In some embodiments, the amount of the monoclonal antibody is less than 1000 mg. In some embodiments, the subject is administered fewer than 3 doses per month. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL. In some embodiments, the subject is human. In some embodiments, the monoclonal antibody is human or humanized. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a method of decreasing use of an anti-headache medication in a subject, comprising administering to the subject a monoclonal antibody (e.g., anti-CGRP antagonist antibody) that modulates the CGRP pathway, wherein the monoclonal antibody is in an amount effective to decrease monthly use of the anti-headache medication by the subject by at least 15% (e.g. 20%, 25%, 30%, 35%, 40%, or more). In some embodiments, the anti-headache medication is selected from the group consisting of 5-HT1 agonists, triptans, opiates, 3-adrenergic antagonists, ergot alkaloids, and non-steroidal anti-inflammatory drugs (NSAIDs). In some embodiments, the anti-headache medication is a triptan. In some embodiments, the amount of the monoclonal antibody is less than 1000 mg. In some embodiments, the subject is administered fewer than 3 doses per month. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL. In some embodiments, the subject is human. In some embodiments, the monoclonal antibody is human or humanized. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a method of treating or reducing incidence of headache (e.g., migraine headache) in a subject comprising administering to the subject a single dose of a monoclonal antibody (e.g., monoclonal anti-CGRP-antagonist antibody) in an amount that modulates the CGRP pathway, wherein the amount of the monoclonal antibody is between 100-2000 mg.

In a further embodiment, the invention provides methods for ameliorating, controlling, reducing incidence of, or delaying the development or progression of headache (e.g., migraine and cluster headache) in an individual comprising administering to the individual an effective amount of an anti-CGRP antagonist antibody in combination with at least one additional agent useful for treating headache. Such additional agents include 5-HT1-like agonists (and agonists acting at other 5-HT1 sites), and non-steroidal anti-inflammatory drugs (NSAIDs).

Examples of 5-HT1 agonists that can be used on combination with an anti-CGRP antibody include a class of compounds known as triptans, such as sumatriptan, zolmitriptan, naratriptan, rizatriptan, eletriptan, almotriptan, and frovatriptan. Ergot alkaloids and related compounds are also known to have 5-HT agonist activity and have been used to treat headache such as migraine. Included among these compounds are ergotamine tartrate, ergonovine maleate, and ergoloid mesylates (e.g., dihydroergocornine, dihydroergocristine, dihydroergocryptine, and dihydroergotamine mesylate (DHE 45)).

Examples of NSAIDs that can be used in combination with an anti-CGRP antibody include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof.

In another aspect, the invention provides a method for ameliorating, controlling, reducing incidence of, or delaying the development or progression of hot flushes in an individual comprising administering to the individual an effective amount of an anti-CGRP antagonist antibody.

In another aspect, the invention provides methods for ameliorating, controlling, reducing incidence of, or delaying the development or progression of hot flushes in an individual comprising administering to the individual an effective amount of an anti-CGRP antagonist antibody in combination with at least one additional agent useful for treating hot flushes. Such additional agents include, but are not limited to, hormone-based treatments, including estrogens and/or progestins.

In one embodiment, the anti-CGRP antagonist antibody used in any of the methods described above is any of the antibodies as described herein.

In some embodiments, the anti-CGRP antagonist antibody recognizes a human CGRP. In some embodiments, the anti-CGRP antagonist antibody binds to both human α-CGRP and β-CGRP. In some embodiments, the anti-CGRP antagonist antibody binds human and rat CGRP. In some embodiments, the anti-CGRP antagonist antibody binds the C-terminal fragment having amino acids 25-37 of CGRP. In some embodiments, the anti-CGRP antagonist antibody binds a C-terminal epitope within amino acids 25-37 of CGRP.

In some embodiments, the anti-CGRP antagonist antibody is a monoclonal antibody. In some embodiments, the anti-CGRP antagonist antibody is humanized. In some embodiments, the antibody is human. In some embodiments, the anti-CGRP antagonist antibody is antibody G1 (as described herein). In some embodiments, the anti-CGRP antagonist antibody comprises one or more CDR(s) (such as one, two, three, four, five, or, in some embodiments, all six CDRs) of antibody G1 or variants of G1 shown in Table 6. In still other embodiments, the anti-CGRP antagonist antibody comprises the amino acid sequence of the heavy chain variable region shown in FIG. 5 (SEQ ID NO: 1) and the amino acid sequence of the light chain variable region shown in FIG. 5 (SEQ ID NO: 2).

In some embodiments, the antibody comprises a modified constant region, such as a constant region that is immunologically inert (including partially immunologically inert), e.g., does not trigger complement mediated lysis, does not stimulate antibody-dependent cell mediated cytotoxicity (ADCC), does not activate microglia, or having reduced one or more of these activities. In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In some embodiments, the heavy chain constant region of the antibody is a human heavy chain IgG1 with any of the following mutations: 1) A327A330P331 to G327S330S331; 2) E233L234L235G236 (SEQ ID NO: 48) to P233V234A235 with G236 deleted; 3) E233L234L235 to P233V234A235; 4) E233L234L235G236A327A330P331 (SEQ ID NO: 49) to P233V234A235G327S330S331 (SEQ ID NO: 50) with G236 deleted; 5) E233L234L235A327A330P331 (SEQ ID NO: 51) to P233V234A235G327S330S331 (SEQ ID NO: 50); and 6) N297 to A297 or any other amino acid except N. In some embodiments, the heavy chain constant region of the antibody is a human heavy chain IgG4 with any of the following mutations: E233F234L235G236 (SEQ ID NO: 52) to P233V234A235 with G236 deleted; E233F234L235 to P233V234A235; and S228L235 to P228E235.

In still other embodiments, the constant region is aglycosylated for N-linked glycosylation. In some embodiments, the constant region is aglycosylated for N-linked glycosylation by mutating the oligosaccharide attachment residue (such as Asn297) and/or flanking residues that are part of the N-glycosylation recognition sequence in the constant region. In some embodiments, the constant region is aglycosylated for N-linked glycosylation. The constant region may be aglycosylated for N-linked glycosylation enzymatically or by expression in a glycosylation deficient host cell.

The binding affinity ($K_D$) of an anti-CGRP antagonist antibody to CGRP (such as human α-CGRP as measured by surface plasmon resonance at an appropriate temperature, such as 25 or 37° C.) can be about 0.02 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM. In some embodiments, the binding affinity is less than about 50 nM.

The anti-CGRP antagonist antibody may be administered prior to, during and/or after headache. In some embodiments, the anti-CGRP antagonist antibody is administered prior to the attack of headache (e.g., migraine and cluster headache). Administration of an anti-CGRP antagonist antibody can be by any means known in the art, including: orally, intravenously, subcutaneously, intraarterially, intramuscularly, intranasally (e.g., with or without inhalation), intracardially, intraspinally, intrathoracically, intraperitoneally, intraventricularly, sublingually, transdermally, and/or via inhalation. Administration may be systemic, e.g. intravenously, or localized.

In some embodiments, the anti-CGRP antagonist antibody may be administered in conjunction with another agent, such as another agent for treating headache.

In another aspect, the invention provides use of an anti-CGRP antagonist antibody for the manufacture of a medicament for use in any of the methods described herein, for example, for treating or preventing headache.

In another aspect, the invention provides a pharmaceutical composition for preventing or treating headache (e.g., migraine and cluster headache) comprising an effective amount of an anti-CGRP antagonist antibody, in combination with one or more pharmaceutically acceptable excipients.

In another aspect, the invention provides a kit for use in any of the methods described herein. In some embodiments, the kit comprises a container, a composition comprising an anti-CGRP antagonist antibody described herein, in combination with a pharmaceutically acceptable carrier, and instructions for using the composition in any of the methods described herein.

The present invention also provides anti-CGRP antagonist antibodies and polypeptides derived from antibody G1 or its variants shown in Table 6. Accordingly, in one aspect, the invention provides an antibody G1 (interchangeably termed "G1") that is produced by expression vectors having ATCC Accession Nos. PTA-6866 and PTA-6867. For example, in one embodiment is an antibody comprising a heavy chain produced by the expression vector with ATCC Accession No. PTA-6867. In a further embodiment is an antibody comprising a light chain produced by the expression vector with ATCC Accession No. PTA-6866. The amino acid sequences of the heavy chain and light chain variable regions of G1 are shown in FIG. 5. The complementarity determining region (CDR) portions of antibody G1 (including Chothia and Kabat CDRs) are also shown in FIG. 5. It is understood that reference to any part of or entire region of G1 encompasses sequences produced by the expression vectors having ATCC Accession Nos. PTA-6866 and PTA-6867, and/or the sequences depicted in FIG. 5. In some embodiments, the invention also provides antibody variants of G1 with amino acid sequences depicted in Table 6.

In one aspect, the invention provides an antibody comprising a $V_H$ domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 1.

In another aspect, the invention provides an antibody comprising a $V_L$ domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 2.

In another aspect, the invention provides an antibody comprising a fragment or a region of the antibody G1 or its variants shown in Table 6. In one embodiment, the fragment is a light chain of the antibody G1. In another embodiment, the fragment is a heavy chain of the antibody G1. In yet another embodiment, the fragment contains one or more variable regions from a light chain and/or a heavy chain of the antibody G1. In yet another embodiment, the fragment contains one or more variable regions from a light chain and/or a heavy chain shown in FIG. 5. In yet another embodiment, the fragment contains one or more CDRs from a light chain and/or a heavy chain of the antibody G1.

In another aspect, the invention provides polypeptides (which may or may not be an antibody) comprising a $V_H$ CDR3 as set forth in SEQ ID NO: 5, or a sequence that differs from SEQ ID NO: 5 by 1, 2, 3, 4, or 5 amino acid substitutions. In a particular embodiment, such amino acid substitutions are conservative substitutions.

In another aspect, the invention provides polypeptides (which may or may not be an antibody) comprising a $V_L$ CDR3 as set forth in SEQ ID NO: 8, or a sequence that differs from SEQ ID NO: 8 by 1, 2, 3, 4, or 5 amino acid substitutions. In a particular embodiment, such amino acid substitutions are conservative substitutions.

In another aspect, the invention provides polypeptides (which may or may not be an antibody) comprising any one or more of the following: a) one or more CDR(s) of antibody G1 or its variants shown in Table 6; b) CDR H3 from the heavy chain of antibody G1 or its variants shown in Table 6; c) CDR L3 from the light chain of antibody G1 or its variants shown in Table 6; d) three CDRs from the light chain of antibody G1 or its variants shown in Table 6; e) three CDRs from the heavy chain of antibody G1 or its variants shown in Table 6; f) three CDRs from the light chain and three CDRs from the heavy chain of antibody G1 or its variants shown in Table 6. In some embodiments, the invention further provides polypeptides (which may or may not be an antibody) comprising any one or more of the following: a) one or more (one, two, three, four, five, or six) CDR(s) derived from antibody G1 or its variants shown in Table 6; b) a CDR derived from CDR H3 from the heavy chain of antibody G1; and/or c) a CDR derived from CDR L3 from the light chain of antibody G1. In some embodiments, the CDR is a CDR shown in FIG. 5. In some embodiments, the one or more CDRs derived from antibody G1 or its variants shown in Table 6 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six CDRs of G1 or its variants.

In some embodiments, the CDR is a Kabat CDR. In other embodiments, the CDR is a Chothia CDR. In other embodiments, the CDR is a combination of a Kabat and a Chothia CDR (also termed "combined CDR" or "extended CDR"). In other words, for any given embodiment containing more than one CDR, the CDRs may be any of Kabat, Chothia, and/or combined.

In some embodiments, the polypeptide (such as an antibody) comprises the amino acid sequence of KASKXaaVXaaTYVS (SEQ ID NO: 53), wherein Xaa at position 5 is R, W, G, L, or N; and wherein Xaa at position 7 is T, A, D, G, R, S, W, or V. In some embodiments, the amino acid sequence of KASKXaaVXaaTYVS (SEQ ID NO: 53) is CDR1 of an antibody light chain.

In some embodiments, the polypeptide (such as an antibody) comprises the amino acid sequence of XaaXaaSNRYXaa (SEQ ID NO: 54), wherein Xaa at position 1 is G or A; wherein Xaa at position 2 is A or H; and wherein Xaa at position 7 is L, T, I, or S. In some embodiments, the amino acid sequence of XaaXaaSNRYXaa (SEQ ID NO: 54) is CDR2 of an antibody light chain.

In some embodiments, the polypeptide (such as an antibody) comprises the amino acid sequence of EIRSXaaSDXaaXaaATXaaYAXaaAVKG (SEQ ID NO: 55), wherein Xaa at position 5 is E, R, K, Q, or N; wherein Xaa at position 8 is A, G, N, E, H, S, L, R, C, F, Y, V, D, or P; wherein Xaa at position 9 is S, G, T, Y, C, E, L, A, P, I, N, R, V, D, or M; wherein Xaa at position 12 is H or F; wherein Xaa at position 15 is E or D. In some embodiments, the amino acid sequence of EIRSXaaSDXaaXaaATXaaYAXaaAVKG (SEQ ID NO: 55) is CDR2 of an antibody heavy chain.

In some embodiments, the polypeptide (such as an antibody) comprises the amino acid sequence of SEQ ID NO:1, wherein amino acid residue at position 99 of SEQ ID NO:1 is L or is substituted by A, N, S, T, V, or R; and wherein amino acid residues at position 100 of SEQ ID NO:1 is A or is substituted by L, R, S, V, Y, C, G, T, K, or P.

In some embodiments, the antibody is a human antibody. In other embodiments, the antibody a humanized antibody. In some embodiments, the antibody is monoclonal. In some embodiments, the antibody (or polypeptide) is isolated. In some embodiments, the antibody (or polypeptide) is substantially pure.

The heavy chain constant region of the antibodies may be from any types of constant region, such as IgG, IgM, IgD, IgA, and IgE; and any isotypes, such as IgG1, IgG2, IgG3, and IgG4.

In some embodiments, the antibody comprises a modified constant region as described herein.

In another aspect, the invention provides a polynucleotide (which may be isolated) comprising a polynucleotide encoding a fragment or a region of the antibody G1 or its variants shown in Table 6. In one embodiment, the fragment is a light chain of the antibody G1. In another embodiment, the fragment is a heavy chain of the antibody G1. In yet another embodiment, the fragment contains one or more variable regions from a light chain and/or a heavy chain of the antibody G1. In yet another embodiment, the fragment contains one or more (i.e., one, two, three, four, five, or six) complementarity determining regions (CDRs) from a light chain and/or a heavy chain of the antibody G1.

In another aspect, the invention provides a polynucleotide (which may be isolated) comprising a polynucleotide that encodes for antibody G1 or its variants shown in Table 6. In some embodiments, the polynucleotide comprises either or both of the polynucleotides shown in SEQ ID NO:9 and SEQ ID NO:10.

In another aspect, the invention provides polynucleotides encoding any of the antibodies (including antibody fragments) or polypeptides described herein.

In another aspect, the invention provides vectors (including expression and cloning vectors) and host cells comprising any of the polynucleotide disclosed herein. In some embodiments, the vector is pDb.CGRP.hFcGI having ATCC No. PTA-6867. In other embodiments, the vector is pEb.CGRP.hKGI having ATCC No. PTA-6866.

In another aspect, the invention provides a host cell comprising a polynucleotide encoding any of the antibodies described herein.

In another aspect, the invention provides a complex of CGRP bound by any of the antibodies or polypeptides described herein. In some embodiments, the antibody is antibody G1 or its variants shown in Table 6.

In another aspect, the invention provides a pharmaceutical composition comprising an effective amount of any of the polypeptides (including antibodies, such as an antibody comprising one or more CDRs of antibody G1) or polynucleotides described herein, and a pharmaceutically acceptable excipient.

In another aspect, the invention provides a method of generating antibody G1 comprising culturing a host cell or progeny thereof under conditions that allow production of antibody G1, wherein the host cell comprises an expression vector that encodes for antibody G1; and, in some embodiments, purifying the antibody G1. In some embodiments, the expression vector comprises one or both of the polynucleotide sequences shown in SEQ ID NO:9 and SEQ ID NO:10.

In another aspect, the invention provides methods of generating any of the antibodies or polypeptides described herein by expressing one or more polynucleotides encoding the antibody (which may be separately expressed as a single light or heavy chain, or both a light and a heavy chain are expressed from one vector) or the polypeptide in a suitable cell, generally followed by recovering and/or isolating the antibody or polypeptides of interest.

The anti-CGRP antagonist antibody and polypeptides, and polynucleotides encoding the antibodies and polypeptides of the present invention may be used for treating, preventing, ameliorating, controlling, or reducing incidence of diseases associated with abnormal function of CGRP, such as headache (e.g., migraine, cluster headache, chronic headache, and tension headache) and other conditions that may be treated or prevented by antagonizing CGRP activity.

In another aspect, the invention provides kits and compositions comprising any one or more of the compositions described herein. These kits, generally in suitable packaging and provided with appropriate instructions, are useful for any of the methods described herein.

In one aspect, the invention provides a composition for use in accordance with any of the methods described herein.

In one aspect, the invention provides a composition for use in treating or reducing incidence of at least one vasomotor symptom and/or headache in a subject. In one embodiment, the use comprises administering to the subject on a plurality of days an amount of monoclonal antibody (e.g., monoclonal anti-CGRP-antagonist antibody) that modulates the CGRP pathway, wherein the amount administered on each of the plurality of days is less than 1000 mg. In one embodiment, the use comprises administering to the subject on a plurality of days an amount of monoclonal antibody (e.g., monoclonal anti-CGRP-antagonist antibody) that modulates the CGRP pathway, wherein the amount administered on each of the plurality of days is between 100-2000 mg. In some embodiments, the headache is migraine headache (e.g. chronic migraine headache or episodic migraine headache). In some embodiments, two of the plurality of days are more than seven days apart. In some embodiments, the incidence of headache is reduced for at least seven days after a single administration. In some embodiments, the amount of the monoclonal antibody administered on a first day is different than (e.g. more than) the amount of the monoclonal antibody administered on a second day. In some embodiments, the subject is administered less than 3 doses per month. In some embodiments, the administering is subcutaneous administration. In some embodiments, the administering is intravenous administration. In some embodiments, the administering comprises utilizing a pre-filled syringe comprising the amount of the monoclonal antibody. In some embodiments, the monoclonal antibody is formulated at a concentration of 150 mg/mL. In some embodiments, the monoclonal antibody is administered in a volume of less than 2 mL. In some embodiments, the amount of monoclonal antibody is less than 1000 mg. In some embodiments, monthly headache hours experienced by the subject after said administering is reduced by 40 or more hours (e.g. 45, 50, 55, 60, 65, 70, 75, 80, or more) from a pre-administration level in the subject. Monthly headache hours may be reduced by more than 60 hours.

In some embodiments, monthly headache hours experienced by the subject after said administering are reduced by 25% or more (e.g. 30%, 35%, 40%, 45%, 50%, or more) relative to a pre-administration level in the subject. Monthly headache hours may be reduced by 40% or more. In some embodiments, monthly headache days experienced by the subject after said administering is reduced by 3 or more days (e.g. 3, 4, 5, 6, 7, 8, 9, 10, 11, 12, 13, 14, 15, 16, 17, 18, 19, 20 or more days) from a pre-administration level in the subject. In some embodiments, the use further comprises administering to the subject a second agent simultaneously or sequentially with the monoclonal antibody. The second agent can be any of 5-HT1 agonists, triptans, ergot alkaloids, and non-steroidal anti-inflammatory drugs. In some embodiments, the second agent is an agent taken by the subject prophylactically. In some embodiments, monthly use of the second agent by the subject is decreased by at least 15% after administering the monoclonal antibody. In some embodiments, the second agent is a triptan. In some embodiments, the subject is a human. In some embodiments, the monoclonal antibody is a human or humanized monoclonal antibody. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a composition for use in decreasing a number of monthly headache hours experienced by a subject. In one embodiment, the use comprises administering to the subject an amount of a monoclonal antibody that modulates the CGRP pathway, wherein the monoclonal antibody is in an amount effective to decrease the number of monthly headache hours by at least 20 (e.g. 25, 30, 35, 40, 45, 50, 55, 60, 65, 70 or more headache hours) after a single dose. In some embodiments, the number of monthly headache hours is reduced by at least about 50 hours. In one embodiment, the use comprises administering to the subject an amount of a monoclonal antibody that modulates the CGRP pathway, wherein the monoclonal antibody is in an amount effective to decrease the number of monthly headache hours by at least 15% (e.g. 20%, 25%, 30%, 35%, 40%, or more) after a single dose. In some embodiments, the number of monthly headache hours is reduced by at least about 30%. In some embodiments, the monoclonal antibody is an anti-CGRP antagonist antibody. In some embodiments, the amount of the monoclonal antibody is less than 1000 mg. In some embodiments, the subject is administered fewer than 3 doses per month. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL. In some embodiments, the subject is human. In some embodiments, the monoclonal antibody is human or humanized. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a composition for use in decreasing a number of monthly headache days experienced by a subject. In one embodiment, the use comprises administering to the subject an amount of a monoclonal antibody that modulates the CGRP pathway, wherein the monoclonal antibody is in an amount effective to decrease the number of monthly headache days by at least 3 (e.g. 3, 4, 5, 6, 7, 8, 9, 10, 11, 12, 13, 14, 15, 16, 17, 18, 19, 20 or more headache days) after a single dose. In some embodiments, the number of monthly headache days is reduced by at least about 6 headache days. In some embodiments, the monoclonal antibody is an anti-CGRP antagonist antibody. In some embodiments, the amount of the monoclonal antibody is less than 1000 mg. In some embodiments, the subject is administered fewer than 3 doses per month. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL. In some embodiments, the subject is human. In some embodiments, the monoclonal antibody is human or humanized. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a composition for use in decreasing use of an anti-headache medication in a subject, comprising administering to the subject a monoclonal antibody (e.g., anti-CGRP antagonist antibody) that modulates the CGRP pathway, wherein the monoclonal antibody is in an amount effective to decrease monthly use of the anti-headache medication by the subject by at least 15% (e.g. 20%, 25%, 30%, 35%, 40%, or more). In some embodiments, the anti-headache medication is selected from the group consisting of 5-HT1 agonists, triptans, opiates, 3-adrenergic antagonists, ergot alkaloids, and non-steroidal anti-inflammatory drugs (NSAIDs). In some embodiments, the anti-headache medication is a triptan. In some embodiments, the amount of the monoclonal antibody is less than 1000 mg. In some embodiments, the subject is administered fewer than 3 doses per month. In some embodiments, the administering is subcutaneous or intravenous administration. In some embodiments, the monoclonal antibody is formulated at a concentration of at least 150 mg/mL. In some embodiments, wherein the monoclonal antibody is administered in a volume of less than 2 mL. In some embodiments, the subject is human. In some embodiments, the monoclonal antibody is human or humanized. In some embodiments, the monoclonal antibody comprises (a) an antibody having a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; or (b) a variant of an antibody according to (a) as shown in Table 6.

In one aspect, the invention provides a composition for use in of treating or reducing incidence of headache (e.g., migraine headache) in a subject comprising administering to the subject a single dose of a monoclonal antibody (e.g., monoclonal anti-CGRP-antagonist antibody) in an amount that modulates the CGRP pathway, wherein the amount of the monoclonal antibody is between 100-2000 mg.

BRIEF DESCRIPTION OF THE DRAWINGS

FIG. 1 is a table showing binding affinities of 12 murine antibodies for different alanine substituted human α-CGRP fragments. Binding affinities were measured at 25° C. using Biacore by flowing Fabs across CGRPs on the chip. The boxed values represent the loss in affinity of alanine mutants relative to parental fragment, 25-37 (italic), except K35A, which was derived from a 19-37 parent. "$^a$" indicates affinities for 19-37 and 25-37 fragments are the mean average ±standard deviation of two independent measurements on different sensor chips. "$^b$" indicates these interactions deviated from a simple bimolecular interaction model due to a biphasic offrate, so their affinities were determined using a conformational change model. Grey-scale key: white (1.0) indicates parental affinity; light grey (less than 0.5) indicates higher affinity than parent; dark grey (more than 2) indicates lower affinity than parent; and black indicates that no binding was detected.

FIGS. 2A and 2B show the effect of administering CGRP 8-37 (400 nmol/kg), antibody 4901 (25 mg/kg), and antibody 7D11 (25 mg/kg) on skin blood flow measured as blood cell flux after electrical pulse stimulation for 30 seconds. CGRP 8-37 was administered intravenously (iv) 3-5 min before electrical pulse stimulation. Antibodies were administered intraperitoneal (IP) 72 hours before electrical pulse stimulation. Each point in the graphs represents AUC of one rat treated under the conditions as indicated. Each line in the graphs represents average AUC of rats treated under the condition as indicated. AUC (area under the curve) equals to Δflux×Δtime. "Δflux" represents the change of flux units after the electrical pulse stimulation; and "Δtime" represents the time period taken for the blood cell flux level to return to the level before the electrical pulse stimulation.

FIG. 5 shows the amino acid sequence of the heavy chain variable region (SEQ ID NO:1) and light chain variable region (SEQ ID NO:2) of antibody G1. The Kabat CDRs are in bold text, and the Chothia CDRs are underlined. The amino acid residues for the heavy chain and light chain variable region are numbered sequentially.

FIG. 8B shows the effect of administering antibody G1 (0.3 mg/kg, 1 mg/kg, 3 mg/kg or 10 mg/kg, i.v.) or vehicle (PBS, 0.01% Tween 20) on skin blood flow measured as blood cell flux after electrical pulse stimulation for 30 seconds 7 days after dosing. Antibody G1 or vehicle was administered intravenously (i.v.) 7 days before nerve electrical pulse stimulation. Y axis represents total AUC. X axis represents varying doses of antibody G1. "*" indicates $P<0.01$, and "*" indicates $P<0.001$, as compared to vehicle. Data were analyzed using one-way ANOVA and Dunn's multiple comparison test.

DETAILED DESCRIPTION

Figure 3:
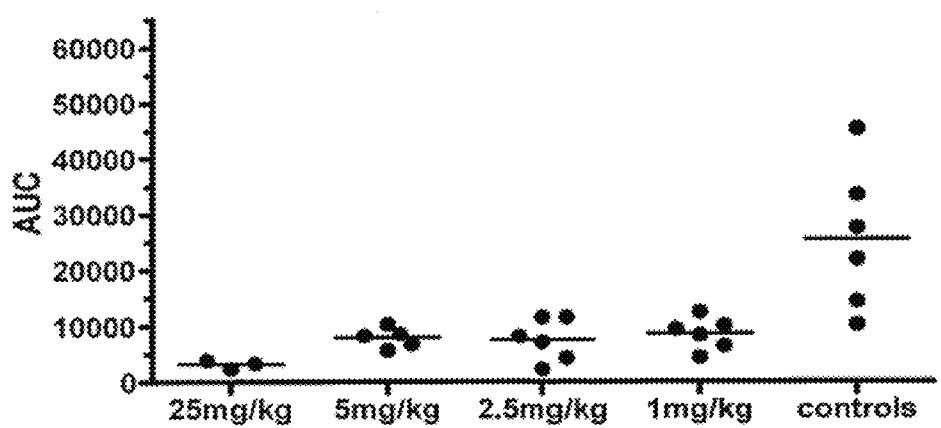
FIG. 3 shows the effect of administering different dosage of antibody 4901 (25 mg/kg, 5 mg/kg, 2.5 mg/kg, or 1 mg/kg) on skin blood flow measured as blood cell flux after electrical pulse stimulation for 30 seconds. Antibodies were administered intravenously (IV) 24 hours before electrical pulse stimulation. Each point in the graph represents AUC of one rat treated under the conditions as indicated. The line in the graph represents average AUC of rats treated under the condition as indicated.

In some aspects, the invention disclosed herein provides methods for treating and/or preventing vasomotor symptoms (e.g., hot flush) in an individual by administering to the individual a therapeutically effective amount of an anti-CGRP antagonist antibody.

In some aspects, the invention disclosed herein provides methods for treating and/or preventing headache (e.g., migraine, cluster headache, chronic headache, and tension headache) in an individual by administering to the individual a therapeutically effective amount of an anti-CGRP antagonist antibody. In some cases, the headache is a migraine headache.

In some aspects, the invention disclosed herein also provides anti-CGRP antagonist antibodies and polypeptides derived from G1 or its variants shown in Table 6. In some embodiments, the invention also provides methods of making and using these antibodies and polypeptides.

Throughout this application various publications (including patents and patent applications) are referenced. The disclosures of these publications in their entireties are hereby incorporated by reference.

General Techniques

The practice of the various aspects of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and, biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

As used herein, the term "calcitonin gene-related peptide" and "CGRP" refers to any form of calcitonin gene-related peptide and variants thereof that retain at least part of the activity of CGRP. For example, CGRP may be α-CGRP or β-CGRP. As used herein, CGRP includes all mammalian species of native sequence CGRP, e.g., human, canine, feline, equine, and bovine.

As used herein, an "anti-CGRP antagonist antibody" (interchangeably termed "anti-CGRP antibody") refers to an antibody that is able to bind to CGRP and inhibit CGRP biological activity and/or downstream pathway(s) mediated by CGRP signaling. An anti-CGRP antagonist antibody encompasses antibodies that modulate, block, antagonize, suppress or reduce (including significantly) CGRP biological activity, or otherwise antagonize the CGRP pathway, including downstream pathways mediated by CGRP signaling, such as receptor binding and/or elicitation of a cellular response to CGRP. For purpose of the present invention, it will be explicitly understood that the term "anti-CGRP antagonist antibody" encompasses all the previously identified terms, titles, and functional states and characteristics whereby CGRP itself, CGRP biological activity (including but not limited to its ability to mediate any aspect of headache), or the consequences of the biological activity, are substantially nullified, decreased, or neutralized in any meaningful degree. In some embodiments, an anti-CGRP antagonist antibody binds CGRP and prevents CGRP binding to a CGRP receptor. In other embodiments, an anti-CGRP antibody binds CGRP and prevents activation of a CGRP receptor. Examples of anti-CGRP antagonist antibodies are provided herein.

As used herein, the terms "G1" and "antibody G1" are used interchangeably to refer to an antibody produced by expression vectors having deposit numbers of ATCC PTA-6867 and ATCC PTA-6866. The amino acid sequence of the heavy chain and light chain variable regions are shown in FIG. 5. The CDR portions of antibody G1 (including Chothia and Kabat CDRs) are diagrammatically depicted in FIG. 5. The polynucleotides encoding the heavy and light chain variable regions are shown in SEQ ID NO:9 and SEQ ID NO:10. The characterization of G1 is described in the Examples.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CGRP epitope is an antibody that binds this epitope with greater affinity, avidity, more readily, and/or with greater duration than it binds to other CGRP epitopes or non-CGRP epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Imunological Interest, 5th Ed. Public Health Service, National Institutes of Health, Bethesda, Md., 1991. The Fc region of an immunoglobulin generally comprises two constant domains, CH2 and CH3.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, at least about 99% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in an animal model such as that disclosed in Clynes et al., 1998, PNAS (USA), 95:652-656.

As used herein, "treatment" is an approach for obtaining beneficial or desired clinical results. For purposes of this invention, beneficial or desired clinical results include, but are not limited to, one or more of the following: improvement in any aspect of a headache including lessening severity, alleviation of pain intensity, and other associated symptoms, reducing frequency of recurrence, increasing the quality of life of those suffering from the headache, and decreasing dose of other medications required to treat the headache. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, Rhinorrhea or nasal congestion, and red flushed face.

"Reducing incidence" of headache means any of reducing severity (which can include reducing need for and/or amount of (e.g., exposure to) other drugs and/or therapies generally used for this condition, including, for example, ergotamine, dihydroergotamine, or triptans for migraine), duration, and/or frequency (including, for example, delaying or increasing time to next episodic attack in an individual). As is understood by those skilled in the art, individuals may vary in terms of their response to treatment, and, as such, for example, a "method of reducing incidence of headache in an individual" reflects administering the anti-CGRP antagonist antibody based on a reasonable expectation that such administration may likely cause such a reduction in incidence in that particular individual.

"Ameliorating" headache or one or more symptoms of headache means a lessening or improvement of one or more symptoms of headache as compared to not administering an anti-CGRP antagonist antibody. "Ameliorating" also includes shortening or reduction in duration of a symptom.

As used herein, "controlling headache" refers to maintaining or reducing severity or duration of one or more symptoms of headache or frequency of headache attacks in an individual (as compared to the level before treatment). For example, the duration or severity of head pain, or frequency of attacks is reduced by at least about any of 10%, 20%, 30%, 40%, 50%, 60%, or 70% in the individual as compared to the level before treatment.

As used herein, a "headache hour" refers to an hour during which a subject experiences headache. Headache hours can be expressed in terms of whole hours (e.g., one headache hour, two headache hours, three headache hours, etc.) or in terms of whole and partial hours (e.g., 0.5 headache hours, 1.2 headache hours, 2.67 headache hours, etc.). One or more headache hours may be described with respect to a particular time interval. For example, "daily headache hours" may refer to the number of headache hours a subject experiences within a day interval (e.g., a 24-hour period). In another example, "weekly headache hours" may refer to the number of headache hours a subject experiences within a week interval (e.g., a 7-day period). As can be appreciated, a week interval may or may not correspond to a calendar week. In another example, "monthly headache hours" may refer to the number of headache hours a subject experiences within a month interval. As can be appreciated, a month interval (e.g., a period of 28-31 days) may vary in terms of number of days depending upon the particular month and may or may not correspond to a calendar month. In yet another example, "yearly headache hours" may refer to the number of headache hours a subject experiences within a year interval. As can be appreciated, a year interval (e.g., a period of 365 or 366 days) may vary in terms of number of days depending upon the particular year and may or may not correspond to a calendar year. In some embodiments, a headache hour may with reference to a particular type of headache (e.g., migraine, cluster headache, chronic headache, and tension headache). For example a "migraine hour" may refer to an hour during which a subject experiences migraine.

As used herein, a "headache day" refers to a day during which a subject experiences headache. Headache days can be expressed in terms of whole days (e.g., one headache day, two headache days, three headache days, etc.) or in terms of whole and partial days (e.g., 0.5 headache days, 1.2 headache days, 2.67 headache days, etc.). One or more headache days may be described with respect to a particular time interval. For example, "weekly headache days" may refer to the number of headache days a subject experiences within a week interval (e.g., a 7-day period). As can be appreciated, a week interval may or may not correspond to a calendar week. In another example, "monthly headache days" may refer to the number of headache days a subject experiences within a month interval. As can be appreciated, a month interval (e.g., a period of 28-31 days) may vary in terms of number of days depending upon the particular month and may or may not correspond to a calendar month. In yet another example, "yearly headache days" may refer to the number of headache days a subject experiences within a year interval. As can be appreciated, a year interval (e.g., a period of 365 or 366 days) may vary in terms of number of days depending upon the particular year and may or may not correspond to a calendar year. In some embodiments, a headache day may be with reference to a particular type of headache (e.g., migraine, cluster headache, chronic headache, and tension headache). For example a "migraine day" may refer to a day during which a subject experiences migraine.

As used therein, "delaying" the development of headache means to defer, hinder, slow, retard, stabilize, and/or postpone progression of the disease. This delay can be of varying lengths of time, depending on the history of the disease and/or individuals being treated. As is evident to one skilled in the art, a sufficient or significant delay can, in effect, encompass prevention, in that the individual does not develop headache (e.g., migraine). A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of headache means initial manifestations and/or ensuing progression of the disorder. Development of headache can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of headache includes initial onset and/or recurrence.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as reducing pain intensity, duration, or frequency of headache attack, and decreasing one or more symptoms resulting from headache (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably a human. Mammals also include, but are not limited to, farm animals, sport animals, pets, primates, horses, dogs, cats, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

As used herein, the term "vasomotor symptom," is intended to refer to conditions related to vasodilation. Such vasodilation can be associated or potentially associated with headache (such as migraine with or without aura; hemiplegic migraine; chronic migraine; episodic migraine; high frequency episodic migraine; cluster headaches; migrainous neuralgia; chronic headaches; tension headaches; headaches resulting from other medical conditions (such as infection or increased pressure in the skull due to a tumor); chronic paroxysmal hemicrania; miscellaneous headache unassociated with a structural lesion; headache associated with a non-vascular intracranial disorder; headache associated with the administration of a substance or its withdrawal; headache associated with noncephalic infection; headache associated with a metabolic disorder; headache associated with a disorder of the cranium, neck, eyes, ears, nose, sinuses, teeth, mouth or other facial or cranial structure; cranial neuralgias; and nerve trunk pain and deafferentiation pain), hot flushing (or hot flashes), cold flashes, insomnia, sleep disturbances, mood disorders, irritability, excessive perspiration, night sweats, day sweats, fatigue, and the like, caused by, inter alia, thermoregulatory dysfunction.

As used herein, the terms "flushing", "hot flush" and "hot flash" are art-recognized terms that refer to an episodic disturbance in body temperature typically consisting of a sudden skin flushing, usually accompanied by perspiration in a subject.

A. Methods for Preventing or Treating Vasomotor Symptoms and/or Headache

In one aspect, the invention provides a method of treating or reducing incidence of at least one vasomotor symptom in a subject. In another aspect, the invention provides a method of treating or reducing incidence of headache (e.g., migraine) in a subject. In some embodiments, the method comprises administering to the individual an effective amount of an antibody or polypeptides derived from the antibody that modulates the CGRP pathway (e.g. a monoclonal anti-CGRP antagonist antibody). In some embodiments, the at least one vasomotor symptom may be associated with headache (e.g., migraine) and/or hot flushes.

In another aspect, the invention provides a method for ameliorating, controlling, reducing incidence of, or delaying the development or progression of at least one vasomotor symptom in an individual comprising administering to the individual an effective amount of an anti-CGRP antagonist antibody. In some embodiments, the at least one vasomotor symptom may be associated with headache (e.g., migraine) and/or hot flushes.

In another aspect, the invention provides methods for ameliorating, controlling, reducing incidence of, or delaying the development or progression of headache (e.g., migraine) in an individual or symptoms associated with headache (e.g., diarrhea or light sensitivity) comprising administering to the individual an effective amount of an antibody that modulates the CGRP pathway or an anti-CGRP antagonist antibody in combination with at least one additional agent useful for treating headache.

Such additional agents include, but are not limited to, 5-HT agonists and NSAIDs. For example, the antibody and the at least one additional agent can be concomitantly administered, i.e., they can be given in close enough temporal proximity to allow their individual therapeutic effects to overlap. For example, the amount of 5-HT agonist or NSAID administered in combination with an anti-CGRP antibody should be sufficient to reduce the frequency of headache relapse in patients or produce longer lasting efficacy compared to the administration of either one of these agents in the absence of the other. This procedure may be used to treat headaches falling into any of a wide variety of classes including: migraine with or without aura; hemiplegic migraine; chronic migraine; episodic migraine; high frequency episodic migraine; cluster headaches; migrainous neuralgia; chronic headaches; tension headaches; headaches resulting from other medical conditions (such as infection or increased pressure in the skull due to a tumor); chronic paroxysmal hemicrania; miscellaneous headache unassociated with a structural lesion; headache associated with a non-vascular intracranial disorder; headache associated with the administration of a substance or its withdrawal; headache associated with noncephalic infection; headache associated with a metabolic disorder; headache associated with a disorder of the cranium, neck, eyes, ears, nose, sinuses, teeth, mouth or other facial or cranial structure; cranial neuralgias; and nerve trunk pain and deafferentiation pain.

Additional non-limiting examples of additional agents that may be administered in combination with an anti-CGRP antagonist antibody include one or more of:

(i) an opioid analgesic, e.g., morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(ii) a nonsteroidal antiinflammatory drug (NSAID), e.g., aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof;

(iii) a barbiturate sedative, e.g., amobarbital, aprobarbital, butabarbital, butalbital, mephobarbital, metharbital, methohexital, pentobarbital, phenobartital, secobarbital, talbutal, theamylal or thiopental or a pharmaceutically acceptable salt thereof;

(iv) a barbiturate analgesic, e.g., butalbital or a pharmaceutically acceptable salt thereof or a composition comprising butalbital.

(v) a benzodiazepine having a sedative action, e.g., chlordiazepoxide, clorazepate, diazepam, flurazepam, lorazepam, oxazepam, temazepam or triazolam or a pharmaceutically acceptable salt thereof;

(vi) an $H_1$ antagonist having a sedative action, e.g., diphenhydramine, pyrilamine, promethazine, chlorpheniramine or chlorocyclizine or a pharmaceutically acceptable salt thereof;

(vii) a sedative such as glutethimide, meprobamate, methaqualone or dichloralphenazone or a pharmaceutically acceptable salt thereof;

(viii) a skeletal muscle relaxant, e.g., baclofen, carisoprodol, chlorzoxazone, cyclobenzaprine, methocarbamol or orphrenadine or a pharmaceutically acceptable salt thereof;

(ix) an NMDA receptor antagonist, e.g., dextromethorphan ((+)-3-hydroxy-N-methylmorphinan) or its metabolite dextrorphan ((+)-3-hydroxy-N-methylmorphinan), ketamine, memantine, pyrroloquinoline quinone or cis-4-(phosphonomethyl)-2-piperidinecarboxylic acid or a pharmaceutically acceptable salt thereof;

(x) an alpha-adrenergic, e.g., doxazosin, tamsulosin, clonidine or 4-amino-6,7-dimethoxy-2-(5-methanesulfonamido-1,2,3,4-tetrahydroisoquinol-2-yl)-5-(2-pyridyl) quinazoline;

(xi) a tricyclic antidepressant, e.g., desipramine, imipramine, amytriptiline or nortriptiline;

(xii) an anticonvulsant, e.g., carbamazepine or valproate;

(xiii) a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant or 3-[[2-methoxy-5-(trifluoromethoxy)phenyl]methylamino]-2-phenyl-piperidine (2S, 3S);

(xiv) a muscarinic antagonist, e.g., oxybutin, tolterodine, propiverine, tropsium chloride or darifenacin; (xv) a COX-2 inhibitor, e.g., celecoxib, rofecoxib or valdecoxib;

(xvi) a non-selective COX inhibitor (preferably with GI protection), e.g., nitroflurbiprofen (HCT-1026);

(xvii) a coal-tar analgesic, in particular paracetamol;

(xviii) a neuroleptic such as droperidol;

(xix) a vanilloid receptor agonist (e.g., resinferatoxin) or antagonist (e.g., capsazepine);

(xix) a beta-adrenergic such as propranolol;

(xx) a local anaesthetic, such as mexiletine;

(xxi) a corticosteriod, such as dexamethasone;

(xxii) a serotonin receptor agonist or antagonist;

(xxiii) a cholinergic (nicotinic) analgesic;

(xxiv) Tramadol (trade mark);

(xxv) a PDEV inhibitor, such as sildenafil, vardenafil or taladafil;

(xxvi) an alpha-2-delta ligand such as gabapentin or pregabalin;

(xxvii) a canabinoid; and (xxviii) an antidepressant, such as amitriptyline (Elavil), trazodone (Desyrel), and imipramine (Tofranil) or anticonvulsants such as phenytoin (Dilantin) or carbamazepine (Tegretol).

Those skilled in the art will be able to determine appropriate dosage amounts for particular agents to be used in combination with an anti-CGRP antibody. For example, sumatriptan may be administered in a dosage from about 0.01 to about 300 mg. In some cases, sumatriptan may be administered in a dosage from 2 mg to 300 mg. When administered non-parenterally, the typical dosage of sumatriptan is from about 25 to about 100 mg with about 50 mg being generally preferred and, when administered parenterally, the preferred dosage is about 6 mg. However, these dosages may be varied according to methods standard in the art so that they are optimized for a particular patient or for a particular combination therapy. Further, for example, celecoxib may be administered in an amount of between 50 and 500 mg.

In another aspect, the invention provides methods for ameliorating, controlling, reducing incidence of, or delaying the development or progression of hot flushes in an individual comprising administering to the individual an effective amount of an anti-CGRP antagonist antibody in combination with at least one additional agent useful for treating hot flushes. Such additional agents include, but are not limited to, hormone-based treatments, including estrogens and/or some progestins.

In another aspect, the disclosure provides a method of treating or reducing incidence of headache (e.g., migraine) in a subject comprising administering to the subject on a plurality of days an amount of a monoclonal antibody (e.g., a monoclonal, anti-CGRP antagonist antibody) that modulates the CGRP pathway. In some embodiments, the amount of the monoclonal antibody administered on each of the plurality of days may be between 0.1 mg-5000 mg, 1 mg-5000 mg, 10 mg-5000 mg, 100 mg-5000 mg, 1000 mg-5000 mg, 0.1 mg-4000 mg, 1 mg-4000 mg, 10 mg-4000 mg, 100 mg-4000 mg, 1000 mg-4000 mg, 0.1 mg-3000 mg, 1 mg-3000 mg, 10 mg-3000 mg, 100 mg-3000 mg, 1000 mg-3000 mg, 0.1 mg-2000 mg, 1 mg-2000 mg, 10 mg-2000 mg, 100 mg-2000 mg, 1000 mg-2000 mg, 0.1 mg-1000 mg, 1 mg-1000 mg, 10 mg-1000 mg or 100 mg-1000 mg. In some embodiments, the amount is between 100-2000 mg.

In another aspect, the disclosure provides a method of treating or reducing incidence of headache (e.g., migraine) in a subject comprising administering to the subject a single dose of a monoclonal antibody (e.g., a monoclonal, anti-CGRP antagonist antibody) in an amount that modulates the CGRP pathway. In some embodiments, the single dose may be an amount of antibody between 0.1 mg-5000 mg, 1 mg-5000 mg, 10 mg-5000 mg, 100 mg-5000 mg, 1000 mg-5000 mg, 0.1 mg-4000 mg, 1 mg-4000 mg, 10 mg-4000 mg, 100 mg-4000 mg, 1000 mg-4000 mg, 0.1 mg-3000 mg, 1 mg-3000 mg, 10 mg-3000 mg, 100 mg-3000 mg, 1000 mg-3000 mg, 0.1 mg-2000 mg, 1 mg-2000 mg, 10 mg-2000 mg, 100 mg-2000 mg, 1000 mg-2000 mg, 0.1 mg-1000 mg, 1 mg-1000 mg, 10 mg-1000 mg or 100 mg-1000 mg. In some embodiments, the single dose may be an amount of antibody between 100-2000 mg.

In another aspect, the disclosure provides a method of treating or reducing incidence of at least one vasomotor symptom in a subject comprising administering to the subject on a plurality of days an amount of a monoclonal antibody (e.g., a monoclonal, anti-CGRP antagonist antibody) that modulates the CGRP pathway. In some embodiments, the amount of the monoclonal antibody administered on each of the plurality of days may be between 0.1 mg-5000 mg, 1 mg-5000 mg, 10 mg-5000 mg, 100 mg-5000 mg, 1000 mg-5000 mg, 0.1 mg-4000 mg, 1 mg-4000 mg, 10 mg-4000 mg, 100 mg-4000 mg, 1000 mg-4000 mg, 0.1 mg-3000 mg, 1 mg-3000 mg, 10 mg-3000 mg, 100 mg-3000 mg, 1000 mg-3000 mg, 0.1 mg-2000 mg, 1 mg-2000 mg, 10 mg-2000 mg, 100 mg-2000 mg, 1000 mg-2000 mg, 0.1 mg-1000 mg, 1 mg-1000 mg, 10 mg-1000 mg or 100 mg-1000 mg. In some embodiments, the amount is between 100-2000 mg.

In another aspect, the disclosure provides a method of decreasing a number of monthly headache hours experienced by a subject, comprising administering to the subject an amount of a monoclonal antibody (e.g., a monoclonal, anti-CGRP antagonist antibody) that modulates the CGRP pathway. In some embodiments, the monoclonal antibody can be in an amount effective to decrease the number of monthly headache hours by at least 0.1, 1, 5, 10, 15, 20, 25, 30, 35, 40, 45, 50, 55, 60, 65, 70, 75, 80, 85, 90, 95, 100 or more headache hours after a single dose. In some embodiments, the monoclonal can be in an amount effective to decrease the number of monthly headache hours by at least 20 headache hours after a single dose. In some embodiments, the monoclonal antibody can be in an amount effective to decrease the number of monthly headache hours by at least 40 headache hours. In some embodiments, the monoclonal antibody can be in an amount effective to decrease the number of monthly headache hours by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or more after a single dose. In some embodiments, the monoclonal can be in an amount effective to decrease the number of monthly headache hours by at least 15% after a single dose.

In another aspect, the disclosure provides a method of decreasing a number of monthly headache days experienced by a subject, comprising administering to the subject an amount of a monoclonal antibody (e.g., a monoclonal, anti-CGRP antagonist antibody) that modulates the CGRP pathway. In some embodiments, the monoclonal antibody can be in an amount effective to decrease the number of monthly headache days by at least 3, 4, 5, 6, 7, 8, 9, 10, 11, 12, 13, 14, 15, 16, 17, 18, 19, 20 or more headache days after a single dose. In some embodiments, the monoclonal antibody can be in an amount effective to decrease the number of monthly headache days by at least 3 headache days after a single dose. In some embodiments, the monoclonal antibody can be in an amount effective to decrease the number of monthly headache days by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or more after a single dose.

In another aspect, the disclosure provides a method of decreasing use of an anti-headache medication in a subject, comprising administering to the subject a monoclonal antibody (e.g., a monoclonal anti-CGRP antagonist antibody) that modulates the CGRP pathway. In some embodiments, the monoclonal antibody can be in an amount effective to decrease monthly use of the anti-headache medication by the subject by at least 0.1%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or more. In some embodiments, the monoclonal antibody can be in an amount effective to decrease monthly use of the anti-headache medication by the subject by at least 15%. The anti-headache medication can be any type of anti-headache medication described elsewhere herein. Non-limiting examples of anti-headache medications include 5-HT1 agonists (and agonists acting at other 5-HT1 sites), triptans (e.g., sumatriptan, zolmitriptan, naratriptan, rizatriptan, eletriptan, almotriptan, afrovatriptan), ergot alkaloids (e.g., ergotamine tartrate, ergonovine maleate, and ergoloid mesylates (e.g., dihydroergocornine, dihydroergocristine, dihydroergocryptine, and dihydroergotamine mesylate (DHE 45)) and non-steroidal anti-inflammatory drugs (NSAIDs) (e.g., aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin or zomepirac, cyclooxygenase-2 (COX-2) inhibitors, celecoxib; rofecoxib; meloxicam; JTE-522; L-745,337; NS398; or a pharmaceutically acceptable salt thereof), opiates (e.g., oxycodone) and β-adrenergic antagonists (e.g., propranolol).

With respect to all methods described herein, references to antibodies (e.g., monoclonal antibodies that modulate the CGRP pathway, anti-CGRP antagonist antibodies, monoclonal anti-CGRP antagonist antibodies) also include compositions comprising one or more of these agents. Accordingly, such a composition may be used according to a method referring to an antibody described herein. These compositions may further comprise suitable excipients, such as pharmaceutically acceptable excipients as described elsewhere herein. The present invention can be used alone or in combination with other conventional methods of treatment.

An antibody described herein (e.g., a monoclonal antibody, an anti-CGRP antagonist antibody, a monoclonal anti-CGRP antagonist antibody) can be administered to an individual or subject in any therapeutic dose, via any suitable route and in any suitable formulation. It should be apparent to a person skilled in the art that the examples described herein are not intended to be limiting but to be illustrative of the techniques available. Accordingly, in some embodiments, an antibody described herein can be administered to an individual in accord with known methods, such as intravenous administration, e.g., as a bolus or by continuous infusion over a period of time, by intramuscular, intraperitoneal, intracerebrospinal, subcutaneous, intra-articular, sublingually, intra-arterial, intrasynovial, via insufflation, intrathecal, oral, inhalation, intranasal (e.g., with or without inhalation), buccal, rectal, transdermal, intracardiac, intraosseous, intradermal, transmucosal, vaginal, intravitreal, peri-articular, local, epicutaneous, or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, an antibody described herein can be aerosolized using a fluorocarbon formulation and a metered dose inhaler, or inhaled as a lyophilized and milled powder.

In some embodiments, an antibody described herein can be administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See e.g., PCT Publication No. WO 00/53211 and U.S. Pat. No. 5,981,568.

Various formulations of an antibody described herein may be used for administration. In some embodiments, an antibody may be administered neat. In some embodiments, antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and non-parenteral drug delivery are set forth in Remington, The Science and Practice of Pharmacy 20th Ed. Mack Publishing (2000).

In some embodiments, these agents, including antibodies described herein, may be formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

In some embodiments, these agents, including antibodies described herein, may be formulated for peripheral administration. Such formulations can be administered peripherally via any suitable peripheral route, including intravenously and subcutaneously. An agent prepared for peripheral administration can include a substance, medicament, and/or antibody that is not delivered centrally, spinally, intrathecally, or directly into the CNS. Non-limiting examples of peripheral administration routes include a route which is oral, sublingual, buccal, topical, rectal, via inhalation, transdermal, subcutaneous, intravenous, intra-arterial, intramuscular, intracardiac, intraosseous, intradermal, intraperitoneal, transmucosal, vaginal, intravitreal, intra-articular, peri-articular, local, or epicutaneous.

Therapeutic formulations of the antibodies used in accordance with the present disclosure can be prepared for storage and/or use by mixing an antibody having the desired degree of purity with optional pharmaceutically acceptable carriers, excipients or stabilizers (Remington, The Science and Practice of Pharmacy 20th Ed. Mack Publishing (2000)), and can in some cases be in the form of lyophilized formulations or aqueous solutions. Acceptable carriers, excipients, or stabilizers are nontoxic to recipients at the dosages and concentrations employed. A therapeutic formulation of an antibody may comprise one or more pharmaceutically acceptable carriers, excipients or stabilizes with non-limiting examples of such species that include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids (e.g., at concentrations of 0.1 mM to 100 mM, 0.1 mM to 1 mM, 0.01 mM to 50 mM, 1 mM to 50 mM, 1 mM to 30 mM, 1 mM to 20 mM, 10 mM to 25 mM) such as glycine, glutamine, methionine, asparagine, histidine, arginine, or lysine; monosaccharides, disaccharides, and other carbohydrates including glucose, mannose, or dextrins; chelating agents (e.g., at concentrations of 0.001 mg/mL to 1 mg/mL, 0.001 mg/mL to 1 mg/mL, 0.001 mg/mL to 0.1 mg/mL, 0.001 mg/mL to 0.01 mg/mL, 0.01 mg/mL to 0.1 mg/mL) such as EDTA (e.g., disodium EDTA dihydrate); sugars (e.g., at concentrations of 1 mg/mL to 500 mg/mL, 10 mg/mL to 200 mg/mL, 10 mg/mL to 100 mg/mL, 50 mg/mL to 150 mg/mL) such as sucrose, mannitol, trehalose or sorbitol; salt-forming counter-ions such as sodium; metal complexes (e.g. Zn-protein complexes); and/or non-ionic surfactants (e.g., at concentrations of 0.01 mg/mL to 10 mg/mL, 0.01 mg/mL to 1 mg/mL, 0.1 mg/mL to 1 mg/mL, 0.01 mg/mL to 0.5 mg/mL) such as TWEEN™ (e.g., polysorbate (e.g., polysorbate 20, polysorbate 40, polysorbate 60, polysorbate 80)), PLURONICS™ or polyethylene glycol (PEG).

An antibody formulation may be characterized in terms of any of a variety of physical properties. For example, a liquid antibody formulation may have any suitable pH for therapeutic efficacy, safety and storage. For example, the pH of a liquid antibody formulation may be from pH 4 to about pH 9, from pH 5 to pH 8, from pH 5 to pH 7 or from pH 6 to pH 8. In some embodiments, a liquid antibody formulation may have a pH of 3.0, 3.5, 4.0, 4.5, 5.0, 5.5, 6.0, 6.5, 7.0, 7.5, 8.0, 8.5, 9.0, 9.5 or 10 or higher or lower.

In another example, a liquid antibody formulation may have any suitable viscosity for therapeutic efficacy, safety and storage. For example, the viscosity of a liquid antibody formulation may be from 0.5 centipoise (cP) to 100 cP, 1 cP to 50 cP, 1 cP to 20 cP, 1 cP to 15 cP or 5 cP to 15 cP at 25° C. In some embodiments, a liquid antibody formulation may have a viscosity of 0.5 cP, 1 cP, 1.2 cP, 1.4 cP, 1.6 cP, 1.8 cP, 2.0 cP, 2.2 cP, 2.4 cP, 2.6 cP, 2.8 cP, 3.0 cP, 3.2 cP, 3.4 cP, 3.6 cP, 3.8 cP, 4.0 cP, 4.2 cP, 4.4 cP, 4.6 cP, 4.8 cP, 5.0 cP, 5.2 cP, 5.4 cP, 5.6 cP, 5.8 cP, 6.0 cP, 6.2 cP, 6.4 cP, 6.6 cP, 6.8 cP, 7.0 cP, 7.2 cP, 7.4 cP, 7.6 cP, 7.8 cP, 8.0 cP, 8.2 cP, 8.4 cP, 8.6 cP, 8.8 cP, 9.0 cP, 9.2 cP, 9.4 cP, 9.6 cP, 9.8 cP, 10.0 cP, 10.2 cP, 10.4 cP, 10.6 cP, 10.8 cP, 11.0 cP, 11.2 cP, 11.4 cP, 11.6 cP, 11.8 cP, 12.0 cP, 12.2 cP, 12.4 cP, 12.6 cP, 12.8 cP, 13.0 cP, 13.2 cP, 13.4 cP, 13.6 cP, 13.8 cP, 14.0 cP, 14.2 cP, 14.4 cP, 14.6 cP, 14.8 cP, or 15.0 cP at 25° C. or the viscosity may be higher or lower.

In another example, a liquid antibody formulation may have any suitable conductivity for therapeutic efficacy, safety and storage. For example, the conductivity of a liquid antibody formulation may be from 0.1 millisiemens per centimeter (mS/cm) to 15 mS/cm, 0.1 mS/cm to 10 mS/cm, 0.1 mS/cm to 5 mS/cm, 0.1 mS/cm to 2 mS/cm or 0.1 mS/cm to 1.5 mS/cm. In some embodiments, a liquid antibody formulation may have a conductivity of 0.19 mS/cm, 0.59 mS/cm, 1.09 mS/cm, 1.19 mS/cm, 1.29 mS/cm, 1.39 mS/cm, 1.49 mS/cm, 1.59 mS/cm, 1.69 mS/cm, 1.79 mS/cm, 1.89 mS/cm, 1.99 mS/cm, 2.09 mS/cm, 2.19 mS/cm, 2.29 mS/cm, 2.39 mS/cm, 2.49 mS/cm, 2.59 mS/cm, 2.69 mS/cm, 2.79 mS/cm, 2.89 mS/cm, 2.99 mS/cm, 3.09 mS/cm, 3.19 mS/cm, 3.29 mS/cm, 3.39 mS/cm, 3.49 mS/cm, 3.59 mS/cm, 3.69 mS/cm, 3.79 mS/cm, 3.89 mS/cm, 3.99 mS/cm, 4.09 mS/cm, 4.19 mS/cm, 4.29 mS/cm, 4.39 mS/cm, 4.49 mS/cm, 4.59 mS/cm, 4.69 mS/cm, 4.79 mS/cm, 4.89 mS/cm, 4.99 mS/cm, 5.09 mS/cm, 6.09 mS/cm, 6.59 mS/cm, 7.09 mS/cm, 7.59 mS/cm, 8.09 mS/cm, 8.59 mS/cm, 9.09 mS/cm, 9.59 mS/cm, 10.09 mS/cm, 10.59 mS/cm, 11.09 mS/cm, 11.59 mS/cm, 12.09 mS/cm, 12.59 mS/cm, 13.09 mS/cm, 13.59 mS/cm, 14.09 mS/cm, 14.59 mS/cm or 15.09 mS/cm or the conductivity may be higher or lower.

In another example, a liquid antibody formulation may have any suitable osmolality for therapeutic efficacy, safety and storage. For example, the osmolality of a liquid antibody formulation may be from 50 milliosmole per kilogram (mOsm/kg) to 5000 mOsm/kg, 50 mOsm/kg to 2000 mOsm/kg, 50 mOsm/kg to 1000 mOsm/kg, 50 mOsm/kg to 750 mOsm/kg or 50 mOsm/kg to 500 mOsm/kg. In some embodiments, a liquid antibody formulation may have an osmolality of 50 mOsm/kg, 60 mOsm/kg, 70 mOsm/kg, 80 mOsm/kg, 90 mOsm/kg, 100 mOsm/kg 120 mOsm/kg, 140 mOsm/kg, 160 mOsm/kg, 180 mOsm/kg, 200 mOsm/kg, 220 mOsm/kg, 240 mOsm/kg, 260 mOsm/kg, 280 mOsm/kg, 300 mOsm/kg, 320 mOsm/kg, 340 mOsm/kg, 360 mOsm/kg, 380 mOsm/kg, 400 mOsm/kg, 420 mOsm/kg, 440 mOsm/kg, 460 mOsm/kg, 480 mOsm/kg, 500 mOsm/kg, 520 mOsm/kg, 540 mOsm/kg, 560 mOsm/kg, 580 mOsm/kg, 600 mOsm/kg, 620 mOsm/kg, 640 mOsm/kg, 660 mOsm/kg, 680 mOsm/kg, 700 mOsm/kg, 720 mOsm/kg, 740 mOsm/kg, 760 mOsm/kg, 780 mOsm/kg, 800 mOsm/kg, 820 mOsm/kg, 840 mOsm/kg, 860 mOsm/kg, 880 mOsm/kg, 900 mOsm/kg, 920 mOsm/kg, 940 mOsm/kg, 960 mOsm/kg, 980 mOsm/kg, 1000 mOsm/kg, 1050 mOsm/kg, 1100 mOsm/kg, 1150 mOsm/kg, 1200 mOsm/kg, 1250 mOsm/kg, 1300 mOsm/kg, 1350 mOsm/kg, 1400 mOsm/kg, 1450 mOsm/kg, 1500 mOsm/kg or the osmolality may be higher or lower.

Liposomes containing antibody can be prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration should generally be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation. In some cases, a unit dosage form may be supplied in a prefilled receptacle (e.g., a prefilled syringe) useful in administering the unit dosage to a subject.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 lm, particularly 0.1 and 0.5 lm, and have a pH in the range of 5.5 to 8.0.

The emulsion compositions can be those prepared by mixing an antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

In some embodiments, a formulation comprising an antibody (e.g., monoclonal antibody that modulates the CGRP pathway, anti-CGRP antagonist antibody, monoclonal anti-CGRP antagonist antibody) described herein may be prepared for any suitable route of administration with an antibody amount ranging from 0.1 mg to 3000 mg, 1 mg to 1000 mg, 100 to 1000 mg, or 100 to 500 mg. In some cases, a formulation comprising an antibody (e.g., monoclonal antibody that modulates the CGRP pathway, anti-CGRP antagonist antibody, monoclonal anti-CGRP antagonist antibody) described herein may comprise an antibody amount of, at most, or at least 0.1 mg, 1 mg, 100 mg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg, or 3000 mg.

In some embodiments, a liquid formulation comprising an antibody (e.g., monoclonal antibody that modulates the CGRP pathway, anti-CGRP antagonist antibody, monoclonal anti-CGRP antagonist antibody) described herein may be prepared for any suitable route of administration with an antibody concentration ranging from 0.1 to 500 mg/mL, 0.1 to 375 mg/mL, 0.1 to 250 mg/mL, 0.1 to 175 mg/mL, 0.1 to 100 mg/mL, 1 mg/mL to 500 mg/mL, 1 mg/mL to 375 mg/mL, 1 mg/mL to 300 mg/mL, 1 mg/mL to 250 mg/mL, 1 mg/mL to 200 mg/mL, 1 mg/mL to 150 mg/mL, 1 mg/mL to 100 mg/mL, 10 mg/mL to 500 mg/mL, 10 mg/mL to 375 mg/mL, 10 mg/mL to 250 mg/mL, 10 mg/mL to 150 mg/mL, 10 mg/mL to 100 mg/mL, 100 mg/mL to 500 mg/mL, 100 mg/mL to 450 mg/mL, 100 mg/mL to 400 mg/mL, 100 mg/mL to 350 mg/mL, 100 mg/mL to 300 mg/mL, 100 mg/mL to 250 mg/mL, 100 mg/mL to 200 mg/mL or 100 mg/mL to 150 mg/mL. In some embodiments, a liquid formulation may comprise an antibody described herein at a concentration of, of at most, of at least, or less than 0.1, 0.5, 1, 5, 10, 15 20, 25, 30, 35, 40, 45, 50, 55, 60, 65, 70, 75, 80, 85, 90, 95, 100, 105 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 mg/mL.

An antibody formulation may comprise one or more components including the antibody and other species described elsewhere herein. The antibody and other components may be in any suitable amount and/or any suitable concentration for therapeutic efficacy of the antibody, safety and storage. In one example, an antibody formulation may be a solution comprising 51.4 mg/mL antibody (e.g., antibody G1, another anti-CGRP antagonist antibody, a monoclonal antibody that modulates the CGRP pathway), 20 mM histidine, 0.1 mg/mL methionine, 84 mg/mL trehalose dihydrate, 0.05 mg/mL disodium EDTA dihydrate, and 0.2 mg/mL polysorbate 80.

In another example, an antibody formulation may comprise 200 mg/mL antibody (e.g., antibody G1, another anti-CGRP antagonist antibody, a monoclonal antibody that modulates the CGRP pathway), 15 mM arginine, 78 mg/mL sucrose, 0.3 mg/mL EDTA, and 0.1 mg/mL polysorbate 80.

In another example, an antibody formulation may comprise 175 mg/mL antibody (e.g., antibody G1, another anti-CGRP antagonist antibody, a monoclonal antibody that modulates the CGRP pathway), 20 mM glycine, 88 mg/mL trehalose dihydrate, 0.015 mg/mL EDTA and 0.25 mg/mL polysorbate 80.

In another example, an antibody formulation may comprise 225 mg/mL antibody (e.g., antibody G1, another anti-CGRP antagonist antibody, a monoclonal antibody that modulates the CGRP pathway), 23 mM asparagine, 84 mg/mL sorbitol, 0.1 mg/mL EDTA and 0.15 mg/mL polysorbate 60.

In another example, an antibody formulation may comprise 150 mg/mL antibody (e.g., antibody G1, another anti-CGRP antagonist antibody, a monoclonal antibody that modulates the CGRP pathway), 17 mM asparagine, 74 mg/mL mannitol, 0.025 mg/mL EDTA and 0.2 mg/mL polysorbate 80.

In another example, an antibody formulation may comprise 100 mg/mL antibody (e.g., antibody G1, another anti-CGRP antagonist antibody, a monoclonal antibody that modulates the CGRP pathway), 16 mM arginine, 87 mg/mL mannitol, 0.025 mg/mL EDTA and 0.15 mg/mL polysorbate 20.

In another example, an antibody formulation may comprise 250 mg/mL antibody (e.g., antibody G1, another anti-CGRP antagonist antibody, a monoclonal antibody that modulates the CGRP pathway), 25 mM histidine, 74 mg/mL mannitol, 0.025 mg/mL EDTA and 0.25 mg/mL polysorbate 20.

In another example, an antibody formulation may comprise 50 mg/mL antibody (e.g., antibody G1, another anti-CGRP antagonist antibody, a monoclonal antibody that modulates the CGRP pathway), 19 mM arginine, 84 mg/mL sucrose, 0.05 mg/mL EDTA and 0.3 mg/mL polysorbate 80.

In another example, an antibody formulation may comprise 125 mg/mL antibody (e.g., antibody G1, another anti-CGRP antagonist antibody, a monoclonal antibody that modulates the CGRP pathway), 22 mM glycine, 79 mg/mL trehalose dihydrate, 0.15 mg/mL EDTA and 0.15 mg/mL polysorbate 80.

In another example, an antibody formulation may be a solution comprising 175 mg/mL antibody (e.g., antibody G1, another anti-CGRP antagonist antibody, a monoclonal antibody that modulates the CGRP pathway), 20 mM histidine, 0.1 mg/mL methionine, 84 mg/mL trehalose dihydrate, 0.05 mg/mL disodium EDTA dihydrate, and 0.2 mg/mL polysorbate 80.

In another example, an antibody formulation may comprise 200 mg/mL antibody (e.g., antibody G1, another anti-CGRP antagonist antibody, a monoclonal antibody that modulates the CGRP pathway), 30 mM arginine, 78 mg/mL sucrose, 0.3 mg/mL EDTA, and 0.1 mg/mL polysorbate 80.

In another example, an antibody formulation may comprise 175 mg/mL antibody (e.g., antibody G1, another anti-CGRP antagonist antibody, a monoclonal antibody that modulates the CGRP pathway), 20 mM glycine, 88 mg/mL trehalose dihydrate, 0.015 mg/mL EDTA and 0.15 mg/mL polysorbate 80.

In another example, an antibody formulation may comprise 150 mg/mL antibody (e.g., antibody G1, another anti-CGRP antagonist antibody, a monoclonal antibody that modulates the CGRP pathway), 20 mM histidine, 84 mg/mL sucrose, 0.05 mg/mL EDTA and 0.2 mg/mL polysorbate 80.

In another example, an antibody formulation may comprise 225 mg/mL antibody (e.g., antibody G1, another anti-CGRP antagonist antibody, a monoclonal antibody that modulates the CGRP pathway), 23 mM histidine, 84 mg/mL sorbitol, 0.1 mg/mL EDTA and 0.15 mg/mL polysorbate 60.

In another example, an antibody formulation may comprise 150 mg/mL antibody (e.g., antibody G1, another anti-CGRP antagonist antibody, a monoclonal antibody that modulates the CGRP pathway), 17 mM asparagine, 74 mg/mL mannitol, 0.3 mg/mL EDTA and 0.2 mg/mL polysorbate 80.

In another example, an antibody formulation may comprise 100 mg/mL antibody (e.g., antibody G1, another anti-CGRP antagonist antibody, a monoclonal antibody that modulates the CGRP pathway), 16 mM arginine, 87 mg/mL mannitol, 0.025 mg/mL EDTA and 0.25 mg/mL polysorbate 20.

In another example, an antibody formulation may comprise 250 mg/mL antibody (e.g., antibody G1, another anti-CGRP antagonist antibody, a monoclonal antibody that modulates the CGRP pathway), 25 mM histidine, 89 mg/mL mannitol, 0.025 mg/mL EDTA and 0.25 mg/mL polysorbate 20.

In another example, an antibody formulation may comprise 125 mg/mL antibody (e.g., antibody G1, another anti-CGRP antagonist antibody, a monoclonal antibody that modulates the CGRP pathway), 29 mM arginine, 84 mg/mL sucrose, 0.05 mg/mL EDTA and 0.3 mg/mL polysorbate 80.

In another example, an antibody formulation may comprise 150 mg/mL antibody (e.g., antibody G1, another anti-CGRP antagonist antibody, a monoclonal antibody that modulates the CGRP pathway), 25 mM asparagine, 84 mg/mL mannitol, 0.05 mg/mL EDTA and 0.2 mg/mL polysorbate 80.

In another example, an antibody formulation may comprise 145 mg/mL antibody (e.g., antibody G1, another anti-CGRP antagonist antibody, a monoclonal antibody that modulates the CGRP pathway), 22 mM histidine, 72 mg/mL trehalose dihydrate, 0.05 mg/mL EDTA and 0.1 mg/mL polysorbate 80.

An antibody described herein can be administered using any suitable method, including by injection (e.g., intraperitoneally, intravenously, subcutaneously, intramuscularly, etc.). Antibodies can also be administered via inhalation, as described herein. In some cases, an antibody may be administered nasally with or without inhalation. Generally, for administration of an antibody described herein, an initial candidate dosage can be about 2 mg/kg. For the purpose of the present invention, a typical daily dosage might range from about any of 3 µg/kg to 30 µg/kg to 300 µg/kg to 3 mg/kg, to 30 mg/kg to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce pain. An exemplary dosing regimen comprises administering an initial dose of about 8.5 mg/kg, followed by a weekly maintenance dose of about 2.8 mg/kg of an antibody, or followed by a maintenance dose of about 2.8 mg/kg every other week. Another exemplary dosing regimen comprises administering a dose of 100 mg, 125 mg, 150 mg, 200 mg, 225 mg, 250 mg, 275 mg, 300 mg, 350 mg, 400 mg, 450 mg, 500 mg, 550 mg, 600 mg, 675 mg, or 900 mg to a subject once per month subcutaneously. Another exemplary dosing regimen comprises administering an initial dose of 675 mg subcutaneously, followed by a monthly dose of 225 mg of the antibody subcutaneously. However, other dosage regimens may be useful, depending on the pattern of pharmacokinetic decay that the practitioner wishes to achieve. For example, in some embodiments, dosing from one-four times a week is contemplated. The progress of this therapy is easily monitored by conventional techniques and assays. The dosing regimen (including the CGRP antagonist(s) used) can vary over time.

In some embodiments, the dose or amount of an antibody (e.g., monoclonal antibody that modulates the CGRP pathway, anti-CGRP antagonist antibody, monoclonal anti-CGRP antagonist antibody) described herein and administered to a subject may range from 0.1 µg to 3000 mg, 1 mg to 1000 mg, 100 to 1000 mg, 100 to 500 mg, 0.1 mg to 5000 mg, 1 mg to 4000 mg, 250 mg to 1000 mg, 500 mg to 1000 mg, 100 mg to 900 mg, 400 mg to 900 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg. In some embodiments, the dose or amount of an antibody described herein and administered to a subject may be, may be at most, may be less than, or may be at least 0.1 µg, 1 µg, 100 µg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg, or 3000 mg. In some embodiments, the amount is between 100 to 2000 mg.

In some embodiments, the dose or amount of an antibody (e.g., monoclonal antibody that modulates the CGRP pathway, anti-CGRP antagonist antibody, monoclonal anti-CGRP antagonist antibody) described herein and administered to a subject may range from 0.1 to 500, 0.1 to 100, 0.1 to 50, 0.1 to 20, 0.1 to 10, 1 to 10, 1 to 7, 1 to 5 or 0.1 to 3 mg/kg of body weight. In some embodiments, the dose or amount of an antibody (e.g., monoclonal antibody that modulates the CGRP pathway, anti-CGRP antagonist antibody, monoclonal anti-CGRP antagonist antibody) described herein and administered to a subject may be, may be at most, may be less than, or may be at least 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, or 500 mg/kg of body weight.

In some embodiments, the frequency at which a dose or amount of an antibody (e.g., monoclonal antibody that modulates the CGRP pathway, anti-CGRP antagonist antibody, monoclonal anti-CGRP antagonist antibody) described herein is administered to a subject may vary. In some embodiments, a single dose of antibody may be given to a subject across therapy. In some embodiments, the frequency at which a dose or amount of an antibody is administered to a subject is constant (e.g., administered once per month). In some embodiments, the frequency at which a dose or amount of an antibody described herein is administered to a subject is variable (e.g., an initial dose followed by a dose at one month, followed by additional doses at three months and seven months). In some embodiments, the frequency at which an antibody is administered to a subject is, is at least, is less than, or is at most one, two, three, four, five, or six times per day. In some embodiments, the frequency at which an antibody (e.g., monoclonal antibody that modulates the CGRP pathway, anti-CGRP antagonist antibody, monoclonal anti-CGRP antagonist antibody) is administered to a subject is, is at least, is less than, or is at most one, two, three, four, five, or six dose(s) per day.

In some embodiments, the frequency at which a dose or amount of an antibody (e.g., monoclonal antibody that modulates the CGRP pathway, anti-CGRP antagonist antibody, monoclonal anti-CGRP antagonist antibody) described herein is administered to a subject is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-five, sixty, sixty-five, seventy, seventy-five, eighty, eighty-five, ninety, ninety-five, one-hundred, one-hundred twenty-five, one-hundred fifty, one-hundred eighty, or two-hundred day(s).

In some embodiments, the frequency at which a dose or amount of an antibody (e.g., monoclonal antibody that modulates the CGRP pathway, anti-CGRP antagonist antibody, monoclonal anti-CGRP antagonist antibody) described herein is administered to a subject is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty-nine, forty, forty-one, forty-two, forty-three, forty-four, forty-five, forty-six, forty-seven, forty-eight, forty-nine, fifty, fifty-five, sixty, sixty-five, seventy, seventy-five, eighty, eighty-five, ninety, ninety-five, or one-hundred week(s). In some embodiments, the frequency at which an antibody (e.g., monoclonal antibody that modulates the CGRP pathway, anti-CGRP antagonist antibody, monoclonal anti-CGRP antagonist antibody) described herein is administered to a subject is less than one, two, three, four, five, six, seven, eight, nine, ten, eleven, twelve, thirteen, fourteen, or fifteen dose(s) per week.

In some embodiments, the frequency at which a dose or amount of an antibody (e.g., monoclonal antibody that modulates the CGRP pathway, anti-CGRP antagonist antibody, monoclonal anti-CGRP antagonist antibody) is administered to a subject is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every month, every two months, every three months, every four months, every five months, every six months, every seven months, every eight months, every nine months, every ten months, every eleven months, every twelve months, every thirteen months, every fourteen months, every fifteen months, every sixteen months, every seventeen months, or every eighteen month(s). In some embodiments, the frequency at which an antibody (e.g., monoclonal antibody that modulates the CGRP pathway, anti-CGRP antagonist antibody, monoclonal anti-CGRP antagonist antibody) described herein is administered to a subject is less than one, two, three, four, five, six, seven, eight, nine, ten, eleven, twelve, thirteen, fourteen, or fifteen dose(s) per month. In some embodiments, a dose or amount of an antibody may be administered (e.g., subcutaneously or intravenously) to a subject one time, two times, three times, four times, five times, six times, seven times, eight times, nine times, ten times or more per month.

In some embodiments, an antibody in a dose or amount of 50 mg, 100 mg 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously) to a subject once per month. In some embodiments, an antibody in a dose or amount of between 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered (e.g., subcutaneously or intravenously) to a subject once per month. In some embodiments, between 100-2000 mg of antibody are administered once per month.

In some embodiments, an antibody in a dose or amount of 50 mg, 100 mg 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously) to a subject every three months. In some embodiments, an antibody in a dose or amount of between 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered (e.g., subcutaneously or intravenously) to a subject every three months. In some embodiments, between 450 mg to 2000 mg is administered once every three months or less.

In some embodiments, an antibody in a dose or amount of 50 mg, 100 mg 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously) to a subject every six months. In some embodiments, an antibody in a dose or amount of between 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered (e.g., subcutaneously or intravenously) to a subject every six months. In some embodiments, between 450 mg to 2000 mg is administered once every six months or less.

In some embodiments, the frequency at which a dose or amount of an antibody (e.g., monoclonal antibody that modulates the CGRP pathway, anti-CGRP antagonist antibody, monoclonal anti-CGRP antagonist antibody) is administered to a subject (e.g., subcutaneously or intravenously) is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every quarter. As can be appreciated, a "quarter" can refer to a time period of a quarter year or may also refer to a calendar quarter such as a time period of January 1-March 31, April 1-June 30, July 1-September 30 or October 1-December 31. In some cases, a "quarter" may refer to a time period of approximately three months.

In some embodiments, an antibody in a dose or amount of 50 mg, 100 mg 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered (e.g., subcutaneously or intravenously) to a subject every quarter. In some embodiments, an antibody in a dose or amount of between 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered (e.g., subcutaneously or intravenously) to a subject every quarter.

In some embodiments, the frequency at which a dose or amount of an antibody (e.g., monoclonal antibody that modulates the CGRP pathway, anti-CGRP antagonist antibody, monoclonal anti-CGRP antagonist antibody) is administered is, is at least, is less than, or is at most one, two, three, four, five, six, seven, eight, nine, ten, eleven, twelve, thirteen, fourteen, fifteen, sixteen, seventeen, eighteen, nineteen, or twenty time(s) per every year, every two years, every three years, every four years, or every five years. In some embodiments, the frequency at which an antibody (e.g., monoclonal antibody that modulates the CGRP pathway, anti-CGRP antagonist antibody, monoclonal anti-CGRP antagonist antibody) is administered to a subject is less than one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four or twenty-five dose(s) per year.

In some embodiments, an antibody in a dose or amount of 50 mg, 100 mg 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, 2000 mg, 2050 mg, 2100 mg, 2150 mg, 2200 mg, 2250 mg, 2300 mg, 2350 mg, 2400 mg, 2450 mg, 2500 mg, 2550 mg, 2600 mg, 2650 mg, 2700 mg, 2750 mg, 2800 mg, 2850 mg, 2900 mg, 2950 mg, 3000 mg, or more may be administered to a subject every once per year. In some embodiments, an antibody in a dose or amount of between 0.1 mg to 5000 mg, 1 mg to 4000 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg may be administered to a subject every once per year. In some embodiments, between 450 mg to 2000 mg is administered once every year or less.

In some embodiments, a method may comprise administering an antibody (e.g., monoclonal antibody that modulates the CGRP pathway, anti-CGRP antagonist antibody, monoclonal anti-CGRP antagonist antibody) described herein to a subject on a plurality of days. Two, three, four, five, six, seven, eight or more days of the plurality of days may be more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75 or more days apart. In some embodiments, two of the plurality of days are more than one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty or more days apart. Moreover, in some embodiments, the amount of antibody administered on a first day of the plurality of days may be different (e.g., higher or lower) than the amount of the antibody administered on a second day.

In some embodiments, an initial dose (e.g., a loading dose) of an antibody (e.g., monoclonal antibody that modulates the CGRP pathway, anti-CGRP antagonist antibody, monoclonal anti-CGRP antagonist antibody) described herein may be administered to a subject, followed by administration of one or more additional doses at desired intervals. In some embodiments, the initial dose and one or more of the additional doses are the same dose. In some embodiments, the one or more additional doses are a different dose than the initial dose. In some embodiments, the frequency at which the one or more additional doses are administered is constant (e.g., every month). In some embodiments, the frequency at which the one or more additional doses are administered is variable (e.g., one additional dose administered at one month following the initial dose, followed by another additional dose at three months following the initial dose). Any desirable and/or therapeutic regimen of initial loading dose, additional doses, and frequency (e.g., including those described herein) of additional doses may be used. An exemplary regimen includes an initial loading dose of 675 mg anti-CGRP antagonist antibody administered subcutaneously, followed by subsequent maintenance doses of 225 mg of the antibody administered subcutaneously at one month intervals.

In some embodiments, an initial dose of an antibody (e.g., monoclonal antibody that modulates the CGRP pathway, anti-CGRP antagonist antibody, monoclonal anti-CGRP antagonist antibody) of 0.1 µg, 1 µg, 100 µg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1500 mg, 2000 mg, or 3000 mg may be administered to a subject followed by one or more additional doses of the antibody of 0.1 µg, 1 µg, 100 µg, 1 mg, 10 mg, 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1500 mg, 2000 mg, or 3000 mg.

In some embodiments, a dose or amount of antibody (e.g., monoclonal antibody that modulates the CGRP pathway, anti-CGRP antagonist antibody, monoclonal anti-CGRP antagonist antibody) described herein may be divided into sub-doses and administered as multiple sub-doses, depending, for example, on the route of administration and/or particular formulation administered. For example, in cases where a dose is administered subcutaneously, the subcutaneous dose may be divided into multiple sub-doses and each sub-dose administered at a different site in order to avoid, for example, a larger, single subcutaneous injection at a single site. For example, a subcutaneous dose of 900 mg may be divided into four sub-doses of 225 mg each and each 225 mg dose administered at a different site, which can help minimize the volume injected at each site. The division of sub-doses may be equal (e.g., 4 equal sub-doses) or may be unequal (e.g., 4 sub-doses, two of the sub-doses twice as large as the other sub-doses).

In some embodiments, the number of doses of antibody administered to a subject over the course of treatment may vary depending upon, for example, achieving reduced incidence of a vasomotor symptom and/or headache in the subject. In some embodiments, the vasomotor symptom is associated with a form of headache (e.g., migraine, chronic migraine, episodic migraine, other type of headache, etc.). For example, the number of doses administered over the course of treatment may be, may be at least, or may be at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some cases (e.g., in cases where a subject has chronic migraine), treatment may be given indefinitely. In some cases, treatment may be acute such that at most 1, 2, 3, 4, 5, or 6 doses are administered to a subject for treatment.

In some embodiments, a dose (or sub-dose) or amount of an antibody (e.g., monoclonal antibody that modulates the CGRP pathway, anti-CGRP antagonist antibody, monoclonal anti-CGRP antagonist antibody) described herein may be formulated in a liquid formulation and administered (e.g., via subcutaneous injection, via intravenous injection) to a subject. In such cases, the volume of liquid formulation comprising antibody may vary depending upon, for example, the concentration of antibody in the liquid formulation, the desired dose of antibody, and/or the route of administration used. For example the volume of liquid formulation comprising an antibody described herein and administered (e.g., via an injection, such as, for example, a subcutaneous injection or an intravenous injection) to a subject may be from 0.001 mL to 10.0 mL, 0.01 mL to 5.0 mL, 0.1 mL to 5 mL, 0.1 mL to 3 mL, 0.5 mL to 2.5 mL, or 1 mL to 2.5 mL. For example, the volume of liquid formulation comprising an antibody (e.g., monoclonal antibody that modulates the CGRP pathway, anti-CGRP antagonist antibody, monoclonal anti-CGRP antagonist antibody) described herein and administered (e.g., via an injection, such as, for example, a subcutaneous injection, an intravenous injection) to a subject may be, may be at least, may be less than, or may be at most 0.001, 0.005, 0.01, 0.02, 0.03, 0.04, 0.05, 0.06, 0.07, 0.08, 0.09, 0.10, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.5, 6.0, 6.5, 7.0, 7.5, 8.0, 8.5, 9.0, 9.5, or 10.0 mL.

In some embodiments, a dose (or sub-dose) or amount of an antibody (e.g., monoclonal antibody that modulates the CGRP pathway, anti-CGRP antagonist antibody, monoclonal anti-CGRP antagonist antibody) described herein may be supplied in prefilled receptacles useful in administering antibody to a subject. Such prefilled receptacles may be designed for self-administration or for administration by another. For example, a dose (or sub-dose) or amount of antibody described herein may be supplied as a liquid formulation in pre-filled syringes. In such examples, the pre-filled syringes may be designed for self-administration or for administration by another. In some cases, pre-filled syringes may be designed for subcutaneous administration and/or intravenous administration.

For the purpose of the present invention, the appropriate dosage of an antibody may depend on the antibody (or compositions thereof) employed, the type and severity of vasomotor symptom, the type and severity of headache (e.g., migraine) or other condition to be treated, whether the agent is administered for preventive or therapeutic purposes, previous therapy, the patient's clinical history and response to the agent, and the discretion of the attending physician. Typically the clinician will administer an antibody, until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of headache (e.g., migraine) or other condition. Alternatively, sustained continuous release formulations of antibodies may be appropriate. Various formulations and devices for achieving sustained release are known in the art.

In one embodiment, dosages for an antibody (e.g., monoclonal antibody that modulates the CGRP pathway, anti-CGRP antagonist antibody, monoclonal anti-CGRP antagonist antibody) described herein may be determined empirically in individuals who have been given one or more administration(s) of the antibody. Individuals are given incremental dosages of an antibody. To assess efficacy of an antibody, an indicator of the disease can be followed.

Administration of an antibody (e.g., monoclonal antibody that modulates the CGRP pathway, anti-CGRP antagonist antibody, monoclonal anti-CGRP antagonist antibody) in accordance with the methods of the present invention can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing headache (e.g., migraine); before; during; before and after; during and after; before and during; or before, during, and after developing headache. Administration can be before, during and/or after any event likely to give rise to headache.

In some embodiments, more than one antibody may be present. At least one, at least two, at least three, at least four, at least five different, or more antibodies can be present. Generally, those antibodies may have complementary activities that do not adversely affect each other. An antibody (e.g., monoclonal antibody that modulates the CGRP pathway, anti-CGRP antagonist antibody, monoclonal anti-CGRP antagonist antibody) described herein can also be used in conjunction with other CGRP antagonists or CGRP receptor antagonists. For example, one or more of the following CGRP antagonists may be used: an anti-sense molecule directed to a CGRP (including an anti-sense molecule directed to a nucleic acid encoding CGRP), a CGRP inhibitory compound, a CGRP structural analog, a dominant-negative mutation of a CGRP receptor that binds a CGRP, and an anti-CGRP receptor antibody. An antibody can also be used in conjunction with other agents that serve to enhance and/or complement the effectiveness of the agents.

Diagnosis or assessment of headache is well-established in the art. Assessment may be performed based on subjective measures, such as patient characterization of symptoms. For example, migraine may be diagnosed based on the following criteria: 1) episodic attacks of headache lasting 4 to 72 hours; 2) with two of the following symptoms: unilateral pain, throbbing, aggravation on movement, and pain of moderate or severe intensity; and 3) one of the following symptoms: nausea or vomiting, and photophobia or phonophobia. Goadsby et al., N. Engl. J. Med. 346:257-270, 2002. In some embodiments, assessment of headache (e.g., migraine) may be via headache hours, as described elsewhere herein. For example assessment of headache (e.g., migraine) may be in terms of daily headache hours, weekly headache hours, monthly headache hours and/or yearly headache hours. In some cases, headache hours may be as reported by the subject.

Treatment efficacy can be assessed by methods well-known in the art. For example, pain relief may be assessed. Accordingly, in some embodiments, pain relief is subjectively observed after 1, 2, or a few hours after administering an anti-CGRP antibody. In some embodiments, frequency of headache attacks is subjectively observed after administering an anti-CGRP antibody.

In some embodiments, a method for treating or reducing incidence of headache in a subject as described herein may reduce incidence of headache after a single administration of an antibody (e.g., monoclonal antibody that modulates the CGRP pathway, anti-CGRP antagonist antibody, monoclonal anti-CGRP antagonist antibody) described herein for an extended period of time. For example, incidence of headache may be reduced for at least 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more days after a single administration.

In some embodiments, a method for treating or reducing incidence of headache in a subject as described herein may reduce the number of headache hours experienced by a subject from a pre-administration level after administration of one or more doses of an antibody (e.g., monoclonal antibody that modulates the CGRP pathway, anti-CGRP antagonist antibody, monoclonal anti-CGRP antagonist antibody) described herein to the subject. For example, daily headache hours experienced by the subject after administering one or more doses of an antibody to the subject may be reduced by 0.5, 1, 2, 3, 4, 5, 6, 7, 8, 9, 10, 11, 12, 13, 14, 15, 16, 17, 18, 19, 20, 21, 22, 23 or 24 headache hours from a pre-administration level in the subject. In some cases, daily headache hours experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99% or more relative to a pre-administration level in the subject. In another example, weekly headache hours experienced by the subject after administering one or more doses of an antibody to the subject may be reduced by 0.5, 1, 5, 10, 15, 20, 25, 30, 35, 40, 45, 50, 55, 60, 65, 70, 75 or more headache hours from a pre-administration level in the subject. In some cases, weekly headache hours experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99% or more relative to a pre-administration level in the subject. In another example, monthly headache hours experienced by the subject after administering one or more doses of an antibody to the subject may be reduced by 0.5, 1, 5, 10, 15, 20, 25, 30, 35, 40, 45, 50, 55, 60, 65, 70, 75, 80, 85, 90, 95, 100, 105, 110, 115, 120, 125 or more headache hours from a pre-administration level. In some cases, weekly headache hours experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99% or more relative to a pre-administration level in the subject.

In some embodiments, a method for treating or reducing incidence of headache in a subject as described herein may reduce the number of headache days experienced by a subject from a pre-administration level after administration of one or more doses of an antibody (e.g., monoclonal antibody that modulates the CGRP pathway, anti-CGRP antagonist antibody, monoclonal anti-CGRP antagonist antibody) described herein to the subject. For example, weekly headache days experienced by the subject after administering one or more doses of an antibody to the subject may be reduced by 0.5, 1, 1.5, 2, 2.5, 3, 3.5, 4, 4.5, 5, 5.5, 6, 6.5, or 7 headache days from a pre-administration level in the subject. In some cases, weekly headache days experienced by the subject after administering one or more doses of an antibody to the subject may be reduced by 0.5%, 1%, 5%, 10%, 15%, 20%, 25%, 30%, 35%, 40%, 45%, 50%, 55%, 60%, 65%, 70%, 75%, 80%, 85%, 90%, 95%, 99% or more relative to a pre-administration level in the subject. In another example, monthly headache days experienced by the subject after administering one or more doses of an antibody to the subject may be reduced by 0.5, 1, 2, 3, 4, 5, 6, 7, 8, 9, 10, 15, 20 or more headache days from a pre-administration level.

In some embodiments, a method may comprise administering to a subject one or more additional agent(s) simultaneously or sequentially with an antibody (e.g., monoclonal antibody that modulates the CGRP pathway, anti-CGRP antagonist antibody, monoclonal anti-CGRP antagonist antibody). In some embodiments, an additional agent may be an anti-headache medication such as an example anti-headache medication (e.g., 5-HT1 agonists, triptans, ergot alkaloids, opiates, 3-adrenergic antagonists, NSAIDs) described elsewhere herein. In some embodiments, a therapeutic effect may be greater as compared to use of an antibody or one or more additional agent(s) alone. Accordingly, a synergistic effect between an antibody and the one or more additional agents may be achieved. In some embodiments, the one or more additional agent(s) may be taken by a subject prophylactically.

B. Anti-CGRP Antagonist Antibodies

In some embodiments, the methods of the invention use an antibody, which can be an anti-CGRP antagonist antibody. An anti-CGRP antagonist antibody can refer to any antibody molecule that blocks, suppresses or reduces (including significantly) CGRP biological activity, including downstream pathways mediated by CGRP signaling, such as receptor binding and/or elicitation of a cellular response to CGRP.

An anti-CGRP antagonist antibody can exhibit any one or more of the following characteristics: (a) bind to CGRP; (b) block CGRP from binding to its receptor(s); (c) block or decrease CGRP receptor activation (including cAMP activation); (d) inhibit CGRP biological activity or downstream pathways mediated by CGRP signaling function; (e) prevent, ameliorate, or treat any aspect of headache (e.g., migraine); (f) increase clearance of CGRP; and (g) inhibit (reduce) CGRP synthesis, production or release. Anti-CGRP antagonist antibodies are known in the art. See e.g., Tan et al., Clin. Sci. (Lond). 89:565-73, 1995; Sigma (Missouri, US), product number C7113 (clone #4901); Plourde et al., Peptides 14:1225-1229, 1993.

In some embodiments, the antibody reacts with CGRP in a manner that inhibits CGRP, and/or the CGRP pathway, including downstream pathways mediated by the CGRP signaling function. In some embodiments, the anti-CGRP antagonist antibody recognizes human CGRP. In some embodiments, the anti-CGRP antagonist antibody binds to both human α-CGRP and β-CGRP. In some embodiments, the anti-CGRP antagonist antibody binds human and rat CGRP. In some embodiments, the anti-CGRP antagonist antibody binds the C-terminal fragment having amino acids 25-37 of CGRP. In some embodiments, the anti-CGRP antagonist antibody binds a C-terminal epitope within amino acids 25-37 of CGRP.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the anti-CGRP antagonist antibody is a monoclonal antibody. In some embodiments, the anti-CGRP antagonist antibody is humanized. In some embodiments, the antibody is human. In some embodiments, the anti-CGRP antagonist antibody is antibody G1 (as described herein).

In some embodiments, the anti-CGRP antagonist antibody comprises one or more CDR(s) (such as one, two, three, four, five, or, in some embodiments, all six CDRs) of antibody G1 or variants of G1 shown in Table 6. In still other embodiments, the anti-CGRP antagonist antibody comprises the amino acid sequence of the heavy chain variable region shown in FIG. 5 (SEQ ID NO:1) and the amino acid sequence of the light chain variable region shown in FIG. 5 (SEQ ID NO:2).

In some embodiments, the antibody comprises a light chain variable region (LCVR) and a heavy chain variable region (HCVR) selected from the groups consisting of: (a) LCVR17 (SEQ ID NO: 58) and HCVR22 (SEQ ID NO: 59); (b) LCVR18 (SEQ ID NO: 60) and HCVR23 (SEQ ID NO: 61); (c) LCVR19 (SEQ ID NO: 62) and HCVR24 (SEQ ID NO: 63); (d) LCVR20 (SEQ ID NO: 64) and HCVR25 (SEQ ID NO: 65); (e) LCVR21 (SEQ ID NO: 66) and HCVR26 (SEQ ID NO: 67); (f) LCVR27 (SEQ ID NO: 68) and HCVR28 (SEQ ID NO: 69); (g) LCVR29 (SEQ ID NO: 70) and HCVR30 (SEQ ID NO: 71); (h) LCVR31 (SEQ ID NO: 72) and HCVR32 (SEQ ID NO: 73); (i) LCVR33 (SEQ ID NO: 74) and HCVR34 (SEQ ID NO: 75); (j) LCVR35 (SEQ ID NO: 76) and HCVR36 (SEQ ID NO: 77); and (k) LCVR37 (SEQ ID NO: 78) and HCVR38 (SEQ ID NO: 79). Sequences of these regions are provided herein. Other examples of antibodies are described in US20110305711, US20120294802, US20120294797, and US20100172895, which are incorporated herein by reference.

In some embodiments, the antibody comprises a modified constant region, such as a constant region that is immunologically inert described herein. In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In some embodiments, the antibody comprises a constant region of IgG4 comprising the following mutations: E233F234L235 to P233V234A235. In still other embodiments, the constant region is aglycosylated for N-linked glycosylation. In some embodiments, the constant region is aglycosylated for N-linked glycosylation by mutating the oligosaccharide attachment residue (such as Asn297) and/or flanking residues that are part of the N-glycosylation recognition sequence in the constant region. In some embodiments, the constant region is aglycosylated for N-linked glycosylation. The constant region may be aglycosylated for N-linked glycosylation enzymatically or by expression in a glycosylation deficient host cell.

The binding affinity ($K_D$) of an anti-CGRP antagonist antibody to CGRP (such as human $\alpha$-CGRP) can be about 0.02 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

One way of determining binding affinity of antibodies to CGRP is by measuring binding affinity of monofunctional Fab fragments of the antibody. To obtain monofunctional Fab fragments, an antibody (for example, IgG) can be cleaved with papain or expressed recombinantly. The affinity of an anti-CGRP Fab fragment of an antibody can be determined by surface plasmon resonance (Biacore3000™ surface plasmon resonance (SPR) system, Biacore, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated human CGRP (or any other CGRP) can be diluted into HBS-EP buffer to a concentration of less than 0.5 ug/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of CGRP on the chip for over 200 injections. Typically, serial dilutions (spanning concentrations of 0.1-10× estimated $K_D$) of purified Fab samples are injected for 1 min at 100 µL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any CGRP, including human CGRP, CGRP of another mammalian (such as mouse CGRP, rat CGRP, primate CGRP), as well as different forms of CGRP (such as a and 3 form). Binding affinity of an antibody is generally measured at 25° C., but can also be measured at 37° C.

Antibodies, including anti-CGRP antagonist antibodies, may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce monoclonal antibodies (e.g., monoclonal the anti-CGRP antibodies) of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for CGRP, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human CGRP, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaradehyde, succinic anhydride, SOCl2, or R1 N=C=NR, where R and R1 are different alkyl groups, can yield a population of antibodies (e.g., monoclonal antibodies).

If desired, an antibody (e.g., monoclonal or polyclonal anti-CGRP antagonist antibody) of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to CGRP and greater efficacy in inhibiting CGRP. It will be apparent to one of skill in the art that one or more polynucleotide changes can be made to the anti-CGRP antagonist antibody and still maintain its binding ability to CGRP.

Humanizing a monoclonal antibody can comprise four general steps. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349:293-299 (1991), Lobuglio et al. Proc. Nat. Acad. Sci. USA 86:4220-4224 (1989), Shaw et al. J Immunol. 138:4534-4538 (1987), and Brown et al. Cancer Res. 47:3577-3583 (1987). Other references describe rodent CDRs grafted into a human supporting framework region (FR) prior to fusion with an appropriate human antibody constant domain. See, for example, Riechmann et al. Nature 332:323-327 (1988), Verhoeyen et al. Science 239:1534-1536 (1988), and Jones et al. Nature 321:522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476 (1991) and in U.S. Pat. Nos. 6,180,377; 6,054,297; 5,997,867; 5,866,692; 6,210,671; and 6,350,861; and in PCT Publication No. WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455 (1994). Alternatively, the phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597 (1991), or Griffith et al., EMBO J. 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., Bio/Technol. 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756 (2001); Lonberg, N. and D. Huszar Int. Rev. Immunol 13:65 (1995); and Pollock, et al., J Immunol Methods 231:147 (1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for CGRP.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-CGRP monoclonal antibody herein.

Antibodies (e.g., anti-CGRP antagonist antibodies) and polypeptides derived from antibodies can be identified or characterized using methods known in the art, whereby reduction, amelioration, or neutralization of an CGRP biological activity is detected and/or measured. For example, anti-CGRP antagonist antibody can also be identified by incubating a candidate agent with CGRP and monitoring any one or more of the following characteristics: (a) bind to CGRP; (b) block CGRP from binding to its receptor(s); (c) block or decrease CGRP receptor activation (including cAMP activation); (d) inhibit CGRP biological activity or downstream pathways mediated by CGRP signaling function; (e) prevent, ameliorate, or treat any aspect of headache (e.g., migraine); (f) increase clearance of CGRP; and (g) inhibit (reduce) CGRP synthesis, production or release. In some embodiments, an anti-CGRP antagonist antibody or polypeptide is identified by incubating a candidate agent with CGRP and monitoring binding and/or attendant reduction or neutralization of a biological activity of CGRP. The binding assay may be performed with purified CGRP polypeptide(s), or with cells naturally expressing, or transfected to express, CGRP polypeptide(s). In one embodiment, the binding assay is a competitive binding assay, where the ability of a candidate antibody to compete with a known anti-CGRP antagonist for CGRP binding is evaluated. The assay may be performed in various formats, including the ELISA format. In other embodiments, an anti-CGRP antagonist antibody is identified by incubating a candidate agent with CGRP and monitoring binding and attendant inhibition of CGRP receptor activation expressed on the surface of a cell.

Following initial identification, the activity of a candidate antibody (e.g., anti-CGRP antagonist antibody) can be further confirmed and refined by bioassays, known to test the targeted biological activities. Alternatively, bioassays can be used to screen candidates directly. For example, CGRP promotes a number of measurable changes in responsive cells. These include, but are not limited to, stimulation of cAMP in the cell (e.g., SK-N-MC cells). Antagonist activity may also be measured using animal models, such as measuring skin vasodilatation induced by stimulation of the rat saphenous nerve. Escott et al., Br. J. Pharmacol. 110: 772-776, 1993. Animal models of headaches (such as, migraine) may further be used for testing efficacy of antagonist antibodies or polypeptides. Reuter, et al., Functional Neurology (15) Suppl. 3, 2000. Some of the methods for identifying and characterizing anti-CGRP antagonist antibody or polypeptide are described in detail in the Examples.

Antibodies, including anti-CGRP antagonist antibodies, may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-CGRP antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-CGRP antagonist antibody. In another example, the epitope to which the anti-CGRP antagonist antibody binds can be determined in a systematic screening by using overlapping peptides derived from the CGRP sequence and determining binding by the anti-CGRP antagonist antibody. According to the gene fragment expression assays, the open reading frame encoding CGRP is fragmented either randomly or by specific genetic constructions and the reactivity of the expressed fragments of CGRP with the antibody to be tested is determined. The gene fragments may, for example, be produced by PCR and then transcribed and translated into protein in vitro, in the presence of radioactive amino acids. The binding of the antibody to the radioactively labeled CGRP fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant CGRP in which various fragments of the CGRP polypeptide have been replaced (swapped) with sequences from a closely related, but antigenically distinct protein (such as another member of the neurotrophin protein family). By assessing binding of the antibody to the mutant CGRP, the importance of the particular CGRP fragment to antibody binding can be assessed.

Yet another method which can be used to characterize an antibody, including an anti-CGRP antagonist antibody, is to use competition assays with other antibodies known to bind to the same antigen, i.e., various fragments on CGRP, to determine if the anti-CGRP antagonist antibody binds to the same epitope as other antibodies. Competition assays are well known to those of skill in the art.

An expression vector can be used to direct expression of an antibody, including an anti-CGRP antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 μg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol. (1994) 14:2411, and in Woffendin, Proc. Natl. Acad. Sci. (1994) 91:1581.

C. Antibody G1 and Related Antibodies, Polypeptides, Polynucleotides, Vectors and Host Cells This invention encompasses compositions, including pharmaceutical compositions, comprising antibody G1 and its variants shown in Table 6 or polypeptide derived from antibody G1 and its variants shown in Table 6; and polynucleotides comprising sequences encoding G1 and its variants or the polypeptide. In some embodiments, compositions comprise one or more antibodies or polypeptides (which may or may not be an antibody) that bind to CGRP, and/or one or more polynucleotides comprising sequences encoding one or more antibodies or polypeptides that bind to CGRP. These compositions may further comprise suitable excipients, such as pharmaceutically acceptable excipients including buffers, which are well known in the art.

In some embodiments, the anti-CGRP antagonist antibodies and polypeptides of the invention are characterized by any (one or more) of the following characteristics: (a) bind to CGRP; (b) block CGRP from binding to its receptor(s); (c) block or decrease CGRP receptor activation (including cAMP activation); (d) inhibit CGRP biological activity or downstream pathways mediated by CGRP signaling function; (e) prevent, ameliorate, or treat any aspect of headache (e.g., migraine); (f) increase clearance of CGRP; and (g) inhibit (reduce) CGRP synthesis, production or release.

In some embodiments, the invention provides any of the following, or compositions (including pharmaceutical compositions) comprising any of the following: (a) antibody G1 or its variants shown in Table 6; (b) a fragment or a region of antibody G1 or its variants shown in Table 6; (c) a light chain of antibody G1 or its variants shown in Table 6; (d) a heavy chain of antibody G1 or its variants shown in Table 6; (e) one or more variable region(s) from a light chain and/or a heavy chain of antibody G1 or its variants shown in Table 6; (f) one or more CDR(s) (one, two, three, four, five or six CDRs) of antibody G1 or its variants shown in Table 6; (g) CDR H3 from the heavy chain of antibody G1; (h) CDR L3 from the light chain of antibody G1 or its variants shown in Table 6; (i) three CDRs from the light chain of antibody G1 or its variants shown in Table 6; (j) three CDRs from the heavy chain of antibody G1 or its variants shown in Table 6; (k) three CDRs from the light chain and three CDRs from the heavy chain, of antibody G1 or its variants shown in Table 6; and (l) an antibody comprising any one of (b) through (k). In some embodiments, the invention also provides polypeptides comprising any one or more of the above.

The CDR portions of antibody G1 (including Chothia and Kabat CDRs) are diagrammatically depicted in FIG. 5. Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

In some embodiments, the invention provides a polypeptide (which may or may not be an antibody) which comprises at least one CDR, at least two, at least three, or at least four, at least five, or all six CDRs that are substantially identical to at least one CDR, at least two, at least three, at least four, at least five or all six CDRs of G1 or its variants shown in Table 6. Other embodiments include antibodies which have at least two, three, four, five, or six CDR(s) that are substantially identical to at least two, three, four, five or six CDRs of G1 or derived from G1. In some embodiments, the at least one, two, three, four, five, or six CDR(s) are at least about 85%, 86%, 87%, 88%, 89%, 90%, 95%, 96%, 97%, 98%, or 99% identical to at least one, two, three, four, five or six CDRs of G1 or its variants shown in Table 6. It is understood that, for purposes of this invention, binding specificity and/or overall activity is generally retained, although the extent of activity may vary compared to G1 or its variants shown in Table 6 (may be greater or lesser).

In some embodiments, the invention also provides a polypeptide (which may or may not be an antibody) which comprises an amino acid sequence of G1 or its variants shown in Table 6 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of G1 or its variants shown in Table 6, wherein at least 3 of the amino acids are from a variable region of G1 (FIG. 5) or its variants shown in Table 6. In one embodiment, the variable region is from a light chain of G1. In another embodiment, the variable region is from a heavy chain of G1. An exemplary polypeptide has contiguous amino acid (lengths described above) from both the heavy and light chain variable regions of G1. In another embodiment, the 5 (or more) contiguous amino acids are from a complementarity determining region (CDR) of G1 shown in FIG. 5. In some embodiments, the contiguous amino acids are from a variable region of G1.

The binding affinity ($K_D$) of an anti-CGRP antagonist antibody and polypeptide to CGRP (such as human α-CGRP) can be about 0.06 to about 200 nM. In some embodiments, the binding affinity is any of about 200 nM, 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

In some embodiments, the invention also provides methods of making any of these antibodies or polypeptides. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody G1 shown in SEQ ID NO:9 and SEQ ID NO:10. In another embodiment, the polynucleotide comprising the nucleotide sequence shown in SEQ ID NO:9 and SEQ ID NO:10 are cloned into one or more vectors for expression or propagation. The sequence encoding the antibody of interest may be maintained in a vector in a host cell and the host cell can then be expanded and frozen for future use. Vectors (including expression vectors) and host cells are further described herein.

In some embodiments, the invention also encompasses single chain variable region fragments ("scFv") of antibodies of this invention, such as G1. Single chain variable region fragments are made by linking light and/or heavy chain variable regions by using a short linking peptide. Bird et al. (1988) Science 242:423-426. An example of a linking peptide is (GGGGS)3 (SEQ ID NO: 57) which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad Sci. USA 90:6444-6448; Poljak, R. J., et al. (1994) Structure 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibody G1 or its variants shown in Table 6, or one or more CDRs derived from antibody G1 or its variants shown in Table 6 can be made using any methods known in the art. For example, four general steps may be used to humanize a monoclonal antibody.

In some embodiments, the invention encompasses modifications to antibody G1 or its variants shown in Table 6, including functionally equivalent antibodies which do not significantly affect their properties and variants which have enhanced or decreased activity and/or affinity. For example, the amino acid sequence of antibody G1 or its variants shown in Table 6 may be mutated to obtain an antibody with the desired binding affinity to CGRP. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
  (1) Non-polar: Norleucine, Met, Ala, Val, Leu, Ile;
  (2) Polar without charge: Cys, Ser, Thr, Asn, Gln;
  (3) Acidic (negatively charged): Asp, Glu;
  (4) Basic (positively charged): Lys, Arg;
  (5) Residues that influence chain orientation: Gly, Pro; and
  (6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of $\beta(1,4)$-N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified G1 polypeptides can be made using established procedures in the art and can be screened using standard assays known in the art, some of which are described below and in the Examples.

In some embodiments of the invention, the antibody comprises a modified constant region, such as a constant region that is immunologically inert or partially inert, e.g., does not trigger complement mediated lysis, does not stimulate antibody-dependent cell mediated cytotoxicity (ADCC), or does not activate microglia; or have reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324 (1995); Lund et al., J. Immunology 157:4963-9 157:4963-4969 (1996); Idusogie et al., J. Immunology 164:4178-4184 (2000); Tao et al., J. Immunology 143: 2595-2601 (1989); and Jefferis et al., Immunological Reviews 163:59-76 (1998). In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601 (1989); and Jefferis et al., Immunological Reviews 163:59-76 (1998). In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

In some embodiments, the invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al, 1992, J. Mol. Biol., 226:889-896; and WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased or no binding are identified. Methods for determining binding affinity are well-known in the art. Binding affinity may be determined using Biacore surface plasmon resonance analysis, which detects differences in binding affinity of about 2-fold or greater. Biacore is particularly useful when the starting antibody already binds with a relatively high affinity, for example a $K_D$ of about 10 nM or lower. Screening using Biacore surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., (1993) Gene 137(1):109-18).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore surface plasmon resonance analysis, and selection using any method known in the art for selection, including phage display, yeast display, and ribosome display.

In some embodiments, the invention also encompasses fusion proteins comprising one or more fragments or regions from the antibodies (such as G1) or polypeptides of this invention. In one embodiment, a fusion polypeptide is provided that comprises at least 10 contiguous amino acids of the variable light chain region shown in SEQ ID NO:2 (FIG. 5) and/or at least 10 amino acids of the variable heavy chain region shown in SEQ ID NO:1 (FIG. 5). In other embodiments, a fusion polypeptide is provided that comprises at least about 10, at least about 15, at least about 20, at least about 25, or at least about 30 contiguous amino acids of the variable light chain region shown in SEQ ID NO:2 (FIG. 5) and/or at least about 10, at least about 15, at least about 20, at least about 25, or at least about 30 contiguous amino acids of the variable heavy chain region shown in SEQ ID NO:1 (FIG. 5). In another embodiment, the fusion polypeptide comprises a light chain variable region and/or a heavy chain variable region of G1, as shown in SEQ ID NO:2 and SEQ ID NO:1 of FIG. 5. In another embodiment, the fusion polypeptide comprises one or more CDR(s) of G1. In still other embodiments, the fusion polypeptide comprises CDR H3 and/or CDR L3 of antibody G1. For purposes of this invention, an G1 fusion protein contains one or more G1 antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag (SEQ ID NO: 56). Tags are well known in the art.

A G1 fusion polypeptide can be created by methods known in the art, for example, synthetically or recombinantly. Typically, the G1 fusion proteins of this invention are made by preparing an expressing a polynucleotide encoding them using recombinant methods described herein, although they may also be prepared by other means known in the art, including, for example, chemical synthesis.

In some aspects, this invention also provides compositions comprising antibodies or polypeptides derived from G1 conjugated (for example, linked) to an agent that facilitate coupling to a solid support (such as biotin or avidin). For simplicity, reference will be made generally to G1 or antibodies with the understanding that these methods apply to any of the CGRP binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide may be linked to a labeling agent (alternatively termed "label") such as a fluorescent molecule, a radioactive molecule or any others labels known in the art. Labels are known in the art which generally provide (either directly or indirectly) a signal.

In some embodiments, the invention also provides compositions (including pharmaceutical compositions) and kits comprising antibody G1, and/or any or all of the antibodies or polypeptides described herein.

In some embodiments, the invention also provides isolated polynucleotides encoding the antibodies and polypeptides of the invention (including an antibody comprising the polypeptide sequences of the light chain and heavy chain variable regions shown in FIG. 5), and vectors and host cells comprising the polynucleotide.

In some embodiments, the invention provides polynucleotides (or compositions, including pharmaceutical compositions), comprising polynucleotides encoding any of the following: (a) antibody G1 or its variants shown in Table 6;

(b) a fragment or a region of antibody G1 or its variants shown in Table 6; (c) a light chain of antibody G1 or its variants shown in Table 6; (d) a heavy chain of antibody G1 or its variants shown in Table 6; (e) one or more variable region(s) from a light chain and/or a heavy chain of antibody G1 or its variants shown in Table 6; (f) one or more CDR(s) (one, two, three, four, five or six CDRs) of antibody G1 or its variants shown in Table 6; (g) CDR H3 from the heavy chain of antibody G1; (h) CDR L3 from the light chain of antibody G1 or its variants shown in Table 6; (i) three CDRs from the light chain of antibody G1 or its variants shown in Table 6; (j) three CDRs from the heavy chain of antibody G1 or its variants shown in Table 6; (k) three CDRs from the light chain and three CDRs from the heavy chain, of antibody G1 or its variants shown in Table 6; and (l) an antibody comprising any one of (b) through (k). In some embodiments, the polynucleotide comprises either or both of the polynucleotide(s) shown in SEQ ID NO: 9 and SEQ ID NO: 10.

In another aspect, the invention provides polynucleotides encoding any of the antibodies (including antibody fragments) and polypeptides described herein, such as antibodies and polypeptides having impaired effector function. Polynucleotides can be made by procedures known in the art.

In another aspect, the invention provides compositions (such as a pharmaceutical compositions) comprising any of the polynucleotides of the invention. In some embodiments, the composition comprises an expression vector comprising a polynucleotide encoding the G1 antibody as described herein. In other embodiment, the composition comprises an expression vector comprising a polynucleotide encoding any of the antibodies or polypeptides described herein. In still other embodiments, the composition comprises either or both of the polynucleotides shown in SEQ ID NO:9 and SEQ ID NO:10. Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to any of the various aspects of the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

In some aspects, the invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to Aϑ1-40 is effected by an immunoassay or FACS. A cell overexpressing the antibody or protein of interest can be identified.

D. Compositions

In some embodiments, compositions used in a method of the invention comprise an effective amount of an antibody (e.g., anti-CGRP antagonist antibody, monoclonal antibody that modulates the CGRP pathway) or an antibody derived polypeptide described herein. Examples of such compositions, as well as how to formulate, are also described in an earlier section and below. In one embodiment, the composition further comprises a CGRP antagonist. In some embodiments, the composition comprises one or more monoclonal antibodies that modulate the CGRP pathway. In some embodiments, the composition comprises one or more anti-CGRP antagonist antibodies. In some embodiments, the anti-CGRP antagonist antibody recognizes human CGRP. In some embodiments, the anti-CGRP antagonist antibody is humanized. In some embodiments, the anti-CGRP antagonist antibody comprises a constant region that does not trigger an unwanted or undesirable immune response, such as antibody-mediated lysis or ADCC. In some embodiments, the anti-CGRP antagonist antibody comprises one or more CDR(s) of antibody G1 (such as one, two, three, four, five, or, in some embodiments, all six CDRs from G1). In some embodiments, the anti-CGRP antagonist antibody is human.

It is understood that the compositions can comprise more than one antibody (e.g., more than one anti-CGRP antagonist antibody—a mixture of anti-CGRP antagonist antibodies that recognize different epitopes of CGRP). Other exemplary compositions comprise more than one anti-CGRP antagonist antibodies that recognize the same epitope(s), or different species of anti-CGRP antagonist antibodies that bind to different epitopes of CGRP.

A composition can further comprise pharmaceutically acceptable carriers, excipients, or stabilizers (Remington: The Science and practice of Pharmacy 20th Ed. (2000) Lippincott Williams and Wilkins, Ed. K. E. Hoover). Acceptable carriers, excipients, or stabilizers are nontoxic to recipients at the dosages and concentrations employed. A therapeutic formulation of an antibody may comprise one or more pharmaceutically acceptable carriers, excipients or stabilizes with non-limiting examples of such species that include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids (e.g., at concentrations of 0.1 mM to 100 mM, 0.1 mM to 1 mM, 0.01 mM to 50 mM, 1 mM to 50 mM, 1 mM to 30 mM, 1 mM to 20 mM, 10 mM to 25 mM) such as glycine, glutamine, methionine, asparagine, histidine, arginine, or lysine; monosaccharides, disaccharides, and other carbohydrates including glucose, mannose, or dextrins; chelating agents (e.g., at concentrations of 0.001 mg/mL to 1 mg/mL, 0.001 mg/mL to 1 mg/mL, 0.001 mg/mL to 0.1 mg/mL, 0.001 mg/mL to 0.01 mg/mL) such as EDTA (e.g., disodium EDTA dihydrate); sugars (e.g., at concentrations of 1 mg/mL to 500 mg/mL, 10 mg/mL to 200 mg/mL, 10 mg/mL to 100 mg/mL, 50 mg/mL to 150 mg/mL) such as sucrose, mannitol, trehalose or sorbitol; salt-forming counter-ions such as sodium; metal complexes (e.g. Zn-protein complexes); and/or non-ionic surfactants (e.g., at concentrations of 0.01 mg/mL to 10 mg/mL, 0.01 mg/mL to 1 mg/mL, 0.1 mg/mL to 1 mg/mL, 0.01 mg/mL to 0.5 mg/mL) such as TWEEN™ (e.g., polysorbate (e.g., polysorbate 20, polysorbate 40, polysorbate 60, polysorbate 80)), PLURONICS™ or polyethylene glycol (PEG). Pharmaceutically acceptable excipients are further described herein.

An antibody (e.g., an anti-CGRP antagonist antibody) and compositions thereof can also be used in conjunction with other agents that serve to enhance and/or complement the effectiveness of the agents.

E. Kits

In one aspect, the invention also provides kits for use in the instant methods. Kits can include one or more containers comprising an antibody described herein (e.g., an anti-CGRP antagonist antibody (such as a humanized antibody)) or polypeptide described herein and instructions for use in accordance with any of the methods described herein. Generally, these instructions comprise a description of administration of the antibody to treat, ameliorate or prevent headache (such as migraine) according to any of the methods described herein. The kit may further comprise a description of selecting an individual suitable for treatment based on identifying whether that individual has headache or whether the individual is at risk of having headache. In still other embodiments, the instructions comprise a description of administering an antibody (e.g., anti-CGRP antagonist antibody) to an individual at risk of having headache (such as migraine).

In some embodiments, the antibody is a humanized antibody. In some embodiments, the antibody is human. In other embodiments, the antibody is a monoclonal antibody. In still other embodiments. In some embodiment, the antibody comprises one or more CDR(s) of antibody G1 (such as one, two, three, four, five, or, in some embodiments, all six CDRs from G1).

The instructions relating to the use of an antibody (e.g., anti-CGRP antagonist antibody) generally include information as to dosage, dosing schedule, and route of administration for the intended treatment. The containers may be unit doses, bulk packages (e.g., multi-dose packages) or sub-unit doses. Instructions supplied in the kits are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, ameliorating and/or preventing headache (such as migraine). Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CGRP antagonist antibody and/or a monoclonal antibody that modulates the CGRP pathway. The container may further comprise a second pharmaceutically active agent.

Kits may optionally provide additional components such as buffers and interpretive information. Normally, the kit comprises a container and a label or package insert(s) on or associated with the container.

The following Examples are provided to illustrate but not limit the invention.

EXAMPLES

Example 1: Generation and Characterization of Monoclonal Antibodies Directed Against CGRP Generation of anti-CGRP antibodies. To generate anti-CGRP antibodies that have cross-species reactivity for rat and human CGRP, mice were immunized with 25-100 µg of human α-CGRP or β-CGRP conjugated to KLH in adjuvant (50 µl per footpad, 100 µl total per mouse) at various intervals. Immunization was generally performed as described in Geerligs H J et al., 1989, J. Immunol. Methods 124:95-102; Kenney J S et al., 1989, J. Immunol. Methods 121:157-166; and Wicher K et al., 1989, Int. Arch. Allergy Appl. Immunol. 89:128-135. Mice were first immunized with 50 µg of human α-CGRP or β-CGRP conjugated to KLH in CFA (complete Freund's adjuvant). After 21 days, mice were secondly immunized with 25 µg of human β-CGRP (for mice first immunized with human α-CGRP) or α-CGRP (for mice first immunized with human β-CGRP) conjugated to KLH in IFA (incomplete Freund's adjuvant). Twenty three days later after the second immunization, third immunization was performed with 25 µg of rat α-CGRP conjugated to KLH in IFA. Ten days later, antibody titers were tested using ELISA. Forth immunization was performed with 25 µg of the peptide (rat α-CGRP-KLH) in IFA 34 days after the third immunization. Final booster was performed with 100 µg soluble peptide (rat α-CGRP) 32 days after the forth immunization.

Splenocytes were obtained from the immunized mouse and fused with NSO myeloma cells at a ratio of 10:1, with polyethylene glycol 1500. The hybrids were plated out into 96-well plates in DMEM containing 20% horse serum and 2-oxaloacetate/pyruvate/insulin (Sigma), and hypoxanthine/aminopterin/thymidine selection was begun. On day 8, 100 µl of DMEM containing 20% horse serum was added to all the wells. Supernatants of the hybrids were screened by using antibody capture immunoassay. Determination of antibody class was done with class-specific second antibodies.

A panel of monoclonal antibody-producing cell lines was selected based on their binding to human and rat CGRP for further characterization. These antibodies and characteristics are shown below in Tables 2 and 3.

Purification and Fab fragment preparation. Monoclonal antibodies selected for further characterization were purified from supernatants of hybridoma cultures using protein A affinity chromatography. The supernatants were equilibrated to pH 8. The supernatants were then loaded to the protein A column MabSelect (Amersham Biosciences #17-5199-02) equilibrated with PBS to pH 8. The column was washed with 5 column volumes of PBS, pH 8. The antibodies were eluted with 50 mM citrate-phosphate buffer, pH 3. The eluted antibodies were neutralized with 1M Phosphate Buffer, pH 8. The purified antibodies were dialyzed with PBS, pH 7.4. The antibody concentrations were determined by SDS-PAGE, using a murine monoclonal antibody standard curve.

Fabs were prepared by papain proteolysis of the full antibodies using Immunopure Fab kit (Pierce #44885) and purified by flow through protein A chromatography following manufacturer instructions. Concentrations were determined by ELISA and/or SDS-PAGE electrophoresis using a standard Fab of known concentration (determined by amino acid analysis), and by A280 using 1OD=0.6 mg/ml (or theoretical equivalent based on the amino acid sequence).

Affinity determination of the Fabs. Affinities of the anti-CGRP monoclonal antibodies were determined at either 25° C. or 37° C. using the Biacore3000™ surface plasmon resonance (SPR) system (Biacore, INC, Piscataway N.J.) with the manufacture's own running buffer, HBS-EP (10 mM HEPES pH 7.4, 150 mM NaCl, 3 mM EDTA, 0.005% v/v polysorbate P20). Affinity was determined by capturing N-terminally biotinylated CGRP peptides (custom ordered from GenScript Corporation, New Jersey or Global Peptide Services, Colorado) via pre-immobilized streptavidin on SA chip and measuring binding kinetics of antibody Fab titrated across the CGRP surface. Biotinylated CGRP was diluted into HBS-EP and injected over the chip at a concentration of less than 0.001 mg/ml. Using variable flow time across the individual chip channels, two ranges of antigen density were achieved: <50 response units (RU) for detailed kinetic studies and about 800 RU for concentration studies and screening. Two- or three-fold serial dilutions typically at concentrations spanning 1 µM-0.1 nM (aimed at 0.1-10× estimated $K_D$) of purified Fab fragments were injected for 1 minute at 100 µL/min and dissociation times of 10 minutes were allowed. After each binding cycle, surfaces were regenerated with 25 mM NaOH in 25% v/v ethanol, which was tolerated over hundreds of cycles. Kinetic association rate ($k_{on}$) and dissociation rate ($k_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Global equilibrium dissociation constants ($K_D$) or "affinities" were calculated from the ratio $K_D = k_{off}/k_{on}$. Affinities of the murine Fab fragments are shown in Tables 2 and 3.

Figure 1:
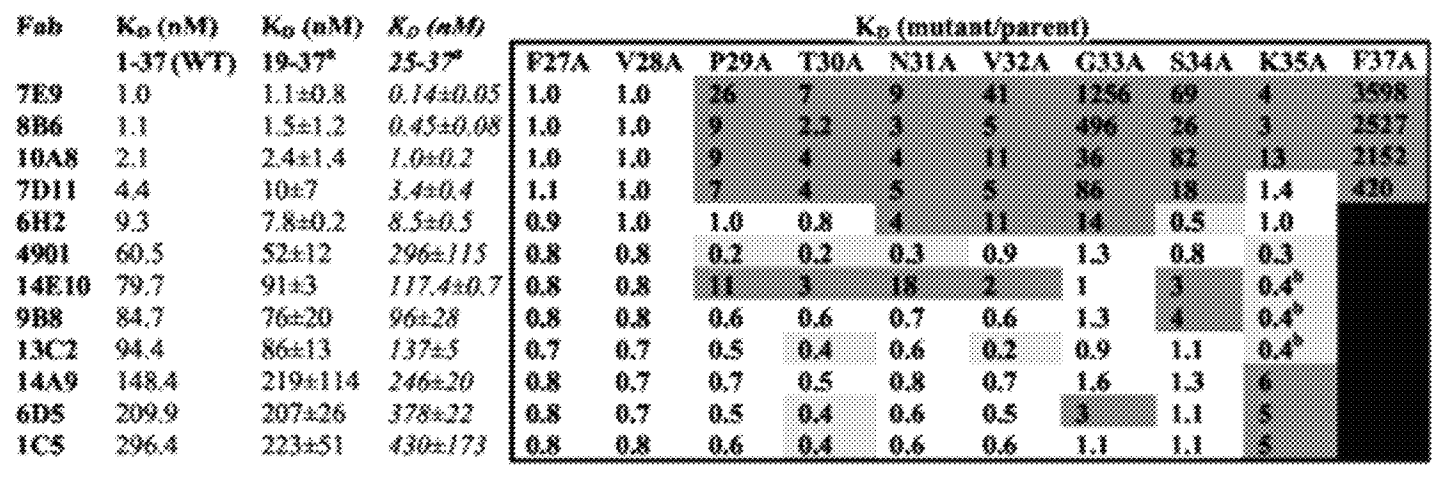

Epitope mapping of the murine anti-CGRP antibodies. To determine the epitope that anti-CGRP antibodies bind on human α-CGRP, binding affinities of the Fab fragments to various CGRP fragments were measured as described above by capturing N-terminally biotinylated CGRP fragments amino acids 19-37 and amino acids 25-37 on a SA sensor chip. FIG. 1 shows their binding affinities measured at 25° C. As shown in FIG. 1, all antibodies, except antibody 4901, bind to human α-CGRP fragments 19-37 and 25-37 with affinity similar to their binding affinity to full length human α-CGRP (1-37). Antibody 4901 binds to human α-CGRP fragment 25-37 with six fold lower affinity than binding to full length human α-CGRP fragment, due mainly to a loss in off-rate. The data indicate that these anti-CGRP antibodies generally bind to the C-terminal end of CGRP.

Alanine scanning was performed to further characterize amino acids in human α-CGRP involved in binding of anti-CGRP antibodies. Different variants of human α-CGRP with single alanine substitutions were generated by peptide synthesis. Their amino acid sequences are shown in Table 4 along with all the other peptides used in the Biacore analysis. Affinities of Fab fragments of the anti-CGRP antibodies to these variants were determined using Biacore as described above. As shown in FIG. 1, all 12 antibodies target a C-terminal epitope, with amino acid F37 being the most crucial residue. Mutation of F37 to alanine significantly lowered the affinity or even completely knocked out binding of the anti-CGRP antibodies to the peptide. The next most important amino acid residue was G33, however, only the high affinity antibodies (7E9, 8B6, 10A8, and 7D11) were affected by alanine replacement at this position. Amino acid residue S34 also plays a significant, but lesser, role in the binding of these four high affinity antibodies.

TABLE 2

Characteristics of the anti-CGRP monoclonal antibodies' binding to human α-CGRP and their antagonist activity

| Antibodies | $K_D$ to human α-CGRP at 25° C. (nM) | $K_D$ to human α-CGRP at 37° C. (nM) | Cell-based blocking human α-CGRP binding to its receptor at 25° C. (measured by cAMP activation) | $IC_{50}$ (nM binding sites) at 25° C. (room temp.) measured in radioligand binding assay. |
|---|---|---|---|---|
| 7E9 | 1.0 | 0.9 | Yes | 2.5 |
| 8B6 | 1.1 | 1.2 | Yes | 4.0 |
| 10A8 | 2.1 | 3.0 | Yes | n.d. |
| 7D11 | 4.4 | 5.4 | Yes | n.d. |
| 6H2 | 9.3 | 42 | Yes | 12.9 |
| 4901 | 61 | 139 | Yes | 58 |
| 14E10 | 80 | 179 | Yes | n.d. |
| 9B8 | 85 | 183 | No | n.d. |
| 13C2 | 94 | 379 | No | n.d. |
| 14A9 | 148 | 581 | No | n.d. |
| 6D5 | 210 | 647 | No | n.d. |
| 1C5 | 296 | 652 | No | n.d. |

Note:
Antibody 4901 is commercially available (Sigma, Product No. C7113).
n.d. = not determined

TABLE 3

Characteristics of the anti-CGRP monoclonal antibodies' binding to rat α-CGRP and antagonist activity

| Antibodies | $K_D$ to rat α-CGRP at 37° C. (nM) | Cell-based blocking of binding of rat α-CGRP to its receptor at 25° C. (measured by cAMP activation) | In vivo blocking in saphenous nerve assay |
|---|---|---|---|
| 4901 | 3.4 | Yes | Yes |
| 7E9 | 47 | Yes | Yes |
| 6H2 | 54 | No | No |
| 8B6 | 75 | Yes | Yes |
| 7D11 | 218 | Yes | Yes |
| 10A8 | 451 | No | n.d. |
| 9B8 | 876 | No | n.d. |
| 14E10 | 922 | No | n.d. |
| 13C2 | >1000 | No | n.d. |
| 14A9 | >1000 | No | n.d. |
| 6D5 | >1000 | No | n.d. |
| 1C5 | >1000 | No | n.d. |

"n.d." indicates no test was performed for the antibody.

TABLE 4

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
|---|---|---|
| 1-37 (WT) | ACDTATCVTHRLAGLLSRSGGVVKNNFVPTNVGSKAF | 15 |
| 8-37 | VTHRLAGLLSRSGGVVKNNFVPTNVGSKAF | 16 |
| 19-37 | SGGVVKNNFVPTNVGSKAF | 17 |
| P29A (19-37) | SGGVVKNNFVATNVGSKAF | 18 |
| K35A (19-37) | SGGVVKNNFVPTNVGSAAF | 19 |
| K35E (19-37) | SGGVVKNNFVPTNVGSEAF | 20 |
| K35M (19-37) | SGGVVKNNFVPTNVGSMAF | 21 |
| K35Q (19-37) | SGGVVKNNFVPTNVGSQAF | 22 |
| F37A (19-37) | SGGVVKNNFVPTNVGSKAA | 23 |
| 25-38A | NNFVPTNVGSKAFA | 24 |
| 25-37 | NNFVPTNVGSKAF | 25 |

TABLE 4-continued

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
| --- | --- | --- |
| F27A (25-37) | NNAVPTNVGSKAF | 26 |
| V28A (25-37) | NNFAPTNVGSKAF | 27 |
| P29A (25-37) | NNFVATNVGSKAF | 28 |
| T30A (25-37) | NNFVPANVGSKAF | 29 |
| N31A (25-37) | NNFVPTAVGSKAF | 30 |
| V32A (25-37) | NNFVPTNAGSKAF | 31 |
| G33A (25-37) | NNFVPTNVASKAF | 32 |
| S34A (25-37) | NNFVPTNVGAKAF | 33 |
| F37A (25-37) | NNFVPTNVGSKAA | 34 |
| 26-37 | NFVPTNVGSKAF | 35 |
| 19-37-COOH | SGGVVKNNFVPTNVGSKAF | 36 |
| 19-36-COOH | SGGVVKNNFVPTNVGSKA | 37 |
| 1-36-COOH | ACDTATCVTHRLAGLLSRSGGVVKNNFVPTNVGSKA | 38 |
| 1-19-COOH | ACDTATCVTHRLAGLLSRS | 39 |
| 1-13-COOH | ACDTATCVTHRLA | 40 |
| rat α (1-37) | SCNTATCVTHRLAGLLSRSGGVVKDNFVPTNVGSEAF | 41 |
| rat α (19-37) | SGGVVKDNFVPTNVGSEAF | 42 |
| human β (1-37) | ACNTATCVTHRLAGLLSRSGGMVKSNFVPTNVGSKAF | 43 |
| rat β (1-37) | SCNTATCVTHRLAGLLSRSGGVVKDNFVPTNVGSKAF | 44 |
| Human calcitonin (1-32) | CGNLSTCMLGTYTQDFNKFHTFPQTAIGVGAP | 45 |
| Human amylin (1-37) | KCNTATCATQRLANFLVHSSNNFGAILSSTNVGSNTY | 46 |
| Human adrenomedullin (1-52) | YRQSMNNFQGLRSFGCRFGTCTVQKLAHQIYQFTDKDKDNVAPRSKISPQGY | 47 |

Example 2: Screening of Anti-CGRP Antagonist Antibodies Using In Vitro Assays

Murine anti-CGRP antibodies were further screened for antagonist activity in vitro using cell based cAMP activation assay and binding assay.

Antagonist activity measured by cAMP assay. Five microliters of human or rat α-CGRP (final concentration 50 nM) in the presence or absence of an anti-CGRP antibody (final concentration 1-3000 nM), or rat α-CGRP or human α-CGRP (final concentration 0.1 nM-10 μM; as a positive control for c-AMP activation) was dispensed into a 384-well plate (Nunc, Cat. No. 264657). Ten microliters of cells (human SK-N-MC if human α-CGRP is used, or rat L6 from ATCC if rat α-CGRP is used) in stimulation buffer (20 mM HEPES, pH 7.4, 146 mM NaCl, 5 mM KCl, 1 mM $CaCl_2$), 1 mM $MgCl_2$, and 500 uM 3-Isobutyl-1-methylxanthine (IBMX)) were added into the wells of the plate. The plate was incubated at room temperature for 30 min.

After the incubation, cAMP activation was performed using HitHunter™ Enzyme Fragment Complementation Assay (Applied Biosystems) following manufacture's instruction. The assay is based on a genetically engineered β-galactosidase enzyme that consists of two fragments—termed Enzyme Acceptor (EA) and Enzyme Donor (ED). When the two fragments are separated, the enzyme is inactive. When the fragments are together they can recombine spontaneously to form active enzyme by a process called complementation. The EFC assay platform utilizes an ED-cAMP peptide conjugate in which cAMP is recognized by anti-cAMP. This ED fragment is capable of reassociation with EA to form active enzyme. In the assay, anti-cAMP antibody is optimally titrated to bind ED-cAMP conjugate and inhibit enzyme formation. Levels of cAMP in cell lysate samples compete with ED-cAMP conjugate for binding to the anti-cAMP antibody. The amount of free ED conjugate in the assay is proportional to the concentration of cAMP. Therefore, cAMP is measured by the formation of active enzyme that is quantified by the turnover of β-galactosidase luminescent substrate. The cAMP activation assay was performed by adding 10 μl of lysis buffer and anti-cAMP antibody (1:1 ratio) following by incubation at room temperature for 60 min. Then 10 μl of ED-cAMP reagent was added into each well and incubated for 60 minutes at room temperature. After the incubation, 20 μl of EA reagent and CL mixture (containing the substrate) (1:1 ratio) was added into each well and incubated for 1-3 hours or overnight at room temperature. The plate was read at 1 second/well on PMT instrument or 30 seconds/place on imager. The antibodies that inhibit activation of cAMP by α-CGRP were identified (referred to as "yes") in Tables 2 and 3 above. Data in Tables 2 and 3 indicate that antibodies that demonstrated antagonist activity in the assay generally have high affinity. For example, antibodies having $K_D$ (determined at 25° C.) of about 80 nM or less to human α-CGRP or having $K_D$ (determined at 37° C.) of about 47 nM or less to rat α-CGRP showed antagonist activity in this assay.

Radioligand binding assay. Binding assay was performed to measure the $IC_{50}$ of anti-CGRP antibody in blocking the CGRP from binding to the receptor as described previously. Zimmermann et al., Peptides 16:421-4, 1995; Mallee et al., J. Biol. Chem. 277:14294-8, 2002. Membranes (25 μg) from SK-N-MC cells were incubated for 90 min at room temperature in incubation buffer (50 mM Tris-HCL, pH 7.4, 5 mM $MgCL_2$, 0.1% BSA) containing 10 pM $^{125}$I-human α-CGRP in a total volume of 1 mL. To determine inhibition concentrations ($IC_{50}$), antibodies or unlabeled CGRP (as a control), from a about 100 fold higher stock solution were dissolved at varying concentrations in the incubation buffer and incubated at the same time with membranes and 10 pM $^{125}$I-human α-CGRP. Incubation was terminated by filtration through a glass microfiber filter (GF/B, 1 μm) which had been blocked with 0.5% polyethylemimine. Dose response curves were plotted and $K_i$ values were determined by using the equation: $K_i=IC_{50}/(1+([ligand]/K_D))$; where the equilibrium dissociation constant $K_D$=8 pM for human α-CGRP to CGRP1 receptor as present in SK-N-MC cells, and $B_{max}$=0.025 pmol/mg protein. The reported $IC_{50}$ value (in terms of IgG molecules) was converted to binding sites (by multiplying it by 2) so that it could be compared with the affinities ($K_D$) determined by Biacore (see Table 2).

Table 2 shows the $IC_{50}$ of murine antibodies 7E9, 8B6, 6H2 and 4901. Data indicate that antibody affinity generally correlates with $IC_{50}$: antibodies with higher affinity (lower $K_D$ values) have lower $IC_{50}$ in the radioligand binding assay.

Example 3: Effect of Anti-CGRP Antagonist Antibodies on Skin Vasodilatation Induced by Stimulation of Rat Saphenous Nerve To test antagonist activity of anti-CGRP antibodies, effect of the antibodies on skin vasodilatation by stimulation of rat saphenous nerve was tested using a rat model described previously. Escott et al., Br. J. Pharmacol. 110:772-776, 1993. In this rat model, electrical stimulation of saphenous nerve induces release of CGRP from nerve endings, resulting in an increase in skin blood flow. Blood flow in the foot skin of male Sprague Dawley rats (170-300 g, from Charles River Hollister) was measured after saphenous nerve stimulation. Rats were maintained under anesthesia with 2% isoflurane. Bretylium tosylate (30 mg/kg, administered i.v.) was given at the beginning of the experiment to minimize vasoconstriction due to the concomitant stimulation of sympathetic fibers of the saphenous nerve. Body temperature was maintained at 37° C. by the use of a rectal probe thermostatically connected to a temperature controlled heating pad. Compounds including antibodies, positive control (CGRP 8-37), and vehicle (PBS, 0.01% Tween 20) were given intravenously through the right femoral vein, except for the experiment shown in FIG. 3, the test compound and the control were injected through tail vein, and for experiments shown in FIGS. 2A and 2B, antibodies 4901 and 7D11 were injected intraperitoneally (IP). Positive control compound CGRP 8-37 (vasodilatation antagonist), due to its short half-life, was given 3-5 min before nerve stimulation at 400 nmol/kg (200 μl). Tan et al., Clin. Sci. 89:656-73, 1995. The antibodies were given in different doses (1 mg/kg, 2.5 mg/kg, 5 mg/kg, 10 mg/kg, and 25 mg/kg).

For experiments shown in FIGS. 2A and 2B, antibody 4901 (25 mg/kg), antibody 7D11 (25 mg/kg), or vehicle control (PBS with 0.01% Tween 20) was administered intraperitoneally (IP) 72 hours before the electrical pulse stimulation. For experiment shown in FIG. 3, antibody 4901 (1 mg/kg, 2.5 mg/kg, 5 mg/kg, or 25 mg/kg) or vehicle control (PBS with 0.01% Tween 20) was administered intravenously 24 hours before the electrical pulse stimulation. After administration of the antibodies or vehicle control, the saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. When a stable base-line flux (less than 5% variation) was established for at least 5 min, the nerve was placed over platinum bipolar electrodes and electrically stimulated with 60 pulses (2 Hz, 10 V, 1 ms, for 30 sec) and then again 20 minutes later. Cumulative change in skin blood flow was estimated by the area under the flux-time curve (AUC, which is equal to change in flux multiplied by change in time) for each flux response to electrical pulse stimulation. The average of the blood flow response to the two stimulations was taken. Animals were kept under anesthesia for a period of one to three hours.

As shown in FIG. 2A and FIG. 2B, blood flow increase stimulated by applying electronic pulses on saphenous nerve was inhibited by the presence of CGRP 8-37 (400 nmol/kg, administered i.v.), antibody 4901 (25 mg/kg, administered ip), or antibody 7D11 (25 mg/kg, administered ip) as compared to the control. CGRP 8-37 was administered 3-5 min before the saphenous nerve stimulation; and antibodies were administered 72 hours before the saphenous nerve stimulation. As shown in FIG. 3, blood flow increase stimulated by applying electronic pulses on saphenous nerve was inhibited by the presence of antibody 4901 at different doses (1 mg/kg, 2.5 mg/kg, 5 mg/kg, and 25 mg/kg) administered intravenously at 24 h before the saphenous nerve stimulation.

Figure 4A:
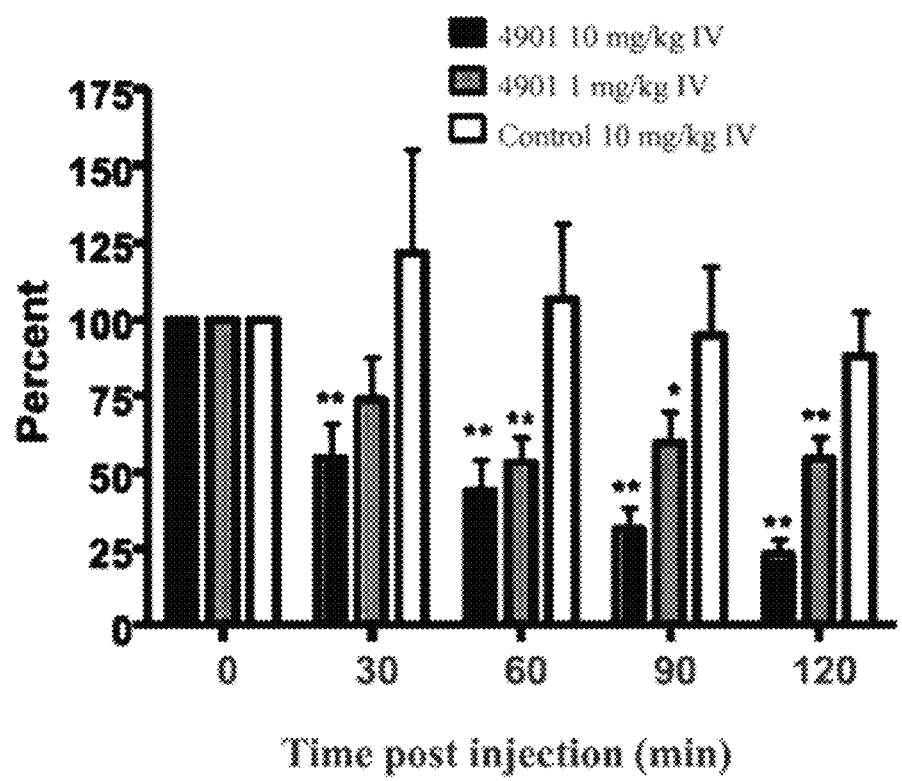
FIGS. 4A and 4B show the effect of administering antibody 4901 (1 mg/kg or 10 mg/kg, i.v.), antibody 7E9 (10 mg/kg, i.v.), and antibody 8B6 (10 mg/kg, i.v.) on skin blood flow measured as blood cell flux after electrical pulse stimulation for 30 seconds. Antibodies were administered intravenously (i.v.) followed by electrical pulse stimulation at 30 min, 60 min, 90 min, and 120 min after antibody administration. Y axis represents percent of AUC as compared to level of AUC when no antibody was administered (time 0). X axis represents time (minutes) period between the administration of antibodies and electrical pulse stimulation. "*" indicates $P<0.05$, and "**" indicates $P<0.01$, as compared to time 0. Data were analyzed using one-way ANOVA with a Dunnett's Multiple comparison test.
Figure 4B:
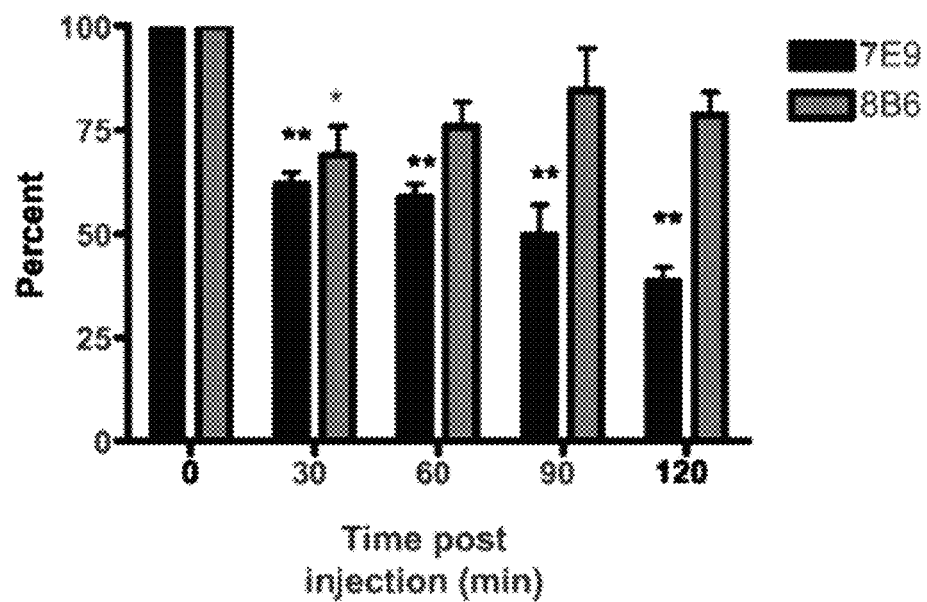

For experiments shown in FIGS. 4A and 4B, saphenous nerve was exposed surgically before antibody administration. The saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. Thirty to forty five minutes after bretylium tosylate injection, when a stable base-line flux (less than 5% variation) was established for at least 5 min, the nerve was placed over platinum bipolar electrodes and electrically stimulated (2 Hz, 10V, 1 ms, for 30 sec) and again 20 minutes later. The average of the blood flow flux response to these two stimulations was used to establish the baseline response (time 0) to electrical stimulation. Antibody 4901 (1 mg/kg or 10 mg/kg), antibody 7E9 (10 mg/kg), antibody 8B6 (10 mg/kg), or vehicle (PBS with 0.01% Tween 20)

were then administered intravenously (i.v.). The nerve was subsequently stimulated (2 Hz, 10V, 1 ms, for 30 sec) at 30 min, 60 min, 90 min, and 120 min after antibody or vehicle administration. Animals were kept under anesthesia for a period of approximately three hours. Cumulative change in skin blood flow was estimated by the area under the flux-time curve (AUC, which is equal to change in flux multiplied by change in time) for each flux response to electrical pulse stimulations.

As shown in FIG. 4A, blood flow increase stimulated by applying electronic pulses on saphenous nerve was significantly inhibited by the presence of antibody 4901 1 mg/kg administered i.v., when electronic pulse stimulation was applied at 60 min, 90 min, and 120 min after the antibody administration, and blood flow increase stimulated by applying electronic pulses on saphenous nerve was significantly inhibited by the presence of antibody 4901 10 mg/kg administered i.v., when electronic pulse stimulation was applied at 30 min, 60 min, 90 min, and 120 min after the antibody administration. FIG. 4B shows that blood flow increase stimulated by applying electronic pulses on saphenous nerve was significantly inhibited by the presence of antibody 7E9 (10 mg/kg, administered i.v.) when electronic pulse stimulation was applied at 30 min, 60 min, 90 min, and 120 min after antibody administration, and by the presence of antibody 8B6 (10 mg/kg, administered i.v.) when electronic pulse stimulation was applied at 30 min after antibody administration.

These data indicate that antibodies 4901, 7E9, 7D11, and 8B6 are effective in blocking CGRP activity as measured by skin vasodilatation induced by stimulation of rat saphenous nerve.

Example 4. Characterization of Anti-CGRP Antibody G1 and its Variants

Amino acid sequences for the heavy chain variable region and light chain variable region of anti-CGRP antibody G1 are shown in FIG. 5. The following methods were used for expression and characterization of antibody G1 and its variants.

Expression vector used. Expression of the Fab fragment of the antibodies was under control of an IPTG inducible lacZ promoter similar to that described in Barbas (2001) Phage display: a laboratory manual, Cold Spring Harbor, N.Y., Cold Spring Harbor Laboratory Press pg. 2.10. Vector pComb3x), however, modifications included addition and expression of the following additional domains: the human Kappa light chain constant domain and the CH1 constant domain of IgG2 human immunoglobulin, Ig gamma-2 chain C region, protein accession number P01859; Immunoglobulin kappa light chain (homosapiens), protein accession number CAA09181.

Small scale Fab preparation. From E. Coli transformed (either using electroporation-competent TG1 cells or chemically-competent Top 10 cells) with a Fab library, single colonies were used to inoculate both a master plate (agar LB+carbenicillin (50 ug/mL)+2% glucose) and a working plate (2 mL/well, 96-well/plate) where each well contained 1.5 mL LB+carbenicillin (50 ug/mL)+2% glucose. A gas permeable adhesive seal (ABgene, Surrey, UK) was applied to the plate. Both plates were incubated at 30° C. for 12-16 h; the working plate was shaken vigorously. The master plate was stored at 4° C. until needed, while the cells from the working plate were pelleted (4000 rpm, 4° C., 20 mins) and resuspended in 1.0 mL LB+carbenicillin (50 ug/mL)+ 0.5 mM IPTG to induce expression of Fabs by vigorous shaking for 5 h at 30° C. Induced cells were centrifuges at 4000 rpm, 4° C. for 20 mins and resuspended in 0.6 mL Biacore HB-SEP buffer (10 mM Hepes pH 7.4, 150 mM NaCl, 3 mM EDTA, 0.005% v/v P20). Lysis of HB-SEP resuspended cells was accomplished by freezing (−80° C.) and then thawing at 37° C. Cell lysates were centrifuged at 4000 rpm, 4° C. for 1 hour to separate the debris from the Fab-containing supernatants, which were subsequently filtered (0.2 um) using a Millipore MultiScreen Assay System 96-Well Filtration Plate and vacuum manifold. Biacore was used to analyze filtered supernatants by injecting them across CGRPs on the sensor chip. Affinity-selected clones expressing Fabs were rescued from the master plate, which provided template DNA for PCR, sequencing, and plasmid preparation.

Large scale Fab preparation. To obtain kinetic parameters, Fabs were expressed on a larger scale as follows. Erlenmeyer flasks containing 150 mL LB+carbenicillin (50 ug/mL)+2% glucose were inoculated with 1 mL of a "starter" overnight culture from an affinity-selected Fab-expressing E. Coli clone. The remainder of the starter culture (~3 mL) was used to prepare plasmid DNA (QIAprep mini-prep, Qiagen kit) for sequencing and further manipulation. The large culture was incubated at 30° C. with vigorous shaking until an $OD_{600nm}$ of 1.0 was attained (typically 12-16 h). The cells were pelleted by centrifuging at 4000 rpm, 4° C. for 20 mins, and resuspended in 150 mL LB+carbenicillin (50 ug/mL)+0.5 mM IPTG. After 5 h expression at 30° C., cells were pelleted by centrifuging at 4000 rpm, 4° C. for 20 mins, resuspended in 10 mL Biacore HBS-EP buffer, and lysed using a single freeze (−80° C.)/thaw (37° C.) cycle. Cell lysates were pelleted by centrifuging at 4000 rpm, 4° C. for 1 hour, and the supernatant was collected and filtered (0.2 um). Filtered supernatants were loaded onto Ni-NTA superflow sepharose (Qiagen, Valencia. Calif.) columns equilibrated with PBS, pH 8, then washed with 5 column volumes of PBS, pH 8. Individual Fabs eluted in different fractions with PBS (pH 8)+300 mM Imidazole. Fractions containing Fabs were pooled and dialyzed in PBS, then quantified by ELISA prior to affinity characterization.

Full antibody preparation. For expression of full antibodies, heavy and light chain variable regions were cloned in mammalian expression vectors and transfected using lipofectamine into HEK 293 cells for transient expression. Antibodies were purified using protein A using standard methods.

Vector pDb.CGRP.hFcGI is an expression vector comprising the heavy chain of the G1 antibody, and is suitable for transient or stable expression of the heavy chain. Vector pDb.CGRP.hFcGI has nucleotide sequences corresponding to the following regions: the murine cytomegalovirus promoter region (nucleotides 7-612); a synthetic intron (nucleotides 613-1679); the DHFR coding region (nucleotides 688-1253); human growth hormone signal peptide (nucleotides 1899-1976); heavy chain variable region of G1 (nucleotides 1977-2621); human heavy chain IgG2 constant region containing the following mutations: A330P331 to S330S331 (amino acid numbering with reference to the wildtype IgG2 sequence; see Eur. J. Immunol. (1999) 29:2613-2624). Vector pDb.CGRP.hFcGI was deposited at the ATCC on Jul. 15, 2005, and was assigned ATCC Accession No. PTA-6867.

Vector pEb.CGRP.hKGI is an expression vector comprising the light chain of the G1 antibody, and is suitable for transient expression of the light chain. Vector pEb.CGRP.hKGI has nucleotide sequences corresponding to the following regions: the murine cytomegalovirus promoter region (nucleotides 2-613); human EF-1 intron (nucleotides 614-1149); human growth hormone signal peptide (nucleotides 1160-1237); antibody G1 light chain variable region (nucleotides 1238-1558); human kappa chain constant region (nucleotides 1559-1882). Vector pEb.CGRP.hKGI was deposited at the ATCC on Jul. 15, 2005, and was assigned ATCC Accession No. PTA-6866.

Biacore assay for affinity determination. Affinities of G1 monoclonal antibody and its variants were determined at either 25° C. or 37° C. using the Biacore3000™ surface plasmon resonance (SPR) system (Biacore, INC, Piscataway N.J.). Affinity was determined by capturing N-terminally biotinylated CGRP or fragments via pre-immobilized streptavidin (SA sensor chip) and measuring the binding kinetics of antibody G1 Fab fragments or variants titrated across the CGRP or fragment on the chip. All Biacore assays were conducted in HBS-EP running buffer (10 mM HEPES pH 7.4, 150 mM NaCl, 3 mM EDTA, 0.005% v/v polysorbate P20). CGRP surfaces were prepared by diluting the N-biotinylated CGRP to a concentration of less than 0.001 mg/mL into HBS-EP buffer and injecting it across the SA sensor chip using variable contact times. Low capacity surfaces, corresponding to capture levels <50 response units (RU) were used for high-resolution kinetic studies, whereas high capacity surfaces (about 800 RU of captured CGRP) were used for concentration studies, screening, and solution affinity determinations. Kinetic data were obtained by diluting antibody G1 Fab serially in two- or three-fold increments to concentrations spanning 1 uM-0.1 nM (aimed at 0.1-10× estimated $K_D$). Samples were typically injected for 1 minute at 100 μL/min and dissociation times of at least 10 minutes were allowed. After each binding cycle, surfaces were regenerated with 25 mM NaOH in 25% v/v ethanol, which was tolerated over hundreds of cycles. An entire titration series (typically generated in duplicate) was fit globally to a 1:1 Langmuir binding model using the BIAevaluation program. This returned a unique pair of association and dissociation kinetic rate constants (respectively, $k_{on}$ and $k_{off}$) for each binding interaction, whose ratio gave the equilibrium dissociation constant ($K_D = k_{off}/k_{on}$). Affinities ($K_D$ values) determined in this way are listed in Tables 6 and 7.

High-resolution analysis of binding interactions with extremely slow offrates. For interactions with extremely slow offrates (in particular, antibody G1 Fab binding to human α-CGRP on the chip at 25° C.), affinities were obtained in a two-part experiment. The protocol described above was used with the following modifications. The association rate constant ($k_{on}$) was determined by injecting a 2-fold titration series (in duplicate) spanning 550 nM-1 nM for 30 sec at 100 uL/min and allowing only a 30 sec dissociation phase. The dissociation rate constant ($k_{off}$) was determined by injecting three concentrations (high, medium, and low) of the same titration series in duplicate for 30 sec and allowing a 2-hour dissociation phase. The affinity ($K_D$) of each interaction was obtained by combining the $k_{on}$ and $k_{off}$ values obtained in both types of experiments, as shown in Table 5.

Determining solution affinity by Biacore. The solution affinity of antibody G1 for rat α-CGRP and F37A (19-37) human α-CGRP was measured by Biacore at 37° C. A high capacity CGRP chip surface was used (the high-affinity human α-CGRP was chosen for detection purposes) and HBS-EP running buffer was flowed at 5 uL/min. Antibody G1 Fab fragment at a constant concentration of 5 nM (aimed to be at or below the expected $K_D$ of the solution-based interaction) was pre-incubated with competing peptide, either rat α-CGRP or F37A (19-37) human α-CGRP, at final concentrations spanning 1 nM to 1 uM in 3-fold serial dilutions. Antibody G1 Fab solutions in the absence or presence of solution-based competing peptide, were injected across CGRP on the chip and the depletion of binding responses detected at the chip surface as a result of solution competition was monitored. These binding responses were converted to "free Fab concentrations" using a calibration curve, which was constructed by titrating antibody G1 Fab alone (5, 2.5, 1.25, 0.625, 0.325 and 0 nM) across the CGRP on the chip. "Free Fab concentrations" were plotted against the concentration of competing solution-based peptide used to generate each data point and fit to a solution affinity model using the BIAevaluation software. The solution affinities determined (indirectly) in this way are shown in Tables 5 and 7 and were used to validate the affinities obtained when Fabs are injected directly across N-biotinylated CGRPs on a SA chip. The close agreement between the affinities determined by these two methods confirms that tethering an N-biotinylated version of the CGRP to the chip does not alter its native solution binding activity.

Table 5 below shows the binding affinities of antibody G1 to human α-CGRP, human β-CGRP, rat α-CGRP, and rat β-CGRP determined by Biacore, by flowing Fab fragments across N-biotinylated CGRPs on a SA chip. To better resolve the affinities of binding interactions with extremely slow offrates, affinities were also determined in a two-part experiment to complement this assay orientation, the solution affinity of the rat α-CGRP interaction was also determined (as described above). The close agreement of the affinities measured in both assay orientations confirms that the binding affinity of the native rat α-CGRP in solution is not altered when it is N-biotinylated and tethered to a SA chip.

TABLE 5

Binding affinities of antibody G1 Fabs titrated across CGRPs on the chip

| CGRP on chip | Temp. (° C.) | $k_{on}$ (1/Ms) | $k_{off}$ (1/s) | $K_D$ (nM) |
|---|---|---|---|---|
| Human α-CGRP | 25 | $1.86 \times 10^5$ | $7.80 \times 10^{-6}$ | 0.042 (7%, n = 4)* |
| Human α-CGRP | 37 | $5.78 \times 10^5$ | $3.63 \times 10^{-5}$ | 0.063 (4%, n = 2)* |
| Human β-CGRP | 37 | $4.51 \times 10^5$ | $6.98 \times 10^{-5}$ | 0.155 |
| Rat α-CGRP | 25 | $5.08 \times 10^4$ | $6.18 \times 10^{-5}$ | 1.22 (12%, n = 2)* |
| Rat α-CGRP | 37 | $1.55 \times 10^5$ | $3.99 \times 10^{-4}$ | 2.57* (Solution $K_D$ = 10 (50%, n = 4)** |
| Rat β-CGRP | 37 | $5.16 \times 10^5$ | $7.85 \times 10^{-5}$ | 0.152 |

*Affinities for α-CGRPs (rat and human) were determined in a high-resolution two-part experiment, in which the dissociation phase was monitored for 2 hours (the values for $k_{on}$, $k_{off}$ and $K_D$ represent the average of n replicate experiments with the standard deviation expressed as a percent variance). Affinities for β-CGRPs (rat and human) were determined by global analysis using only a 20-min dissociation phase, which was not accurate enough to quantify their extremely offrates (their offrates are likely slower than stated here and therefore their affinities are likely even higher). Antibody G1 Fab dissociated extremely slowly from all CGRPs (except α-rat CGRP) with offrates that approached the resolution limit of the Biacore assay (especially at 25° C.).
**Solution affinity determined by measuring the depletion of binding responses detected at CGRP on the chip for antibody G1 Fab pre-incubated with solution-based rat α-CGRP competitor.

Table 6 below shows antibodies having the amino acid sequence variation as compared to antibody G1 and their affinities to both rat α-CGRP and human α-CGRP. All amino acid substitutions of the variants shown in Table 6 are described relative to the sequence of G1. The binding affinities of Fab fragments were determined by Biacore by flowing them across CGRPs on a SA chip.

TABLE 6

Amino acid sequences and binding affinity data for antibody G1 variants determined at 37° C. by Biacore.

| Clone | L1 | L2 | H2 | HC-FW3 | α-rat $k_{off}$ (1/s) | α-rat $K_D$ (nM) | α-human $k_{off}$ (1/s) | α-human $K_D$ (nM) |
|---|---|---|---|---|---|---|---|---|
| G1 | | | | | $\underline{3.99 \times 10^{-4}}$ | $\underline{2.57}$ | $\underline{3.63 \times 10^{-5}}$ | $\underline{0.063}$ |
| M1 | | | | A100L | $\underline{1.10 \times 10^{-3}}$ | | $\underline{1.73 \times 10^{-4}}$ | |
| M2 | | | | L99A A100R | $2.6 \times 10^{-3}$ | $\underline{58}$ | $3.1 \times 10^{-4}$ | $\underline{3}$ |
| M3 | | | | L99A A100S | $2.0 \times 10^{-3}$ | $\underline{61}$ | $2.1 \times 10^{-4}$ | $\underline{1.7}$ |
| M4 | | | | L99A A100V | $1.52 \times 10^{-3}$ | 84.4 | $6.95 \times 10^{-5}$ | 0.43 |
| M5 | | | | L99A A100Y | $7.35 \times 10^{-4}$ | 40.8 | $3.22 \times 10^{-5}$ | 0.20 |
| M6 | | | | L99N | $7.84 \times 10^{-4}$ | 43.6 | $1.33 \times 10^{-4}$ | 0.83 |
| M7 | | | | L99N A100C | $9.18 \times 10^{-4}$ | 51.0 | $2.43 \times 10^{-4}$ | 1.52 |
| M8 | | | | L99N A100G | $7.45 \times 10^{-4}$ | 41.4 | $9.20 \times 10^{-5}$ | 0.58 |
| M9 | | | | L99N A100Y | n.d. | n.d. | $1.00 \times 10^{-5}$ | 0.06 |
| M10 | | | | L99S A100S | $1.51 \times 10^{-3}$ | 83.9 | $1.73 \times 10^{-4}$ | 1.08 |
| M11 | | | | L99S A100T | $4.83 \times 10^{-3}$ | 268.3 | $2.83 \times 10^{-4}$ | 1.77 |
| M12 | | | | L99S A100V | $1.94 \times 10^{-3}$ | 107.8 | $1.01 \times 10^{-4}$ | 0.63 |
| M13 | | | | L99T A100G | $1.84 \times 10^{-3}$ | 102.2 | $1.86 \times 10^{-4}$ | 1.16 |
| M14 | | | | L99T A100K | n.d. | n.d. | $1.00 \times 10^{-5}$ | 0.06 |
| M15 | | | | L99T A100P | $1.15 \times 10^{-3}$ | 63.9 | $1.58 \times 10^{-5}$ | 0.10 |
| M16 | | | | L99T A100S | $9.96 \times 10^{-4}$ | 55.3 | $1.65 \times 10^{-4}$ | 1.03 |
| M17 | | | | L99T A100V | $2.06 \times 10^{-3}$ | 114.4 | $1.85 \times 10^{-4}$ | 1.16 |
| M18 | | | | L99V A100G | $1.22 \times 10^{-3}$ | 67.8 | $7.03 \times 10^{-5}$ | 0.44 |
| M19 | | | | L99V A100R | n.d. | n.d. | $1.00 \times 10^{-5}$ | 0.06 |
| M20 | R28W | | | L99R A100L | $1.44 \times 10^{-3}$ | 80.0 | $1.36 \times 10^{-4}$ | 0.85 |
| M21 | R28W | | | L99S | $\underline{6.95 \times 10^{-4}}$ | $\underline{15.2}$ | $\underline{1.42 \times 10^{-4}}$ | $\underline{1.23}$ |
| M22 | R28W | | | L99T | $\underline{1.10 \times 10^{-3}}$ | 61.1 | $\underline{1.16 \times 10^{-4}}$ | 0.73 |
| M23 | R28G | | | L99T A100V | $7.99 \times 10^{-4}$ | 44.4 | $1.30 \times 10^{-4}$ | 0.81 |
| M24 | R28L | | | L99T A100V | $1.04 \times 10^{-3}$ | 57.8 | $1.48 \times 10^{-4}$ | 0.93 |
| M25 | R28N | | | L99T A100V | $\underline{1.4 \times 10^{-3}}$ | $\underline{76}$ | $\underline{1.4 \times 10^{-4}}$ | $\underline{1.3}$ |
| M26 | R28N | | A57G | L99T A100V | $9.24 \times 10^{-4}$ | 51.3 | $1.48 \times 10^{-4}$ | 0.93 |
| M27 | R28N T30A | | | L99T A100V | $3.41 \times 10^{-3}$ | 189.4 | $3.57 \times 10^{-4}$ | 2.23 |
| M28 | R28N T30D | E54R | A57N | L99T A100V | $1.25 \times 10^{-3}$ | 69.4 | $9.96 \times 10^{-5}$ | 0.62 |
| M29 | R28N T30G | | | L99T A100V | $3.59 \times 10^{-3}$ | 199.4 | $3.80 \times 10^{-4}$ | 2.38 |
| M30 | R28N T30G | E54K | A57E | L99T A100V | $6.38 \times 10^{-3}$ | 354.4 | $5.90 \times 10^{-4}$ | 3.69 |
| M31 | R28N T30G | E54K | A57G | L99T A100V | $3.61 \times 10^{-3}$ | 200.6 | $3.47 \times 10^{-4}$ | 2.17 |
| M32 | R28N T30G | E54K | A57H | L99T A100V | $2.96 \times 10^{-3}$ | 164.4 | $2.71 \times 10^{-4}$ | 1.69 |
| M33 | R28N T30G | E54K | A57N S58G | L99T A100V | $9.22 \times 10^{-3}$ | 512.2 | $7.50 \times 10^{-4}$ | 4.69 |
| M34 | R28N T30G | E54K | A57N S58T | L99T A100V | $2.17 \times 10^{-3}$ | 120.6 | $6.46 \times 10^{-4}$ | 4.04 |
| M35 | R28N T30G | E54K | A57S | L99T A100V | $3.99 \times 10^{-3}$ | 221.7 | $3.39 \times 10^{-4}$ | 2.12 |
| M36 | R28N T30R | | | L99T A100V | $4.79 \times 10^{-3}$ | 266.1 | $2.39 \times 10^{-4}$ | 1.49 |
| M37 | R28N T30S | | A57G | L99T A100V | $1.45 \times 10^{-3}$ | 80.6 | $2.26 \times 10^{-4}$ | 1.41 |

TABLE 6-continued

Amino acid sequences and binding affinity data for antibody G1 variants determined at 37° C. by Biacore.

| Clone | L1 | L2 | H2 | HC-FW3 | α-rat $k_{off}$ (1/s) | α-rat $K_D$ (nM) | α-human $k_{off}$ (1/s) | α-human $K_D$ (nM) |
|---|---|---|---|---|---|---|---|---|
| M38 | R28N T30W | | | L99T A100V | $5.11 \times 10^{-3}$ | 283.9 | $2.18 \times 10^{-4}$ | 1.36 |
| M39 | R28N | G50A L56T | A57N S58Y | L99T A100V | $9.95 \times 10^{-3}$ | 552.8 | $4.25 \times 10^{-4}$ | 2.66 |
| M40 | R28N | G50A L56T | E54K A57L | L99T A100V | 0.36 | 20000.0 | $1.28 \times 10^{-3}$ | 8.00 |
| M41 | R28N | G50A L56T | E54K A57N E64D | L99T A100V | $4.53 \times 10^{-3}$ | 251.7 | $2.10 \times 10^{-4}$ | 1.31 |
| M42 | R28N | G50A L56T | E54K A57N H61F | L99T A100V | $7.52 \times 10^{-3}$ | 417.8 | $4.17 \times 10^{-4}$ | 2.61 |
| M43 | R28N | G50A L56T | E54K A57N S58C | L99T A100V | $4.53 \times 10^{-3}$ | 251.7 | $2.63 \times 10^{-4}$ | 1.64 |
| M44 | R28N | G50A L56T | E54K A57N S58E | L99T A100V | $\underline{6.13 \times 10^{-3}}$ | $\underline{443}$ | $\underline{2.10 \times 10^{-4}}$ | $\underline{2.05}$ |
| M45 | R28N | G50A L56T | E54K A57N S58E E64D | L99T A100V | $\underline{5.58 \times 10^{-3}}$ | $\underline{259}$ | $\underline{2.11 \times 10^{-4}}$ | $\underline{1.85}$ |
| M46 | R28N | G50A L56T | E54K A57N S58E H61F | L99T A100V | $2.94 \times 10^{-3}$ | 163.3 | $5.39 \times 10^{-4}$ | 3.37 |
| M47 | R28N | G50A L56T | E54K A57N S58G | L99T A100V | $8.23 \times 10^{-3}$ | 457.2 | $3.32 \times 10^{-4}$ | 2.08 |
| M48 | R28N | G50A L56T | E54K A57N S58L | L99T A100V | 0.0343 | 1905.6 | $8.42 \times 10^{-4}$ | 5.26 |
| M49 | R28N | G50A L56T | E54K A57N S58Y H61F | L99T A100V | 0.0148 | 822.2 | $5.95 \times 10^{-4}$ | 3.72 |
| M50 | R28N | G50A L56T | E54K A57R | L99T A100V | $5.30 \times 10^{-3}$ | 294.4 | $4.06 \times 10^{-4}$ | 2.54 |
| M51 | R28N | L56I | E54K A57G | L99T A100V | $1.18 \times 10^{-3}$ | 65.6 | $1.31 \times 10^{-4}$ | 0.82 |
| M52 | R28N | L56I | E54K A57N S58A | L99T A100V | $2.29 \times 10^{-3}$ | 127.2 | $2.81 \times 10^{-4}$ | 1.76 |
| M53 | R28N | L56I | E54K A57N S58G | L99T A100V | $1.91 \times 10^{-3}$ | 106.1 | $3.74 \times 10^{-4}$ | 2.34 |
| M54 | R28N T30A | G50A | E54K A57N S58P | L99T A100V | $2.16 \times 10^{-3}$ | 120.0 | $1.79 \times 10^{-3}$ | 11.19 |
| M55 | R28N T30A | L56S | E54K A57N S58E E64D | L99T A100V | $5.85 \times 10^{-3}$ | 325.0 | $4.78 \times 10^{-4}$ | 2.99 |
| M56 | R28N T30D | L56S | E54K A57N H61F | L99T A100V | $9.35 \times 10^{-3}$ | 519.4 | $4.79 \times 10^{-4}$ | 2.99 |
| M57 | R28N T30D | L56S | E54K A57N S58E | L99T A100V | $\underline{0.0104}$ | $\underline{1.200}$ | $\underline{3.22 \times 10^{-4}}$ | $\underline{3.08}$ |
| M58 | R28N T30D | L56S | E54K A57N S58I H61F | L99T A100V | No binding | n.d. | $1.95 \times 10^{-3}$ | 12.19 |
| M59 | R28N T30D | L56S | E54K A57N S58N H61F | L99T A100V | 0.0123 | 683.3 | $5.24 \times 10^{-4}$ | 3.28 |
| M60 | R28N T30D | L56S | E54K A57N S58R H61F | L99T A100V | 0.0272 | 1511.1 | $9.11 \times 10^{-4}$ | 5.69 |
| M61 | R28N T30G | A51H | E54Q A57N H61F | L99T A100V | $5.21 \times 10^{-3}$ | 289.4 | $4.59 \times 10^{-4}$ | 2.87 |

TABLE 6-continued

Amino acid sequences and binding affinity data for antibody G1 variants determined at 37° C. by Biacore.

| Clone | L1 | L2 | H2 | HC-FW3 | α-rat $k_{off}$ (1/s) | α-rat $K_D$ (nM) | α-human $k_{off}$ (1/s) | α-human $K_D$ (nM) |
|---|---|---|---|---|---|---|---|---|
| M62 | R28N T30G | A51H L56T | E54K A57N S58E | L99T A100V | <u>5.75 × 10⁻³</u> | <u>242</u> | <u>5.57 × 10⁻⁴</u> | <u>5.86</u> |
| M63 | R28N T30G | G50A | E54K A57N S58T | L99T A100V | 2.65 × 10⁻³ | 147.2 | 1.50 × 10⁻³ | 9.38 |
| M64 | R28N T30G | G50A | E54K A57N S58V | L99T A100V | 0.0234 | 1300.0 | 1.32 × 10⁻³ | 8.25 |
| M65 | R28N T30G | G50A L56I | E54K A57C | L99T A100V | 4.07 × 10⁻³ | 226.1 | 8.03 × 10⁻⁴ | 5.02 |
| M66 | R28N T30G | L56I | E54K A57E | L99T A100V | 5.11 × 10⁻³ | 283.9 | 5.20 × 10⁻⁴ | 3.25 |
| M67 | R28N T30G | L56I | E54K A57F | L99T A100V | 1.71 × 10⁻³ | 95.0 | 8.20 × 10⁻⁴ | 5.13 |
| M68 | R28N T30G | L56I | E54K A57N S58D E64D | L99T A100V | 6.76 × 10⁻³ | 375.6 | 4.28 × 10⁻⁴ | 2.68 |
| M69 | R28N T30G | L56I | E54K A57N S58E | L99T A100V | 1.81 × 10⁻³ | 100.6 | 7.33 × 10⁻⁴ | 4.58 |
| M70 | R28N T30G | L56I | E54K A57S | L99T A100V | 6.07 × 10⁻³ | 337.2 | 5.59 × 10⁻⁴ | 3.49 |
| M71 | R28N T30G | L56I | E54K A57Y | L99T A100V | 2.12 × 10⁻³ | 117.8 | 1.28 × 10⁻³ | 8.00 |
| M72 | R28N T30G | L56S | E54K | L99T A100V | 3.95 × 10⁻³ | 219.4 | 4.00 × 10⁻⁴ | 2.50 |
| M73 | R28N T30G | L56S | E54K A57N S58Y E64D | L99T A100V | 3.00 × 10⁻³ | 166.7 | 2.55 × 10⁻⁴ | 1.59 |
| M74 | R28N T30G | L56S | E54K A57S | L99T A100V | 6.03 × 10⁻³ | 335.0 | 5.97 × 10⁻⁴ | 3.73 |
| M75 | R28N T30G | L56S | E54K A57V | L99T A100V | 1.87 × 10⁻² | 1038.9 | 1.16 × 10⁻³ | 7.25 |
| M76 | R28N T30S | G50A L56T | A57G | L99T A100V | 1.16 × 10⁻³ | 64.4 | 3.64 × 10⁻⁴ | 2.28 |
| M77 | R28N T30S | G50A L56T | E54K A57D | L99T A100V | 0.0143 | 794.4 | 4.77 × 10⁻⁴ | 2.98 |
| M78 | R28N T30S | G50A L56T | E54K A57N S58T | L99T A100V | 0.167 | 9277.8 | 1.31 × 10⁻³ | 8.19 |
| M79 | R28N T30S | G50A L56T | E54K A57P | L99T A100V | 0.19 | 10555.6 | 1.29 × 10⁻³ | 8.06 |
| M80 | R28N T30S | L56I | E54K A57N S58V | L99T A100V | 0.0993 | 5516.7 | 2.09 × 10⁻³ | 13.06 |
| M81 | R28N T30S | L56S | E54K A57N S58E | L99T A100V | 4.29 × 10⁻³ | 238.3 | 4.90 × 10⁻⁴ | 3.06 |
| M82 | R28N T30V | A51H L56T | A57N | L99T A100V | 6.99 × 10⁻³ | 388.3 | 8.77 × 10⁻⁴ | 5.48 |
| M83 | R28N T30V | A51H L56T | E54K A57N S58M H61F | L99T A100V | No binding | n.d. | 9.33 × 10⁻⁴ | 5.83 |
| M84 | R28N T30V | A51H L56T | E54N A57N | L99T A100V | 1.76 × 10⁻² | 977.8 | 1.08 × 10⁻³ | 6.75 |

Figure 6:
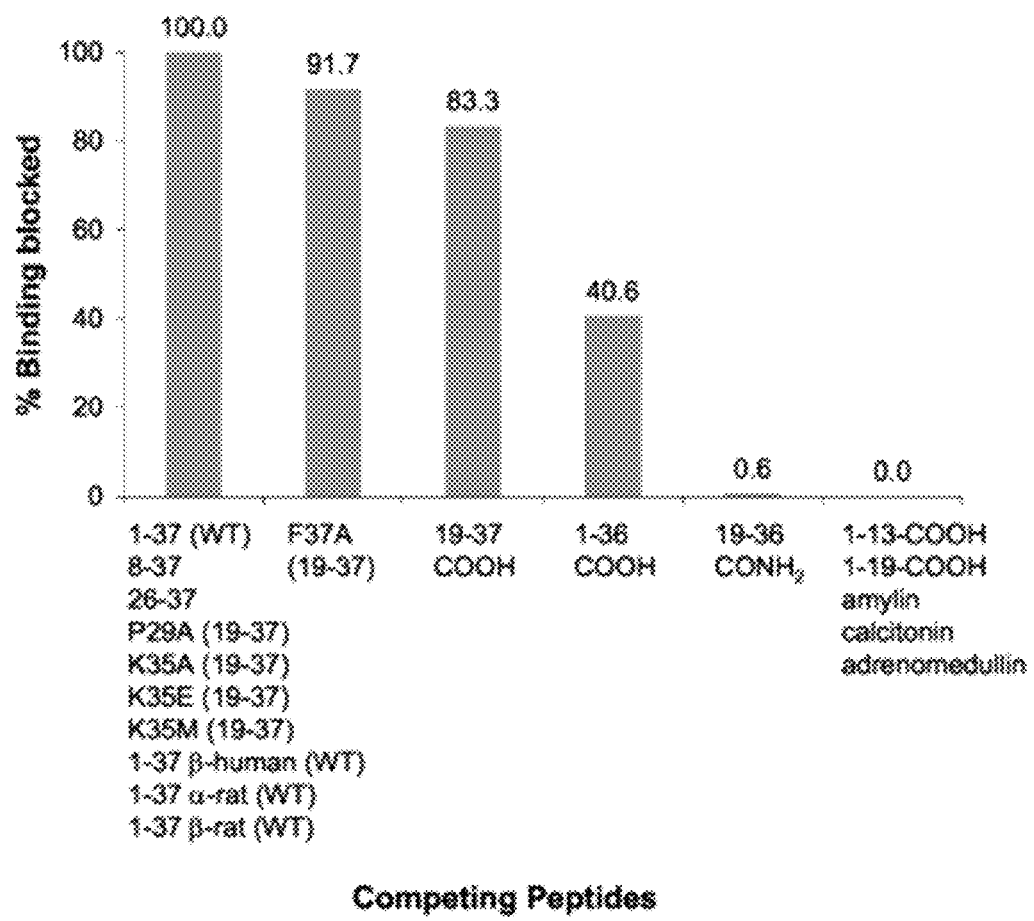
FIG. 6 shows epitope mapping of antibody G1 by peptide competition using Biacore. N-biotinylated human α-CGRP was captured on SA sensor chip. G1 Fab (50 nM) in the absence of a competing peptide or pre-incubated for 1 h with 10 uM of a competing peptide was flowed onto the chip. Binding of G1 Fab to the human α-CGRP on the chip was measured. Y axis represents percentage of binding blocked by the presence of the competing peptide compared with the binding in the absence of the competing peptide.

All CDRs including both Kabat and Chothia CDRs. Amino acid residues are numbered sequentially (see FIG. 5). All clones have L3+H1+H3 sequences identical to G1.
$K_D = k_{off}/k_{on}$. All $k_{off}$ values were determined in a screening mode except those that are underlined, which were obtained by global analysis of a Fab concentration series (G1 was analyzed in a high-resolution mode). Underlined $K_D$ values were therefore determined experimentally by measuring $k_{on}$. Other $k_{on}$ values were estimated to be the same as M25.
n.d.=not determined To determine the epitope on human α-CGRP that is recognized by antibody G1, Biacore assays described above were used. Human α-CGRP was purchased as an N-biotinylated version to enable its high-affinity capture via SA sensor chips. The binding of G1 Fab fragment to the human α-CGRP on the chip in the absence or presence of a CGRP peptide was determined. Typically, a 2000:1 mol peptide/Fab solution (e.g., 10 uM peptide in 50 nM G1 Fab) was injected across human α-CGRP on the chip. FIG. 6 shows the percentage of binding blocked by competing peptide. Data shown in FIG. 6 indicate that peptides that block 100% binding of G1 Fab to human α-CGRP are 1-37 (VVT), 8-37, 26-37, P29A (19-37), K35A (19-37), K35E (19-37), and K35M (19-37) of human α-CGRP; 1-37 of β-CGRP (VVT); 1-37 of rat α-CGRP (VVT); and 1-37 of rat β-CGRP (VVT). All these peptides are amidated at the C-terminus. Peptides F37A (19-37) and 19-37 (the latter not amidated at the C-terminus) of human α-CGRP also blocked about 80% to 90% of binding of G1 Fab to human α-CGRP. Peptide 1-36 (not amidated at the C-terminus) of human α-CGRP blocked about 40% of binding of G1 Fab to human α-CGRP. Peptide fragment 19-36 (amidated at the C-terminus) of human α-CGRP; peptide fragments 1-13 and 1-19 of human α-CGRP (neither of which are amidated at the C-terminus); and human amylin, calcitonin, and adrenomedullin (all amidated at the C-terminus) did not compete with binding of G1 Fab to human α-CGRP on the chip. These data demonstrate that G1 targets a C-terminal epitope of CGRP and that both the identity of the most terminal residue (F37) and its amidation is important for binding.

Binding affinities of G1 Fab to variants of human α-CGRP (at 37° C.) was also determined. Table 7 below shows the affinities as measured directly by titrating G1 Fab across N-biotinylated human α-CGRP and variants on the chip. Data in Table 7 indicate that antibody G1 binds to a C-terminal epitope with F37 and G33 being the most important residues. G1 does not bind to CGRP when an extra amino acid residue (alanine) is added at the C-terminal (which is amidated).

TABLE 7

Binding affinities of G1 Fab to human α-CGRP and variants measured at 37° C. (see Table 4 for their amino acid sequences)

| CGRP on chip | $k_{on}$ (1/Ms) | $k_{off}$ (1/s) | $K_D$ (nM) |
|---|---|---|---|
| 1-37 (WT) | $4.68 \times 10^5$ | $7.63 \times 10^{-5}$ | 0.16 (high resolution $K_D$ = 0.06) |
| 19-37 | $4.60 \times 10^5$ | $7.30 \times 10^{-5}$ | 0.16 |
| 25-37 | $3.10 \times 10^5$ | $8.80 \times 10^{-5}$ | 0.28 |
| F27A (25-37) | $3.25 \times 10^5$ | $1.24 \times 10^{-4}$ | 0.38 |
| V28A (25-37) | $3.32 \times 10^5$ | $9.38 \times 10^{-5}$ | 0.28 |
| P29A (25-37) | $2.26 \times 10^5$ | $1.78 \times 10^{-4}$ | 0.79 |
| T30A (25-37) | $1.79 \times 10^5$ | $8.41 \times 10^{-5}$ | 0.47 |
| N31A (25-37) | $2.17 \times 10^5$ | $1.14 \times 10^{-4}$ | 0.53 |
| V32A (25-37) | $2.02 \times 10^5$ | $3.46 \times 10^{-4}$ | 1.71 |
| G33A (25-37) | $2.07 \times 10^5$ | 0.0291 | 141 |
| S34A (25-37) | $2.51 \times 10^5$ | $7.64 \times 10^{-4}$ | 3.04 |
| K35A (19-37) | $2.23 \times 10^5$ | $2.97 \times 10^{-4}$ | 1.33 |
| K35E (19-37) | $5.95 \times 10^4$ | $5.79 \times 10^{-4}$ | 9.73 |
| K35M (19-37) | $2.63 \times 10^5$ | $1.34 \times 10^{-4}$ | 0.51 |
| K35Q (19-37) | $1.95 \times 10^5$ | $2.70 \times 10^{-4}$ | 1.38 |
| F37A (25-37) | $8.90 \times 10^4$ | $8.48 \times 10^{-3}$ | 95 (solution $K_D$ = 172 nM) |
| 38A (25-38A) | — | — | No binding detected |

The above data indicate that the epitope that antibody G1 binds is on the C-terminal end of human α-CGRP, and amino acids 33 and 37 on human α-CGRP are important for binding of antibody G1. Also, the amidation of residue F37 is important for binding.

Example 5: Effect of Anti-CGRP Antagonist Antibody G1 on Skin Vasodilatation Induced by Stimulation of Rat Saphenous Nerve To test antagonist activity of anti-CGRP antibody G1, effect of the antibody on skin vasodilatation by stimulation of rat saphenous nerve was tested using a rat model described in Example 3. Briefly, rats were maintained anesthesia with 2% isoflurane. Bretylium tosylate (30 mg/kg, administered i.v.) was given at the beginning of the experiment to minimize vasoconstriction due to the concomitant stimulation of sympathetic fibers of the saphenous nerve. Body temperature was maintained at 37° C. by the use of a rectal probe thermostatically connected to a temperature controlled heating blanket. The saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. In experiments to determine effects of antibody within two hours of injection thirty to forty five minutes after bretylium tosylate injection, when a stable base-line flux (less than 5% variation) was established for at least 5 min, the nerve was placed over platinum bipolar electrodes and electrically stimulated (2 Hz, 10V, 1 ms, for 30 sec) and again 20 minutes later. The average of the blood flow flux response to these two stimulations was used to establish the baseline response (time 0) to electrical stimulation. Antibody G1 (1 mg/kg or 10 mg/kg) or vehicle (PBS with 0.01% Tween 20 equal volume to 10 mg/kg G1) were then administered intravenously (i.v.). The nerve was subsequently stimulated (2 Hz, 10V, 1 ms, for 30 sec) at 30 min, 60 min, 90 min, and 120 min after the antibody administration. Animals were kept under anesthesia for a period of approximately three hours. Cumulative change in skin blood flow was estimated by the area under the flux-time curve (AUC, which is equal to change in flux multiplied by change in time) for each flux response to electrical pulse stimulations.

Figure 7:
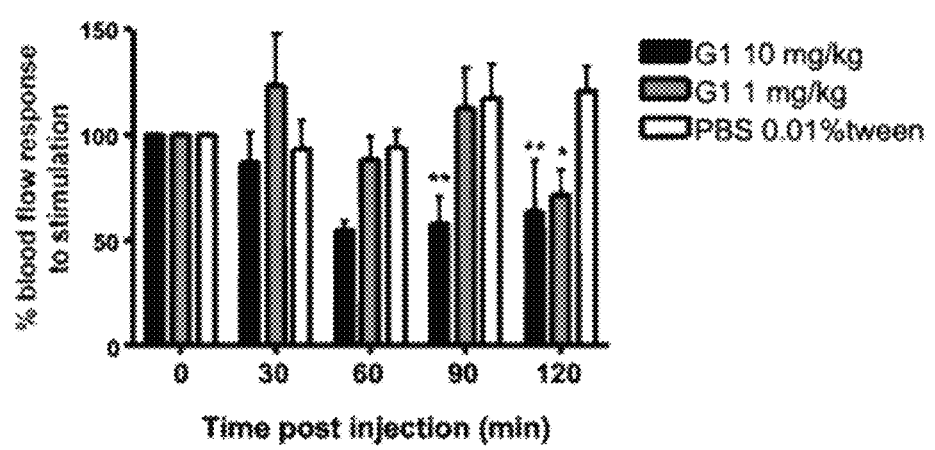
FIG. 7 shows the effect of administering antibody G1 (1 mg/kg or 10 mg/kg, i.v.) or vehicle (PBS, 0.01% Tween 20) on skin blood flow measured as blood cell flux after electrical pulse stimulation for 30 seconds. Antibody G1 or vehicle was administered intravenously (i.v.) followed by nerve electrical pulse stimulation at 30 min, 60 min, 90 min, and 120 min after antibody administration. Y axis represents percent of AUC as compared to level of AUC when no antibody or vehicle (defined as 100%) was administered (time 0). X axis represents time (minutes) period between the administration of antibodies and electrical pulse stimulation. "*" indicates $P<0.05$, and "**" indicates $P<0.01$, as compared to vehicle. Data were analyzed using two-way ANOVA and Bonferroni post tests.

As shown in FIG. 7, blood flow increase stimulated by applying electronic pulses on saphenous nerve was significantly inhibited by the presence of antibody G1 at 1 mg/kg (administered i.v.) as compared to the vehicle, when the saphenous nerve was electrically stimulated at 90 min after the antibody administration. Blood flow increase stimulated by applying electronic pulses on saphenous nerve was significantly inhibited by the presence of antibody G1 at 10 mg/kg (administered i.v.) as compared to the vehicle, when the saphenous nerve was electrically stimulated at 90 minutes and 120 minutes after antibody administration.

In experiments to determine effects of the antibodies at longer time points in the saphenous assay, rats were injected i.v. with the indicated doses of antibody 24 hours or 7 days prior to preparing the animal for saphenous nerve stimulation as described above. In these experiments it was impossible to establish a baseline response in individual rats to electrical pulse stimulation prior to dosing, so treated groups were compared to animals dosed with vehicle (PBS, 0.01% Tween 20) at 24 hours or 7 days.

Figure 8A:
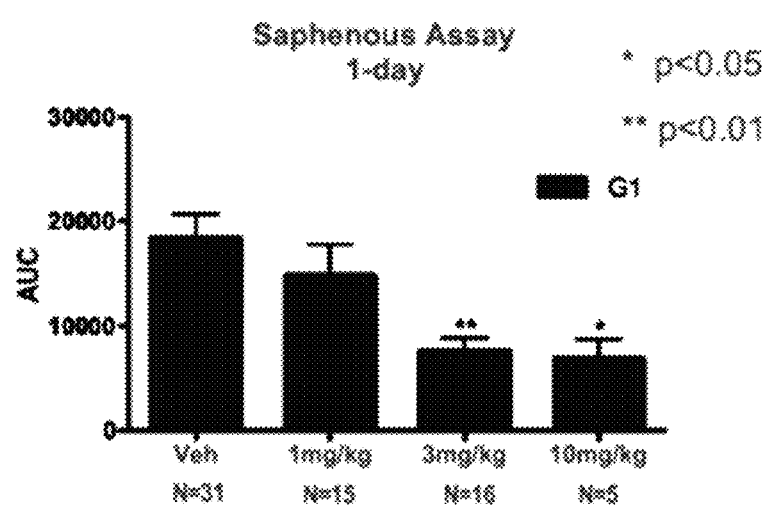
FIG. 8A shows the effect of administering antibody G1 (1 mg/kg, 3 mg/kg or 10 mg/kg, i.v.) or vehicle (PBS, 0.01% Tween 20) on skin blood flow measured as blood cell flux after electrical pulse stimulation for 30 seconds 24 hours after dosing. Antibody G1 or vehicle was administered intravenously (i.v.) 24 hours before nerve electrical pulse stimulation. Y axis represents total area under curve (change in blood cell flux multiplied by the change in time from stimulation until flux returns to baseline, AUC). X axis represents varying doses of antibody G1. "*" indicates $P<0.05$, and "**" indicates $P<0.01$, as compared to vehicle. Data were analyzed using one-way ANOVA and Dunn's multiple comparison test.

As shown in FIGS. 8A and 8B blood flow increases in the dorso-medial hindpaw skin evoked by saphenous nerve stimulation were significantly inhibited in the groups of animals dosed with either 10 mg/kg or 3 mg/kg G1 at either 24 hours or 7 days prior to stimulation as compared to vehicle groups dosed at the same time points.

Figure 8C:
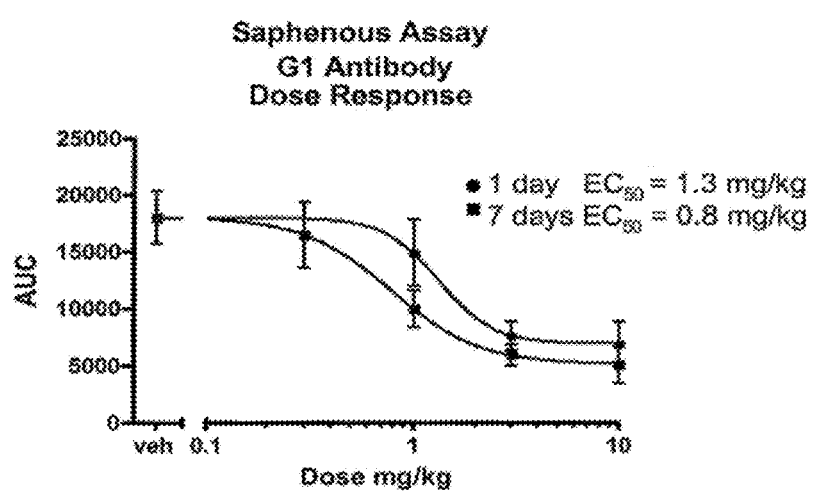
FIG. 8C is a curve fit analysis of the data from FIGS. 8A and 8B. Antibody G1 or vehicle was administered intravenously (i.v.) either 24 hours or 7 days before nerve electrical pulse stimulation. Y axis represents total AUC. X axis represents varying doses of antibody G1 in "mg/kg" on a logarithmic scale to determine $EC_{50}$.

FIG. 8C represents a curve fit analysis applied to the dose response data represented in FIGS. 8A and 8B to determine the dose required for 50% maximal effect ($EC_{50}$). The $EC_{50}$ at 24 hours is 1.3 mg/kg and the $EC_{50}$ at 7 days is slightly lower (0.8 mg/kg).

Example 6: Acute Effect of Anti-CGRP Antagonist Antibody mu7E9 in a Dural Artery (Closed Cranial Window) Assay Closed Cranial Window Model: The purpose of this experiment was to determine the acute effect of anti-CGRP antagonist antibodies and compare it with the acute effect of the CGRP receptor antagonist BIBN4096BS. Experiments were carried out as previously described (Williamson et al., Cephalalgia 17(4):518-24 (1997)) with the following modifications. Sprague Dawley rats (300-400 g) were anesthetized with 70 mg/kg i.p. pentobarbital. Anesthesia was maintained with 20 mg/kg/hr i.v. pentobarbital. Rats were cannulated through the jugular vein for delivery of all drugs. Blood pressure was monitored with a probe (mikro-tip catheter, Millar Instruments) threaded through the femoral artery into the abdominal aorta. The rats were tracheotomized and breathing rate was maintained at 75 breaths per minute at a volume of 3.5 mL. After fixating the head in a stereotactic instrument and removing the scalp, a 2×6 mm window in the left parietal area just lateral to the sagittal suture was made by thinning the bone with a dental drill. Using a micromanipulator, a platinum bipolar electrode was lowered onto the surface and covered with heavy mineral oil. Lateral to the electrode window another window of 5×6 mm was created and filled with heavy mineral oil through which the diameter of a branch of the middle meningeal artery (MMA) was continuously monitored with a CCD camera and a video dimension analyzer (Living Systems). The rats were rested for no less than 45 minutes after the preparation. A baseline response to electrical stimulation was established (15 V, 10 hz, 0.5 ms pulses, 30 seconds) and then rats were dosed i.v. with experimental compound (10 mg/kg mu7E9, 300 µg/kg BIBN4096BS or PBS 0.01% Tween 20). Additional electrical stimulations were done at 5 (BIBN4096BS), 30, 60, 90 and 120 minutes after dosing. All data was recorded using chart software (ADInstruments).

Figure 9:
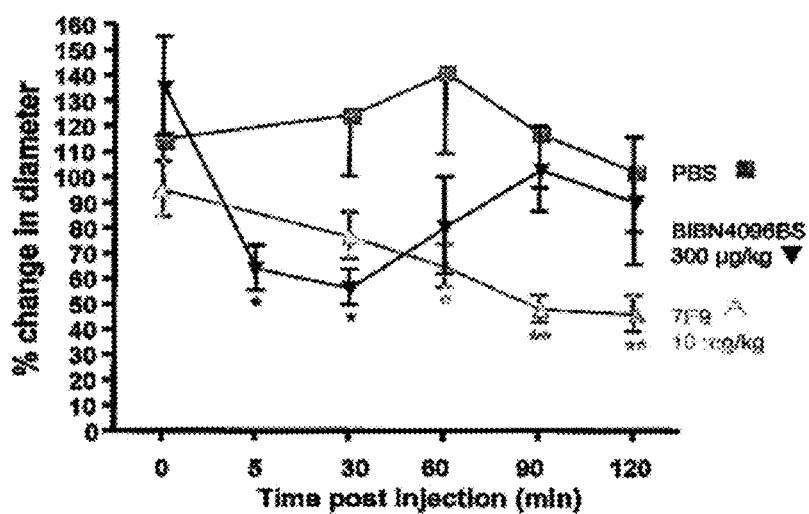
FIG. 9 shows the effect of antibody mu7E9 (10 mg/kg), BIBN4096BS or vehicle (PBS, 0.01% Tween 20) on the change in diameter of the middle meningeal artery after electrical field stimulation. Antibody mu7E9, BIBN4096BS or vehicle were administered intravenously (i.v.) at time point 0 minutes after a baseline response to electrical stimulation was established. Y axis represents change in diameter of the middle meningeal artery after electrical field stimulation. Resting diameter corresponds to 0%. X axis represents time (minutes) of electrical pulse stimulation. "*" indicates $P<0.05$, and "**" indicates $P<0.01$, as compared to vehicle. Data were analyzed using one-way ANOVA and Dunett's multiple comparison test.

As shown in FIG. 9 mu7E9 at 10 mg/kg significantly blocks MMA dilation evoked by electrical field stimulation within 60 minutes after dosing and maintains the effect throughout the duration of the assay (120 minutes). For comparison BIBN4096BS blocks MMA dilation within 5 minutes of dosing but the effect has completely disappeared by 90 minutes. The magnitude of the block is comparable between BIBN4096BS and mu7E9.

Example 7: Chronic Effect of Anti-CGRP Antagonist Antibody G1 in a Dural Artery (Closed Cranial Window) Assay The purpose of this experiment was to determine if the anti CGRP antibody could still block electrically stimulated MMA dilation 7 days after dosing. Preparation of the rats was identical to the above described acute experiment (Example 6) with the following exceptions. Rats were injected i.v. (10 mg/kg, 3 mg/kg or 1 mg/kg G1) 7 days prior to creating the closed cranial window prep and stimulation. It was impossible to establish a baseline dilation response to electrical stimulation prior to dosing as in the acute experiment so the antibody groups were compared to dilation of the MMA in a vehicle (PBS, 0.01% Tween 20) dosed control group. After the rats were allowed to rest for no less than 45 minutes the dura was electrically stimulated at 30 minute intervals. Stimulations were at 2.5V, 5V, 10V, 15V and 20V, all at 10 Hz, 0.5 ms pulses for 30 seconds.

Figure 10:
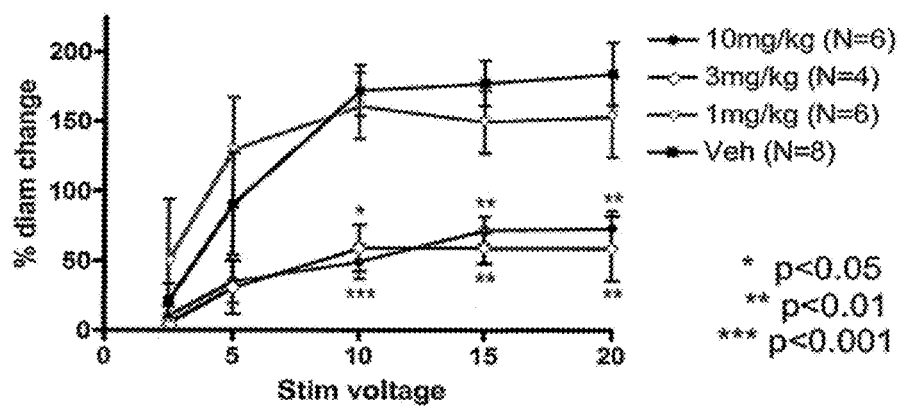
FIG. 10 shows the effect of varying doses of antibody G1 (1 mg/kg, 3 mg/kg or 10 mg/kg, i.v.) or vehicle (PBS, 0.01% Tween 20) on the change in diameter of the middle meningeal artery after electrical field stimulation. Antibody G1 or vehicle was administered intravenously (i.v.) 7 days before electrical field stimulation. Y axis represents change in diameter of the middle meningeal artery. Resting diameter corresponds to 0%. X axis represents stimulation voltage. "*" indicates $P<0.05$, "" indicates $P<0.01$, and "*" indicates $P<0.001$, as compared to vehicle. Data were analyzed using two-way ANOVA and Bonferroni posttests.

As shown in FIG. 10 G1 at 10 mg/kg and 3 mg/kg significantly blocked MMA dilation evoked by electrical stimulation in the range of 10 to 20 volts. This data demonstrates that G1 can block electrically stimulated MMA dilation up to 7 days after dosing.

Example 8: Morphine Withdrawal Hot Flush Model

The morphine withdrawal rat model is an established rodent model for menopausal hot flush mechanisms (Sipe et al., Brain Res. 1028(2):191-202 (2004); Merchenthaler et al., Maturitas 30:307-316 (1998); Katovich et al., Brain Res. 494:85-94 (1989); Simpkins et al., Life Sciences 32:1957-1966 (1983)). Basically the rats are addicted to morphine by implanting morphine pellets under the skin. Upon addiction the animals are injected with naloxone (opioid antagonist) which sends them into withdrawal immediately. This withdrawal is accompanied by a skin temperature increase, a core body temperature decrease, an increase in heart rate and an increase in serum luteinizing hormone. These are all similar in magnitude and timing to what occurs in human hot flush (Simpkins et al., Life Sciences 32:1957-1966 (1983)). Furthermore, if rats are treated with estradiol prior to inducing withdrawal, the symptoms of hot flush are reduced (Merchenthaler et al., Maturitas 30:307-316 (1998)). This is why the morphine withdrawal model is believed to mimic clinical hot flush.

Figure 11A:
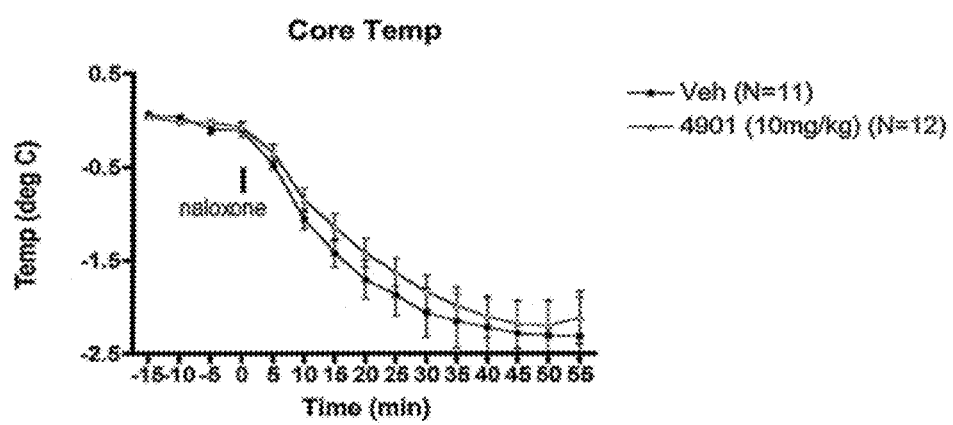
FIG. 11A shows the effect of antibody mu4901 (10 mg/kg) or vehicle (PBS, 0.01% Tween 20), administered intravenously (i.v.) 24 hours prior, on the decrease in core temperature induced by subcutaneous injection of naloxone (1 mg/kg) in morphine addicted rats. The Y axis represents temperature difference from baseline. The X axis represents time measured from the point of naloxone injection.
Figure 11B:
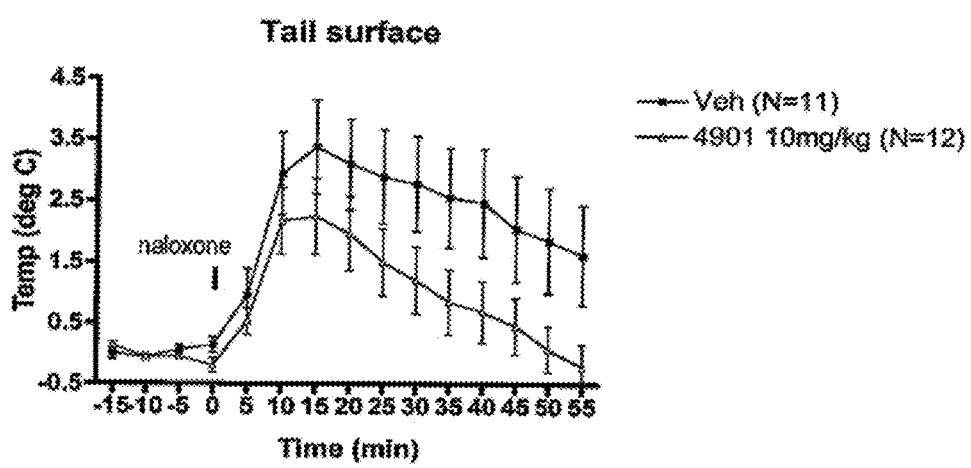
FIG. 11B shows the effect of antibody mu4901 (10 mg/kg) or vehicle (PBS, 0.01% Tween 20), administered intravenously (i.v.) 24 hours prior, on the increase in tail surface temperature induced by subcutaneous injection of naloxone (1 mg/kg) in morphine addicted rats. The Y axis represents temperature difference from baseline. The X axis represents time measured from the point of naloxone injection.

Ovariectomized rats were ordered from Charles River Laboratories. Not less than 7 days post ovariectomy morphine dependency was created by implanting a morphine pellet (75 mg morphine base) subcutaneously. Two days later 2 more pellets were implanted. The following day rats were injected intravenously with either 10 mg/kg 4901 [**] or vehicle (PBS, 0.01% tween). Two days after the second pelleting the rats were anesthetized with ketamine (90 mg/kg) and lightly restrained. A surface temperature thermocouple was taped to the base of the tail and a rectal thermocouple is used to measure core temperature. Data was recorded using Chart software (ADInstruments). After recording 15 minutes of stable baseline temperature, naloxone (1 mg/kg) was injected subcutaneously. Temperature was recorded continuously for the next 60 minutes. The results are shown in FIGS. 11A and 11B.

Example 9: Treatment of Chronic Migraine

A male human subject age 45 years old is identified as having had chronic migraine for at least three months. Identification of having had chronic migraine is achieved by observing a history of frequent headaches suggestive of chronic migraine (e.g., 15 days per month) for at least three months prior to screening. Verification of headache frequency is achieved through prospectively collected baseline information demonstrating headaches on at least 15 days, with at least 8 days per month fulfilling any one of the following: i. qualify as being a migraine attack; and/or ii. preceded or accompanied by migraine aura.

In order to reduce incidence of migraine in the subject, the subject is administered with a dose of 225 mg of anti-CGRP antagonist antibody (e.g., antibody G1). The anti-CGRP antagonist antibody is supplied as a liquid formulation at a concentration of 150 mg/mL. The 225 mg dose is administered as a subcutaneous injection of 1.5 mL the back of an upper arm of the subject's body. Alternatively, the dose may be provided to the subject via intravenous infusion. In such cases, 5.85 mL of 150 mg/mL anti-CGRP antibody may be combined with 0.9% Sodium Chloride Solution (Normal Saline) in an IV bag for a total volume of 130 mL in the bag. 100 mL of the IV bag volume is intravenously infused to the subject over the course of one hour, for a total dose of 225 mg. Dosing is repeated every twenty-eight days until a reduced incidence of migraine is observed. A reduced incidence of chronic migraine is examined using a variety of criteria that include the number of headache days, the number of hours for which headaches occur (e.g., headache hours), the severity of headaches, and the number of migraine days observed in the subject.

Example 10: Treatment of Chronic Migraine

A female human subject age 37 years old is identified as having had chronic migraine for at least three months.

Identification of having had chronic migraine is achieved by observing a history of frequent headaches suggestive of chronic migraine (e.g., 15 days per month) for at least three months prior to screening. Verification of headache frequency is achieved through prospectively collected baseline information demonstrating headaches on at least 15 days, with at least 8 days per month fulfilling any one of the following: i. qualify as being a migraine attack; and/or ii. preceded or accompanied by migraine aura.

In order to reduce incidence of migraine in the subject, the subject is administered with an initial loading dose of 675 mg of anti-CGRP antagonist antibody (e.g., antibody G1). The anti-CGRP antagonist antibody is supplied as a liquid formulation at a concentration of 150 mg/mL. The 675 mg loading dose is administered as three 225 mg subcutaneous injections of 1.5 mL to various regions (e.g., back of upper arms, lower abdomen/belly/waistline, front of thighs, etc.) of the subject's body. Dosing is repeated every twenty-eight days at 225 mg (e.g., via one 1.5 mL subcutaneous injection in the subject's arm) until a reduced incidence of migraine is observed. A reduced incidence of chronic migraine is examined using a variety of criteria that include the number of headache days, the number of hours for which headaches occur (e.g., headache hours), the severity of headaches, and the number of migraine days observed in the subject.

Example 11: Treatment of Chronic Migraine

A male human subject age 23 years old is identified as having had chronic migraine for at least three months. Identification of having had chronic migraine is achieved by observing a history of frequent headaches suggestive of chronic migraine (e.g., 15 days per month) for at least three months prior to screening. Verification of headache frequency is achieved through prospectively collected baseline information demonstrating headaches on at least 15 days, with at least 8 days per month fulfilling any ONE of the following: i. qualify as being a migraine attack; and/or ii. preceded or accompanied by migraine aura.

In order to reduce incidence of migraine in the subject, the subject is administered with a dose of 900 mg of anti-CGRP antagonist antibody (e.g., antibody G1). The anti-CGRP antagonist antibody is supplied as a liquid formulation at a concentration of 150 mg/mL. The 900 mg dose is administered as four 225 mg subcutaneous injections of 1.5 mL to various regions (e.g., back of upper arms, lower abdomen/belly/waistline, front of thighs, etc.) of the subject's body. Dosing is repeated every twenty-eight days until a reduced incidence of migraine is observed. A reduced incidence of chronic migraine is examined using a variety of criteria that include the number of headache days, the number of hours for which headaches occur (e.g., headache hours), the severity of headaches, and the number of migraine days observed in the subject.

Example 12: Treatment of Episodic Migraine

A male human subject age 28 years old is identified as having had episodic migraine at high frequency. Subjects are identified as having episodic migraine at high frequency using criteria that include: having a history of headaches on more than 8 days per month for at least 3 months prior to screening; and verification of headache frequency through prospectively collected baseline information demonstrating headaches (of any type) on 8 to 14 days with at least 8 days fulfilling criteria for at least one of the following: i. migraine; ii. probable migraine; and/or iii. use of triptans or ergot compounds.

In order to reduce incidence of migraine in the subject, the subject is administered with a dose of 675 mg of anti-CGRP antagonist antibody (e.g., antibody G1). The anti-CGRP antagonist antibody is supplied as a liquid formulation at a concentration of 150 mg/mL. The 675 mg dose is administered as three 225 mg subcutaneous injections of 1.5 mL to various regions (e.g., back of upper arms, lower abdomen/belly/waistline, front of thighs, etc.) of the subject's body. Dosing is repeated every twenty-eight days until a reduced incidence of migraine is observed. A reduced incidence of episodic migraine is examined using a variety of criteria that include the number of headache days, the number of hours for which headaches occur (e.g., headache hours), the severity of headaches, and the number of migraine days observed in the subject.

Example 13: Treatment of Episodic Migraine

A female human subject age 52 years old is identified as having had episodic migraine at high frequency. Subjects are identified as having episodic migraine at high frequency using criteria that include: having a history of headaches on more than 8 days per month for at least 3 months prior to screening; and verification of headache frequency through prospectively collected baseline information demonstrating headaches (of any type) on 8 to 14 days with at least 8 days fulfilling criteria for at least one of the following: i. migraine; ii. probable migraine; and/or iii. use of triptans or ergot compounds.

In order to reduce incidence of migraine in the subject, the subject is administered with a dose of 225 mg of anti-CGRP antagonist antibody (e.g., antibody G1). The anti-CGRP antagonist antibody is supplied as a liquid formulation at a concentration of 150 mg/mL. The 225 mg dose is administered as a subcutaneous injection of 1.5 mL to the back of an upper arm of the subject's body. Dosing is repeated every twenty-eight days until a reduced incidence of migraine is observed. A reduced incidence of episodic migraine is examined using a variety of observations that include observing the number of headache days, the number of hours for which headaches occur, the severity of headaches, and the number of migraine days in the subject.

Example 14: Non-Clinical Toxicology and Pharmacokinetics

Anti-CGRP antagonist antibody G1 was well-tolerated in 1-month IV repeat-dose toxicity studies in Sprague-Dawley (SD) rats and cynomolgus monkeys and no target organ toxicity was determined in either of these studies. A no adverse event level (NOAEL) of 100 mg/kg/week was established for both the rat and monkey studies. This dose level corresponded to systemic exposure with a maximum concentration (Cmax) of 2,570 and 3,440 µg/mL and areas under the curve (AUC(0-168 h)) of 194,000 µg·h/mL and 299,000 µg·h/mL (Day 22) in rats and monkeys, respectively.

In a 3-month IV/SC rat study, no target organ toxicities were identified and G1 was well-tolerated up to the highest tested dose, 300 mg/kg. In a 3-month monkey study, perivascular inflammation of the ciliary artery, as the result of the deposition of immune complexes was observed at 2100 mg/kg. This finding was attributed to the monkey's immunogenic response to a humanized antibody and was not considered to be clinically relevant. The highest tested dose of 300 mg/kg in this monkey study are at least 10-fold greater than the highest anticipated clinical dose of 2,000 mg or 29 mg/kg on a mg/kg basis (assuming an average subject weight of 70 kg).

Example 15: Clinical Pharmacokinetics

The PK of antibody G1 following single IV exposure was examined in four randomized, placebo-controlled, double-blind studies examining doses between 10 and 2,000 mg. Maximum plasma concentrations (Cmax) were reached shortly after the end of the 1-hour IV infusion. Median time to Cmax (Tmax) ranged from 1.0 to 3.0 hours, followed by a multiphasic decline. Cmax and total exposure increased approximately linearly with escalating doses of G1. Terminal half-life (t½) ranged from 36.4 to 48.3 days. There is no evidence of G1 metabolism in the liver, the primary mode of metabolism is by proteosomic degradation.

One study defined the pharmacokinetics of 30 mg and 300 mg doses given twice, two weeks apart. Maximum concentrations and area under the concentration-time profile increased with increasing dose. The apparent terminal half-life (t½) after the second dose was 41.2 days (30 mg) and 50.0 days (300 mg) (arithmetic mean). The plasma accumulation ratios of G1 after two IV doses administered 15 days apart were 1.5 (30 mg) and 1.4 (300 mg).

Example 16: Clinical Safety and Pharmacokinetics

In six studies, antibody G1 was administered to 118 healthy males and females, while 57 male and female subjects received placebo. The study included single IV doses ranging from 0.2 mg up to 2,000 mg, two IV doses of up to 300 mg given once every 14 days, and SC administration of 225 and 900 mg. The six studies included: two IV single dose escalation PK and pharmacodynamics (PD) studies in healthy males (studies B0141001 and B0141002); a two-cohort, placebo controlled cross-over study to examine the acute effects of IV administration of antibody G1 on capsaicin flare response in healthy volunteers (B0141006); a parallel group repeat dose study of antibody G1 in healthy male and female volunteers (B0141007); a single dose study evaluating the safety and tolerability of doses up to 2,000 mg administered IV to healthy female volunteers (B0141008), and a study comparing the relative safety and bioavailability between IV and SC administration (G1-SC-IV).

The six studies are summarized below in Table 11. Of the five IV studies (B0141001, B0141002, B0141006, B0141007 and B0141008), three had virtually identical designs and assessments. Study B014100 tested doses of 0.2 mg, 1 mg, and 3 mg given as a single one-hour IV infusion. The study had a parallel design. Participants were confined in the clinic for seven days after the infusion, with multiple assessments on each of these days. After discharge, patients were reassessed one week after discharge (day 14), and then one, two, and three months after the infusion. Study B0141002 tested doses ranging from 10 mg to 1000 mg as a single administration. Finally, Study B0141008 tested doses of 300 mg, 1000 mg, 1500 mg, or 2000 mg. Study B0141006 was distinct from the others since it also aimed to integrate pharmacodynamic readouts through measuring capsaicin flare inhibition up to one week after IV infusion of antibody G1.

For the IV studies, adverse events (AEs) profiles were reported for the first dosed period only. Study B0141007 tested multiple doses of antibody G1 at either 30 or 300 mg IV given two weeks apart, using a parallel design. Each eligible subject was assigned a randomization sequence via an interactive Web-based system that contained the treatment assignment. The randomization schema was developed by the lead statistician. Participants in all studies were generally healthy men and women (from 18 to 65 years of age); all participants signed informed consent forms. All studies were approved by investigation review boards (IRBs). AEs were defined as any untoward medical occurrence in clinical study participants, with or without causal relationship to study drug. AEs observed after administration of the study drug or placebo were termed "treatment-emergent" AE (TEAEs) regardless of potential causality with the study drug. All subjects experiencing TEAEs were followed at appropriate time intervals until the event had resolved or until the event had stabilized and/or reached a new baseline. All TEAEs were ranked as being mild, moderate, or severe. Serious AEs (SAEs) were defined a priori as any untoward medical occurrence that at any dose resulted in death, was life threatening (i.e. the subject was at immediate risk of death at the time of the event), required inpatient hospitalization or prolongation of existing hospitalization, resulted in persistent or significant disability/incapacity (e.g., a substantial disruption of the subject's ability to carry out normal life functions), resulted in a congenital anomaly/birth defect, or any other medically important event. Treatment-related AE (TRAEs) were to be considered when one of the following situations was present: 1) a plausible temporal relationship between the onset of the AE and administration of the investigational product could be identified; 2) the AE could not be readily explained by the patient's clinical state, intercurrent illness, or concomitant therapies; 3) the AE abated on discontinuation of the investigational product or dose reduction.

Blood pressure, pulse rate and oral temperature were measured at screening, pre-dose, immediately after the end of the infusion and multiple times during the patients' confinements in the clinics, as well as at all clinic visits. Laboratory tests included serum chemistries, hematology, and urinalysis. Hematology, chemistry, coagulation, and urine safety laboratory tests were performed at multiple study times. ECGs were recorded at screening, pre-dose on Day 1, immediately after the end of the infusion and five other times during the first day, as well as in all clinic visits. QTcF values were derived using Fridericia's (QTcF) heart rate correction formula. Absolute values and changes from baseline for the ECG parameters QT interval, heart rate, QTcF interval, PR interval and QRS interval were assessed by cohort, treatment, and time post-dose. In addition to the safety assessments described above, Protocol B014008 included complete ophthalmic assessments at baseline and at three time points after dosing (Day 28, Day 84, and Day 168).

Clinical data and vital signs were summarized using descriptive tables and summary statistics. Laboratory and other safety data were summarized as a function of any change (values outside of the reference range), as well as any clinical relevant changes, which were defined a priori. Summary tables were stratified by dose and data were pooled across studies. In addition, comparisons for consolidated data for all antibody G1 exposures were contrasted with placebo. Placebo was also contrasted with antibody G1 doses of 100 mg and higher (100 mg, 300 mg, 1000 mg, 1500 mg, and 2000 mg), and with antibody G1 doses of 1000 mg and higher (1000 mg, 1500 mg, and 2000 mg).

In the IV/SC study (G1-SC-IV), thirty-six subjects were randomized to receive a single administration of antibody G1 (225 or 900 mg) or placebo, delivered as either a subcutaneous (SC) bolus injection or a 1-hour IV infusion. Subjects were confined in the clinical research unit for seven days after dosing, and returned to the clinic periodically for additional outpatient visits up to Study Day 90. ECGs were performed extensively on Day 1 (pre-dose, Hours 1, 6, 12), Day 3, Day 7 while the subjects were confined and once at the completion of the study (Day 90). Vital signs, including temperature, blood pressure and heart rate, were collected pre-dose, Days 1, 3, 7 and 90.

TABLE 11

| Study | Study population | Treatment with Antibody G1 |
|---|---|---|
| B0141001 | Healthy adult men (n = 24) | Single intravenous (IV) infusion of 0.2, 1 or 3 mg in cohorts of eight (six/cohort, active treatment; two in placebo cohort) |
| B0141002 | Healthy adult men (n = 40) | Single IV infusion of 10, 30, 100, 300 or 1000 mg in cohorts of eight (six/cohort, active treatment; 10 in placebo cohort) |
| B0141006 | Healthy adult men (n = 12) | Two cohorts modified cross-over, placebo or 300 mg IV infusion in cohorts of six. In the first period, all participants received placebo. For the second period (included herein), 12 participants received placebo and 11 received 300 mg. |
| B0141007 | Healthy adult men and women (n = 21) | Two IV infusions two weeks apart at 30 or 300 mg in cohorts of 10 or 11 (six/cohort, active treatment; nine in placebo cohort) |
| B0141008 | Healthy adult women (n = 31) | Single IV infusion of 300, 1000, 1500, or 2000 mg (five in 2000 mg cohort; six/cohort remaining treatment groups; eight in placebo cohort) |
| G1-SC-IV | Thirty-six subjects (n = 36) | Single subcutaneous (SC) bolus injection or single IV infusion of 225 or 900 mg |

Across the broad range of dosages evaluated in the five IV studies (0.2 to 2,000 mg), IV antibody G1 was acceptably tolerated. Table 8 summarizes the overall adverse event (AE) rate by dose for the IV studies. Based on these tolerability results, overt safety concerns have not emerged. Across all trials in the IV studies, participants receiving placebo reported an average of 1.3 treatment emergent adverse events (TEAEs). These are all reported events, regardless of the investigator's opinion of relationship to study drug. Across all IV G1 doses, the rate was 1.4 TEAEs/subject. Subjects receiving G1 doses of 100 mg or higher had an average of 1.5 TEAEs; those receiving doses of 1,000 mg or higher had an average of 1.6 TEAEs.

TABLE 8

| | Subjects Evaluated for AE | Number of AEs - n (N) | Subjects with AE - n (N) | Subject with Serious AE - n (N) | Subject with Severe AE - n(N) | Subjects discontinued for AEs - n (N) | Dose reduced or temporary discontinuations - n (N) |
|---|---|---|---|---|---|---|---|
| Placebo | 45 | 57 (11) | 23 (8) | 0 | 0 | 2 (1) | 0 |
| 0.2 mg | 6 | 5 (0) | 2 (0) | 0 | 0 | 0 | 0 |
| 1 mg | 6 | 1 (1) | 3 (0) | 0 | 0 | 0 | 0 |
| 3 mg | 6 | 10 (2) | 4 (1) | 0 | 0 | 0 | 0 |
| 10 mg | 6 | 5 (1) | 4 (1) | 0 | 0 | 0 | 0 |
| 30 mg | 12 | 21 (11) | 8 (5) | 0 | 0 | 0 | 0 |
| 100 mg | 6 | 5 (1) | 4 (1) | 0 | 0 | 0 | 0 |
| 300 mg | 29 | 47 (10) | 20 (7) | 1 (1) | 1 (1) | 0 | 0 |
| 1000 mg | 12 | 17 (4) | 8 (4) | 0 | 0 | 0 | 0 |
| 1500 mg | 6 | 8 (0) | 3 (0) | 0 | 1 (0) | 0 | 0 |
| 2000 mg | 5 | 12 (2) | 4 (1) | 0 | 0 | 0 | 1 (1) |

AE = adverse events;
n = any event, treatment related or not;
(N) = considered treatment related by investigator.
Note:
For protocol B0141006 (placebo and 300 mg), only data for the first active treatment period was included, due to its cross-over nature In the IV studies, treatment-related adverse events (TRAEs, or AEs that might be related to the therapy according to the primary investigator) were reported in 21.2% of subjects receiving IV G1, compared to 17.7% in those receiving placebo. At doses of 100 mg of G1 or higher, TRAEs occurred in 22.4% of participants. At doses of 1,000 mg or higher, TRAEs occurred in 21.7% of participants.

Antibody G1 does not appear to be associated with any clinically relevant patterns of change in vital signs (systolic and diastolic blood pressure [BP], temperature and heart rate [HR]), electrocardiogram (ECG) abnormalities (including QTcB and QTcF), infusion site reactions, or clinical laboratory findings. There were limited effects on liver function tests (aspartate aminotransferase [AST], alanine aminotransferase [ALT], total bilirubin, and alkaline phosphatase) with a grade 1 increase in total bilirubin in one subject receiving placebo (Study B0141001), and a grade 1 increase in ALT in one subject receiving placebo (Study B0141002). Clinically significant liver function abnormalities were not seen among subjects receiving any of the studied doses of G1. There was no evidence of differences between G1 and placebo in hematological tests assessing renal function, electrolytes, or in urine tests.

In the IV/SC study (G1-SC-IV), safety and tolerability were comparable between SC and IV routes of delivery. Mean heart rate and blood pressure (diastolic and systolic) were not affected by antibody G1 treatment, nor were there any meaningful changes in any cardiovascular parameter after treatment with SC antibody G1. A summary of TRAEs observed during the SC study is shown below in Table 12.

TABLE 12

|  | 900 mg (N = 6) | 225 mg (N = 6) | Placebo (N = 6) |
|---|---|---|---|
| GI disorders | 2 (33.3%) | 0 | 1 (16.7%) |
| CNS | 0 | 1 (16.7%) | 0 |
| Infections and Infestations | 0 | 0 | 0 |
| Musculoskeletal and connective tissue | 0 | 0 | 0 |
| Respiratory | 0 | 0 | 0 |
| Reproductive and Breast Disorders | 0 | 0 | 0 |
| Injuries | 0 | 0 | 0 |
| Pregnancy | 0 | 0 | 0 |
| Renal | 1 (16.7%) | 0 | 0 |
| Vascular | 0 | 0 | 0 |

In the single dose studies (B0141001, B0141002, B0141006 and B0141008), pharmacokinetic (PK) parameters were calculated for doses ranging from 30 mg to 2,000 mg. Group mean terminal half-life ($t_{1/2}$) ranged from approximately 40 to 48 days. $C_{max}$ and total exposure (assessed by $AUC_{inf}$) increased with increasing dose. The increase in $AUC_{inf}$ appeared to be approximately dose proportional between 30 and 1,000 mg and appeared to be greater than dose proportional between 1,000 and 2,000 mg. The volume of distribution was low, between 6-10 L.

In the two dose study (B0141007), the apparent terminal half-life after a second dose was between 41 and 50 days. Plasma concentrations accumulated after the second dose, with an accumulation ratio of approximately 1.5. Moreover, in the IV/SC study (G1-SC-IV), pharmacokinetic assessments indicated G1 had a similar terminal half-life when delivered SC as IV.

Example 17: Prevention of Chronic Migraine in a Clinical Study of Antibody G1

A multicenter, randomized, double-blind, double-dummy, placebo-controlled, parallel group, multi-dose study comparing anti-CGRP antagonist antibody G1 to placebo was performed in subjects having chronic migraine. Qualifying subjects entered a baseline, 28-day run-in period. Subjects had their headache and health information captured daily during the entire study, using an electronic headache diary system. No changes in migraine medication were allowed during the run-in period or study. Inclusion criteria were as follows: (1) males or females aged 18 to 65; (2) a signed and dated informed consent document indicating that the subject has been informed of all pertinent aspects of the study including any known and potential risks and available alternative treatments; (3) chronic migraine meeting the diagnostic criteria listed in the International Classification of Headache Disorders (ICHD-III beta version, 2013); (4) subjects may use up to two different daily migraine preventive medications for migraine (e.g., topiramate, propranolol, amitriptyline) or for other medical conditions (e.g. propranolol being used for hypertension) if the dose and regimen has been stable for at least 2 months prior to beginning the 28-day run in period; (5) Body Mass Index (BMI) of 17.5 to 34.5 kg/m², and a total body weight between 50 kg and 120 kg, inclusive; (6) subject is either not of reproductive potential as defined in the methods or if subject is of reproductive potential, they agree either to remain abstinent or use (or have their partner use) an acceptable method of birth control within the projected duration of the study; (7) demonstrated compliance with the electronic headache diary during the run-in period by entry of headache data on a minimum of 24/28 days (85% compliance). Chronic migraine diagnostic criteria under (3) above were as follows: (a) history of frequent headaches suggesting of chronic migraine (15 days per month) for at least three months prior to screening; (b) verification of headache frequency through prospectively collected baseline information during the 28-day run-in phase demonstrating headaches on at least 15 days, with at least 8 days per month fulfilling any one of (i) qualify as being a migraine attack, (ii) preceded or accompanied by migraine aura, or (iii) relieved by ergot or triptan derivatives.

Exclusion criteria required that subjects not meet any of the following: (1) Onset of chronic migraine after the age of 50 years; (2) subject has received onabotulinum toxin A for migraine or for any medical or cosmetic reasons requiring injections in the head, face, or neck during the six months prior to screening; (3) subject uses medications containing opioids (including codeine) or barbiturates (including Fiorinal®, Fioracet®, or any other combination containing butalbital) on more than 4 days per month for the treatment of migraine or for any other reason (4) failed >2 medication categories or >3 preventive medications (within two medication categories) due to lack of efficacy for prophylactic treatment of episodic or chronic migraine after an adequate therapeutic trial; (5) clinically significant hematological, renal, endocrine, pulmonary, gastrointestinal, genitourinary, neurologic, or ocular disease, at the discretion of the investigator; (6) subjects with evidence or medical history of clinically significant psychiatric issues including major depression, panic disorder, or generalized anxiety disorder (according to Diagnostic and Statistical Manual 5th edition [DSM-5] criteria); (7) systolic blood pressure at screening above 160 mm Hg or below 90 mm Hg; (8) diastolic blood pressure at screening above 110 mm Hg or below 50 mm Hg; (9) history of clinically significant cardiovascular disease or vascular ischemia (such as myocardial, neurological [e.g., cerebral ischemia], peripheral extremity ischemia, or other ischemic event); (10) past or current history of cancer, with the exception of those subjects with basal cell carcinoma that has been excised; (11) pregnant or nursing females; (12) History of hypersensitivity reactions to injected proteins, including monoclonal antibodies; (13) treatment with an investigational drug within 30 days of study entry (14) a clinically significant abnormality in the baseline 12-lead surface ECG, including sinus pauses >2 seconds, second or third degree heart block or other abnormalities judged clinically significant by the investigator. (15) a baseline 12-lead ECG demonstrating QTcF >450 msec for males and 470 msec for females at screening (if QTcF exceeded these values, the ECG was repeated and the average of the three QTcF values used to determine the potential subject's eligibility; QTc obtained using Fridericia calculation); (16) any finding that, in the judgment of the investigator, is clinically significantly abnormal, including hematology values, blood chemistries, coagulation tests or urinalysis (abnormal tests were permitted to be repeated for confirmation) (17) hepatic enzymes (alanine aminotransferase [ALT], aspartate aminotransferase [AST], alkaline phosphatase) >1.3 times the upper limit of normal (ULN) after confirmation in a repeat test; (18) serum creatinine >1.5 times the ULN, clinically significant proteinuria (urine dipstick+4) or evidence of renal disease.

Subjects confirmed to have chronic migraine and high compliance with the daily headache diary during the run-in period were randomized at visit 2 (day 1) into one of three treatment arms. Randomization was performed using an electronic interactive web response system. Subjects were stratified based on gender and baseline migraine medication use. Treatment was administered once monthly (every 28 days) for a total of three treatments over a 3-month period. Treatment administration occurred at visit 2 (day 1; first dose), visit 3 (day 29; second dose), and visit 4 (day 57; third and final dose). Final study exit assessments were performed at visit 5 (day 85), approximately 28 days following the third and final dose. Injections were administered subcutaneously over a 3-month period (every 28 days) to subjects in each of the following groups: (1) those randomized to the 900 mg arm received four active injections every 28 days; (2) those randomized to the 675/225 mg arm received three active and one placebo injection for the first treatment, and one active and three placebo injections for the second and third treatments; (3) those randomized to placebo received four placebo injections every 28 days. Active injections contained 225 mg of antibody G1. Endpoints were derived from an electronic daily headache diary, a web-based interactive system that recorded data for the previous 24-hour period. Overall headache duration was recorded numerically, in hours, as well as number of hours with headache at each level of severity. Headache severity was subjectively rated by the subject at predefined time points as follows: no pain, mild pain, moderate pain, and severe pain. Subjects were also asked to record whether the following associate symptoms were present or absent at predefined time points: photophobia, phonophobia, nausea, and vomiting. An additional endpoint was derived from monitoring the use triptans (e.g., sumatriptan) as an acute anti-headache medication by study subjects throughout the course of the study. A summary of the disposition and demographics of subjects in the study is provided in Table 9.

TABLE 9

|  | Placebo | 675/225 mg | 900 mg | Total |
|---|---|---|---|---|
| Randomized | 89 | 88 | 87 | 264 |
| Completed | 77 (86.5%) | 72 (81.8%) | 76 (87.4%) | 225 |
| Analyzed as ITT | 89 (100%) | 87 (98.9%) | 85 (97.7%) | 261 (98.9%) |
| In Safety Analysis | 89 (100%) | 88 (100%) | 86 (98.9%) | 263 (99.6%) |
| Did Not Complete | 12 (13.5%) | 16 (18.2%) | 11 (12.6%) | 39 (14.8%) |
| Age (mean years) | 40.7 | 40 | 41.5 | 40.75 |
| % women | 85.4% | 86.3% | 86.2% | 85.9% |
| Years with migraine | 20.4 | 15.8 | 18.7 | 18.3 |

Figure 15:
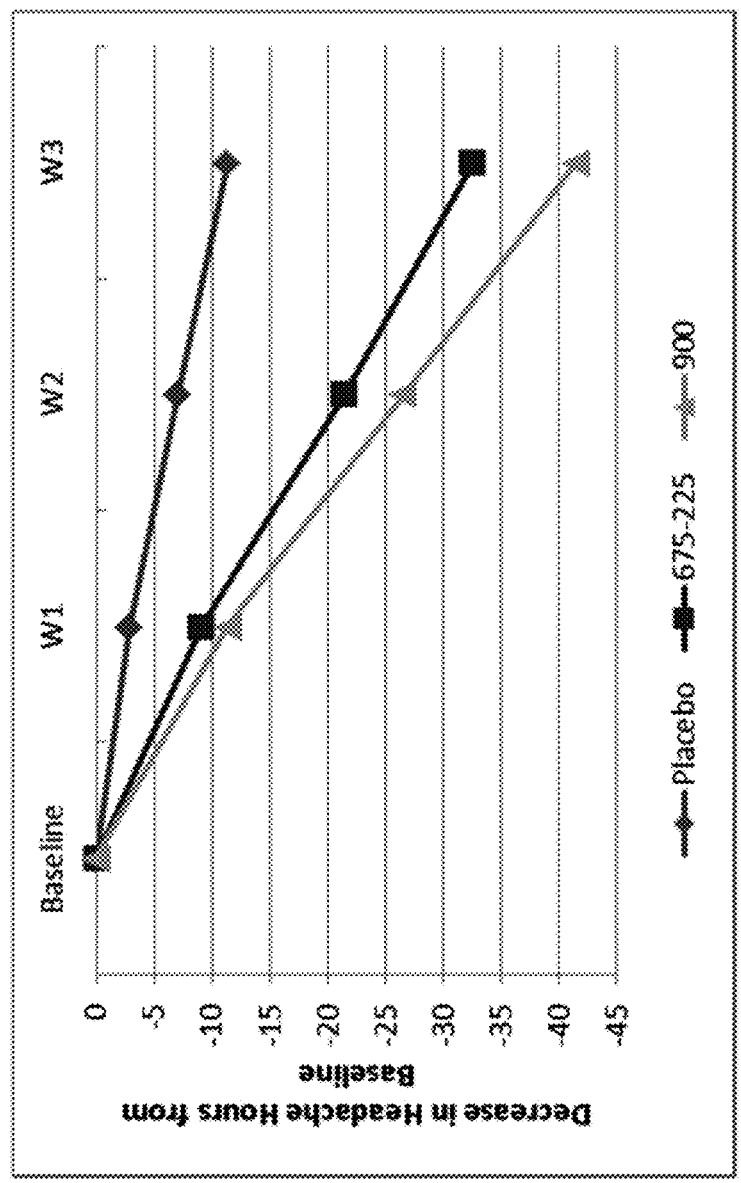
FIG. 15 is a graph illustrating results of a clinical study comparing the effects of different doses of antibody G1 to placebo.

Average decrease in number of headache hours relative to baseline at each of weeks 1, 2 and 3 (W1, W2, and W3, respectively) for each of the groups are represented graphically in FIG. 15. Results show a significant decrease in both treatment groups relative to the placebo group at each of W1, W2 and W3, including the very first week.

Figure 12:
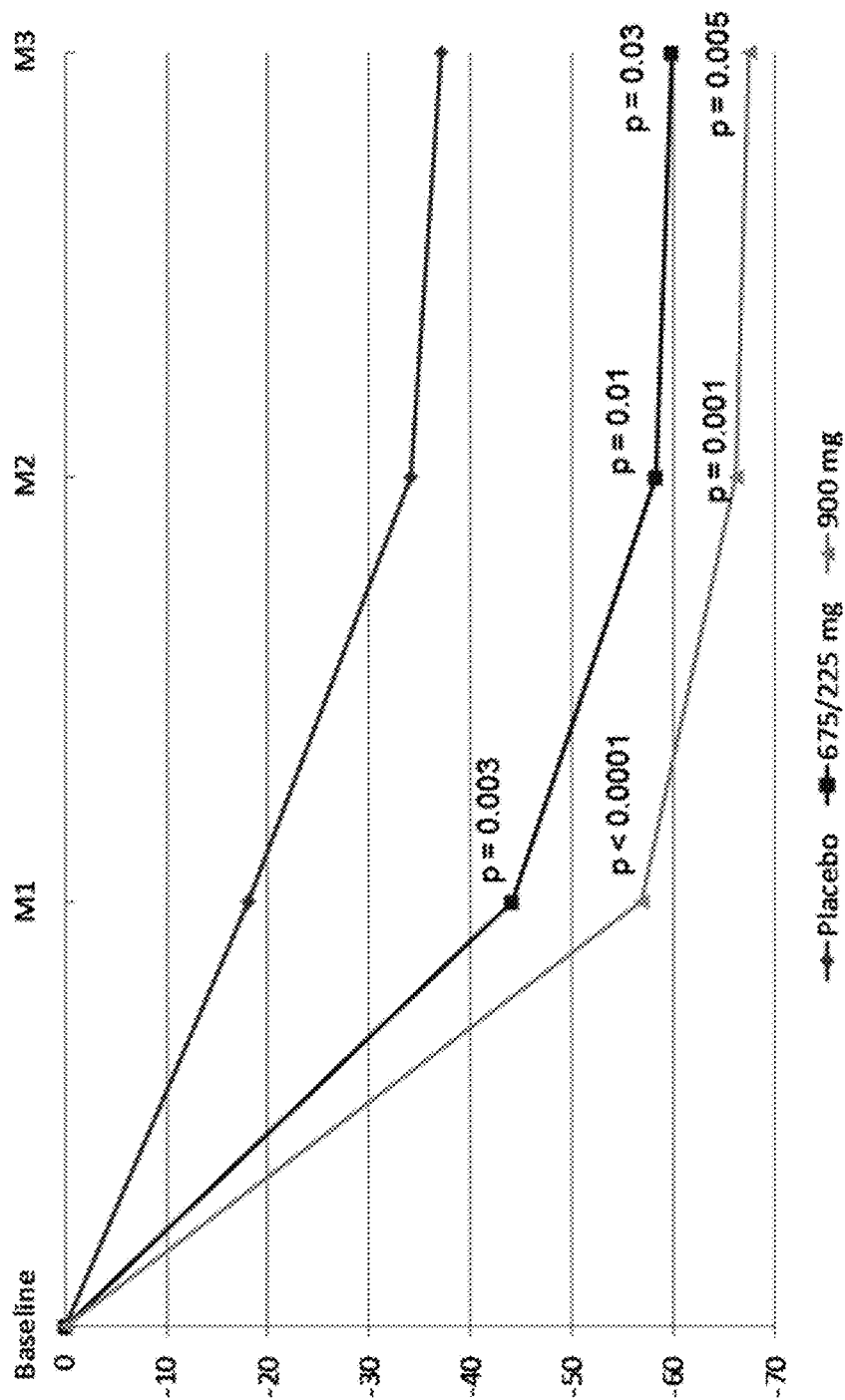
FIG. 12 is a graph illustrating results of a clinical study comparing the effects of different doses of antibody G1 to placebo.

Average decrease in number of headache hours relative to baseline at each of months 1, 2, and 3 (M1, M2, and M3, respectively) for each of the groups are represented graphically in FIG. 12. Results show a significant decrease in both treatment groups relative to the placebo group at all three time-points, including after the very first dose. Statistical significance relative to the placebo group for data in FIG. 12 is provided by the indicated p-values.

Figure 13:
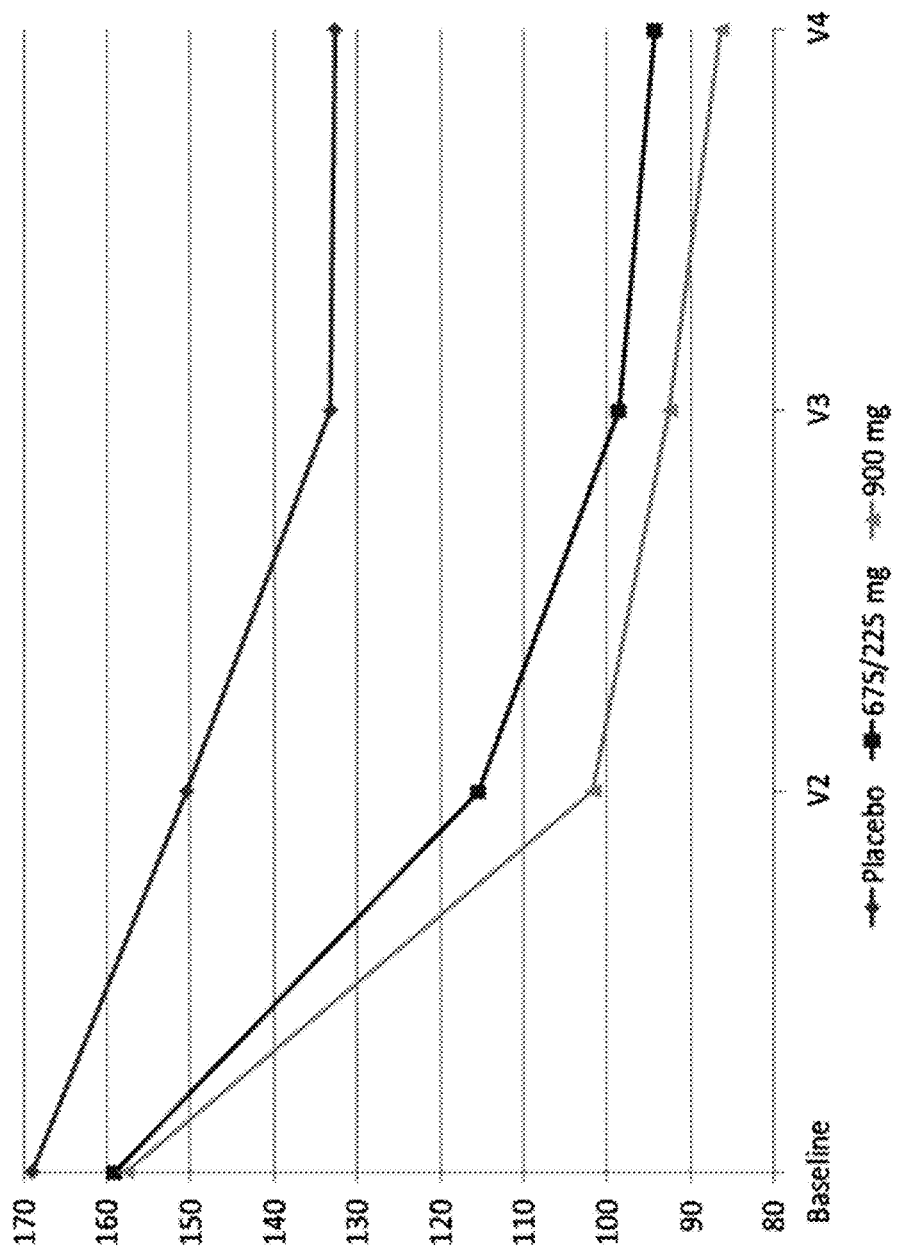
FIG. 13 is a graph illustrating results of a clinical study comparing the effects of different doses of antibody G1 to placebo.

Average number of headache hours in each group at baseline, and at visits 2, 3, and 4 (V2, V3, and V4, respectively) is represented graphically in FIG. 13. Results show a significant decrease in both treatment groups relative to the placebo group at all three time-points, including after the very first dose.

Figure 14:
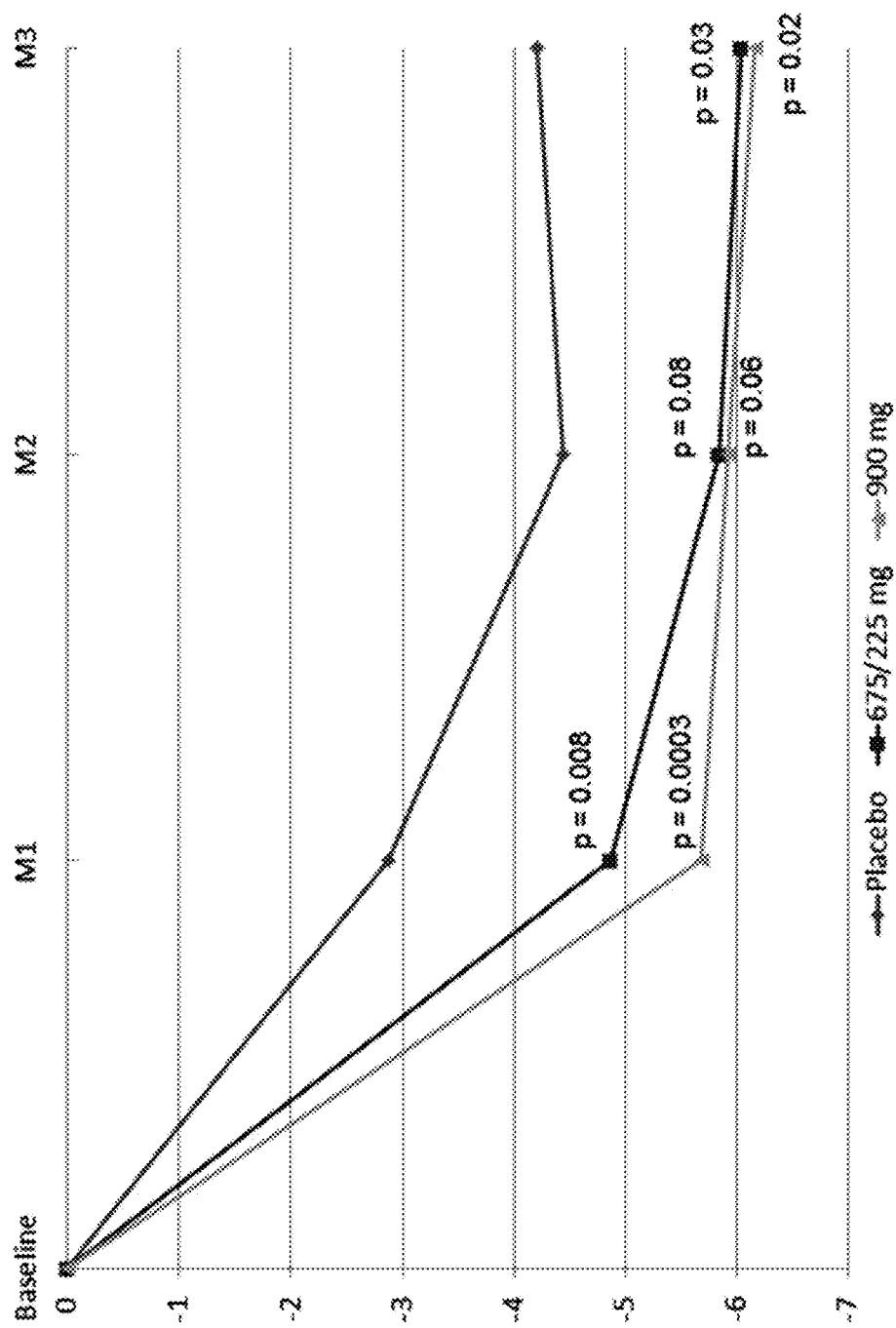
FIG. 14 is a graph illustrating results of a clinical study comparing the effects of different doses of antibody G1 to placebo.

Average decrease in number of headache days of moderate or severe intensity relative to baseline at each of months 1, 2, and 3 (M1, M2, and M3, respectively) for each of the groups are represented in FIG. 14. Results show a statistically significant decrease in both treatment groups relative to the placebo group at all three time-points, including after the very first dose. Statistical significance relative to the placebo group is provided by the indicated p-values.

Figure 16:
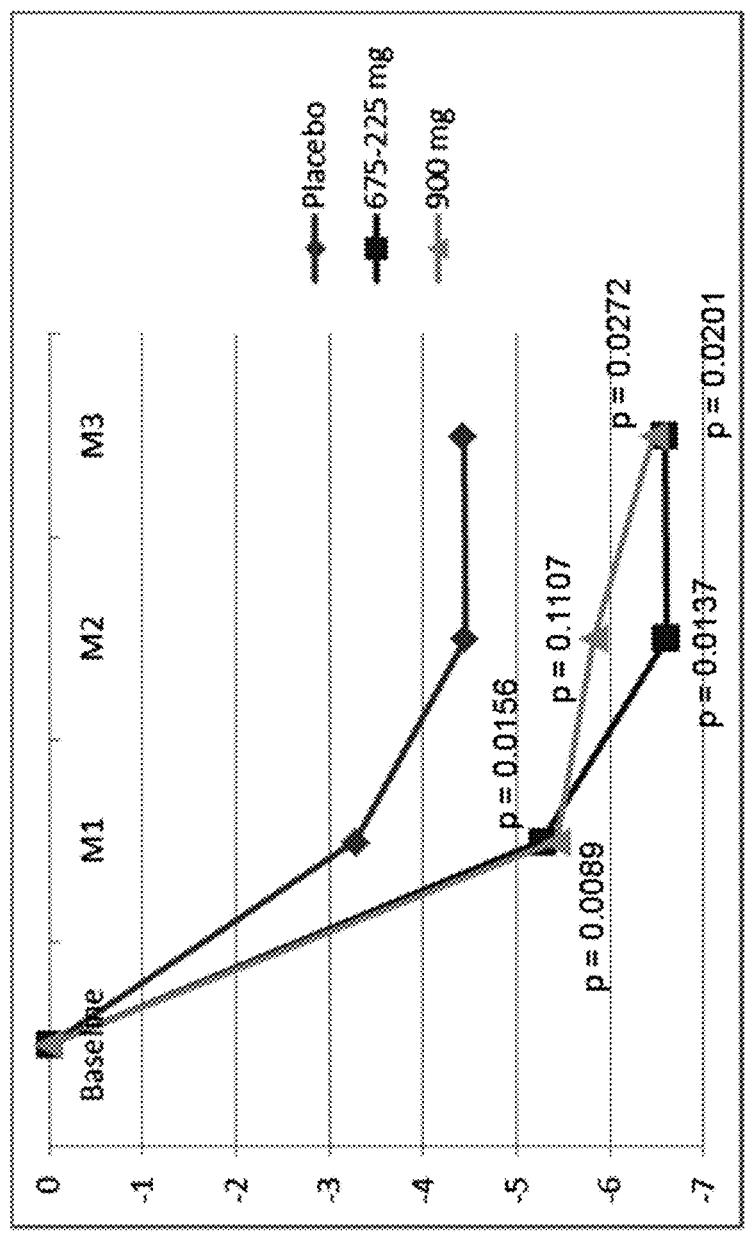
FIG. 16 is a graph illustrating results of a clinical study comparing the effects of different doses of antibody G1 to placebo.

Average decrease in number of uses of triptans as an acute rescue medication relative to baseline at each of months 1, 2, and 3 (M1, M2, and M3, respectively) for each of the groups are represented graphically in FIG. 16. Results show a significant decrease in triptan uses in both treatment groups relative to the placebo group at all three time-points, including after the very first dose. Statistical significance relative to the placebo group is provided by the indicated p-values in FIG. 16.

A significant decrease in number of headache hours was also observed in subjects using prevention medications (e.g., topiramate and amitriptyline or propranolol) relative to a placebo group.

Both doses were well tolerated, and no safety issues emerged. A summary of treatment emergent adverse events (TEAE) by group is provided in Table 10. The difference in related TEAE is almost totally explained by injection related mild events (erythema, some discomfort). The serious TEAE were not related to drug (no drug-related adverse events).

TABLE 10

|  | Placebo N (%) | 675/225 mg N (%) | 900 mg N (%) |
|---|---|---|---|
| TEAE | 36 (40.4) | 47 (53.4) | 41 (47.7) |
| Related TEAE | 15 (16.9) | 25 (28.4) | 28 (32.6) |
| Serious TEAE | 1 (1.1) | 1 (1.1) | 2 (2.3) |
| TEAE Causing Discontinuation | 1 (1.1) | 6 (6.8) | 5 (5.8) |
| Deaths | 0 | 0 | 0 |

Example 18: Prevention of High-Frequency Episodic Migraine in a Clinical Study of Antibody G1

A multicenter, randomized, double-blind, placebo-controlled, parallel-group study comparing anti-CGRP antibody G1 to placebo was performed in subjects with high-frequency episodic migraine (HFEM). Study design followed that of Example 17, with two differences. First, inclusion criteria (3) was for subjects fulfilling criteria for episodic migraine as per the Second Edition of The International Headache Society (Olesen and Steiner 2004), who experience migraine at high frequency as follows: (a) History of headaches on more than 8 days per month for at least 3 months prior to screening; (b) verification of headache frequency through prospectively collected baseline information during the 28-day run-in phase demonstrating headaches (of any type) on 8 to 14 days with at least 8 days fulfilling criteria for at least one of (i) migraine, (ii) probable migraine, or (iii) use of triptans or ergot compounds. Second, dosing schedules were changed for the groups receiving G1. Specifically, injections were administered subcutaneously over a 3-month period (every 28 days) to subjects in each of the following groups: (1) those randomized to the 675 mg arm received 675 mg of G1 every 28 days; (2) those randomized to the 225 mg arm receive 225 mg of G1 every 28 days; and (3) those randomized to placebo receive a placebo injection every 28 days. A summary of the disposition and demographics of subjects in the study is provided in Table 13. Endpoints of the study included decrease in number of migraine days and decrease in number of headache days of any severity.

TABLE 13

|  | Placebo | 225 mg | 675 mg | Total |
|---|---|---|---|---|
| Randomized | 104 | 96 | 97 | 297 |
| Analyzed as ITT | 104 (100%) | 95 (99%) | 96 (99%) | 295 (99%) |
| In Safety Analysis | 104 (100%) | 96 (100%) | 97 (100%) | 297 (100%) |
| Age (mean years) | 42.0 | 40.8 | 40.7 | 41.2 |
| % women | 88% | 91% | 85% | 88% |
| % white | 82% | 77% | 76% | 78% |

Figure 17:
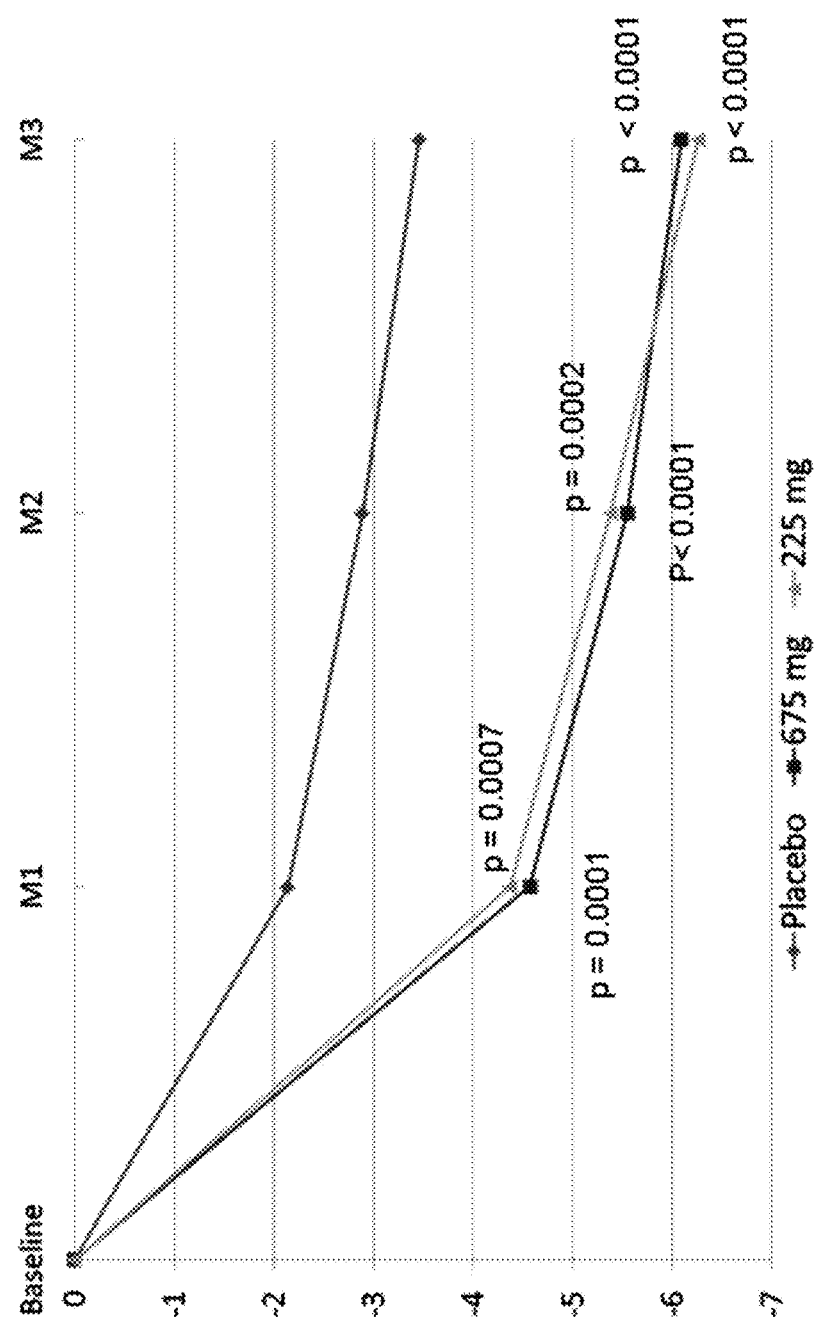
FIG. 17 is a graph illustrating results of a clinical study comparing the effects of different doses of antibody G1 to placebo.

Average decrease in number of migraine days relative to baseline at each of months 1, 2, and 3 (M1, M2, and M3, respectively) for each of the groups are represented in FIG. 17. Results show a statistically significant decrease in both treatment groups relative to the placebo group at all three time-points, including after the very first dose. Statistical significance relative to the placebo group is provided by the indicated p-values.

Figure 18:
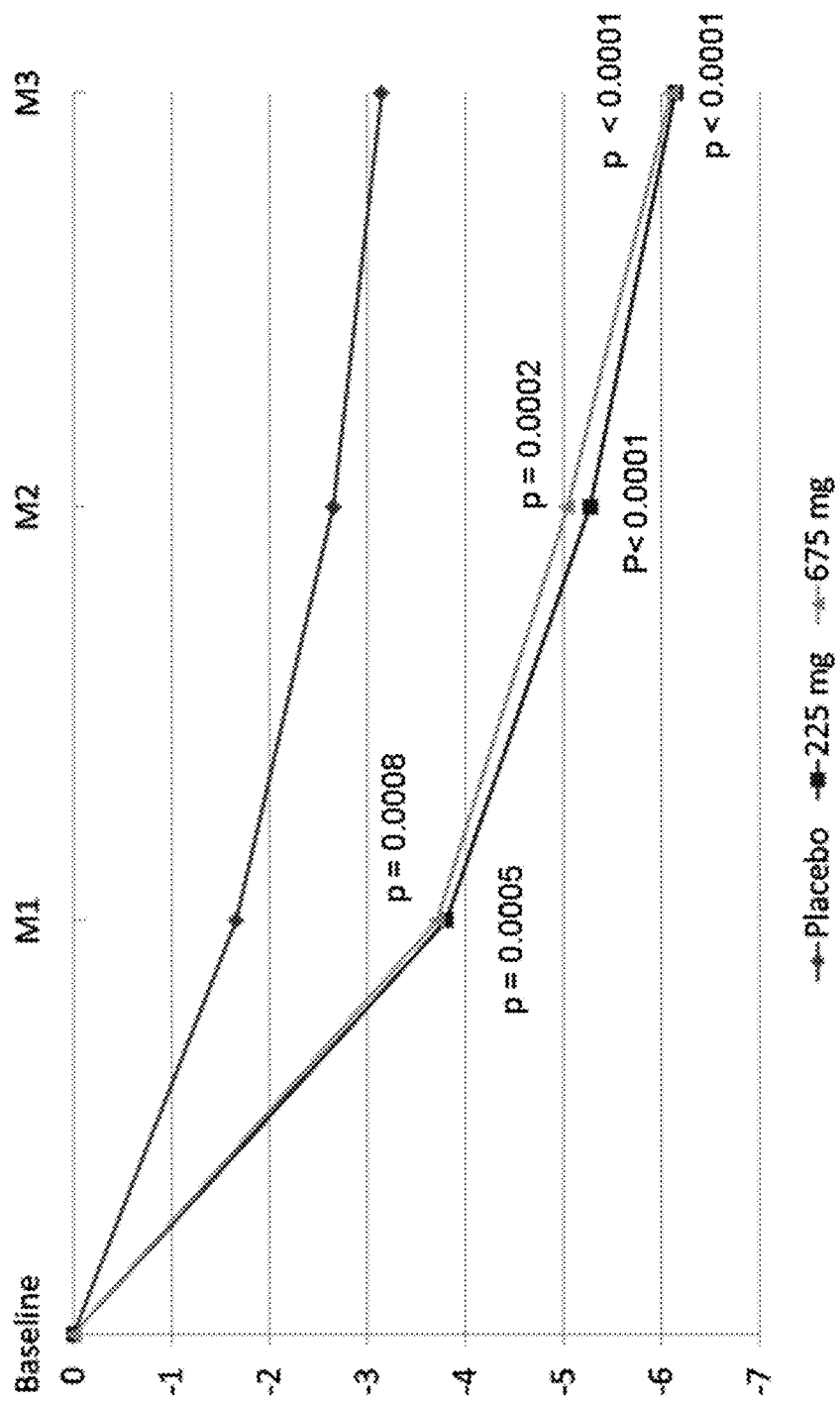
FIG. 18 is a graph illustrating results of a clinical study comparing the effects of different doses of antibody G1 to placebo.

Average decrease in number of headache days of any severity relative to baseline at each of months 1, 2, and 3 (M1, M2, and M3, respectively) for each of the groups are represented in FIG. 18. Results show a statistically significant decrease in both treatment groups relative to the placebo group at all three time-points, including after the very first dose. Statistical significance relative to the placebo group is provided by the indicated p-values.

Both doses were well tolerated, and no safety issues emerged. A summary of treatment emergent adverse events (TEAE) by group is provided in Table 14. The four serious TEAEs were due to one case of fibula fracture, one case of tremor due to stopping medication and two migraine cases requiring emergency room (ER) treatment.

TABLE 14

|  | Placebo N (%) | 225 mg N (%) | 675 mg N (%) |
|---|---|---|---|
| TEAE | 58 (56) | 44 (46) | 57 (59) |
| Related TEAE | 24 (23%) | 26 (27%) | 24 (25%) |
| Serious TEAE | 0 | 2 (2%) | 2 (2%) |
| Related serious TEAE | 0 | 0 | 0 |
| TEAE Causing Discontinuation | 0 | 4 (4%) | 2 (2%) |
| Deaths | 0 | 0 | 0 |

Example 19: Non-Clinical Safety

Two studies assessing the safety of antibody G1 were conducted in cynomolgus monkeys. In the first study, safety of a single dose of antibody G1 was evaluated. In the second study, safety of repeated dosing of antibody G1 was evaluated. Each of the studies and their results are further described in detail below. For both the single and repeat-dose studies, antibody G1 was formulated as a 51.4 mg/mL solution in 20 mM histidine, 84 mg/mL trehalose dihydrate, 0.2 mg/mL polysorbate 80, 0.05 mg/mL disodium EDTA dihydrate and 0.1 mg/mL L-methionine, pH ~5.5. Vehicle was formulated identically without antibody G1. Additionally, in both studies, blood samples were taken periodically for analysis of antibody G1 plasma concentration using a validated ELISA method.

Data were first aggregated in summary tables and figures using GraphPad Prism (version 6.0) and Excel 2010 (Microsoft). For the single exposure study, telemetry data were analyzed using ANOVA. Analysis was performed using SAS Release 8.2. In order to normalize the QT interval over a range of R-R intervals, Individual Animal Correction Factors (IACFs) were generated for each animal by relating each RR-interval with its associated QT-interval. The linear regression of this QT/RR-interval relationship was determined for the data set. The slope of this linear regression was used as the IACF for the associated animal across all treatments. This IACF was used to calculate the corrected QT-interval (QTc) using the following equation:

$$QT\text{-}I(c) = QT \text{ interval corrected for heart rate} = QT\text{-}I - [(RR-300)*(IACF)].$$

For the multiple-dose study, one-way ANOVA was also used to analyze data. If the ANOVA was significant ($P \leq 0.05$), Dunnett's post-test was used for in-between group comparisons. For each gender, the treated group was compared with the control (vehicle) group at the 5% two-tailed probability level.

Single-Dose Telemetry Study

Eight adult male cynomolgus monkeys (Charles River Primates) were surgically instrumented with telemeters and allowed to recover for at least two weeks. Implants (DSI TL11M2-D70-PCT) and receivers (RMC-1) were manufactured by Data Sciences International.

Animals were acclimated to telemetry data acquisition cages at least overnight prior to dosing. During acclimation, pre-study recording of hemodynamic parameters was conducted to verify that the transducers and equipment were functioning correctly. During telemetered data acquisition, animals were housed individually in cages equipped with telemetry receivers. On non-collection days, animals were housed in cages without telemetry receivers. Animals were maintained on a 12-hours light, 12-hours dark day cycle, with ad libitum water and fed with certified primate diet.

For the first phase of the study, animals (8 males) were administered vehicle only, and telemetry data were collected beginning ~1 hour pre-dose through 22 hours post-dose. Six days after vehicle administration, the same animals received a single IV administration of antibody G1 (100 mg/kg, an ~10-fold greater dose than the pharmacological EC50 in cynomolgus monkeys). Telemetered electrocardiographic and hemodynamic data were again continuously recorded from all animals. In addition, these animals were monitored for ~24 hours on days 3, 7, 10 and 14 after receiving their single dose of antibody G1. Telemetered ECG and blood pressure signals were transmitted via the implanted radio-telemetry devices to receivers mounted in each cage. The acquired signals were passed through a data exchange matrix (DSI model DEM) and on to a PC-based data acquisition system (DSI software Ponemah P3 version 3.4); the data analysis software was Emka Technologies version 2.4.0.20 (Emka Technologies). The analog/digital sampling rate was 1,000 Hz for telemetered ECG data and 500 Hz for blood pressure data. Data were logged as 1 min means.

Group mean systolic blood pressure (SBP) was similar before and after treatment with antibody G1 throughout the first day after dosing and on subsequent days (animals telemetered on days 3, 7, 10 and 14 at identical time intervals as day 1). At hours 1-4 post-dosing when antibody G1 blood concentrations were at maximal levels (mean concentration of 3,500 µg/mL at 4 hours), mean SBP was 111 mmHg compared with 113 mmHg at the same time interval following vehicle administration. Furthermore, SBP was 110 mmHg on days 3 and 7, 109 mmHg on day 10 and 110 mmHg on day 14 after antibody G1 administration. Similar SBP data were recorded for other time intervals. Since this was a crossover designed study, the treated animals served as their own controls. When the data were analyzed as differences in blood pressure after antibody G1 administration compared with vehicle treatment, there are minor statistically significant reductions in SBP at the latter time interval on days 7, 10 and 14.

Following treatment with antibody G1, diastolic blood pressure (DBP) was noted to be around 3 mmHg lower than the mean values obtained after vehicle administration. From hours 5-22, the group mean for the vehicle and antibody G1 group were similar. The same trend was seen on other days, when a slight decrease in the DBP (ranging from 2.62-3.5 mmHg) occurred in the first interval measured, with a few changes of similar magnitude seen sporadically on days 7-10 in the 7-22 hour interval. Similar to what was seen for the DBP, minor decreases in the heart rate were seen during the first assessment (hours 1-4) relative to vehicle treatment. Differences were undetectable during the intermediate assessments and were once more seen between hours 18-22 on all days.

Moreover, with respect to ECG findings, there were no statistically significant changes in QTc interval at any time point, relative to vehicle treatment. Although statistically significant changes in RR, PR, RS and QT were seen over the 14 day period when compared with vehicle, they were all minor in absolute value.

Repeat-Dose Safety Study

The repeat-dose safety study included 48 adult, gender-matched (6 per gender per group) antibody G1-naïve cynomolgus monkeys (Charles River Primates). Animals received vehicle or antibody G1 as an intravenous injection once weekly for 14 weeks at doses of 10 mg/kg, 100 mg/kg, or 300 mg/kg. In each group, two animals of each gender were allowed to recover for an additional 4 months following the end of dosing.

ECG and blood pressure measurements were recorded once during the pre-study phase, twice after steady-state was achieved (prior to dosing and 4 hours post-dose on Day 85) and once ~1 week after the end of dosing (day 103 of the recovery phase). Animals were anesthetized with ketamine and ECGs were recorded using eight leads. Measurement of ECGs (including heart rate) was done with the captured data using the Life Science Suite Ponemah Physiology Platform software system via DSI, using leads I, II, aVF, CG4RL and CV4LL, as standard. A heart rate correction for the QT interval (QTc) was calculated using the Bazett formula.

Blood pressure was recorded prior to the first dose, after 12 weeks of dosing (13 doses) and approximately 1 week after the end of dosing. No significant changes were noted in SBP or DBP in any of the treated groups of animals relative to vehicle-treated animals. Group mean heart rates were relatively consistent across the dose groups and time points measured, with no statistical differences measured. Plasma concentrations of antibody G1 were measured during the first week of dosing and at the time of blood pressure and ECG assessments, demonstrating accumulation with repeated, weekly dosing.

Moreover, with respect to ECG findings, there were no significant differences in QTc interval across all doses and time points. Additionally, no significant or relevant ECG changes were seen for any of the ECG parameters assessed over the course of the study.

In summary, antibody G1 was very well tolerated in both studies, with no clinically significant changes noted in any hemodynamic parameter, nor any relevant changes noted in any ECG parameter. In cynomolgus monkeys, cardiovascular and hemodynamic parameters do not appear to be affected by long-term inhibition of CGRP with antibody G1.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

Deposit of Biological Material

The following materials have been deposited with the American Type Culture Collection, 10801 University Boulevard, Manassas, Va. 20110-2209, USA (ATCC):

| Material | Antibody No. | ATCC Accession No. | Date of Deposit |
|---|---|---|---|
| pDb.CGRP.hFcGI | G1 heavy chain | PTA-6867 | Jul. 15, 2005 |
| pEb.CGRP.hKGI | G1 light chain | PTA-6866 | Jul. 15, 2005 |

Vector pEb.CGRP.hKGI is a polynucleotide encoding the G1 light chain variable region and the light chain kappa constant region; and vector pDb.CGRP.hFcGI is a polynucleotide encoding the G1 heavy chain variable region and the heavy chain IgG2 constant region containing the following mutations: A330P331 to S330S331 (amino acid numbering with reference to the wildtype IgG2 sequence; see Eur. J. Immunol. (1999) 29:2613-2624).

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Rinat Neuroscience Corp. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

```
Antibody sequences
G1 heavy chain variable region amino acid sequence
                                                        (SEQ ID NO: 1)
EVQLVESGGGLVQPGGSLRLSCAASGFTFSNYWISWVRQAPGKGLEWVAEIRSESDASATHYAEAVKG

RFTISRDNAKNSLYLQMNSLRAEDTAVYYCLAYFDYGLAIQNYWGQGTLVTVSS

G1 light chain variable region amino acid sequence
                                                        (SEQ ID NO: 2)
EIVLTQSPATLSLSPGERATLSCKASKRVTTYVSWYQQKPGQAPRLLIYGASNRYLGIPARFSGSGSGTD

FTLTISSLEPEDFAVYYCSQSYNYPYTFGQGTKLEIK

G1 CDR H1 (extended CDR)
                                                        (SEQ ID NO: 3)
GFTFSNYWIS G1 CDR H2 (extended CDR)
                                                        (SEQ ID NO: 4)
EIRSESDASATHYAEAVKG G1 CDR H3
                                                        (SEQ ID NO: 5)
YFDYGLAIQNY G1 CDR L1
                                                        (SEQ ID NO: 6)
KASKRVTTYVS G1 CDR L2
                                                        (SEQ ID NO: 7)
GASNRYL G1 CDR L3
                                                        (SEQ ID NO: 8)
SQSYNYPYT G1 heavy chain variable region nucleotide sequence
                                                        (SEQ ID NO: 9)
GAAGTTCAGCTGGTTGAATCCGGTGGTGGTCTGGTTCAGCCAGGTGGTTCCCTGCGTCTGTCCTGC

GCTGCTTCCGGTTTCACCTTCTCCAACTACTGGATCTCCTGGGTTCGTCAGGCTCCTGGTAAAGGTC

TGGAATGGGTTGCTGAAATCCGTTCCGAATCCGACGCGTCCGCTACCCATTACGCTGAAGCTGTTAA

AGGTCGTTTCACCATCTCCCGTGACAACGCTAAGAACTCCCTGTACCTGCAGATGAACTCCCTGCGT

GCTGAAGACACCGCTGTTTACTACTGCCTGGCTTACTTTGACTACGGTCTGGCTATCCAGAACTACT

GGGGTCAGGGTACCCTGGTTACCGTTTCCTCC

G1 light chain variable region nucleotide sequence
                                                        (SEQ ID NO: 10)
GAAATCGTTCTGACCCAGTCCCCGGCTACCCTGTCCCTGTCCCCAGGTGAACGTGCTACCCTGTCCTGC

AAAGCTTCCAAACGGGTTACCACCTACGTTTCCTGGTACCAGCAGAAACCCGGTCAGGCTCCTCGTCTG

CTGATCTACGGTGCTTCCAACCGTTACCTCGGTATCCCAGCTCGTTTCTCCGGTTCCGGTTCCGGTACC

GACTTCACCCTGACCATCTCCTCCCTGGAACCCGAAGACTTCGCTGTTTACTACTGCAGTCAGTCCTACA

ACTACCCCTACACCTTCGGTCAGGGTACCAAACTGGAAATCAAA

G1 heavy chain full antibody amino acid sequence (including modified
IgG2 as described herein)
                                                        (SEQ ID NO: 11)
EVQLVESGGGLVQPGGSLRLSCAASGFTFSNYWISWVRQAPGKGLEWVAEIRSESDASATHYAEAVKG

RFTISRDNAKNSLYLQMNSLRAEDTAVYYCLAYFDYGLAIQNYWGQGTLVTVSSASTKGPSVFPLAPCSR

STSESTAALGCLVKDYFPEPVTVSWNSGALTSGVHTFPAVLQSSGLYSLSSVVTVPSSNFGTQTYTCNVD

HKPSNTKVDKTVERKCCVECPPCPAPPVAGPSVFLFPPKPKDTLMISRTPEVTCVVVDVSHEDPEVQFN

WYVDGVEVHNAKTKPREEQFNSTFRVVSVLTVVHQDWLNGKEYKCKVSNKGLPSSIEKTISKTKGQPRE

PQVYTLPPSREEMTKNQVSLTCLVKGFYPSDIAVEWESNGQPENNYKTTPPMLDSDGSFFLYSKLTVDK

SRWQQGNVFSCSVMHEALHNHYTQKSLSLSPGK
```

G1 light chain full antibody amino acid sequence
(SEQ ID NO: 12)
EIVLTQSPATLSLSPGERATLSCKASKRVTTYVSWYQQKPGQAPRLLIYGASNRYLGIPARFSGSGSGTD

FTLTISSLEPEDFAVYYCSQSYNYPYTFGQGTKLEIKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPVTKSF

NRGEC

G1 heavy chain full antibody nucleotide sequence (including modified IgG2 as described herein)
(SEQ ID NO: 13)
GAAGTTCAGCTGGTTGAATCCGGTGGTGGTCTGGTTCAGCCAGGTGGTTCCCTGCGTCTGTCCTGC

GCTGCTTCCGGTTTCACCTTCTCCAACTACTGGATCTCCTGGGTTCGTCAGGCTCCTGGTAAAGGTC

TGGAATGGGTTGCTGAAATCCGTTCCGAATCCGACGCGTCCGCTACCCATTACGCTGAAGCTGTTAA

AGGTCGTTTCACCATCTCCCGTGACAACGCTAAGAACTCCCTGTACCTGCAGATGAACTCCCTGCGT

GCTGAAGACACCGCTGTTTACTACTGCCTGGCTTACTTTGACTACGGTCTGGCTATCCAGAACTACT

GGGGTCAGGGTACCCTGGTTACCGTTTCCTCCGCCTCCACCAAGGGCCCATCTGTCTTCCCACTGG

CCCCATGCTCCCGCAGCACCTCCGAGAGCACAGCCGCCCTGGGCTGCCTGGTCAAGGACTACTTCC

CAGAACCTGTGACCGTGTCCTGGAACTCTGGCGCTCTGACCAGCGGCGTGCACACCTTCCCAGCTG

TCCTGCAGTCCTCAGGTCTCTACTCCCTCAGCAGCGTGGTGACCGTGCCATCCAGCAACTTCGGCA

CCCAGACCTACACCTGCAACGTAGATCACAAGCCAAGCAACACCAAGGTCGACAAGACCGTGGAGA

GAAAGTGTTGTGTGGAGTGTCCACCTTGTCCAGCCCCTCCAGTGGCCGGACCATCCGTGTTCCTGTT

CCCTCCAAAGCCAAAGGACACCCTGATGATCTCCAGAACCCCAGAGGTGACCTGTGTGGTGGTGGA

CGTGTCCCACGAGGACCCAGAGGTGCAGTTCAACTGGTATGTGGACGGAGTGGAGGTGCACAACG

CCAAGACCAAGCCAAGAGAGGAGCAGTTCAACTCCACCTTCAGAGTGGTGAGCGTGCTGACCGTGG

TGCACCAGGACTGGCTGAACGGAAAGGAGTATAAGTGTAAGGTGTCCAACAAGGGACTGCCATCCA

GCATCGAGAAGACCATCTCCAAGACCAAGGGACAGCCAAGAGAGCCACAGGTGTATACCCTGCCCC

CATCCAGAGAGGAGATGACCAAGAACCAGGTGTCCCTGACCTGTCTGGTGAAGGGATTCTATCCATC

CGACATCGCCGTGGAGTGGGAGTCCAACGGACAGCCAGAGAACAACTATAAGACCACCCCTCCAAT

GCTGGACTCCGACGGATCCTTCTTCCTGTATTCCAAGCTGACCGTGGACAAGTCCAGATGGCAGCA

GGGAAACGTGTTCTCTTGTTCCGTGATGCACGAGGCCCTGCACAACCACTATACCCAGAAGAGCCT

GTCCCTGTCTCCAGGAAAGTAA

G1 light chain full antibody nucleotide sequence
(SEQ ID NO: 14)
GAAATCGTTCTGACCCAGTCCCCGGCTACCCTGTCCCTGTCCCCAGGTGAACGTGCTACCCTGTCC

TGCAAAGCTTCCAAACGGGTTACCACCTACGTTTCCTGGTACCAGCAGAAACCCGGTCAGGCTCCTC

GTCTGCTGATCTACGGTGCTTCCAACCGTTACCTCGGTATCCCAGCTCGTTTCTCCGGTTCCGGTTC

CGGTACCGACTTCACCCTGACCATCTCCTCCCTGGAACCCGAAGACTTCGCTGTTTACTACTGCAGT

CAGTCCTACAACTACCCCTACACCTTCGGTCAGGGTACCAAACTGGAAATCAAACGCACTGTGGCTG

CACCATCTGTCTTCATCTTCCCTCCATCTGATGAGCAGTTGAAATCCGGAACTGCCTCTGTTGTGTGC

CTGCTGAATAACTTCTATCCGCGCGAGGCCAAAGTACAGTGGAAGGTGGATAACGCCCTCCAATCC

GGTAACTCCCAGGAGAGTGTCACAGAGCAGGACAGCAAGGACAGCACCTACAGCCTCAGCAGCAC

CCTGACCCTGAGCAAAGCAGACTACGAGAAACACAAAGTCTACGCCTGCGAAGTCACCCATCAGGG

CCTGAGTTCTCCAGTCACAAAGAGCTTCAACCGCGGTGAGTGCTAA

-continued

Amino acid sequence comparison of human and rat CGRP (human α-CGRP (SEQ ID NO: 15); human β-CGRP (SEQ ID NO: 43); rat α-CGRP (SEQ ID NO: 41); and rat β-CGRP (SEQ ID NO: 44)):

NH₂-ACDTATCVTHRLAGLLSRSGGVVKNNFVPTNVGSKAF-CONH₂ (human α-CGRP)

NH₂-ACNTATCVTHRLAGLLSRSGGMVKSNFVPTNVGSKAF-CONH₂ (human β-CGRP)

NH₂-SCNTATCVTHRLAGLLSRSGGVVKDNFVPTNVGSEAF-CONH₂ (rat α-CGRP)

NH₂-SCNTATCVTHRLAGLLSRSGGVVKDNFVPTNVGSKAF-CONH₂ (rat β-CGRP)

Light chain variable region LCVR17 amino acid sequence
(SEQ ID NO: 58)
DIQMTQSPSSLSASVGDRVTITCRASQDIDNYLNWYQQKPGKAPKLLIYYTSEYHSGVPSRFSGSGSGTD

FTFTISSLQPEDIATYYCQQGDALPPTFGQGTKLEIK

Heavy chain variable region HCVR22 amino acid sequence
(SEQ ID NO: 59)
QVQLVQSGAEVKKPGASVKVSCKASGYTFGNYWMQVVVRQAPGQGLEWMGAIYEGTGDTRYIQKFAGR

VTMTRDTSTSTVYMELSSLRSEDTAVYYCARLSDYVSGFSYWGQGTLVTVSS

Light chain variable region LCVR18 amino acid sequence
(SEQ ID NO: 60)
DIQMTQSPSSLSASVGDRVTITCRASQDIDNYLNWYQQKPGKAPKLLIYYTSEYHSGVPSRFSGSGSGTD

FTFTISSLQPEDIATYYCQQGDALPPTFGQGTKLEIK

Heavy chain variable region HCVR23 amino acid sequence
(SEQ ID NO: 61)
QVQLVQSGAEVKKPGASVKVSCKASGYTFGNYWMQWVRQAPGQGLEWMGAIYEGTGKTVYIQKFAGR

VTMTRDTSTSTVYMELSSLRSEDTAVYYCARLSDYVSGFSYWGQGTLVTVSS

Light chain variable region LCVR19 amino acid sequence
(SEQ ID NO: 62)
DIQMTQSPSSLSASVGDRVTITCRASKDISKYLNWYQQKPGKAPKLLIYYTSGYHSGVPSRFSGSGSGTD

FTLTISSLQPEDFATYYCQQGDALPPTFGGGTKVEIK

Heavy chain variable region HCVR24 amino acid sequence
(SEQ ID NO: 63)
QVQLVQSGAEVKKPGSSVKVSCKASGYTFGNYWMQWVRQAPGQGLEWMGAIYEGTGKTVYIQKFADR

VTITADKSTSTAYMELSSLRSEDTAVYYCARLSDYVSGFGYWGQGTTVTVSS

Light chain variable region LCVR20 amino acid sequence
(SEQ ID NO: 64)
DIQMTQSPSSLSASVGDRVTITCRASRPIDKYLNWYQQKPGKAPKLLIYYTSEYHSGVPSRFSGSGSGTD

FTFTISSLQPEDIATYYCQQGDALPPTFGQGTKLEIK

Heavy chain variable region HCVR25 amino acid sequence
(SEQ ID NO: 65)
QVQLVQSGAEVKKPGASVKVSCKASGYTFGNYWMQWVRQAPGQGLEWMGAIYEGTGKTVYIQKFAGR

VTMTRDTSTSTVYMELSSLRSEDTAVYYCARLSDYVSGFGYWGQGTLVTVSS

Light chain variable region LCVR21 amino acid sequence
(SEQ ID NO: 66)
DIQMTQSPSSLSASVGDRVTITCRASQDIDKYLNWYQQKPGKAPKLLIYYTSGYHSGVPSRFSGSGSGTD

FTLTISSLQPEDFATYYCQQGDALPPTFGGGTKVEIK

Heavy chain variable region HCVR26 amino acid sequence
(SEQ ID NO: 67)
QVQLVQSGAEVKKPGSSVKVSCKASGYTFGNYWMQWVRQAPGQGLEWMGAIYEGTGKTVYIQKFAGR

VTITADKSTSTAYMELSSLRSEDTAVYYCARLSDYVSGFGYWGQGTTVTVSS

Light chain variable region LCVR27 amino acid sequence
(SEQ ID NO: 68)
QVLTQSPSSLSASVGDRVTINCQASQSVYHNTYLAWYQQKPGKVPKQLIYDASTLASGVPSRFSGSGSG

TDFTLTISSLQPEDVATYYCLGSYDCTNGDCFVFGGGTKVEIKR

-continued

Heavy chain variable region HCVR28 amino acid sequence
(SEQ ID NO: 69)
EVQLVESGGGLVQPGGSLRLSCAVSGIDLSGYYMNWVRQAPGKGLEWVGVIGINGATYYASWAKGRFTI

SRDNSKTTVYLQMNSLRAEDTAVYFCARGDIWGQGTLVTVSS

Light chain variable region LCVR29 amino acid sequence
(SEQ ID NO: 70)
QVLTQSPSSLSASVGDRVTINCQASQSVYDNNYLAWYQQKPGKVPKQLIYSTSTLASGVPSRFSGSGSG

TDFTLTISSLQPEDVATYYCLGSYDCSSGDCFVFGGGTKVEIKR

Heavy chain variable region HCVR30 amino acid sequence
(SEQ ID NO: 71)
EVQLVESGGGLVQPGGSLRLSCAVSGLDLSSYYMQWVRQAPGKGLEWVGVIGINDNTYYASWAKGRFT

ISRDNSKTTVYLQMNSLRAEDTAVYFCARGDIWGQGTLVTVSS

Light chain variable region LCVR31 amino acid sequence
(SEQ ID NO: 72)
QVLTQSPSSLSASVGDRVTINCQASQSVYDNNYLAWYQQKPGKVPKQLIYSTSTLASGVPSRFSGSGSG

TDFTLTISSLQPEDVATYYCLGSYDCSSGDCFVFGGGTKVEIKR

Heavy chain variable region HCVR32 amino acid sequence
(SEQ ID NO: 73)
EVQLVESGGGLVQPGGSLRLSCAVSGLDLSSYYMQWVRQAPGKGLEWVGVIGINDNTYYASWAKGRFT

ISRDNSKTTVYLQMNSLRAEDTAVYFCARGDIWGQGTLVTVSS

Light chain variable region LCVR33 amino acid sequence
(SEQ ID NO: 74)
QVLTQTPSPVSAAVGSTVTINCQASQSVYHNTYLAWYQQKPGQPPKQLIYDASTLASGVPSRFSGSGSG

TQFTLTISGVQCNDAAAYYCLGSYDCTNGDCFVFGGGTEVVVKR

Heavy chain variable region HCVR34 amino acid sequence
(SEQ ID NO: 75)
QSLEESGGRLVTPGTPLTLTCSVSGIDLSGYYMNWVRQAPGKGLEWIGVIGINGATYYASWAKGRFTISK

TSSTTVDLKMTSLTTEDTATYFCARGDIWGPGTLVTVSS

Light chain variable region LCVR35 amino acid sequence
(SEQ ID NO: 76)
QVLTQSPSSLSASVGDRVTINCQASQSVYHNTYLAWYQQKPGKVPKQLIYDASTLASGVPSRFSGSGSG

TDFTLTISSLQPEDVATYYCLGSYDCTNGDCFVFGGGTKVEIKR

Heavy chain variable region HCVR36 amino acid sequence
(SEQ ID NO: 77)
EVQLVESGGGLVQPGGSLRLSCAVSGIDLSGYYMNWVRQAPGKGLEWVGVIGINGATYYASWAKGRFTI

SRDNSKTTVYLQMNSLRAEDTAVYFCARGDIWGQGTLVTGSS

Light chain variable region LCVR37 amino acid sequence
(SEQ ID NO: 78)
QSVLTQPPSVSAAPGQKVTISCSGSSSNIGNNYVSWYQQLPGTAPKLLIYDNNKRPSGIPDRFSGSKSGT

STTLGITGLQTGDEADYYCGTWDSRLSAVVFGGGTKLTVL

Heavy chain variable region HCVR38 amino acid sequence
(SEQ ID NO: 79)
QVQLVESGGGVVQPGRSLRLSCAASGFTFSSFGMHWVRQAPGKGLEWVAVISFDGSIKYSVDSVKGRF

TISRDNSKNTLFLQMNSLRAEDTAVYYCARDRLNYYDSSGYYHYKYYGMAVWGQGTTVTVSS

The invention claimed is:

1. A method of treating or reducing incidence of headache in a subject comprising administering to the subject a dose once every three months of a monoclonal antibody that inhibits the calcitonin gene-related peptide (CGRP) pathway, wherein the dose administered every three months is between 100-2000 mg, and wherein the monoclonal antibody comprises a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8.

2. The method of claim 1, wherein the headache is migraine headache.

3. The method of claim 2, wherein the migraine headache is chronic migraine headache.

4. The method of claim 2, wherein the migraine headache is episodic migraine headache.

5. The method of claim 1, wherein the incidence of headache is reduced for at least seven days after a single administration.

6. The method of claim 1, wherein monthly headache hours experienced by the subject after said administering is reduced by 40 or more hours from a pre-administration level in the subject.

7. The method of claim 1, wherein monthly headache days experienced by the subject after said administering is reduced by 3 or more days from a pre-administration level in the subject.

8. The method of claim 1, wherein monthly headache hours experienced by the subject after said administering is reduced by 25% or more relative to a pre-administration level in the subject.

9. The method of claim 1, wherein the administering is subcutaneous or intravenous administration.

10. The method of claim 1, wherein the administering comprises utilizing a pre-filled syringe comprising the monoclonal antibody.

11. The method of claim 1, wherein the monoclonal antibody is formulated at a concentration of at least 150 mg/mL.

12. The method of claim 1, comprising administering to the subject a second agent simultaneously or sequentially with the monoclonal antibody.

13. The method of claim 12, wherein the second agent is selected from the group consisting of: 5-HT1 agonists, triptans, ergot alkaloids, and non-steroidal anti-inflammatory drugs.

14. The method of claim 13, wherein the second agent is a triptan.

15. The method of claim 12, wherein use of the second agent by the subject is decreased by at least 15% after administering the monoclonal antibody.

16. The method of claim 1, wherein the subject is human.

17. The method of claim 1, wherein the monoclonal antibody is human or humanized.

18. The method of claim 1, wherein the dose administered once every three months is 675 mg.

19. The method of claim 18, wherein the dose of 675 mg is administered as three injections of 225 mg each.

20. The method of claim 19, wherein each 225 mg injection is 1.5 mL.

21. The method of claim 19, wherein the injections are subcutaneous injections.

22. The method of claim 19, wherein the injections are injections into the abdomen, thigh, or upper arm of the subject's body.

23. A method of treating or reducing incidence of headache in a subject comprising administering to the subject a 675 mg dose of a monoclonal antibody that inhibits the calcitonin gene-related peptide (CGRP) pathway once every three months;
wherein the monoclonal antibody comprises a CDR H1 as set forth in SEQ ID NO: 3; a CDR H2 as set forth in SEQ ID NO: 4; a CDR H3 as set forth in SEQ ID NO: 5; a CDR L1 as set forth in SEQ ID NO: 6; a CDR L2 as set forth in SEQ ID NO: 7; and a CDR L3 as set forth in SEQ ID NO: 8; and
wherein the 675 mg dose is administered as three consecutive 225 mg subcutaneous injections of 1.5 mL to the abdomen, thigh, or upper arm of the subject's body.

* * * * *